US009040518B2

(12) United States Patent
Aquino et al.

(10) Patent No.: US 9,040,518 B2
(45) Date of Patent: May 26, 2015

(54) CHEMICAL COMPOUNDS

(75) Inventors: Christopher Joseph Aquino, Research Triangle Park, NC (US); Jon Loren Collins, Research Triangle Park, NC (US); David John Cowan, Research Triangle Park, NC (US); Yulin Wu, Research Triangle Park, NC (US)

(73) Assignee: GlaxoSmithKline LLC, Wilmington, New Castle, DE (US)

( * ) Notice: Subject to any disclaimer, the term of this patent is extended or adjusted under 35 U.S.C. 154(b) by 132 days.

(21) Appl. No.: 13/640,166

(22) PCT Filed: Apr. 27, 2011

(86) PCT No.: PCT/US2011/034024
§ 371 (c)(1),
(2), (4) Date: Oct. 9, 2012

(87) PCT Pub. No.: WO2011/137135
PCT Pub. Date: Nov. 3, 2011

(65) Prior Publication Data
US 2013/0029938 A1 Jan. 31, 2013

Related U.S. Application Data

(60) Provisional application No. 61/328,212, filed on Apr. 27, 2010, provisional application No. 61/329,225, filed on Apr. 29, 2010.

(51) Int. Cl.
| | | |
|---|---|---|
| A61K 31/554 | (2006.01) | |
| C07D 281/10 | (2006.01) | |
| C07D 417/06 | (2006.01) | |
| C07F 9/6541 | (2006.01) | |

(52) U.S. Cl.
CPC ............ *C07D 281/10* (2013.01); *C07D 417/06* (2013.01); *C07F 9/6541* (2013.01)

(58) Field of Classification Search
CPC ........................... A61K 31/554; C07D 281/10
USPC ...................... 514/211.09; 540/552
See application file for complete search history.

(56) References Cited

U.S. PATENT DOCUMENTS

| | | |
|---|---|---|
| 2003/0195218 A1 | 10/2003 | Koeller et al. |
| 2004/0077625 A1 | 4/2004 | Tremont et al. |
| 2004/0110785 A1 | 6/2004 | Wang et al. |
| 2006/0100218 A1 | 5/2006 | Ibrahim et al. |
| 2010/0130472 A1* | 5/2010 | Young et al. ............. 514/211.09 |

FOREIGN PATENT DOCUMENTS

| | | |
|---|---|---|
| WO | WO 94/18183 | 8/1994 |
| WO | WO 96/05188 | 2/1996 |
| WO | WO 02/08211 | 1/2002 |
| WO | WO 02/053548 | 7/2002 |
| WO | WO 03/022825 | 3/2003 |
| WO | WO 2004/076430 | 9/2004 |

OTHER PUBLICATIONS

Zhang et al. Topology Scanning and Putative Three-Dimensional Structure of the Extracellular Binding Domains of the Apical Sodium-Dependent Bile Acid Transporter (SLC10A2). Biochemistry, 2004, vol. 43, pp. 11380-11392, p. 11383; p. 11385-11390.
Christ et al. "Rational design of small-molecule inhibitors of the LEDGF/75-integrase interaction and HIV replication." Nature Chemical Biology, 2010, vol. 6(6), pp. 442-448.
EP Search Report for PCT/US2012046354 dated Feb. 6, 2015.
Examination Search Report for Singapore Patent Application No. 2012074860 (national Phase Entry Application of PCT/US2011/034024), Aug. 22, 2014.

* cited by examiner

*Primary Examiner* — Brenda Coleman
(74) *Attorney, Agent, or Firm* — Robert H. Brink

(57) ABSTRACT

Compounds of Formula I and methods for treating metabolic disorders are disclosed.

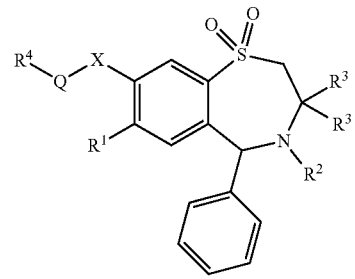

22 Claims, No Drawings

CHEMICAL COMPOUNDS

CROSS-REFERENCE TO RELATED APPLICATIONS

This application is filed pursuant to 35 USC 371 as a United States National Phase Application of International Patent Application Serial No. PCT/US2011/034024 filed on Apr. 27, 2011, which claims priority from 61/328,212 filed on Apr. 27, 2010 and 61/329,225 filed on Apr. 29, 2010 in the United States.

FIELD OF THE INVENTION

The present invention relates to compounds that are useful in the treatment and prevention of metabolic disorders, including diabetes mellitus (Type I and Type II), obesity, and related disorders, and also includes methods for making the compounds, pharmaceutical compositions containing the compounds, and therapeutic uses for such compounds.

BACKGROUND OF THE INVENTION

More than 200 million people worldwide have diabetes. The World Health Organization estimates that 1.1 million people died from diabetes in 2005 and projects that worldwide deaths from diabetes will double between 2005 and 2030. New chemical compounds that effectively treat diabetes could save millions of human lives.

Diabetes refers to metabolic disorders resulting in the body's inability to effectively regulate glucose levels. Approximately 90% of all diabetes cases are a result of type 2 diabetes whereas the remaining 10% are a result of type 1 diabetes, gestational diabetes, and latent autoimmune diabetes of adulthood (LADA). All forms of diabetes result in elevated blood glucose levels and, if left untreated chronically, can increase the risk of macrovascular (heart disease, stroke, other forms of cardiovascular disease) and microvascular [kidney failure (nephropathy), blindness from diabetic retinopathy, nerve damage (diabetic neuropathy)] complications.

Type 1 diabetes, also known as juvenile or insulin-dependent diabetes mellitus (IDDM), can occur at any age, but it is most often diagnosed in children, adolescents, or young adults. Type 1 diabetes is caused by the autoimmune destruction of insulin-producing beta cells, resulting in an inability to produce sufficient insulin. Insulin controls blood glucose levels by promoting transport of blood glucose into cells for energy use. Insufficient insulin production will lead to decreased glucose uptake into cells and result in accumulation of glucose in the bloodstream. The lack of available glucose in cells will eventually lead to the onset of symptoms of type 1 diabetes: polyuria (frequent urination), polydipsia (thirst), constant hunger, weight loss, vision changes, and fatigue. Within 5-10 years of being diagnosed with type 1 diabetes, patient's insulin-producing beta cells of the pancreas are completely destroyed, and the body can no longer produce insulin. As a result, patients with type 1 diabetes will require daily administration of insulin for the remainder of their lives.

Type 2 diabetes, also known as non-insulin-dependent diabetes mellitus (NIDDM) or adult-onset diabetes, occurs when the pancreas produces insufficient insulin and/or tissues become resistant to normal or high levels of insulin (insulin resistance), resulting in excessively high blood glucose levels. Multiple factors can lead to insulin resistance including chronically elevated blood glucose levels, genetics, obesity, lack of physical activity, and increasing age. Unlike type 1 diabetes, symptoms of type 2 diabetes are more salient, and as a result, the disease may not be diagnosed until several years after onset with a peak prevalence in adults near an age of 45 years. Unfortunately, the incidence of type 2 diabetes in children is increasing.

The primary goal of treatment of type 2 diabetes is to achieve and maintain glycemic control to reduce the risk of microvascular (diabetic neuropathy, retinopathy, or nephropathy) and macrovascular (heart disease, stroke, other forms of cardiovascular disease) complications. Current guidelines for the treatment of type 2 diabetes from the American Diabetes Association (ADA) and the European Association for the Study of Diabetes (EASD) [*Diabetes Care*, 2008, 31 (12), 1] outline lifestyle modification including weight loss and increased physical activity as a primary therapeutic approach for management of type 2 diabetes. However, this approach alone fails in the majority of patients within the first year, leading physicians to prescribe medications over time. The ADA and EASD recommend metformin, an agent that reduces hepatic glucose production, as a Tier 1a medication; however, a significant number of patients taking metformin can experience gastrointestinal side effects and, in rare cases, potentially fatal lactic acidosis. Recommendations for Tier 1b class of medications include sulfonylureas, which stimulate pancreatic insulin secretion via modulation of potassium channel activity, and exogenous insulin. While both medications rapidly and effectively reduce blood glucose levels, insulin requires 1-4 injections per day and both agents can cause undesired weight gain and potentially fatal hypoglycemia. Tier 2a recommendations include newer agents such as thiazolidinediones (TZDs pioglitazone and rosiglitazone), which enhance insulin sensitivity of muscle, liver and fat, as well as GLP-1 analogs, which enhance postprandial glucose-mediated insulin secretion from pancreatic beta cells. While TZDs show robust, durable control of blood glucose levels, adverse effects include weight gain, edema, bone fractures in women, exacerbation of congestive heart failure, and potential increased risk of ischemic cardiovascular events. GLP-1 analogs also effectively control blood glucose levels, however, this class of medications requires injection and many patients complain of nausea. The most recent addition to the Tier 2 medication list is DPP-4 inhibitors, which, like GLP-1 analogs, enhance glucose-medicated insulin secretion from beta cells. Unfortunately, DPP-4 inhibitors only modestly control blood glucose levels, and the long-term safety of DPP-4 inhibitors remains to be firmly established. Other less prescribed medications for type 2 diabetes include α-glucosidase inhibitors, glinides, and amylin analogs. Clearly, new medications with improved efficacy, durability, and side effect profiles are needed for patients with type 2 diabetes.

GLP-1 and GIP are peptides, known as incretins, that are secreted by L and K cells, respectively, from the gastrointestinal tract into the blood stream following ingestion of nutrients. This important physiological response serves as the primary signaling mechanism between nutrient (glucose/fat) concentration in the gastrointestinal tract and other peripheral organs. Upon secretion, both circulating peptides initiate signals in beta cells of the pancreas to enhance glucose-stimulated insulin secretion, which, in turn, controls glucose concentrations in the blood stream (For reviews see: *Diabetic Medicine* 2007, 24(3), 223; *Molecular and Cellular Endocrinology* 2009, 297(1-2), 127; *Experimental and Clinical Endocrinology & Diabetes* 2001, 109(Suppl. 2), S288).

The association between the incretin hormones GLP-1 and GIP and type 2 diabetes has been extensively explored. The majority of studies indicate that type 2 diabetes is associated with an acquired defect in GLP-1 secretion as well as GIP action (see *Diabetes* 2007, 56(8), 1951 and *Current Diabetes Reports* 2006, 6(3), 194). The use of exogenous GLP-1 for treatment of patients with type 2 diabetes is severely limited due to its rapid degradation by the protease DPP-4. Multiple modified peptides have been designed as GLP-1 mimetics that are DPP-4 resistant and show longer half-lives than endogenous GLP-1. Agents with this profile that have been shown to be highly effective for treatment of type 2 diabetes include exenatide and liraglutide, however, these agents require injection. Oral agents that inhibit DPP-4, such as sitagliptin vildagliptin, and saxagliptin, elevate intact GLP-1 and modestly control circulating glucose levels (see *Pharmacology & Therapeutics* 2010, 125(2), 328; *Diabetes Care* 2007, 30(6), 1335; *Expert Opinion on Emerging Drugs* 2008, 13(4), 593). New oral medications that increase GLP-1 secretion would be desirable for treatment of type 2 diabetes.

Bile acids have been shown to enhance peptide secretion from the gastrointestinal tract. Bile acids are released from the gallbladder into the small intestine after each meal to facilitate digestion of nutrients, in particular fat, lipids, and lipid-soluble vitamins. Bile acids also function as hormones that regulate cholesterol homeostasis, energy, and glucose homeostasis via nuclear receptors (FXR, PXR, CAR, VDR) and the G-protein coupled receptor TGR5 (for reviews see: *Nature Drug Discovery* 2008, 7, 672; *Diabetes, Obesity and Metabolism* 2008, 10, 1004). TGR5 is a member of the Rhodopsin-like subfamily of GPCRs (Class A) that is expressed in intestine, gall bladder, adipose tissue, liver, and select regions of the central nervous system. TGR5 is activated by multiple bile acids with lithocholic and deoxycholic acids as the most potent activators (Journal of Medicinal Chemistry 2008, 51(6), 1831). Both deoxycholic and lithocholic acids increase GLP-1 secretion from an enteroendocrine STC-1 cell line, in part through TGR5 (*Biochemical and Biophysical Research Communications* 2005, 329, 386). A synthetic TGR5 agonist INT-777 has been shown to increase intestinal GLP-1 secretion in vivo in mice (*Cell Metabolism* 2009, 10, 167). Bile salts have been shown to promote secretion of GLP-1 from colonic L cells in a vascularly perfused rat colon model (*Journal of Endocrinology* 1995, 145(3), 521) as well as GLP-1, peptide YY (PYY), and neurotensin in a vascularly perfused rat ileum model (*Endocrinology* 1998, 139(9), 3780). In humans, infusion of deoxycholate into the sigmoid colon produces a rapid and marked dose responsive increase in plasma PYY and enteroglucagon concentrations (*Gut* 1993, 34(9), 1219). Agents that increase ileal and colonic bile acid or bile salt concentrations will increase gut peptide secretion including, but not limited to, GLP-1 and PYY.

Bile acids are synthesized from cholesterol in the liver then undergo conjugation of the carboxylic acid with the amine functionality of taurine and glycine. Conjugated bile acids are secreted into the gall bladder where accumulation occurs until a meal is consumed. Upon eating, the gall bladder contracts and empties its contents into the duodenum, where the conjugated bile acids facilitate absorption of cholesterol, fat, and fat-soluble vitamins in the proximal small intestine (For reviews see: *Frontiers in Bioscience* 2009, 14, 2584; *Clinical Pharmacokinetics* 2002, 41(10), 751; *Journal of Pediatric Gastroenterology and Nutrition* 2001, 32, 407). Conjugated bile acids continue to flow through the small intestine until the distal ileum where 90% are reabsorbed into enterocytes via the apical sodium-dependent bile acid transporter (ASBT, also known as iBAT). The remaining 10% are deconjugated to bile acids by intestinal bacteria in the terminal ileum and colon of which 5% are then passively reabsorbed in the colon and the remaining 5% being excreted in feces. Bile acids that are reabsorbed by ASBT in the ileum are then transported into the portal vein for recirculation to the liver. This highly regulated process, called enterohepatic recirculation, is important for the body's overall maintenance of the total bile acid pool as the amount of bile acid that is synthesized in the liver is equivalent to the amount of bile acids that are excreted in feces. Pharmacological disruption of bile acid reabsorption with an inhibitor of ASBT leads to increased concentrations of bile acids in the colon and feces, a physiological consequence being increased conversion of hepatic cholesterol to bile acids to compensate for fecal loss of bile acids. Many pharmaceutical companies have pursued this mechanism as a strategy for lowering serum cholesterol in patients with dyslipidemia/hypercholesterolemia (For a review see: *Current Medicinal Chemistry* 2006, 13, 997). Importantly, ASBT-inhibitor mediated increase in colonic bile acid/salt concentration also will increase intestinal GLP-1, PYY, GLP-2, and other gut peptide hormone secretion. Thus, inhibitors of ASBT could be useful for treatment of type 2 diabetes, type 1 diabetes, dyslipidemia, obesity, short bowel syndrome, Chronic Idiopathic Constipation, Irritable bowel syndrome (IBS), Crohn's disease, and arthritis.

Certain 1,4-thiazepines are disclosed, for example in WO 94/18183 and WO 96/05188. These compounds are said to be useful as ileal bile acid reuptake inhibitors (ASBT).

SUMMARY OF THE INVENTION

Briefly, in one aspect, the present invention discloses compound of Formula I

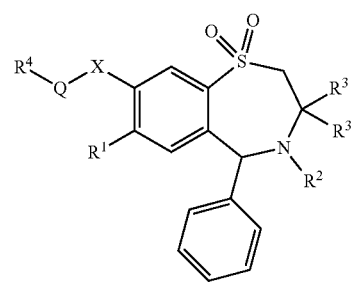

wherein $R^1$ is H, Cl, Br, N(CH$_3$)$_2$, or methoxy;
$R^2$ is H or OH;
each $R^3$ is independently C$_{1-6}$alkyl;
X is CH$_2$, C(O), or CH=CH;
Q is C$_{0-6}$alkyl;
$R^4$ is OH, SO$_3$H, CO$_2$H, PO$_3$H$_2$, CONR$^5$R$^5$, NR$^5$R$^5$; or NHC(O)CH$_2$NR$^5$R$^5$;
each $R^5$ is independently H, OH, C$_{1-6}$alkyl, C$_{0-6}$alkylCO$_2$H, C$_{0-6}$alkylSO$_3$H, C$_{0-6}$alkylPO$_3$H$_2$, C(O)C$_{0-6}$alkylCO$_2$H, C(O)C$_{0-6}$alkylSO$_3$H, C(O)C$_{0-6}$alkylPO$_3$H$_2$, or CH(R$^7$)C$_{0-6}$alkylCO$_2$H; and
$R^7$ is C$_{0-6}$alkylCO$_2$H, C$_{0-6}$alkylOH, C$_{0-6}$alkylSO$_3$H, or C$_{0-6}$alkylPO$_3$H$_2$.

In another aspect, the present invention discloses pharmaceutically acceptable salts of the compounds of Formula I.

In another aspect, the present invention discloses pharmaceutical compositions comprising a compound of Formula I or a pharmaceutically acceptable salt thereof.

In another aspect, the present invention discloses a method for treating or preventing metabolic disorders, including diabetes mellitus (Type I and Type II), obesity, and related disorders in a human, comprising administration of a compound of Formula I or a pharmaceutically acceptable salt thereof.

DETAILED DESCRIPTION OF THE INVENTION

Preferably, $R^1$ is methoxy.
Preferably, $R^2$ is H.
Preferably, each $R^3$ is independently $C_{2-4}$ alkyl. Most preferably, each $R^3$ is independently ethyl or n-butyl.

When the $R^3$ groups are different, the carbon to which they are bonded is chiral. In those chiral compounds, the preferred stereochemistry at that carbon atom is R.

The carbon atom to which the unsubstituted phenyl ring is bonded, is chiral. The preferred stereochemistry at that carbon atom is R.

Preferably, X is $CH_2$ or C(O). Most preferably X is $CH_2$.
Preferably Q is $C_{0-2}$alkyl. Most preferably Q is a $C_0$alkyl (i.e. absent).

Preferably, $R^4$ is $PO_3H_2$ or $NR^5R^5$. Most preferably $R^4$ is $NR^5R^5$.

Preferably, one $R^5$ is H and the other is OH, methyl, $C_{1-4}$alkyl$CO_2H$, $C_{0-2}$alkylSO$_3$H, $C_{1-2}$alkylPO$_3$H$_2$, C(O)CO$_2$H, C(O)C$_{1-2}$alkylSO$_3$H, C(O)C$_{1-2}$alkylPO$_3$H$_2$, or CH(R$^7$) C$_{0-1}$alkyCO$_2$H. Most preferably, one $R^5$ is H and the other is CH$_2$CO$_2$H, CH$_2$SO$_3$H, CH$_2$CH$_2$SO$_3$H, or CH(R$^7$) C$_{0-1}$alkyCO$_2$H.

Preferably, $R^7$ is $C_{0-1}$alkylCO$_2$H or $C_{0-2}$alkylSO$_3$H. Most preferably $R^7$ is $C_{0-1}$alkylCO$_2$H.

As used herein, "alkyl" can be straight chain or branched chain alkyl, unless clearly indicated otherwise.

For a review of suitable pharmaceutically acceptable salts see, for example, Berge et al, J. Pharm, Sci., 66, 1-19, 1977. In an embodiment, acid addition salts are selected from the hydrochloride, hydrobromide, hydroiodide, sulphate, bisulfate, nitrate, phosphate, hydrogen phosphate, acetate, benzoate, succinate, saccharate, fumarate, maleate, lactate, citrate, tartrate, gluconate, camsylate, methanesulfonate, ethanesulfonate, benzenesulfonate, p-toluenesulfonate and pamoate. In an embodiment, base addition salts include metal salts (such as sodium, potassium, aluminium, calcium, magnesium and zinc) and ammonium salts (such as isopropylamine, diethylamine, diethanolamine salts). Other salts (such as trifluoroacetates and oxalates) may be used in the manufacture of compounds of formula (I) and their pharmaceutically acceptable salts, and are included within the scope of the invention. Acid and base addition salts may be prepared by the skilled chemist, by treating a compound of formula (I) with the appropriate acid or base in a suitable solvent, followed by crystallisation and filtration.

The method of treating or preventing metabolic disorders may comprise administration of a compound or salt of this invention alone as mono-therapy. The compounds and salts of this invention may also be used in combination with other therapeutic agents. Suitable agents for use in combination with the compounds and salts of this invention include, for example, insulin sensitivity enhancers, glucose absorption inhibitors, biquanides, insulin secretion enhancers, or metformin.

EXAMPLES

The compounds of this invention may be made by a variety of methods, including well-known standard synthetic methods. Illustrative general synthetic methods are set out below and then specific compounds of the invention are prepared in the working examples.

In all of the schemes described below, protecting groups for sensitive or reactive groups are employed where necessary in accordance with general principles of synthetic chemistry. Protecting groups are manipulated according to standard methods of organic synthesis (T. W. Green and P. G. M. Wuts, (1991) *Protecting Groups in Organic Synthesis*, John Wiley & Sons, incorporated by reference with regard to protecting groups). These groups are removed at a convenient stage of the compound synthesis using methods that are readily apparent to those skilled in the art. The selection of processes as well as the reaction conditions and order of their execution shall be consistent with the preparation of compounds of the present invention. Compounds of the invention can be readily prepared according to Schemes 1 through 9 by those skilled in the art.

As illustrated in Scheme 1, several key intermediates can be prepared from (3R,5R)-3-butyl-3-ethyl-7,8-bis(methyloxy)-5-phenyl-2,3,4,5-tetrahydro-1,4-benzothiazepine 1,1-dioxide (Brieaddy, L. E. WO9605188, 1996). Lewis acid-mediated demethylation followed by reaction with triflic anhydride provided an intermediate triflate (A). Reaction of A with carbon monoxide and palladium catalyst in MeOH provided ester intermediate (B). Reaction of A in the presence of cyanide and palladium catalyst provided intermediate nitrile (C), which was reduced with Diisobutylaluminum hydride (DiBAL-H) to give intermediate aldehyde (D) or subjected to hydrogenation in the presence of palladium and acid gave rise to aminomethyl intermediate (E).

Scheme 1: Preparation of key intermediates

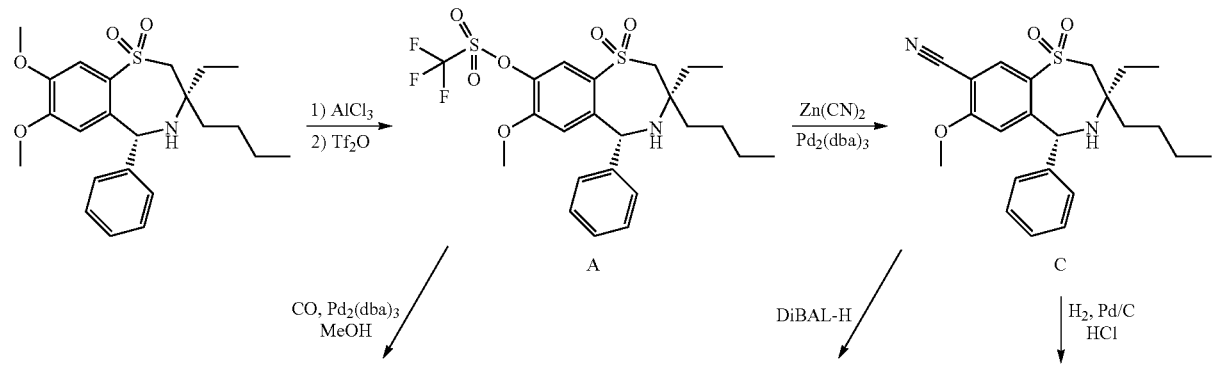

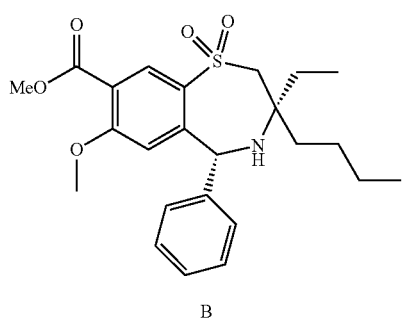

B

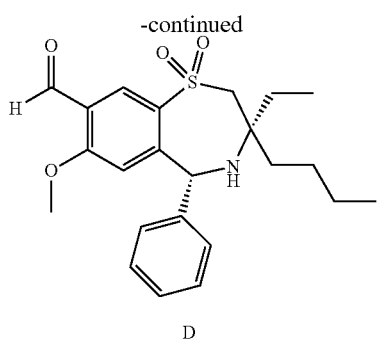

D

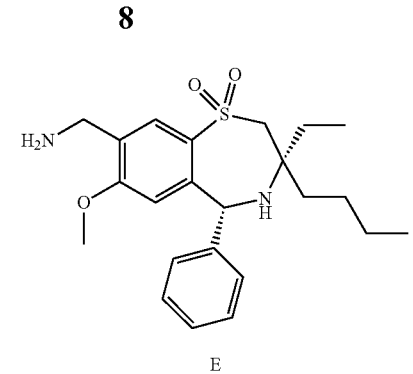

E

Compounds of the invention can be prepared as In Scheme 2. Subjection of intermediate aldehyde (D) to reductive amination conditions with a substituted amine followed by, if necessary, deprotection with acid, base or functionalization (oxidation) gave rise to 8-aminomethyl examples (F). Alternatively, Intermediate (E) was acylated with chloroalkyl acid chlorides then subjected to reaction with various nucleophiles including sulphite, phosphite, hydroxide, and substituted amines followed by, if required, deprotection of a protecting group to give acylated 8-aminomethyl examples (F). Third and fourth procedures to prepare 8-aminomethyl compounds of the invention involved reaction of Intermediate (E) with functionalized bromides in the presence of base or paraformaldehyde and triethylphospite to give other substituted 8-aminomethyl compounds (F).

Scheme 2: Preparation of aminomethyl substituted compounds

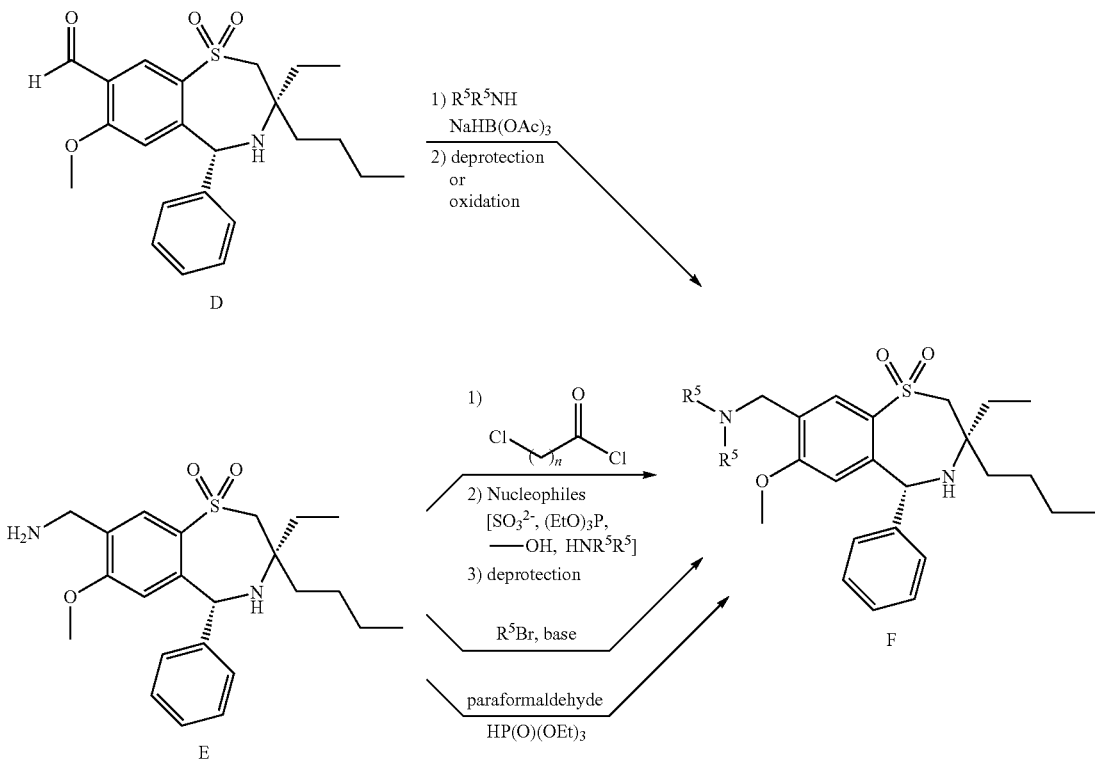

Compounds of the invention can be prepared as in Scheme 3. Ester intermediate (B) was saponified under basic conditions to give carboxylic acid (G) which was then subjected to standard amide coupling conditions in the presence of a substituted amine to give amide examples (H). Ester intermediate (B) was also reduced with DiBAL-H to alcohol (I) which was then converted to bromide (J). Bromide (J) was reacted with various nuclephiles (sulphite, phosphite, hydroxide, amines) followed by, if necessary, deprotection to give examples (K).

Scheme 3: Preparation of examples from ester intermediate (B)

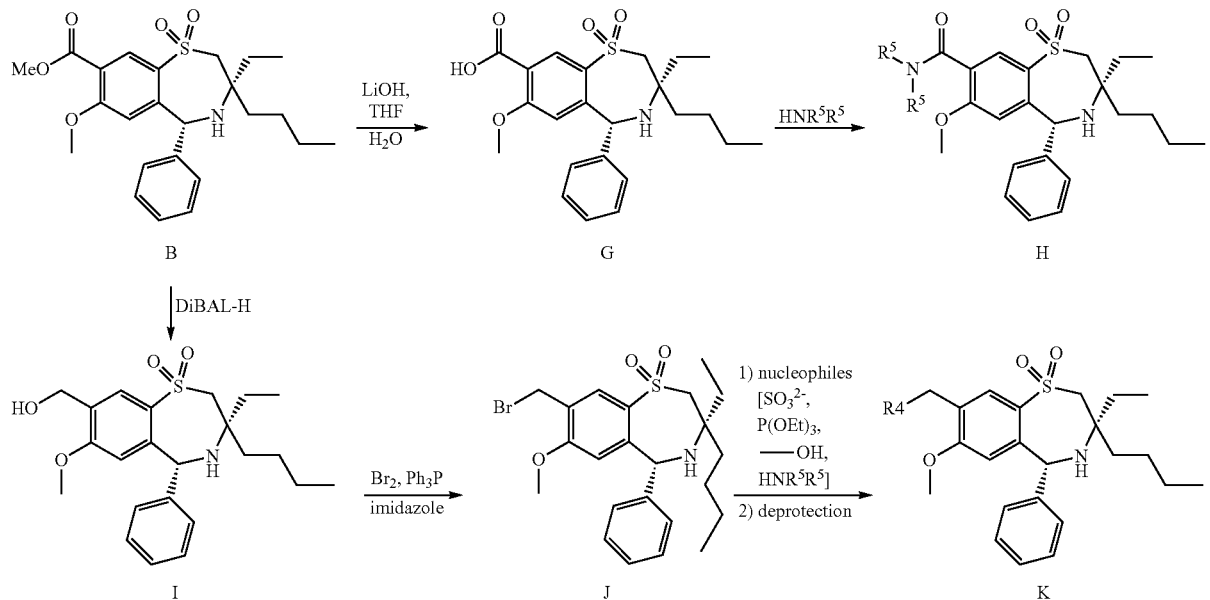

Compounds of the invention can be prepared as In Scheme 4 from triflate intermediate (A). Subjection of intermediate (A) to a Heck reaction provided unsaturated ester (L) which was saponified to unsaturated acid (M). Ester (L) was subjected to hydrogenation conditions followed by saponification to give acid (N). Standard amide formation with substituted amines provided amide examples (O). Reduction of acid (N) with borane followed by mesylation or bromide formation provided compounds (P), which were reacted with various nucleophiles (cyanide, diethyl phosphite, hydroxide, sulphite) then, if necessary, hydrolyzed, oxidized, or deprotected to give examples (Q).

Scheme 4: Preparation of examples from triflate intermediate (A)
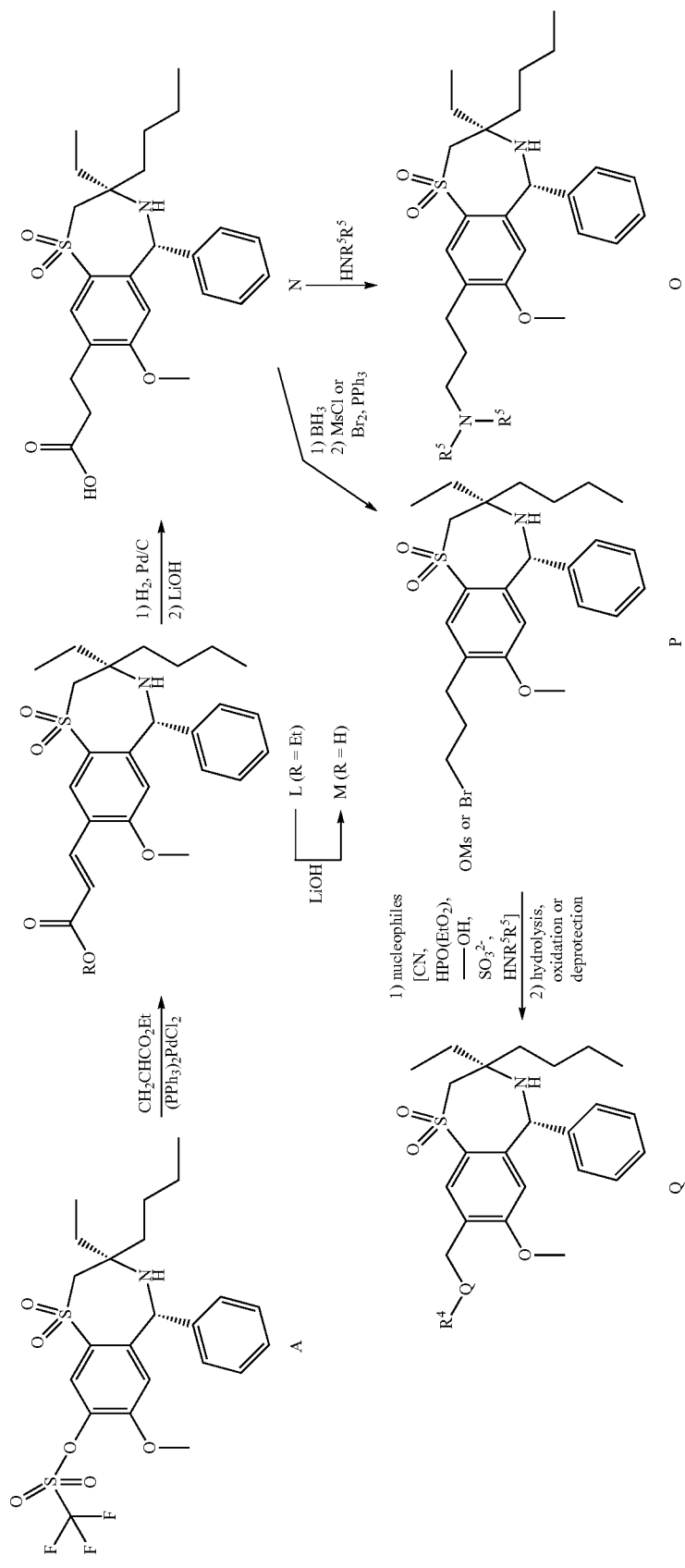

Compounds of the invention can be prepared as In Scheme 5. Intermediate aldehyde (D) was converted to unsaturated phosphonate (R) which was then deprotected with TMSBr to give unsaturated phosphonic acid example (S). Phosponate (R) was subjected to hydrogenation then deprotected with TMSBr to give saturated phosphonic acid example (T).

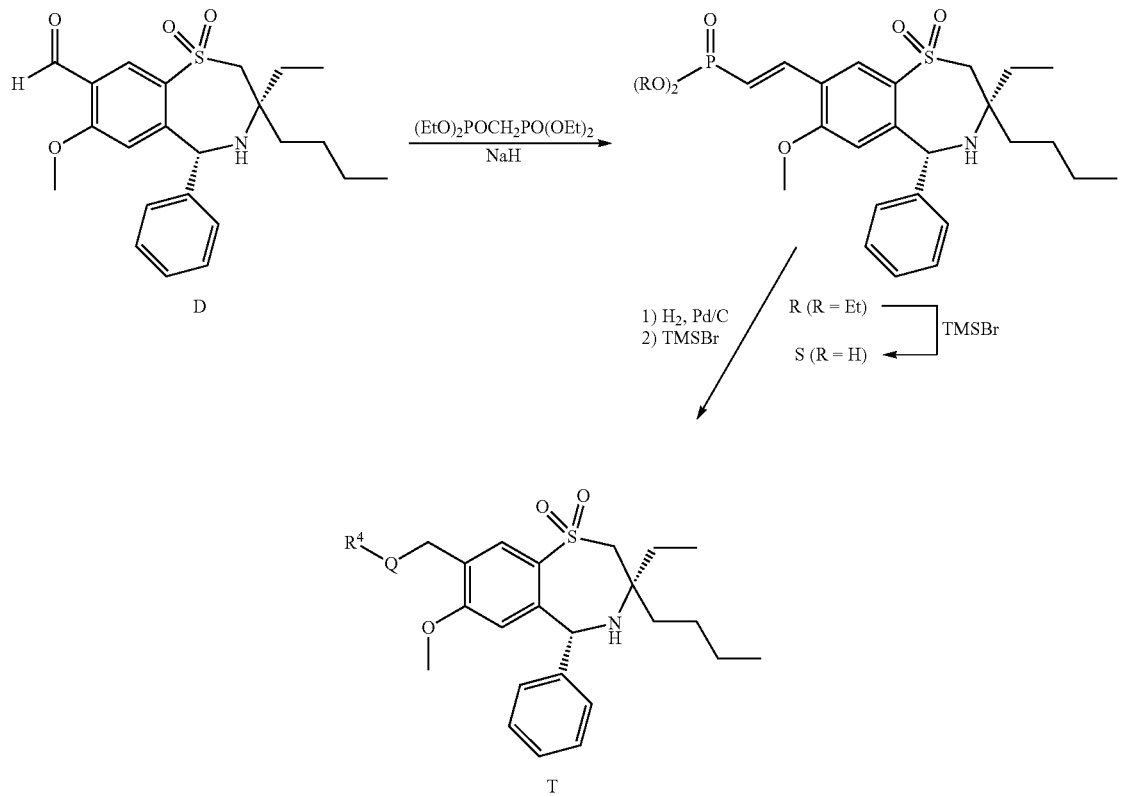

Scheme 5: Preparation of alkylphosphonic acid derivatives

Compounds of the invention can be prepared as In Scheme 6. Compound J (from Scheme 3) was oxidized to the N-hydroxyl derivative which was subjected to triethylphosphite followed by deprotection to give N-hydroxyl example (U). Intermediate nitrile (C) was oxidized then the nitrile was reduced to an aldehyde (V), which was then subjected to substituted amines under reductive amination conditions to give examples (W). Compound X (prepared as in Scheme 2) was oxidized, reduced, and deprotected to give N-hydroxyl example (Y).

Scheme 6: Preparation of N-hydroxyl examples

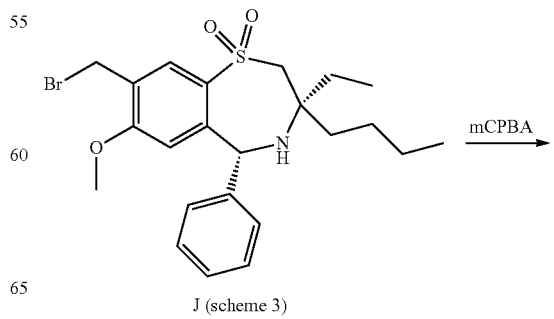

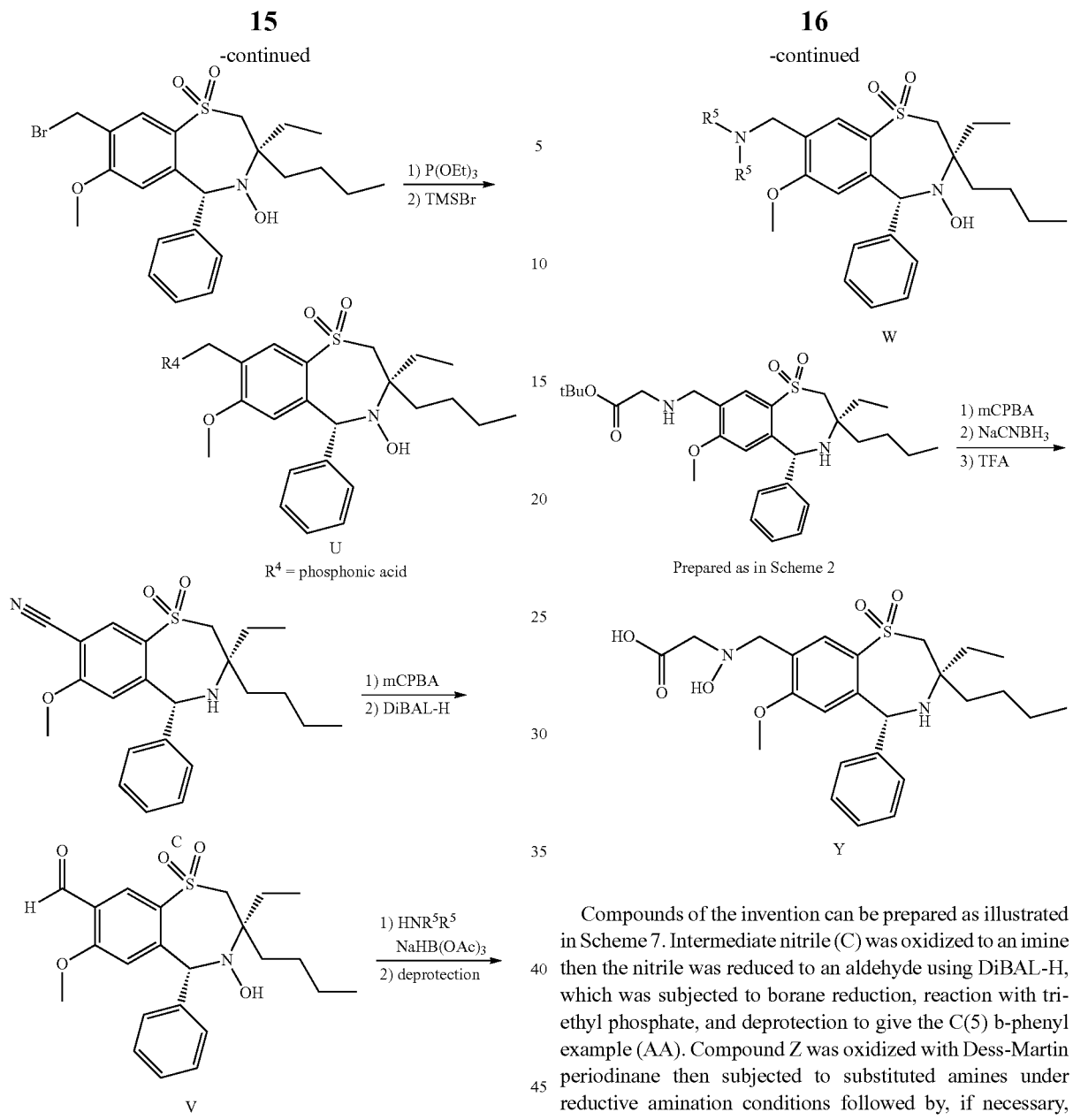

Compounds of the invention can be prepared as illustrated in Scheme 7. Intermediate nitrile (C) was oxidized to an imine then the nitrile was reduced to an aldehyde using DiBAL-H, which was subjected to borane reduction, reaction with triethyl phosphate, and deprotection to give the C(5) b-phenyl example (AA). Compound Z was oxidized with Dess-Martin periodinane then subjected to substituted amines under reductive amination conditions followed by, if necessary, deprotection to additional examples (BB).

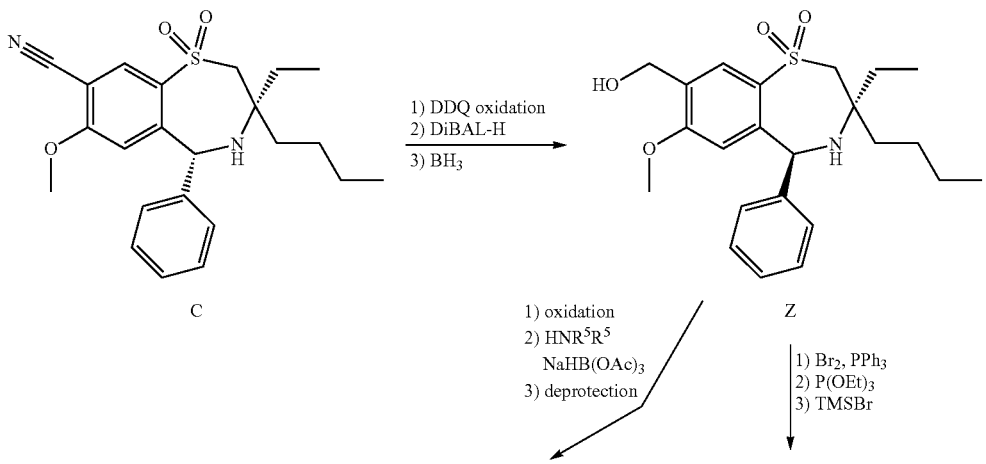

Scheme 7: Preparation of C5 β-epimer

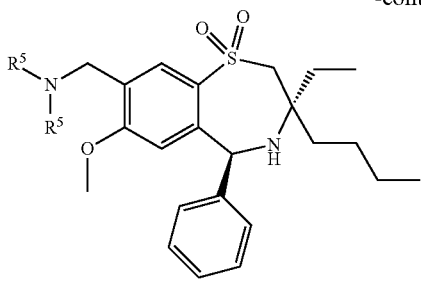

BB ($R^5$ = phosphonic acid)

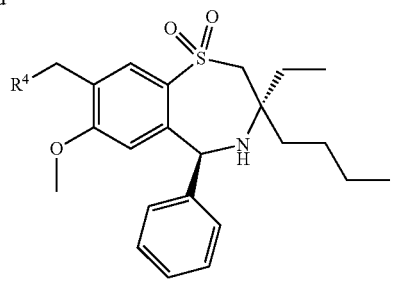

AA ($R^4$ = phosphonic acid)

Compounds of the invention can be prepared as illustrated in Scheme 8. Conversion of norleucine to an ethyl ester followed by imine formation with benzaldehyde and alkylation with iodobutane provided an intermediate compound (CC). Hydroylsis of the imine followed by reduction with LAH and sulfate formation provided aminosulfate intermediate (DD). Acylation of 2-bromo-1,4-bis(methyloxy)benzene with benzoyl chloride followed by selective demethylation provided an intermediate phenol. Acylation followed by Newman-Kwart rearrangement provided Intermediate (EE). One pot deprotection of (EE) and alkylation with aminosulfate (DD) gave rise to product (FF). Intramolecular cyclization to an imine followed by palladium-mediated carbonylation provided an ester intermediate, which was reduced with LAH to give intermediate (GG). Reduction of the imine followed by oxidation of the sulfide provided intermediate (HH). Conversion of (HH) to examples of the invention (II and JJ) could be accomplished according to the chemistry depicted in Schemes 2 and 3, respectively.

Scheme 8: Preparation of C(3)-dibutyl examples

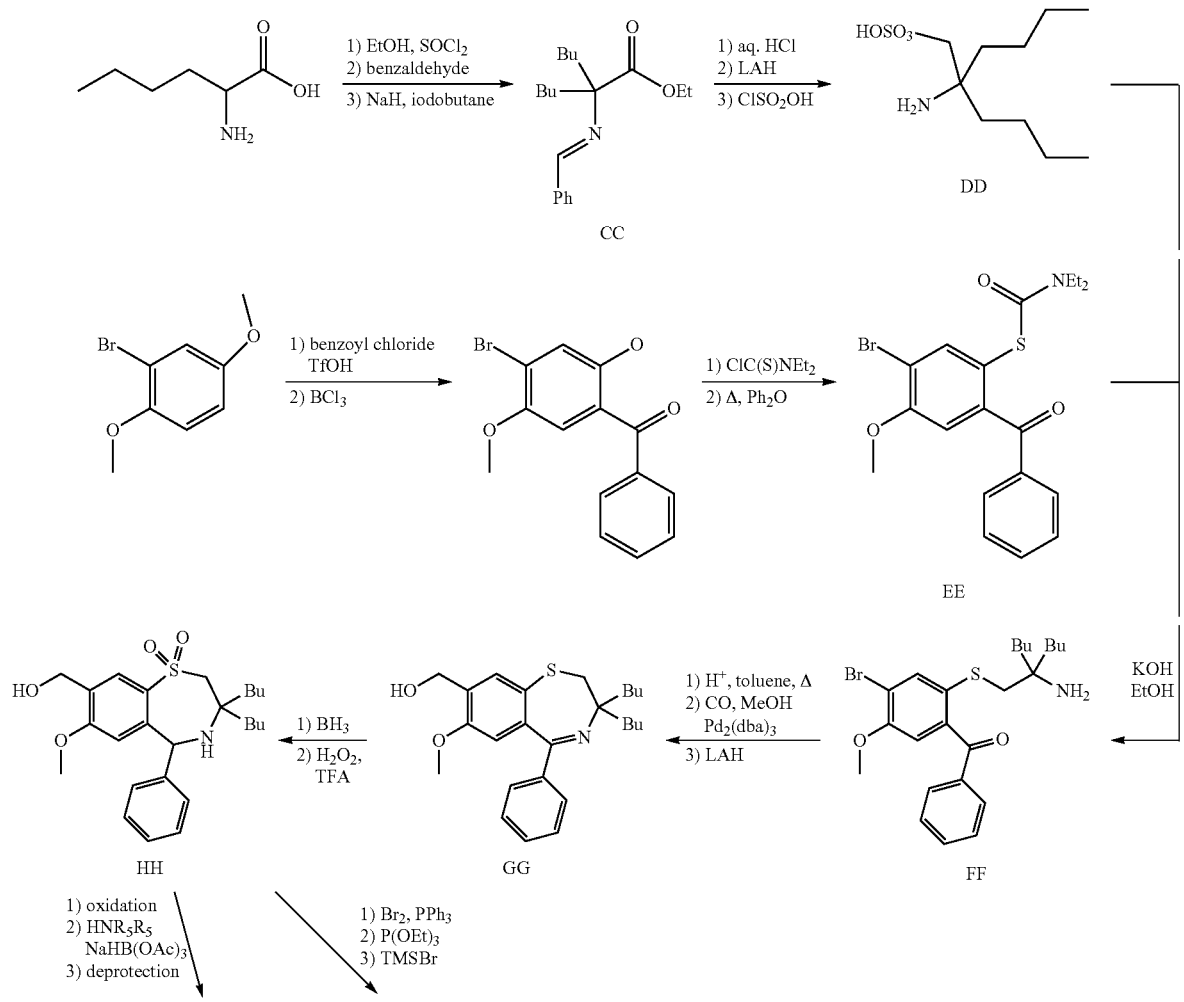

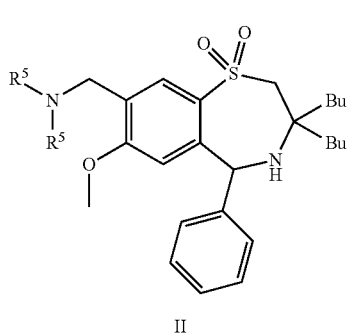

II

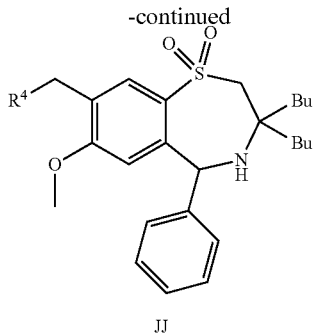

JJ

Compounds of the invention can be prepared as illustrated in Scheme 9. Demethylation of (3R,5R)-3-butyl-3-ethyl-7,8-bis(methyloxy)-5-phenyl-2,3,4,5-tetrahydro-1,4-benzothiazepine 1,1-dioxide (Brieaddy, L. E. WO9605188, 1996) followed by triflate formation and palladium-mediated amination provided derivative (KK). Demethylation, triflate formation, and palladium-mediated cyanation gave rise to a nitrile (LL). Reduction of the nitrile with DiBAL-H to an aldehyde (MM) followed by subjection to substituted amines under reductive amination conditions and, if necessary, deprotection provided examples (NN).

Scheme 9: Preparation of 7-N,N-dimethyl examples

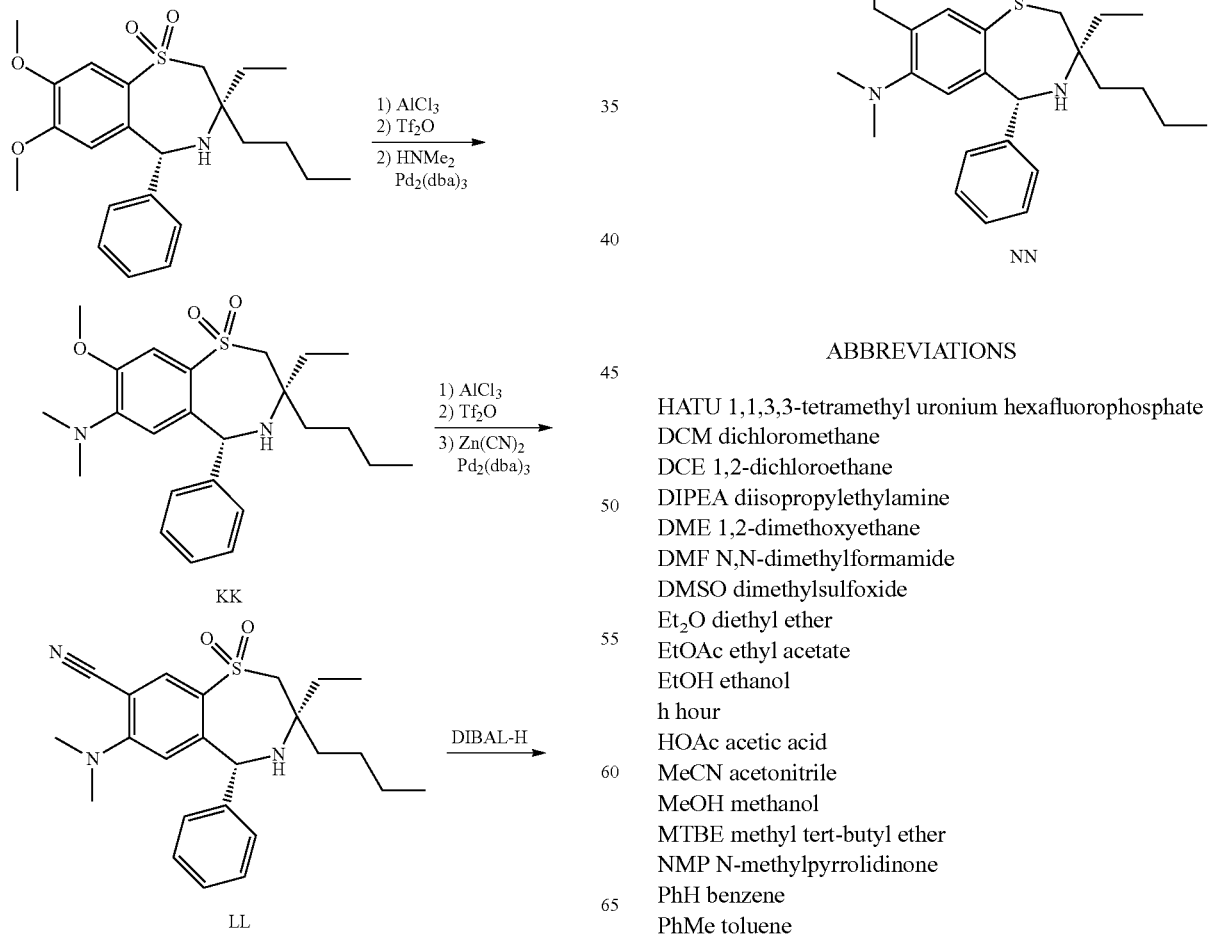

ABBREVIATIONS

HATU 1,1,3,3-tetramethyl uronium hexafluorophosphate
DCM dichloromethane
DCE 1,2-dichloroethane
DIPEA diisopropylethylamine
DME 1,2-dimethoxyethane
DMF N,N-dimethylformamide
DMSO dimethylsulfoxide
$Et_2O$ diethyl ether
EtOAc ethyl acetate
EtOH ethanol
h hour
HOAc acetic acid
MeCN acetonitrile
MeOH methanol
MTBE methyl tert-butyl ether
NMP N-methylpyrrolidinone
PhH benzene
PhMe toluene
THF tetrahydrofuran

I. Preparation of Intermediates

Intermediates 1a and 1b: (3R,5R)-3-butyl-3-ethyl-7-(methyloxy)-5-phenyl-2,3,4,5-tetrahydro-1,4-benzothiazepin-8-ol-1,1-dioxide (1a) and (3R,5R)-3-butyl-3-ethyl-8-(methyloxy)-5-phenyl-2,3,4,5-tetrahydro-1,4-benzothiazepin-7-ol 1,1-dioxide (1b)

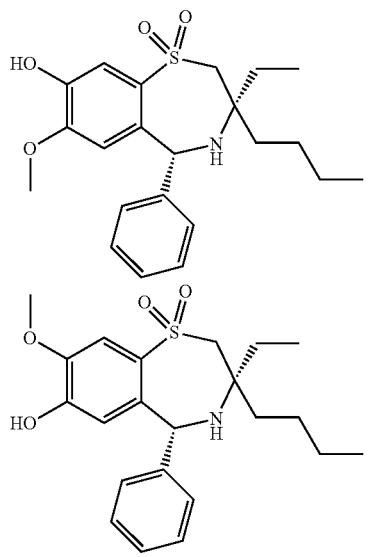

Method 1: A solution of (3R,5R)-3-butyl-3-ethyl-7,8-bis(methyloxy)-5-phenyl-2,3,4,5-tetrahydro-1,4-benzothiazepine 1,1-dioxide (200 g, 479 mmol) (prepared as in Brieaddy, L. E. WO9605188, 1996) in DCE (1 L) was saturated with HCl(g) then treated with aluminum chloride (200 g, 1.5 mol) in one portion. The reaction mixture was stirred while slowly cooling to ambient temperature then stirred for 2.5 h. The reaction mixture was added to an ice-H$_2$O mixture with vigorous stirring. The biphasic mixture was treated with 1N HCl (~200 mL) then the phases were separated after stirring for 30 min. The organic phase was isolated, washed twice with dilute HCl (1.5 L H$_2$O/~200 mL 1N NCl), dried over MgSO$_4$, filtered, and concentrated to dryness to give a regioisomeric mix of 7-OH and 8-OH products (185 g, 458 mmol, 96% yield) as a white foam. $^1$H NMR indicated a 47:53 mix of 7/8-phenols, respectively. The regioisomers were separated by chiral chromatography [stationary phase (CSP)-cellulose tris(3,5-dichlorophenylcarbamate) polymer immobilized on silica (CHIRALPAK IC®, 20 micron, 20 cm×25 cm), DCM and isopropanol (98/2 v/v) as mobile phase] to give intermediates 1a and 1b:

Intermediate 1b (faster eluting peak): (3R,5R)-3-butyl-3-ethyl-8-(methyloxy)-5-phenyl-2,3,4,5-tetrahydro-1,4-benzothiazepin-7-ol 1,1-dioxide (86.3 g, white solid, purity=98.2%): $^1$H NMR (400 MHz, DMSO-d$_6$) δ ppm 0.74 (t, J=7.0 Hz, 3H), 0.79 (t, J=7.4 Hz, 3H), 0.94-1.28 (m, 4H), 1.30-1.53 (m, 2H), 1.64-1.81 (m, 1H), 1.91-2.10 (m, 1H), 2.45 (d, J=9.8 Hz, 1H), 3.04 (d, J=14.8 Hz, 1H), 3.49 (d, J=14.8 Hz, 1H), 3.80 (s, 3H), 5.85 (d, J=10.0 Hz, 1H), 6.06 (s, 1H), 7.19-7.52 (m, 6H), 9.93 (s, 1H)

Intermediate 1a (slower eluting peak): (3R,5R)-3-butyl-3-ethyl-7-(methyloxy)-5-phenyl-2,3,4,5-tetrahydro-1,4-benzothiazepin-8-ol 1,1-dioxide (72.5 g) as a white solid: $^1$H NMR (400 MHz, DMSO-d$_6$) δ ppm 0.75 (t, J=7.1 Hz, 3H), 0.79 (t, J=7.5 Hz, 3H), 0.95-1.28 (m, 4H), 1.31-1.53 (m, 2H), 1.64-1.76 (m, 1H), 1.98-2.10 (m, 1H), 2.43 (d, J=9.8 Hz, 1H), 3.06 (d, J=14.8 Hz, 1H), 3.42 (s, 3H), 3.49 (d, J=14.8 Hz, 1H), 5.85 (d, J=9.8 Hz, 1H), 6.04 (s, 1H), 7.24-7.35 (m, 1H), 7.35-7.48 (m, 5H), 9.72 (s, 1H).

Method 2: A stirred solution of (3R,5R)-3-butyl-3-ethyl-7,8-bis(methyloxy)-5-phenyl-2,3,4,5-tetrahydro-1,4-benzothiazepine 1,1-dioxide (1250 g, 2.99 mol) in 1,2-dichloroethane (6 L) was saturated with HCl gas at ambient temperature (the internal temperature increased to 39° C. during this step). Bubbling of HCl gas through the solution was continued for 5 min after reaching 39° C. Aluminum chloride (1250 g, 9.37 mol) was added portion-wise over 40 min with some external cooling while maintaining the reaction temp between 38-42° C. The reaction mixture was stirred for 2 h and then poured slowly onto 10 kg of ice/water. Two additional batches of 1250 g and 500 g of (3R,5R)-3-butyl-3-ethyl-7,8-bis(methyloxy)-5-phenyl-2,3,4,5-tetrahydro-1,4-benzothiazepine 1,1-dioxide were processed with aluminum chloride and HCl in a similar fashion. The three ice/water quenched reaction mixtures (7.19 mole combined theoretical) were combined and the phases were separated. The aqueous phase was extracted with CH$_2$Cl$_2$ (3 L) and the combined organic layers were washed with water (3×4 L) and concentrated until the product began to crystallize. The mixture was diluted with heptane and aged with stirring. The precipitate was collected by filtration, air dried for 2 days and then dried in a vacuum oven at 55° C. for 48 h to afford a ca. 9:8 mixture of (3R,5R)-3-butyl-3-ethyl-7-(methyloxy)-5-phenyl-2,3,4,5-tetrahydro-1,4-benzothiazepin-8-ol 1,1-dioxide and (3R,5R)-3-butyl-3-ethyl-8-(methyloxy)-5-phenyl-2,3,4,5-tetrahydro-1,4-benzothiazepin-7-ol 1,1-dioxide (2.8 kg). Purification of the mixture according to the procedure in Method 1 provided 1235 grams of (3R,5R)-3-Butyl-3-ethyl-7-(methyloxy)-5-phenyl-2,3,4,5-tetrahydro-1,4-benzothiazepin-8-ol 1,1-dioxide as a white solid.

Method 3: A solution of (3R,5R)-3-butyl-3-ethyl-7,8-bis(methyloxy)-5-phenyl-2,3,4,5-tetrahydro-1,4-benzothiazepine 1,1-dioxide (11.1 kg, 26.58 mol) in DCE (69.7 kg) was treated with water (0.48 kg, 26.67 mol) then the temperature was adjusted to 35°-40° C. The solution was charged with oxalyl chloride (3.4 kg, 26.78 mol) and stirred for thirty minutes. The solution was then charged successively with aluminium trichloride (3.6 kg, 26.9 mol; 3.6 kg, 26.9 mol; 1.8 kg, 13.4 mol; 1.8 kg, 13.4 mol, 0.9 kg, 6.8 mol) allowing thirty minutes between charges. The reaction mixture was stirred at 35°-40° C. until the reaction was complete. The reaction was quenched by slow addition of the reaction solution to water (119 kg). The organic phase was separated, then further extracted twice with water (60 kg) and once with a saturated sodium chloride solution (30 kg). The dichloroethane solution of the product mixture was concentrated to a final mass of 39 kg. This solution was used as the feed solution for preparative chromatography as described in Method 1.

Fractions with the desired product were partially concentrated to a volume of approximately 12 L. The solutions were then further concentrated by atmospheric distillation to an internal pot temperature of 80° C. Upon cooling, crystallization occurred. The initial slurry was diluted with water (6-12 L) and stirred for two hours. The product was collected by filtration, washed with water (4 L) then dried at 60° C. under vacuum to a constant mass. From the above, 4.1 kg (10.22 mol) of (3R,5R)-3-butyl-3-ethyl-8-(methyloxy)-5-phenyl-2,3,4,5-tetrahydro-1,4-benzothiazepin-7-ol 1,1-dioxide (Intermediate 1b) and 3.9 kg (9.72 mol) of (3R,5R)-3-butyl-3- ethyl-7-(methyloxy)-5-phenyl-2,3,4,5-tetrahydro-1,4-benzothiazepin-8-ol 1,1-dioxide (Intermediate 1a) was obtained.

Recycling of intermediate 1b to (3R,5R)-3-butyl-3-ethyl-7,8-bis(methyloxy)-5-phenyl-2,3,4,5-tetrahydro-1,4-benzothiazepine 1,1-dioxide: A solution of (3R,5R)-3-butyl-3-ethyl-8-(methyloxy)-5-phenyl-2,3,4,5-tetrahydro-1,4-benzothiazepin-7-ol 1,1-dioxide (4.1 kg 10.22 mol) in acetone (19.7 kg) was treated with potassium carbonate (3.84 kg) and adjusted to 25°-30° C. Methyl Iodide (5.84 kg, 41.14 mol) was charged and the reaction held at 25°-30° C. until complete. The reaction was concentrated to ~8 L total volume by distillation, then dichloroethane (31 kg) was charged. The reaction was extracted twice with water (20.8 kg) and a further dichloroethane charge (26 kg) made. The product solution was concentrated to ~23 L to form a solution suitable for redeprotection to intermediates 1a and 1b as described above in Method 3.

Intermediate 2: (3R,5R)-3-butyl-3-ethyl-7-(methyloxy)-1,1-dioxido-5-phenyl-2,3,4,5-tetrahydro-1,4-benzothiazepin-8-yl trifluoromethanesulfonate

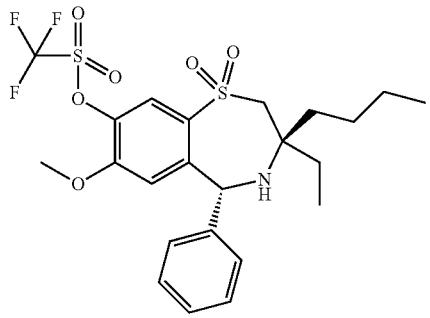 [SMILES: CCCC[C@]1(CC)CS(=O)(=O)c2cc(OS(=O)(=O)C(F)(F)F)c(OC)cc2[C@@H](c2ccccc2)N1]

Method 1: To a DCM solution of (3R,5R)-3-butyl-3-ethyl-7-(methyloxy)-5-phenyl-2,3,4,5-tetrahydro-1,4-benzothiazepin-8-ol 1,1-dioxide (105 g, 26 mmol) and pyridine (27.3 mL, 34 mmol) cooled to 0° C. under nitrogen was added trifluoromethanesulfonic anhydride (57.1 mL, 34 mmol) slowly over 30 min while maintaining an internal temperature between 5-10° C. Upon complete addition the reaction was stirred until TLC and LCMS indicated complete conversion to product. H$_2$O (250 mL) was slowly added to the mixture, and the mixture stirred for 10 min after which the layers separated. The aqueous was extracted an additional time with DCM, and the combined organics washed with 10% HCl, brine, then dried (Na$_2$SO$_4$), filtered, and concentrated to half volume. Hexanes was added until the solution became turbid, and crystallization began to occur. The solids were then filtered from the solution to give the title compounds (134.6 g, 95%) as a white solid which was used without further purification: $^1$H NMR (400 MHz, CDCl$_3$) δ ppm 0.76-0.96 (m, 6H), 1.03-1.40 (m, 4H), 1.40-1.67 (m, 4H), 1.77-1.97 (m, 1H), 2.10-2.28 (m, 1H), 3.07 (d, J=14.8 Hz, 1H), 3.48 (d, J=14.9 Hz, 1H), 3.62 (s, 3H), 6.09 (s, 1H), 6.34 (s, 1H), 7.32-7.50 (m, 5H), 7.96 (s, 1H); ES-LCMS m/z 536 (M+H)$^+$.

Method 2: Pyridine (441 mL, 5.45 mol) was added to a stirred suspension of (3R,5R)-3-butyl-3-ethyl-7-(methyloxy)-5-phenyl-2,3,4,5-tetrahydro-1,4-benzothiazepin-8-ol 1,1-dioxide (1099 g, 2.72 mol) in tert-butyl methyl ether (16 L) with cooling to 15° C. Neat triflic anhydride (1076 g, 3.81 mol) was added dropwise over 45 min while maintaining the reaction temperature between 14-16° C. Following the addition, the reaction mixture was stirred at ambient temperature for 2 h. Water (6 L) was added slowly and the mixture was stirred rapidly for 15 min. The layers were separated and the organic phase was washed with 1:1 water/brine (5 L), dried over MgSO$_4$ and filtered. The filtrate was concentrated to remove most of the tert-butyl methyl ether (ca. 13-14 L was removed). The resulting slurry was filtered and the filter cake was washed with heptane. Further drying of the filter cake in a vacuum overnight at 40° C. afforded (3R,5R)-3-butyl-3-ethyl-7-(methyloxy)-1,1-dioxido-5-phenyl-2,3,4,5-tetrahydro-1,4-benzothiazepin-8-yl trifluoromethanesulfonate as an off-white solid (1342 g). A second crop of product was obtained from the mother liquor (63 g). The combined yield was 1405 g.

Method 3: A reactor was charged with 2.75 Kg (6.8 mol) of (3R,5R)-3-butyl-3-ethyl-7-(methyloxy)-5-phenyl-2,3,4,5-tetrahydro-1,4-benzothiazepin-8-ol-1,1-dioxide, 19.9 Kg of 1,4-dioxane, 1.08 Kg (13.6 mol) of pyridine at 25° C. and stirred at this temperature until dissolved. The solution was then cooled to about 10° C. whereupon triflic anhydride (2.8 Kg, 9.9 mol) was then added at such a rate that the internal temperature was approximately 5-15° C. The reaction mixture was stirred at this temperature for about 45 minutes. The jacket temperature was then raised to about 25° C., and the reaction was stirred at this temperature until complete. Toluene (16.3 Kg) and 10% brine (8.3 L) were then added to the reactor, and the mixture was agitated for at least 5 minutes before settling for another 5 minutes. The aqueous layer was removed. Water (8.3 Kg) was added, and the mixture stirred for about 5 minutes before settling for at least 10 minutes. The aqueous layer was removed, and the water wash repeated. Following removal of the aqueous layer, the organic layer was reduced to about 11 L by vacuum distillation. Heptane (18.8 Kg) was added, and the total volume was again reduced by vacuum distillation to about 14 L. Another 4 Kg of heptanes was added, and the mixture was slowly cooled to about 5° C. overnight. The product was collected by filtration and washed twice with heptanes (3.6 Kg and 4.0 Kg). The cake was pulled dry under a N$_2$ blanket then dried in vacuo (~60° C.) to give 3.47 Kg (95%) of (3R,5R)-3-butyl-3-ethyl-7-(methyloxy)-1,1-dioxido-5-phenyl-2,3,4,5-tetrahydro-1,4-benzothiazepin-8-yl trifluoromethanesulfonate.

Intermediate 3: methyl (3R,5R)-3-butyl-3-ethyl-7-(methyloxy)-5-phenyl-2,3,4,5-tetrahydro-1,4-benzothiazepine-8-carboxylate 1,1-dioxide

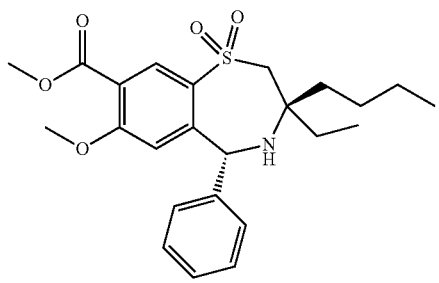 [SMILES: CCCC[C@]1(CC)CS(=O)(=O)c2cc(C(=O)OC)c(OC)cc2[C@@H](c2ccccc2)N1]

To a reaction tube containing (3R,5R)-3-butyl-3-ethyl-7-(methyloxy)-1,1-dioxido-5-phenyl-2,3,4,5-tetrahydro-1,4-benzothiazepin-8-yl trifluoromethanesulfonate (0.103 g, 0.192 mmol), Pd$_2$(dba)$_3$ (0.011 g, 0.012 mmol), dppf (0.013 g, 0.024 mmol), and triethylamine (0.040 mL, 0.288 mmol) in DMF (1 mL) was bubbled in carbon monoxide gas for a period of 15 min. Anhydrous MeOH (0.039 mL, 0.962 mmol) was added, and the reaction vessel was sealed under a carbon monoxide atmosphere then heated at 70° C. overnight. The reaction was cooled to room temperature, and the contents diluted with $Et_2O$ then poured into $H_2O$. The layers were separated, the aqueous extracted one additional time with $Et_2O$, and the combined organics washed with brine, dried ($Na_2SO_4$), filtered, and concentrated. The crude material was chromatographed on silica gel using hexanes/EtOAc to give the title compound (0.080 g, 91%) as a white solid: $^1$H NMR (400 MHz, $CDCl_3$) δ ppm 0.75-0.96 (m, 6H), 0.99-1.36 (m, 4H), 1.36-1.59 (m, 5H), 1.86 (ddd, J=14.4, 12.0, 4.4 Hz, 1H), 2.07-2.23 (m, 1H), 3.02 (d, J=14.8 Hz, 1H), 3.45 (d, J=14.9 Hz, 1H), 3.57 (s, 3H), 3.86 (s, 3H), 6.08 (s, 1H), 6.27 (s, 1H), 7.29-7.48 (m, 5H), 8.52 (s, 1H); ES-LCMS m/z 446 (M+H)$^+$.

Intermediate 4: (3R,5R)-3-butyl-3-ethyl-7-(methyloxy)-5-phenyl-2,3,4,5-tetrahydro-1,4-benzothiazepine-8-carboxylic acid 1,1-dioxide

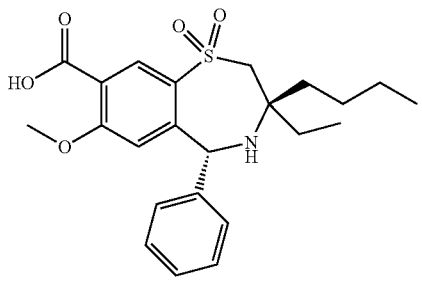 [SMILES: CCCC[C@]1(CC)CS(=O)(=O)c2cc(C(=O)O)c(OC)cc2[C@@H](c2ccccc2)N1]

$H_2O$ (0.333 mL), MeOH (0.333 mL), and THF (1 mL) were added to methyl (3R,5R)-3-butyl-3-ethyl-7-(methyloxy)-5-phenyl-2,3,4,5-tetrahydro-1,4-benzothiazepine-8-carboxylate 1,1-dioxide (0.046 g, 0.103 mmol) along with LiOH (0.013 g, 0.310 mmol), and the mixture stirred for 2 h at ambient temperature to hydrolyze to the benzoic acid. The rxn mixture was concentrated to half volume then 6N HCl was added. The mixture was extracted with EtOAc (2×), washed with brine, dried ($Na_2SO_4$), filtered, and concentrated in vacuo to give the title compound (0.039 g, 86%): $^1$H NMR (400 MHz, $CDCl_3$) δ ppm 0.67-0.99 (m, 6H), 0.99-1.64 (m, 7H), 1.87 (t, J=11.8 Hz, 1H), 2.08-2.29 (m, 1H), 3.09 (d, J=14.8 Hz, 1H), 3.46 (d, J=14.9 Hz, 1H), 3.70 (br. s., 3H), 6.11 (br. s., 1H), 6.33 (br. s., 1H), 7.30-7.60 (m, 5H), 8.73 (br. s., 1H); ES-LCMS m/z 432 (M+H)$^+$.

Intermediate 5: [(3R,5R)-3-butyl-3-ethyl-7-(methyloxy)-1,1-dioxido-5-phenyl-2,3,4,5-tetrahydro-1,4-benzothiazepin-8-yl]methanol

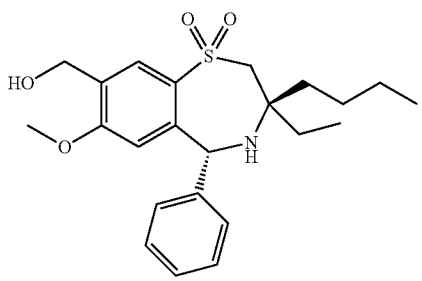 [SMILES: CCCC[C@]1(CC)CS(=O)(=O)c2cc(CO)c(OC)cc2[C@@H](c2ccccc2)N1]

To a DCM (2 mL) solution of methyl (3R,5R)-3-butyl-3-ethyl-7-(methyloxy)-5-phenyl-2,3,4,5-tetrahydro-1,4-benzothiazepine-8-carboxylate 1,1-dioxide (0.275 g, 0.617 mmol) at 0° C. under nitrogen was added a 1M solution of DIBAL-H in toluene (1.3 mL, 1.30 mmol). The reaction was warmed to ambient temperature and stirred for 1.5 h then MeOH was added followed by $H_2O$. The reaction mixture was concentrated then redissolved in EtOAc. The layers were separated, the aqueous layer was extracted an additional time with EtOAc, then the combined organics washed with brine, dried ($Na_2SO_4$), filtered, and concentrated. Chromatography on silica using hexanes/EtOAc provided the title compound (0.238 g, 91%): $^1$H NMR (400 MHz, $CDCl_3$) δ ppm 0.76-0.93 (m, 6H), 1.04-1.36 (m, 6H), 1.36-1.59 (m, 6H), 1.76-1.93 (m, 1H), 2.05-2.24 (m, 2H), 3.02 (d, J=14.8 Hz, 1H), 3.42 (d, J=14.8 Hz, 1H), 3.54 (s, 3H), 4.65 (qd, J=13.2, 6.3 Hz, 2H), 6.07 (br. s., 1H), 6.17 (s, 1H), 7.29-7.50 (m, 5H), 8.03 (s, 2H); ES-LCMS m/z 418 (M+H)$^+$.

Intermediate 6: (3R,5R)-3-butyl-3-ethyl-7-(methyloxy)-5-phenyl-2,3,4,5-tetrahydro-1,4-benzothiazepine-8-carbonitrile-1,1-dioxide

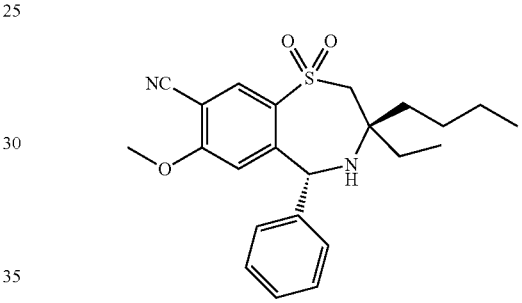

Method 1: A mixture of (3R,5R)-3-butyl-3-ethyl-7-(methyloxy)-1,1-dioxido-5-phenyl-2,3,4,5-tetrahydro-1,4-benzothiazepin-8-yl trifluoromethanesulfonate (0.535 g, 1.0 mmol), $Pd_2(dba)_3$ (0.055 g, 0.06 mmol), DPPF (0.066 g, 0.12 mmol), zinc powder (0.004 g, 0.06 mmol) and $Zn(CN)_2$ (0.117 g, 0.99 mmol) in DMF (10 mL) was stirred at ambient temperature for 15 min under a stream of nitrogen. The reaction was heated to 80° C. and stirred for 8 h. After the mixture was cooled to ambient temperature, DMF was removed in vacuo, $Et_2O$ was added, and the organics were washed with 2N $NH_4OH$(aq) followed by brine. The organics were dried ($Na_2SO_4$), filtered, and concentrated. The residue was triturated with hexanes/EtOAc, and a white solid was collected by filtration to give the title compound (0.386 g, 92%): $^1$H NMR (400 MHz, $CDCl_3$) δ ppm 0.73-0.97 (m, 6H), 0.98-1.62 (m, 8H), 1.77-1.92 (m, 1H), 2.08-2.24 (m, 1H), 3.01 (d, J=14.9 Hz, 1H), 3.45 (d, J=14.9 Hz, 1H), 3.62 (s, 3H), 6.08 (br. s., 1H), 6.26 (s, 1H), 7.32-7.49 (m, 5H), 8.28 (s, 1H); ES-LCMS m/z 413 (M+H)$^+$.

Method 2: A solution of (3R,5R)-3-butyl-3-ethyl-7-(methyloxy)-1,1-dioxido-5-phenyl-2,3,4,5-tetrahydro-1,4-benzothiazepin-8-yl trifluoromethanesulfonate (1.346 kg, 2.51 mol) in DMF (2.5 L) was charged with $Zn(CN)_2$ (440 g, 3.75 mol) and the stirred mixture was degassed by passing $N_2$ through the mixture for 60 min. Water (25 mL) was added and degassing was continued for 30 min. DPPF (14.5 g, 26.16 mmol) and $Pd_2(dba)_3$ (10.5 g, 11.47 mmol) were added and the reaction mixture was heated to 80-85° C. with continued degassing. The reaction was judged to be complete after 2 h at this temperature. After cooling the reaction mixture to 60° C., toluene (500 mL) was added and the mixture was stirred overnight with cooling to ambient temperature. Toluene (8 L) was added and the mixture was washed with water (4×2 L). The organic phase was dried over MgSO₄ and filtered and the filtrate was stirred over PL-BnSH resin (460 g, to scavange heavy metal impurities) for 3 d. The resin was removed by filtration and the filtrate was concentrated until crystallization of the product ensued. Heptane (12 L) was added and the resulting solids were collected by filtration and washed with heptane. The white solids were further dried under vacuum to afford (3R,5R)-3-butyl-3-ethyl-7-(methyloxy)-5-phenyl-2,3,4,5-tetrahydro-1,4-benzothiazepine-8-carbonitrile 1,1-dioxide (1.010 kg).

Method 3: (3R,5R)-3-butyl-3-ethyl-7-(methyloxy)-1,1-dioxido-5-phenyl-2,3,4,5-tetrahydro-1,4-benzothiazepin-8-yl trifluoromethanesulfonate (2160 g, 4.05 moles) and Zinc Cyanide (266 g, 2.23 moles) were placed in a reactor followed by water (1084 ml) and N-methylpyrrolidinone (10830 ml). The contents are placed under nitrogen then evacuated three times. The reaction was heated to 100° C. and treated with a slurry of palladium acetate (4.8 g, 0.02 moles) and 1,1'-Bis(diphenylphosphino)ferrocene (15.7 g, 0.03 moles) in NMP (50 ml). The reaction was immediately treated with polymethylhydrosiloxane (PMHS, 22 g) in NMP (50 ml) and maintained at 100° C. for approximately one hour when HPLC analysis indicated the reaction was complete. The reaction was cooled to approximately 35° C. and treated with a prepared solution of water (8685 g), ammonium hydroxide (1958 g) and ethanol (17130 g) over approximately ten minutes. The resulting slurry was heated to approx 80° C. to dissolve. The solution was cooled to 20° C. over approximately 60 minutes and maintained at 20° C. for approximately 90 minutes. The solids were filtered, washed with a prepared solution of 50% ethanol/water (4330 ml) followed by heptane (4300 ml), and pulled dry. The solids were dried an vacuum oven at 50° C. to provide (3R,5R)-3-butyl-3-ethyl-7-(methyloxy)-5-phenyl-2,3,4,5-tetrahydro-1,4-benzothiazepine-8-carbonitrile 1,1-dioxide (1482 g, 89%).

Intermediate 7: (3R,5R)-8-(bromomethyl)-3-butyl-3-ethyl-7-(methyloxy)-5-phenyl-2,3,4,5-tetrahydro-1,4-benzothiazepine-1,1-dioxide

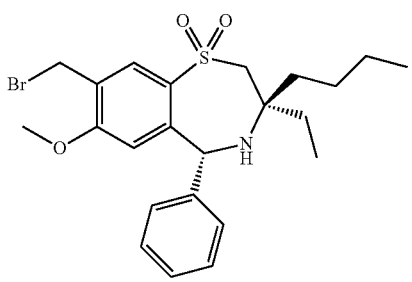 [SMILES: CCCC[C@]1(CC)CS(=O)(=O)c2cc(CBr)c(OC)cc2[C@@H](c2ccccc2)N1]

Imidazole (0.153 g, 0.563 mmol) was dissolved in DCM (2 mL), and the solution was cooled to 0° C. Triphenylphosphine (0.295 g, 1.126 mmol) was added followed by bromine (0.058 mL, 1.126 mmol). A solution of [(3R,5R)-3-butyl-3-ethyl-7-(methyloxy)-1,1-dioxido-5-phenyl-2,3,4,5-tetrahydro-1,4-benzothiazepin-8-yl]methanol (0.235 g, 0.563 mmol) in DCM (1 mL) was added slowly at 0° C. The reaction was stirred at 0° C. for 2 h followed by addition of Na₂SO₃(aq), and the resulting mixture separated. The organic layer was dried (Na₂SO₄), filtered through a silica pad, and concentrated to give a thick oil which solidified upon standing to give the title compound (0.265 g, 84%): ¹H NMR (400 MHz, CDCl₃) δ ppm 0.73-0.95 (m, 6H), 1.02-1.36 (m, 5H), 1.38-1.65 (m, 5H), 1.76-1.92 (m, 1H), 2.08-2.23 (m, 1H), 3.02 (d, J=14.8 Hz, 1H), 3.43 (d, J=14.8 Hz, 1H), 3.57 (s, 3H), 4.38-4.56 (m, 2H), 6.06 (s, 1H), 6.16 (s, 1H), 7.28-7.45 (m, 5H), 8.05 (s, 1H); LC-MS m/z 480 (M+H)⁺, LC-MS 482 (M+H+2)⁺.

Intermediate 8: (3R,5R)-3-butyl-3-ethyl-4-hydroxy-7-(methyloxy)-5-phenyl-2,3,4,5-tetrahydro-1,4-benzothiazepine-8-carbonitrile 1,1-dioxide

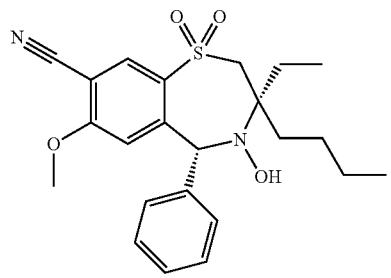 [SMILES: CCCC[C@]1(CC)CS(=O)(=O)c2cc(C#N)c(OC)cc2[C@@H](c2ccccc2)N1O]

(3R,5R)-3-butyl-3-ethyl-7-(methyloxy)-5-phenyl-2,3,4,5-tetrahydro-1,4-benzothiazepine-8-carbonitrile 1,1-dioxide (6.00 g, 14.54 mmol) dissolved in DCM (100 mL) was treated with m-CPBA (2.51 g, 11.20 mmol) with stirring at 22° C. for 3 h. Additional m-CPBA (0.77 g, 3.44 mmol) was added, and the mixture was stirred an additional 2 h. The reaction mixture was treated with 10% Na₂SO₃ then vigorously stirred for 1 h. The organic layer was isolated, dried over MgSO₄, filtered, and concentrated to dryness. The residue was purified on 330 g silica gel eluting with 10 to 60% EtOAc/hexanes to give recovered nitrile starting material (1.33 g, 3.23 mmol, 22.2% yield) and the desired (3R,5R)-3-butyl-3-ethyl-4-hydroxy-7-(methyloxy)-5-phenyl-2,3,4,5-tetrahydro-1,4-benzothiazepine-8-carbonitrile 1,1-dioxide (impure) (1.99 g, 31.9% yield): ¹H NMR (400 MHz, DMSO-d₆) δ ppm 0.78 (t, J=7.1 Hz, 3H), 0.85 (t, J=7.2 Hz, 3H), 1.05-1.37 (m, 4H), 1.38-1.51 (m, 1H), 1.57-1.70 (m, 1H), 1.78-1.89 (m, 1H), 2.01-2.12 (m, 1H), 3.40-3.53 (m, 2H), 3.56 (s, 3H), 6.28 (s, 1H), 6.39 (s, 1H), 7.34-7.58 (m, 5H), 8.16 (s, 1H), 8.26 (s, 1H).

Intermediate 9: (3R,5R)-3-butyl-3-ethyl-7-(methyloxy)-5-phenyl-2,3,4,5-tetrahydro-1,4-benzothiazepine-8-carbaldehyde 1,1-dioxide

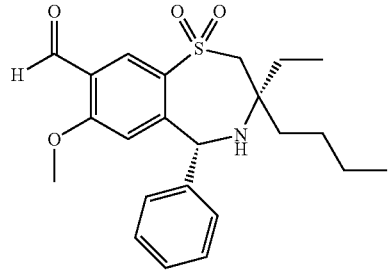 [SMILES: CCCC[C@]1(CC)CS(=O)(=O)c2cc(C=O)c(OC)cc2[C@@H](c2ccccc2)N1]

Method 1: (3R,5R)-3-butyl-3-ethyl-7-(methyloxy)-5-phenyl-2,3,4,5-tetrahydro-1,4-benzothiazepine-8-carbonitrile 1,1-dioxide (7.42 g, 17.99 mmol) dissolved in DCM (150 mL) was treated with 1M DIBAL-H in toluene (36.0 mL, 36.0 mmol) at 0° C. with stirring for 1 h after which time LCMS indicated complete conversion. The reaction mixture was poured into an ice/1 N HCl mixture and stirred vigorously for 1 h. The organic phase was isolated, dried over MgSO₄, filtered, and concentrated to give a yellow solid. The crude product was dissolved in 80 mL hot EtOAc to which was added 250 mL hexanes until cloudy. The mixture was allowed to cool slowly to ambient temperature and then cooled in an ice bath. The resultant precipitate was filtered off, washed with cold 20% EtOAc/hexanes, and air dried to give (3R,5R)-3-butyl-3-ethyl-7-(methyloxy)-5-phenyl-2,3,4,5-tetrahydro-1,4-benzothiazepine-8-carbaldehyde 1,1-dioxide (4.00 g, 53.5% yield) as a white crystalline solid. The mother liquor was concentrated to dryness, and the residue was purified on 120 g silica gel eluting with 20 to 40% EtOAc/hexanes to give additional product as a white solid: $^1$H NMR (400 MHz, DMSO-$d_6$) δ ppm 0.74 (t, J=7.0 Hz, 3H) 0.81 (t, J=7.4 Hz, 3H) 0.96-1.29 (m, 4H) 1.33-1.54 (m, 2H) 1.68-1.81 (m, 1H) 2.01-2.13 (m, 1H) 2.80 (d, J=9.8 Hz, 1H) 3.13 (d, J=15.0 Hz, 1H) 3.58 (s, 3H) 3.63 (d, J=15.0 Hz, 1H) 5.98 (d, J=9.8 Hz, 1H) 6.27 (s, 1H) 7.32-7.40 (m, 1H) 7.40-7.49 (m, 4H) 8.23 (s, 1H) 10.27 (s, 1H); LC-MS (ES$^+$) m/z 416.3 [M+H].

Method 2: A 1.5 M solution of Dibal-H in toluene (1.467 L, 2.20 mol) was added over 50 min to a stirred solution of (3R,5R)-3-butyl-3-ethyl-7-(methyloxy)-5-phenyl-2,3,4,5-tetrahydro-1,4-benzothiazepine-8-carbonitrile 1,1-dioxide (673.3 g, 1.63 mol) in CH$_2$Cl$_2$ (3.3 L) while maintaining the reaction temp below 0° C. The reaction mixture was stirred for 30 min with cooling to −10° C. The reaction mixture was quenched by very slow addition of 1M HCl (8 L) over 1.25 h while maintaining the reaction temperature below +15° C. (caution: addition of the first 500 mL of HCl is very exothermic!). Toluene (7 L) was added and the mixture was stirred for 3 h. The aqueous phase was removed and the organic layer was washed with 1M HCl (5 L). The combined aqueous layers were extracted with CH$_2$Cl$_2$ (2.5 L) and the CH$_2$Cl$_2$ and CH$_2$Cl$_2$/toluene layers were combined and washed with 10% Na$_2$CO$_3$ (5 L), dried over MgSO$_4$, filtered and partially concentrated until a thick slurry formed. The slurry was diluted with heptane (2-3 volumes) and aged with stirring for 15 min. The solids were collected by filtration and washed with heptane. The filter cake was air dried for 3 h and then dried in a vacuum oven overnight at 50° C. to afford (3R,5R)-3-butyl-3-ethyl-7-(methyloxy)-5-phenyl-2,3,4,5-tetrahydro-1,4-benzothiazepine-8-carbaldehyde 1,1-dioxide as a white solid (533 g).

Method 3: (3R,5R)-3-butyl-3-ethyl-7-(methyloxy)-5-phenyl-2,3,4,5-tetrahydro-1,4-benzothiazepine-8-carbaldehyde 1,1-dioxide (2402 g, 5.82 moles) and toluene (20714 g) were added to a reactor and stirred at 40° C. to form a solution. The solution was then cooled to approximately −35° C. and treated with a solution of DIBAL-H (1.5 M in toluene, 4472 g, 7.85 moles) while maintaining the internal temperature at less than −30° C. The reaction was stirred at approximately −30° C. for one hour until completion and then quenched by slow addition of 1N HCl solution (approximately 40 Kg) until pH 1.0. The reaction was warmed to approximately 30° C. and stirred for one hour. Stirring was stopped and the lower aqueous layer was separated, and the organic was washed twice more with 1N HCl solution (7200 ml each) while maintaining the temperature at approximately 40° C. The aqueous layers were combined and back-washed with toluene (4126 g). The combined organic layers were washed with saturated aqueous sodium chloride (9000 ml) and then evaporated under reduced pressure to approximately 12 liters. The solvent was further evaporated at atmospheric pressure to a final volume of approximately 7 liters and treated with heptanes (16420 g). The contents were cooled to approximately 15° C. and stirred for approximately two hours. The solids were manually broken up and rinsed from the reactor with heptanes (2×3260 g) and collected by filtration. The collected solid material was washed with additional heptanes (3180 g) then dried at 50° C. to give (3R,5R)-3-butyl-3-ethyl-7-(methyloxy)-5-phenyl-2,3,4,5-tetrahydro-1,4-benzothiazepine-8-carbaldehyde 1,1-dioxide (2128 g, 88%).

Intermediate 10: dimethyl 3-({[(3R,5R)-3-butyl-3-ethyl-4-hydroxy-7-(methyloxy)-1,1-dioxido-5-phenyl-2,3,4,5-tetrahydro-1,4-benzothiazepin-8-yl]methyl}amino)pentanedioate

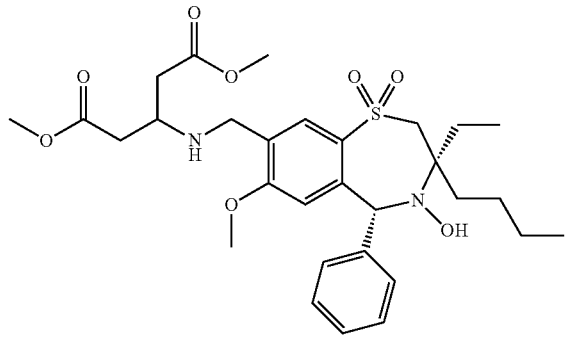 [SMILES: CCCC[C@]1(CC)CS(=O)(=O)c2cc(CNC(CC(=O)OC)CC(=O)OC)c(OC)cc2[C@@H](c2ccccc2)N1O]

(3R,5R)-3-butyl-3-ethyl-4-hydroxy-7-(methyloxy)-5-phenyl-2,3,4,5-tetrahydro-1,4-benzothiazepine-8-carbaldehyde 1,1-dioxide (298 mg, 0.691 mmol) and dimethyl 3-aminopentanedioate (181 mg, 1.036 mmol) (prepared as in *Journal of the American Chemical Society* 2005, 127, 247) were combined in DCM (4 mL) and stirred for 30 min. The reaction mixture was treated with NaHB(OAc)$_3$ (293 mg, 1.381 mmol) and stirred at 22° C. for 16 h after which time LCMS appeared to be complete. The mixture was diluted with DCM, washed twice with H$_2$O, dried over MgSO$_4$, filtered, and concentrated to dryness. The residue was purified on 40 g silica gel eluting with 20 to 100% EtOAc/hexanes to give dimethyl 3-({[(3R,5R)-3-butyl-3-ethyl-4-hydroxy-7-(methyloxy)-1,1-dioxido-5-phenyl-2,3,4,5-tetrahydro-1,4-benzothiazepin-8-yl]methyl}amino)pentanedioate (304 mg, 0.515 mmol, 74.5 yield) as an amber oil: LC-MS (ES$^+$) m/z 591.3 [M+H].

Intermediate 11: diethyl {(E)-2-[(3R,5R)-3-butyl-3-ethyl-7-(methyloxy)-1,1-dioxido-5-phenyl-2,3,4,5-tetrahydro-1,4-benzothiazepin-8-yl]ethenyl}phosphonate

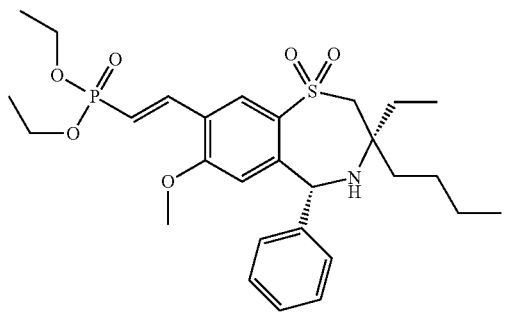 [SMILES: CCCC[C@]1(CC)CS(=O)(=O)c2cc(/C=C/P(=O)(OCC)OCC)c(OC)cc2[C@@H](c2ccccc2)N1]

Tetraethyl methanediylbis(phosphonate) (645 mg, 2.24 mmol) dissolved in THF (7 mL) was treated with NaH (83 mg, 2.075 mmol, 60% dispersion in oil) with stirring at 22° C. for 30 min. (3R,5R)-3-butyl-3-ethyl-7-(methyloxy)-5-phenyl-2,3,4,5-tetrahydro-1,4-benzothiazepine-8-carbaldehyde 1,1-dioxide (300 mg, 0.722 mmol) was added, and the mixture was stirred for 1 h at ambient temperature after which time LCMS indicated complete conversion. The mixture was quenched with H$_2$O, partitioned between EtOAc and brine, and the phases were separated. The organic phase was dried over MgSO$_4$, filtered, and concentrated to an oil. The residue was purified on 40 g silica gel eluting with 40 to 100% EtOAc/hexanes to give diethyl {(E)-2-[(3R,5R)-3-butyl-3-ethyl-7-(methyloxy)-1,1-dioxido-5-phenyl-2,3,4,5-tetrahydro-1,4-benzothiazepin-8-yl]ethenyl}phosphonate (342 mg, 86% yield) as a clear oil: LC-MS (ES⁺) m/z 550.4 [M+H].

Intermediate 12: dimethyl N-{[(3R,5R)-3-butyl-3-ethyl-7-(methyloxy)-1,1-dioxido-5-phenyl-2,3,4,5-tetrahydro-1,4-benzothiazepin-8-yl]methyl}-L-cystinate

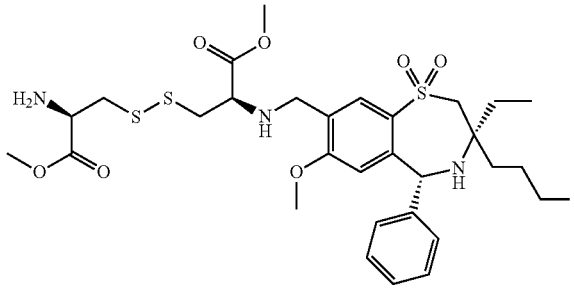 [SMILES: CCCC[C@]1(CC)CS(=O)(=O)c2cc(CN[C@@H](CSSC[C@H](N)C(=O)OC)C(=O)OC)c(OC)cc2[C@@H](c2ccccc2)N1]

(3R,5R)-3-butyl-3-ethyl-7-(methyloxy)-5-phenyl-2,3,4,5-tetrahydro-1,4-benzothiazepine-8-carbaldehyde 1,1-dioxide (231 mg, 0.556 mmol) and dimethyl L-cystinate (95 mg, 0.278 mmol) were combined in DCM (8 mL) and treated with TEA (0.077 mL, 0.556 mmol) at ambient temperature for 1 h. NaHB(OAc)₃ (295 mg, 1.390 mmol) was added, and the reaction mixture was stirred for 16 h. The mixture was partitioned between DCM and saturated NaHCO₃, and the phases were separated. The aqueous phase was extracted with DCM, and the organic phases were combined, dried over MgSO₄, filtered and concentrated to a clear oil. The crude material was purified on 40 g silica eluting with 20 to 100% EtOAc/hexanes to give dimethyl N-{[(3R,5R)-3-butyl-3-ethyl-7-(methyloxy)-1,1-dioxido-5-phenyl-2,3,4,5-tetrahydro-1,4-benzothiazepin-8-yl]methyl}-L-cystinate (167 mg, 45.0% yield): ¹H NMR (400 MHz, DMSO-d₆) δ ppm 0.67-0.88 (m, 12H) 0.96-1.29 (m, 8H) 1.32-1.53 (m, 4H) 1.66-1.80 (m, 2H) 2.00-2.13 (m, 2H) 2.54 (d, J=10.0 Hz, 2H) 2.57-2.70 (m, 2H) 2.93-3.13 (m, 6H) 3.42 (s, 7H) 3.46-3.78 (m, 13H) 5.94 (d, J=9.6 Hz, 2H) 6.07 (s, 2H) 7.26-7.36 (m, 2H) 7.37-7.46 (m, 8H) 7.87-8.01 (m, 2H); LC-MS (ES⁺) m/z 668.22 [M+H].

Intermediate 13: 1,1-dimethylethyl N-{[(3R,5R)-3-butyl-3-ethyl-7-(methyloxy)-1,1-dioxido-5-phenyl-2,3,4,5-tetrahydro-1,4-benzothiazepin-8-yl]methyl}-L-methioninate

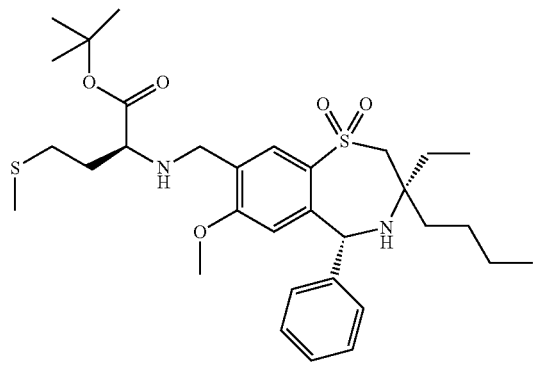 [SMILES: CCCC[C@]1(CC)CS(=O)(=O)c2cc(CN[C@@H](CCSC)C(=O)OC(C)(C)C)c(OC)cc2[C@@H](c2ccccc2)N1]

A slurry of 1,1-dimethylethyl L-methioninate (218 mg, 0.902 mmol) in DCM (3 mL) was treated with TEA (126 μl, 0.902 mmol) at ambient temperature for 15 min after which time (3R,5R)-3-butyl-3-ethyl-7-(methyloxy)-5-phenyl-2,3, 4,5-tetrahydro-1,4-benzothiazepine-8-carbaldehyde 1,1-dioxide (250 mg, 0.602 mmol) was added, and the mixture was stirred for 1 h. NaHB(OAc)₃ (255 mg, 1.203 mmol) was added, and the reaction mixture was stirred overnight at ambient temperature after which time LCMS indicated conversion to desired product. The mixture was partitioned between DCM and brine, and the phases were separated. The aqueous phase was extracted with DCM, and the combined organic phases were dried over MgSO₄, filtered, and concentrated to a clear oil. The residue was purified on 40 g silica eluting with 20 to 60% EtOAc/hexanes to give 1,1-dimethylethyl N-{[(3R,5R)-3-butyl-3-ethyl-7-(methyloxy)-1,1-dioxido-5-phenyl-2,3,4,5-tetrahydro-1,4-benzothiazepin-8-yl]methyl}-L-methioninate as a white solid (270 mg, 74% yield): ¹H NMR (400 MHz, DMSO-d₆) δ ppm 0.75 (t, J=7.0 Hz, 3H) 0.80 (t, J=7.4 Hz, 3H) 0.98-1.28 (m, 4H) 1.36 (s, 9H) 1.38-1.53 (m, 2H) 1.65-1.85 (m, 3H) 2.03 (s, 3H) 2.03-2.13 (m, 1H) 2.33-2.43 (m, 1H) 2.53 (br. s., 2H) 2.55 (d, J=4.3 Hz, 1H) 3.03 (d, J=14.8 Hz, 1H) 3.09-3.17 (m, 1H) 3.43 (s, 3H) 3.52 (d, J=14.8 Hz, 1H) 3.62 (br. s., 2H) 5.93 (d, J=9.6 Hz, 1H) 6.07 (s, 1H) 7.25-7.36 (m, 1H) 7.36-7.47 (m, 4H) 7.94 (s, 1H); LC-MS (ES⁺) m/z 605.3 [M+H].

Intermediate 14: (3R,5R)-3-butyl-3-ethyl-4-hydroxy-7-(methyloxy)-5-phenyl-2,3,4,5-tetrahydro-1,4-benzothiazepine-8-carbaldehyde 1,1-dioxide

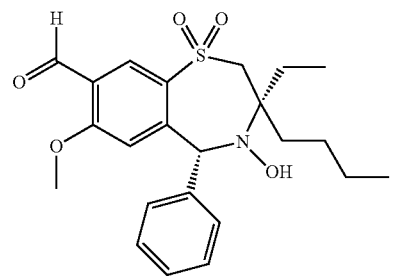 [SMILES: CCCC[C@]1(CC)CS(=O)(=O)c2cc(C=O)c(OC)cc2[C@@H](c2ccccc2)N1O]

(3R,5R)-3-butyl-3-ethyl-4-hydroxy-7-(methyloxy)-5-phenyl-2,3,4,5-tetrahydro-1,4-benzothiazepine-8-carbonitrile 1,1-dioxide (1.99 g, 4.64 mmol) dissolved in DCM (25 mL) was treated with 1M DIBAL-H in toluene (5.34 mL, 5.34 mmol) at 0° C. dropwise with stirring for 1 h. A second portion of 1M DIBAL-H (5.34 mL, 5.34 mmol) was added, and the mixture was stirred further for 2 h at 0° C. after which time LCMS indicated conversion to product. 1N HCl (10 mL) was added to the mixture and the mixture was vigorously stirred for 16 h. The organic phase was isolated, and the aqueous phase was extracted three times with DCM. The organic layers were combined, dried over MgSO₄, filtered, and concentrated to dryness. The residue was purified on 40 g silica gel eluting with 10 to 50% EtOAc/hexanes to give (3R,5R)-3-butyl-3-ethyl-4-hydroxy-7-(methyloxy)-5-phenyl-2,3,4,5-tetrahydro-1,4-benzothiazepine-8-carbaldehyde 1,1-dioxide (1.42 g, 70.9% yield) as a white foam: ¹H NMR (400 MHz, DMSO-d₆) δ ppm 0.78 (t, J=7.1 Hz, 3H), 0.85 (t, J=7.3 Hz, 3H), 1.02-1.38 (m, 4H), 1.38-1.52 (m, 1H), 1.56-1.73 (m, 1H), 1.78-1.91 (m, 1H), 2.01-2.15 (m, 1H), 3.39-3.51 (m, 2H), 3.55 (s, 3H), 6.31 (s, 1H), 6.38 (s, 1H), 7.32-7.75 (m, 5H), 8.20 (s, 1H), 8.22 (s, 1H), 10.26 (s, 1H). LC-MS (ES⁺) m/z 432.2 [M+H].

Intermediate 15: {[(3R,5R)-3-butyl-3-ethyl-7-(methyloxy)-1,1-dioxido-5-phenyl-2,3,4,5-tetrahydro-1,4-benzothiazepin-8-yl]methyl}amine

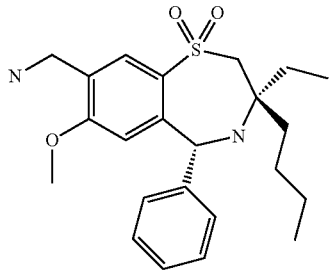 [SMILES: CCCC[C@]1(CC)CS(=O)(=O)c2cc(CN)c(OC)cc2[C@@H](c2ccccc2)N1]

A mixture of (3R,5R)-3-butyl-3-ethyl-7-(methyloxy)-5-phenyl-2,3,4,5-tetrahydro-1,4-benzothiazepine-8-carbonitrile 1,1-dioxide (468 mg, 1.134 mmol) and 10% palladium on carbon (60.4 mg, 0.567 mmol) in ethanol (20 mL) was added hydrochloric acid (0.279 mL, 3.40 mmol) and hydrogenated at 40 psi overnight then filtered and concentrated. The residue was purified via HPLC (eluting with MeCN/H$_2$O with 0.05% TFA-H$_2$O and 0.05% TFA-MeCN) to give the title compound (621 mg, 79%, TFA salt) as a white solid: $^1$H NMR (CDCl$_3$) δ ppm 8.07-8.46 (br.s, 2H), 7.98 (s, 1H), 7.31-7.57 (m, 5H), 6.27 (s, 1H), 6.17 (s, 1H), 4.12-4.27 (m, 1H), 3.98-4.12 (m, 1H), 3.55 (s, 3H), 3.38-3.48 (m, 1H), 3.29 (d, J=15.0 Hz, 1H), 2.14-2.38 (m, 1H), 1.80-1.99 (m, 1H), 1.44-1.75 (m, 2H), 1.14-1.38 (m, 3H), 0.97-1.15 (m, 1H), 0.90 (t, J=7.2 Hz, 3H), 0.82 (t, J=6.8 Hz, 3H); ES-LCMS m/z 417 (M+H)$^+$.

Intermediate 16: N-{[(3R,5R)-3-butyl-3-ethyl-7-(methyloxy)-1,1-dioxido-5-phenyl-2,3,4,5-tetrahydro-1,4-benzothiazepin-8-yl]methyl}-2-chloroacetamide

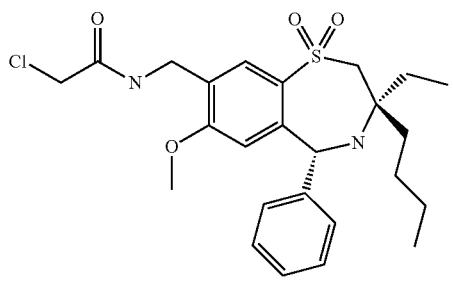 [SMILES: CCCC[C@]1(CC)CS(=O)(=O)c2cc(CNC(=O)CCl)c(OC)cc2[C@@H](c2ccccc2)N1]

To an ice-cold solution of {[(3R,5R)-3-butyl-3-ethyl-7-(methyloxy)-1,1-dioxido-5-phenyl-2,3,4,5-tetrahydro-1,4-benzothiazepin-8-yl]methyl}amine (50 mg, 0.120 mmol) in DCM (6 mL) was added pyridine (0.097 mL, 1.20 mmol) and chloroacetyl chloride (0.048 mL, 0.60 mmol). The reaction mixture was stirred at room temperature overnight then concentrated under reduced pressure to give a light yellow oil. The crude title compound (55 mg, 92%) was used without further purification: $^1$H NMR (CDCl$_3$) δ ppm 7.27-7.45 (m, 5H), 6.91-7.13 (m, 1H), 6.17 (s, 1H), 6.05 (s, 1H), 4.44 (d, J=6.1 Hz, 2H), 4.05 (d, J=7.0 Hz, 3H), 3.53 (s, 3H), 3.37 (s, 1H), 3.02 (s, 2H), 2.09-2.24 (m, 1H), 1.69-1.90 (m, 1H), 0.99-1.60 (m, 6H), 0.86 (t, J=7.4 Hz, 3H), 0.80 (t, J=7.0 Hz, 3H); ES-LCMS m/z 494 (M+H)$^+$.

Intermediate 17: ethyl (2E)-3-[(3R,5R)-3-butyl-3-ethyl-7-(methyloxy)-1,1-dioxido-5-phenyl-2,3,4,5-tetrahydro-1,4-benzothiazepin-8-yl]-2-propenoate

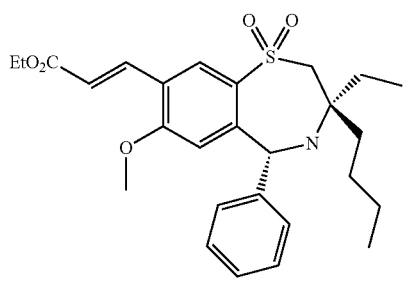 [SMILES: CCCC[C@]1(CC)CS(=O)(=O)c2cc(/C=C/C(=O)OCC)c(OC)cc2[C@@H](c2ccccc2)N1]

In a sealed tube, a solution of (3R,5R)-3-butyl-3-ethyl-7-(methyloxy)-1,1-dioxido-5-phenyl-2,3,4,5-tetrahydro-1,4-benzothiazepin-8-yl trifluoromethanesulfonate (3.5 g, 6.53 mmol) in DMF (30 mL) was treated with triethyamine (4.55 mL, 32.7 mmol), followed by ethyl acrylate (3.56 mL, 32.7 mmol) and bis(triphenylphosphine)palladium(II) chloride (0.459 g, 0.653 mmol). The reaction mixture was stirred at 120° C. overnight, cooled to room temperature and partitioned between H$_2$O and EtOAc. The organic layer was washed with saturated brine, dried (Na$_2$SO$_4$), filtered, and concentrated under reduced pressure. Purification on silica gel (EtOAc: hexanes=1:6 to 2:1) afforded the title compound (3.06 g, 94%) as a white solid: $^1$H NMR (CDCl$_3$): δ ppm 8.21 (s, 1H), 7.85 (d, J=16.2 Hz, 1H), 7.30-7.48 (m, 5H), 6.56 (d, J=16.0 Hz, 1H), 6.19 (s, 1H), 6.06 (d, J=6.8 Hz, 1H), 4.18-4.30 (m, 2H), 3.55 (s, 3H), 3.44 (d, J=14.9 Hz, 1H), 3.02 (d, J=14.9 Hz, 1H), 2.08-2.26 (m, 1H), 1.76-1.93 (m, 1H), 1.38-1.54 (m, 3H), 1.28-1.35 (m, 3H), 1.03-1.21 (m, 2H), 0.88 (t, J=7.4 Hz, 3H), 0.81 (t, J=7.0 Hz, 3H); ES-LCMS m/z 486 (M+H)$^+$.

Intermediate 18: diethyl 3-aminopentanedioate

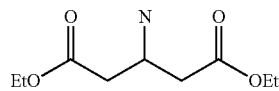 [SMILES: CCOC(=O)CC(N)CC(=O)OCC]

To a solution of β-glutamic acid (500 mg, 3.40 mmol) in EtOH (10 mL) was added thionyl chloride (0.992 mL, 13.59 mmol) dropwise. The reaction mixture was stirred at room temperature overnight and concentrated under reduced pressure. The residue was partitioned between DCM and saturated potassium carbonate solution. The organic layer was washed with saturated brine, dried (Na$_2$SO$_4$), filtered, and concentrated under reduced pressure to give the title compound (702 mg, 97%) as a colorless oil: $^1$H NMR (CDCl$_3$) δ ppm 4.04-4.27 (m, 4H), 3.46-3.74 (m, 1H), 2.24-2.60 (m, 4H), 1.09-1.29 (m, 6H).

Intermediate 19: (3R,5R)-8-(3-bromopropyl)-3-butyl-3-ethyl-7-(methyloxy)-5-phenyl-2,3,4,5-tetrahydro-1,4-benzothiazepine 1,1-dioxide

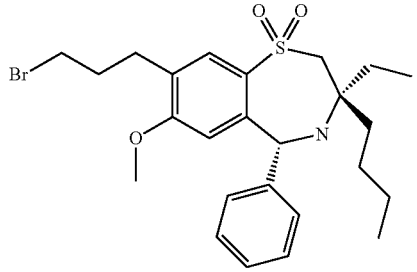 [SMILES: CCCC[C@]1(CC)CS(=O)(=O)c2cc(CCCBr)c(OC)cc2[C@@H](c2ccccc2)N1]

To a solution of 3-[(3R,5R)-3-butyl-3-ethyl-7-(methyloxy)-1,1-dioxido-5-phenyl-2,3,4,5-tetrahydro-1,4-benzothiazepin-8-yl]-1-propanol (84.2 mg, 0.189 mmol) in THF (5 mL) was added triphenylphosphine (99 mg, 0.378 mmol) and carbon tetrabromide (125 mg, 0.378 mmol). The reaction mixture was stirred at room temperature overnight and partitioned between H$_2$O and DCM. The organic layer was washed with brine, dried (Na$_2$SO$_4$), filtered, and concentrated under reduced pressure. Purification using silica gel (EtOAc:hexanes=10:90 to 50:50) afforded the title compound (78 mg, 80%) as a clear oil: ES-LCMS m/z 508 (M+H)$^+$.

Intermediate 20: 3-[(3R,5R)-3-butyl-3-ethyl-7-(methyloxy)-1,1-dioxido-5-phenyl-2,3,4,5-tetrahydro-1,4-benzothiazepin-8-yl]propyl methanesulfonate

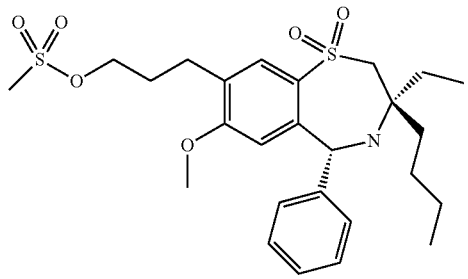 [SMILES: CCCC[C@]1(CC)CS(=O)(=O)c2cc(CCCOS(C)(=O)=O)c(OC)cc2[C@@H](c2ccccc2)N1]

To an ice-cold solution of 3-[(3R,5R)-3-butyl-3-ethyl-7-(methyloxy)-1,1-dioxido-5-phenyl-2,3,4,5-tetrahydro-1,4-benzothiazepin-8-yl]-1-propanol (250 mg, 0.561 mmol) in DCM (10 mL) was added triethylamine (0.235 mL, 1.683 mmol) and methanesulfonyl chloride (0.048 mL, 0.617 mmol). The reaction mixture was stirred at room temperature overnight and partitioned between H$_2$O and DCM. The organic layer was washed with saturated brine, dried (Na$_2$SO$_4$), filtered, and concentrated under reduced pressure to give the title product (280 mg, 91%) as a light yellow solid: $^1$H NMR (CDCl$_3$) δ ppm 7.82 (s, 1H), 7.27-7.52 (m, 5H), 6.11 (s, 1H), 6.01 (d, J=8.0 Hz, 1H), 4.04-4.26 (m, 2H), 3.47 (s, 3H), 3.31-3.43 (m, 1H), 2.85-3.07 (m, 4H), 2.46-2.78 (m, 4H), 1.73-2.27 (m, 4H), 1.35-1.61 (m, 4H), 0.97-1.34 (m, 8H), 0.86 (t, J=7.4 Hz, 3H), 0.80 (t, J=6.8 Hz, 3H).

Intermediate 21: 4-[(3R,5R)-3-butyl-3-ethyl-7-(methyloxy)-1,1-dioxido-5-phenyl-2,3,4,5-tetrahydro-1,4-benzothiazepin-8-yl]butanenitrile

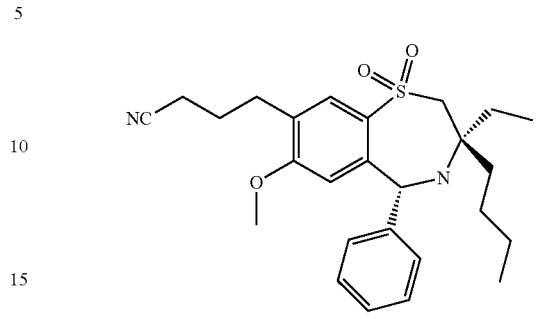

To a solution of 3-[(3R,5R)-3-butyl-3-ethyl-7-(methyloxy)-1,1-dioxido-5-phenyl-2,3,4,5-tetrahydro-1,4-benzothiazepin-8-yl]propyl methanesulfonate (90 mg, 0.172 mmol) in DMSO (5 mL) was added sodium cyanide (16.84 mg, 0.344 mmol). The reaction mixture was stirred at 60° C. over the weekend and partitioned between H$_2$O and EtOAc. The organic layer was washed with saturated brine, dried (Na$_2$SO$_4$), filtered, and concentrated under reduced pressure. Purification using silica gel (EtOAc:hexanes=10:90 to 1:1) afforded the title compound (76 mg, 95%) as a white solid: $^1$H NMR (CDCl$_3$) δ ppm 7.81 (s, 1H), 7.26-7.48 (m, 5H), 6.12 (s, 1H), 6.02 (s, 1H), 3.40 (d, J=14.8 Hz, 1H), 3.01 (d, J=14.6 Hz, 1H), 2.64-2.80 (m, 2H), 2.29 (t, J=7.2 Hz, 2H), 2.08-2.21 (m, 1H), 1.75-1.98 (m, 3H), 1.37-1.51 (m, 2H), 0.99-1.35 (m, 4H), 0.86 (t, J=7.4 Hz, 3H), 0.80 (t, J=7.0 Hz, 3H); ES-LCMS m/z 455 (M+H)$^+$.

Intermediate 22: (3R,5R)-8-(bromomethyl)-3-butyl-3-ethyl-7-(methyloxy)-5-phenyl-2,3-dihydro-1,4-benzothiazepin-4(5H)-ol 1,1-dioxide

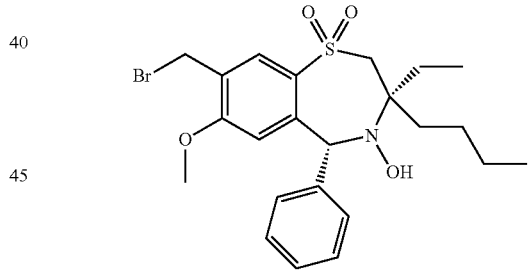

(3R,5R)-8-(bromomethyl)-3-butyl-3-ethyl-7-(methyloxy)-5-phenyl-2,3,4,5-tetrahydro-1,4-benzothiazepine 1,1-dioxide (627 mg, 1.305 mmol) dissolved in DCM (20 mL) was treated with m-CPBA (292 mg, 1.305 mmol) with stirring at 0° C. for 1 h after which time LCMS indicated complete conversion to product. The reaction mixture was treated with 10% Na$_2$SO$_3$ with vigorous stirring for 15 min, diluted with DCM, and the organic phase was isolated, dried over MgSO$_4$, filtered, and concentrated to dryness. The residue was purified on 40 g silica gel eluting with DCM to give (3R,5R)-8-(bromomethyl)-3-butyl-3-ethyl-7-(methyloxy)-5-phenyl-2,3-dihydro-1,4-benzothiazepin-4(5H)-ol 1,1-dioxide (621 mg, 96% yield) as a white foam: $^1$H NMR (400 MHz, DMSO-d$_6$) δ ppm 0.79 (t, J=7.1 Hz, 3H), 0.85 (t, J=7.3 Hz, 3H), 1.04-1.37 (m, 4H), 1.37-1.49 (m, 1H), 1.58-1.71 (m, 1H), 1.77-1.89 (m, 1H), 2.01-2.14 (m, 1H), 3.36-3.44 (m, 2H), 3.45-3.55 (m, 3H), 4.69 (s, 2H), 6.15 (s, 1H), 6.35 (s, 1H), 7.30-7.72 (m, 5H), 7.98 (s, 1H), 8.10 (s, 1H); LC-MS (ES$^+$) m/z 496.1, 498.1 [M+H].

Intermediate 23: diethyl {[(3R,5R)-3-butyl-3-ethyl-4-hydroxy-7-(methyloxy)-1,1-dioxido-5-phenyl-2,3,4,5-tetrahydro-1,4-benzothiazepin-8-yl]methyl}phosphonate

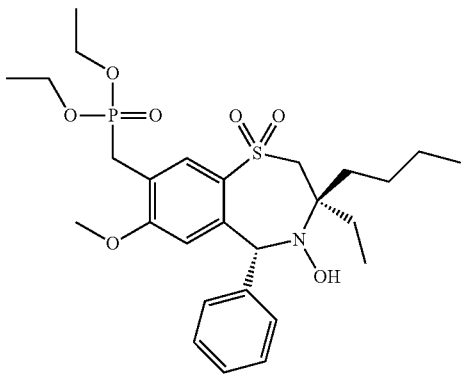 [SMILES: CCCC[C@]1(CC)CS(=O)(=O)c2cc(CP(=O)(OCC)OCC)c(OC)cc2[C@@H](c2ccccc2)N1O]

(3R,5R)-8-(bromomethyl)-3-butyl-3-ethyl-7-(methyloxy)-5-phenyl-2,3-dihydro-1,4-benzothiazepin-4(5H)-ol 1,1-dioxide (171 mg, 0.344 mmol) dissolved in toluene (10 mL) was treated with triethyl phosphite (1.189 mL, 6.80 mmol) then heated at reflux for 16 h. The reaction mixture was washed with $H_2O$, dried over $MgSO_4$, filtered and concentrated to dryness. The residue was purified by RP-HPLC (30×150 mm, C18 5 um $H_2O$ Sunfire Column; MeCN+0.05% TFA & $H_2O$+0.05% TFA were used as the solvent system; 15 to 100%) to give diethyl {[(3R,5R)-3-butyl-3-ethyl-4-hydroxy-7-(methyloxy)-1,1-dioxido-5-phenyl-2,3,4,5-tetrahydro-1,4-benzothiazepin-8-yl]methyl}phosphonate (48.5 mg, 25.4% yield) as a clear oil: $^1$H NMR (400 MHz, DMSO-$d_6$) δ ppm 0.79 (t, J=6.6 Hz, 3H), 0.82-0.93 (m, 3H), 1.04-1.71 (m, 12H), 1.91-2.02 (m, 1H), 2.02-2.13 (m, 1H), 3.13-3.28 (m, 2H), 3.29-3.40 (m, 2H), 3.41 (s, 3H), 3.95 (m, J=7.2, 7.2, 7.2, 7.2, 2.5 Hz, 4H), 6.12 (s, 1H), 6.28-6.38 (m, 1H), 7.31-7.39 (m, 1H), 7.42 (t, J=7.4 Hz, 2H), 7.46-7.60 (m, 2H), 7.82 (d, J=1.8 Hz, 1H), 7.99-8.08 (m, 1H); LC-MS (ES$^+$) m/z 554.31 [M+H].

Intermediates 24: tetraethyl [({[(3R,5R)-3-butyl-3-ethyl-7-(methyloxy)-1,1-dioxido-5-phenyl-2,3,4,5-tetrahydro-1,4-benzothiazepin-8-yl]methyl}imino)dimethanediyl]bis(phosphonate)

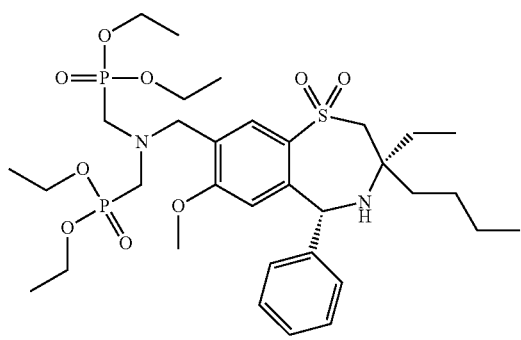 [SMILES: CCCC[C@]1(CC)CS(=O)(=O)c2cc(CN(CP(=O)(OCC)OCC)CP(=O)(OCC)OCC)c(OC)cc2[C@@H](c2ccccc2)N1]

{[(3R,5R)-3-butyl-3-ethyl-7-(methyloxy)-1,1-dioxido-5-phenyl-2,3,4,5-tetrahydro-1,4-benzothiazepin-8-yl]methyl}amine (155 mg, 0.37 mmol) was combined with tosic acid (catalytic) in toluene (20 mL) and concentrated to dryness to azeotrope off any residual $H_2O$. Paraformaldehyde (11.2 mg, 0.37 mmol) and toluene (5 mL) were added, and the mixture was heated at 75° C. with vigorous stirring for 30 minutes after which time diethyl phosphite (0.048 mL, 0.37 mmol) was added. After 30 min THF (20 mL) was added to the mixture, and the resultant homogeneous reaction mixture was stirred overnight at 75° C. The mixture was concentrated to dryness and purified by RP-HPLC (30×150 Sunfire column under acidic conditions; MeCN+0.05% TFA and $H_2O$+0.05% TFA were used as the solvent system; 30% to 100% over 10 minutes, 100% to 100% to 12 minutes) to give tetraethyl [({[(3R,5R)-3-butyl-3-ethyl-7-(methyloxy)-1,1-dioxido-5-phenyl-2,3,4,5-tetrahydro-1,4-benzothiazepin-8-yl]methyl}imino)dimethanediyl]bis(phosphonate) (49.7 mg, 18.6% yield) as a yellow oil: LC-MS (ES$^+$) m/z 717.4 [M+H].

Intermediate 25: diethyl [({[(3R,5R)-3-butyl-3-ethyl-7-(methyloxy)-1,1-dioxido-5-phenyl-2,3,4,5-tetrahydro-1,4-benzothiazepin-8-yl]methyl}amino)methyl]phosphonate

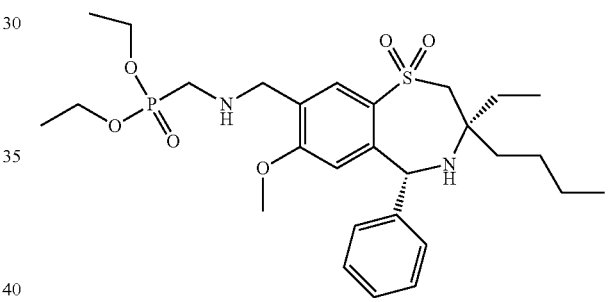

{[(3R,5R)-3-butyl-3-ethyl-7-(methyloxy)-1,1-dioxido-5-phenyl-2,3,4,5-tetrahydro-1,4-benzothiazepin-8-yl]methyl}amine (45.8 mg, 0.110 mmol) was combined with paraformaldehyde (3.47 mg, 0.110 mmol) and diethyl phosphite (0.014 mL, 0.11 mmol) in THF (4 mL) and stirred for 16 h at 75° C. after which time all solvent was gone, and LCMS indicated <20% conversion. The THF was replaced and additional diethyl phosphite (0.043 mL, 0.330 mmol) was added, and the mixture was heated an additional 24 h at 75° C. after which time LCMS indicated ~50% conversion. Additional diethyl phosphite (0.150 mL, 1.16 mmol) was added and heating was continued for 24 h after which time LCMS indicated 70% completion. Additional paraformaldehyde (1.651 mg, 0.055 mmol) was added and heating was continued for 24 h after which time LCMS indicated complete conversion of starting material to mono and disubstituted products. The mixture was concentrated to dryness and purified on 24 g silica gel eluting with 0 to 20% MeOH/DCM to give the desired diethyl [({[(3R,5R)-3-butyl-3-ethyl-7-(methyloxy)-1,1-dioxido-5-phenyl-2,3,4,5-tetrahydro-1,4-benzothiazepin-8-yl]methyl}amino)methyl]phosphonate (36.3 mg, 58.3% yield) as a clear oil: LC-MS (ES$^+$) m/z 567.30 [M+H].

Intermediate 26: [(3R,5S)-3-butyl-3-ethyl-7-(methyloxy)-1,1-dioxido-5-phenyl-2,3,4,5-tetrahydro-1,4-benzothiazepin-8-yl]methanol

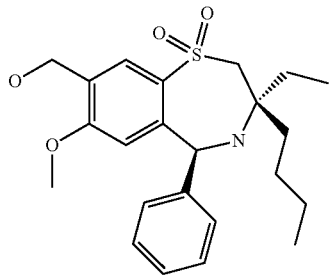 [SMILES: CCCC[C@]1(CC)CS(=O)(=O)c2cc(CO)c(OC)cc2[C@H](c2ccccc2)N1]

Step 1: To an ice-cold solution of (3R,5R)-3-butyl-3-ethyl-7-(methyloxy)-5-phenyl-2,3,4,5-tetrahydro-1,4-benzothiazepine-8-carbonitrile 1,1-dioxide (2.37 g, 5.74 mmol) in DCM (50 mL) was added DDQ (1.956 g, 8.62 mmol). The reaction mixture was warmed to room temperature and stirred for 72 hrs. The reaction mixture was partitioned between $H_2O$ and DCM. The organic layer was washed with saturated brine, dried, ($Na_2SO_4$), filtered, and concentrated under reduced pressure. Purification using silica gel (EtOAc/hexanes=1:4 to 3:1), followed by further purification using silica gel (MeOH:DCM=0:100 to 5:95) afforded (3R)-3-butyl-3-ethyl-7-(methyloxy)-5-phenyl-2,3-dihydro-1,4-benzothiazepine-8-carbonitrile 1,1-dioxide (1.42 g, 59%) as a white solid: $^1$H NMR (CDCl$_3$) δ ppm 8.27 (s, 1H), 7.60 (d, J=7.2 Hz, 2H), 7.44-7.54 (m, 1H), 7.35-7.45 (m, 2H), 6.77 (s, 1H), 3.90 (s, 3H), 3.63-3.86 (m, 3H), 1.02-1.76 (m, 8H), 0.89 (t, J=7.2 Hz, 3H), 0.83 (t, J=6.8 Hz, 3H); ES-LCMS m/z 411 (M+H)$^+$.

Step 2: To an ice-cold solution of (3R)-3-butyl-3-ethyl-7-(methyloxy)-5-phenyl-2,3-dihydro-1,4-benzothiazepine-8-carbonitrile 1,1-dioxide (1.32 g, 3.22 mmol) in DCM (30 mL) was added dropwise DIBAL-H (6.43 mL, 6.43 mmol) as a 1M solution in toluene. The reaction mixture was stirred at room temperature for 2 h, treated with 1N hydrochloric acid solution, and stirred for 1 h whereupon the layers were separated. The aqueous layer was extracted with DCM, and the combined organic layers were washed with $H_2O$, saturated brine, dried ($Na_2SO_4$), filtered, and concentrated under reduced pressure to give (3R)-3-butyl-3-ethyl-7-(methyloxy)-5-phenyl-2,3-dihydro-1,4-benzothiazepine-8-carbaldehyde 1,1-dioxide (1.0 g, 75%) as a white solid: $^1$H NMR (CDCl$_3$) δ ppm 10.48 (s, 1H), 8.50 (s, 1H), 7.59-7.68 (m, 2H), 7.43-7.52 (m, 1H), 7.34-7.43 (m, 2H), 6.80 (s, 1H), 3.89 (s, 3H), 3.63-3.83 (m, 2H), 0.99-1.36 (m, 5H), 0.88 (t, J=7.0 Hz, 3H), 0.82 (t, J=7.0 Hz, 3H); ES-LCMS m/z 414 (M+H)$^+$.

Step 3: To a solution of (3R)-3-butyl-3-ethyl-7-(methyloxy)-5-phenyl-2,3-dihydro-1,4-benzothiazepine-8-carbaldehyde 1,1-dioxide (720 mg, 1.741 mmol) in THF (20 mL) was added borane-THF complex (3.48 mL, 1M solution in THF, 3.48 mmol) dropwise. The reaction mixture was stirred overnight then at 40° C. for an additional 24 h. The reaction mixture was cooled to room temperature, quenched with MeOH, stirred for 30 min, and concentrated under reduced pressure. MeOH was added several times and evaporated under reduced pressure. Purification using silica gel (EtOAc:hexanes=20:80 to 50:50) afforded the title compound (306 mg, 42%) as a white solid: $^1$H NMR (CDCl$_3$) δ ppm 8.05 (s, 1H), 7.30-7.53 (m, 5H), 6.18 (s, 1H), 6.08 (br. s., 1H), 4.53-4.82 (m, 2H), 3.56 (s, 3H), 3.43 (d, J=14.9 Hz, 1H), 3.08 (d, J=14.9 Hz, 1H), 2.38 (dd, J=14.7, 7.4 Hz, 1H), 2.14 (t, J=5.9 Hz, 1H), 1.71-1.87 (m, 1H), 1.44-1.57 (m, 2H), 1.09-1.42 (m, 5H), 0.91 (t, J=6.8 Hz, 3H), 0.79 (t, J=7.2 Hz, 3H); ES-LCMS m/z 418 (M+H)$^+$.

Intermediate 27: (3R,5S)-3-butyl-3-ethyl-7-(methyloxy)-5-phenyl-2,3,4,5-tetrahydro-1,4-benzothiazepine-8-carbaldehyde 1,1-dioxide

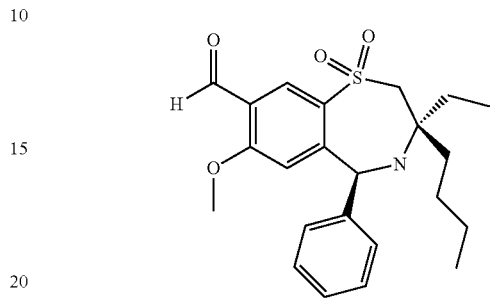

To a solution of [(3R,5S)-3-butyl-3-ethyl-7-(methyloxy)-1,1-dioxido-5-phenyl-2,3,4,5-tetrahydro-1,4-benzothiazepin-8-yl]methanol (460 mg, 1.102 mmol) in DCM (10 mL) was added Dess-Martin Periodinane (491 mg, 1.157 mmol). The reaction mixture was stirred at room temperature for 2 hrs and filtered through a pad of silica gel. The filtrate was concentrated under reduced pressure to give the title compound (391 mg, 85% yield) as a white solid: $^1$H NMR (CDCl$_3$) δ ppm 10.35 (s, 1H), 8.55 (s, 1H), 7.33-7.52 (m, 5H), 6.30 (s, 1H), 6.13 (s, 1H), 3.63 (s, 3H), 3.47 (d, J=14.9 Hz, 1H), 3.08 (d, J=14.9 Hz, 1H), 2.40 (dd, J=14.9, 7.4 Hz, 1H), 1.83 (dd, J=14.9, 7.4 Hz, 1H), 1.11-1.47 (m, 5H), 0.91 (t, J=6.8 Hz, 3H), 0.78 (t, J=7.4 Hz, 3H); ES-LCMS m/z 416 (M+H)$^+$.

Intermediate 28: 2-amino-2-butylhexanesyl hydrogen sulfate

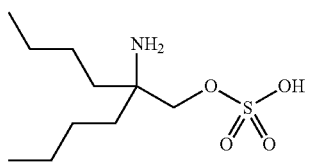 [SMILES: CCCCC(N)(CCCC)COS(=O)(=O)O]

Step 1: To a stirred slurry of norleucine (100 g, 762 mmol) in EtOH (715 mL) at 0° C. was added thionyl chloride (58.4 mL, 800 mmol) over 1 h maintaining a temperature of <5° C. The reaction was allowed to slowly warm to 25° C. and stirred overnight. The solution was heated at 65° C. for 3 h then concentrated under reduced pressure to provide ethyl norleucinate hydrochloride (149 g, 761 mmol, 100% yield) as a white solid after drying at 50° C. under high vacuum for 15 h.

Step 2: A slurry of ethyl norleucinate hydrochloride salt (149 g, 761 mmol) in DCM (1352 mL) at 25° C. was treated with MgSO$_4$ (92 g, 761 mmol) followed by TEA (223 mL, 1599 mmol) in a dropwise fashion over 1 h. After stirring for 1 h, benzaldehyde (77 mL, 761 mmol) was added via addition funnel over 30 min followed by additional MgSO$_4$, (92 g, 761 mmol). The slurry was stirred at 25° C. for 60 h then filtered washing with DCM. The filtrate was concentrated in vacuo then triturated with MTBE. The mixture was filtered, and the solid was washed with MTBE. The filtrate was concentrated in vacuo to give a light yellow oil (>95% yield).

Step 3: A mixture of NaH (16.53 g, 413 mmol) in DMF (293 mL) at 25° C. was stirred for 10 min then cooled to 0° C. whereupon a solution of ethyl N-(phenylmethylidene)norleucinate (81.8 g, 331 mmol) in DMF (58.5 mL) was added via cannula in a dropwise fashion. The reaction was warmed to 25° C. and stirred for 2 h. A solution of iodobutane (44.6 mL, 364 mmol) in DMF (29.3 mL) was added via cannula, and the rxn mixture was stirred at 25° C. for 20 h. The reaction was poured into saturated NH$_4$Cl (250 mL) and MTBE (250 mL) then stirred for 10 min. The layers were separated, and the aqueous layer was extracted with MTBE (1×). The combined organic layers were dried (MgSO$_4$,), filtered, and concentrated in vacuo to give a yellow oil in >95% yield.

Step 4: Neat ethyl 2-butyl-N-(phenylmethylidene)norleucinate (112.3 g, 370 mmol) was treated with 1N HCl (444 mL, 444 mmol) and stirred at 25° C. for 30 min. The reaction was washed with hexanes (2×200 mL) then the aqueous layer was cooled to 0° C. and adjusted to pH 12 with a combination of 3N and 6N NaOH. The aqueous mixture was extracted with MTBE (4×) then the combined organic layers were washed with brine, dried (MgSO$_4$), filtered, and concentrated in vacuo to give ethyl 2-butylnorleucinate (74 g, 93% yield) as a yellow oil.

Step 5: A solution of ethyl 2-butylnorleucinate (37 g, 172 mmol) in THF (275 mL) at 25° C. was treated with 2M LAH (86 mL, 172 mmol) via an addition funnel over 30 min. The reaction mixture was heated to 65° C. and stirred for 2 h then allowed to come to ambient temperature while stirring overnight. The reaction was cooled to 0° C. then treated sequentially with H$_2$O (7.82 mL), 15% NaOH (7.82 mL), and H$_2$O (23.5 mL). The mixture was stirred for 2 h then filtered washing with THF. The filtrate was concentrated in vacuo to give 2-amino-2-butyl-1-hexanol (29.8 g, >95% yield) as a thick yellow oil which solidified upon standing.

Step 6: A solution of 2-amino-2-butyl-1-hexanol (62.8 g, 362 mmol) in EtOAc (454 mL) at 25° C. was treated with chlorosulfonic acid (29.1 mL, 435 mmol). The reaction was heated to 40° C. and stirred for 3 h then cooled to 25° C. The thick mixture was placed in refrigerator overnight then filtered washing with cold EtOAc. The solid was dried to give 2-amino-2-butylhexanesyl hydrogen sulfate as a white solid in >50% yield: $^1$H NMR (D$_2$O) δ ppm 3.92 (s, 2H), 1.42-1.65 (m, 4H), 1.02-1.25 (m, 8H), 0.72 (t, J=6.7 Hz, 6H).

Intermediate 29: S—[5-bromo-4-(methyloxy)-2-(phenylcarbonyl)phenyl]diethylthiocarbamate

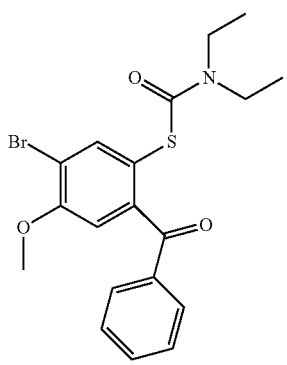 [SMILES: CCN(CC)C(=O)Sc1cc(Br)c(OC)cc1C(=O)c1ccccc1]

Step 1: To a solution of 2-bromo-1,4-bis(methyloxy)benzene (203 g, 934 mmol) and benzoyl chloride (125 mL, 1074 mmol) in DCM (800 mL) at 5° C. was added triflic acid (83 mL, 934 mmol) over 1 h. The reaction mixture was allowed to warm to ambient temperature and then slowly heated to gentle reflux and stirred for 48 h. The reaction mixture was cooled, and MeOH (20 mL) was added and stirring was continued for 30 min. The reaction mixture was poured into ice H$_2$O and stirred for 1 h. The layers were separated and the organic phase was washed with H$_2$O, dried over MgSO$_4$, and concentrated to an orange solid. MTBE (500 mL) was added and the mixture was stirred overnight. The resulting solid was filtered, rinsed with 1:1 MTBE/hexanes and air dried to afford [4-bromo-2,5-bis(methyloxy)phenyl](phenyl)methanone (210.6 g, 70%) as a light grey solid: $^1$H NMR (DMSO-d$_6$) δ ppm 7.68 (d, J=8.0 Hz, 2H), 7.62 (t, J=8.0 Hz, 1H), 7.48 (t, J=7.4 Hz, 2H), 7.42 (s, 1H), 7.07 (s, 1H), 3.76 (s, 3H), 3.59 (s, 3H).

Step 2: A solution of [4-bromo-2,5-bis(methyloxy)phenyl](phenyl)methanone (290 g, 0.903 mol) in DCM (1.5 L) was added dropwise over 1 h to a stirred solution of 1M BCl$_3$ in DCM (1.13 L, 1.13 mol) while maintaining the reaction temperature below 5° C. The reaction mixture was stirred at or below 0° C. for 30 min and then quenched by slow addition of MeOH (500 mL) over 30 min at 10° C. 2N HCl (1 L) was added at 15° C. over 30 min. The layers were separated, and the organic phase was concentrated by rotovap to around 500 mL then diluted with hexanes. The resulting yellow crystals were collected by filtration and air dried to afford [4-bromo-2-hydroxy-5-(methyloxy)phenyl](phenyl)methanone (258 g, 93%): $^1$H NMR (CDCl$_3$) δ ppm 11.67 (s, 1H), 7.64-7.72 (m, 2H), 7.59 (t, J=7.4 Hz, 1H), 7.51 (t, J=7.2 Hz, 2H), 7.33 (s, 1H), 7.02 (s, 1H), 3.71 (s, 3H)

Step 3: Solid potassium tert-butoxide (116 g, 1.03 mol) was added portionwise to a stirred solution of [4-bromo-2-hydroxy-5-(methyloxy)phenyl](phenyl)methanone (253.33 g, 0.825 mol) in DMF (800 mL) while maintaining the internal temperature below 20° C. Stirring was maintained with cooling for 15 min until the internal temperature was ca. 0° C. The cooling bath was removed and stirring was continued for 30 min with warming to 6° C. internal temp. A solution of N,N-diethyl thiocarbamoyl chloride (150 g, 0.99 mol) in DMF (300 mL) was then added in a slow stream over 5 min. The resulting dark mixture was then heated to 60° C. and maintained for 3 h. The mixture was diluted with MTBE (1.5 L) and H$_2$O (1.5 L) then stirred rapidly. The layers were separated, and the aqueous phase was extracted with MTBE (1.5 L). The combined organic layers were washed with 0.2N NaOH (2×1.5 L) and once with brine (1 L). The dark red organic phase was dried over MgSO$_4$, filtered and concentrated to 1 L of a thick slurry, chasing with heptane. The solids were collected by filtration washing with heptane and air dried to afford O—[5-bromo-4-(methyloxy)-2-(phenylcarbonyl)phenyl]diethylthiocarbamate (301.3 g, 86%) as a light orange solid: $^1$H NMR (CDCl$_3$) δ ppm 7.81 (d, J=8.0 Hz, 2H), 7.52 (t, J=7.6 Hz, 1H), 7.36-7.45 (m, 3H), 7.00 (s, 1H), 3.86 (s, 3H), 3.63 (q, J=7.0 Hz, 2H), 3.22 (q, J=7.2 Hz, 2H), 1.06 (q, 6H)

Step 4: A stirred mixture of 0-[5-bromo-4-(methyloxy)-2-(phenylcarbonyl)phenyl]diethylthiocarbamate (301 g, 0.71 mol) in diphenyl ether (10 was heated gradually to 215° C. internal temperature over 1 h and maintained at this temperature for 3.5 h. The dark solution was cooled to 100° C. and treated with Darco G-60 (20 g). The mixture was further cooled to 70° C. with stirring and filtered through celite washing with heptane. The filtrate was diluted with heptane (4 L) with cooling to 5° C. and aged to 0° C. over 30 min. The supernatant was removed by decantation, and the remaining solids were triturated with hexanes. The remaining solids were dissolved in DCM and concentrated in vacuo to a solid which was triturated with hexanes and collected by filtration. The material was dried under high vacuum to afford S—[5-bromo-4-(methyloxy)-2-(phenylcarbonyl)phenyl]diethylthiocarbamate (224 g, 74%) as a dark-gray solid: $^1$H NMR (CDCl$_3$) δ ppm 7.72-7.82 (m, 3H), 7.52 (t, J=7.4 Hz, 1H), 7.39 (t, J=7.6 Hz, 2H), 6.90 (s, 1H), 3.87 (s, 3H), 3.15-3.29 (br. s., 2H), 3.02-3.15 (br. s., 2H), 0.68-1.09 (m, 6H).

Intermediate 30: [2-[(2-amino-2-butylhexanesyl)thio]-4-bromo-5-(methyloxy)phenyl]phenyl)methanone

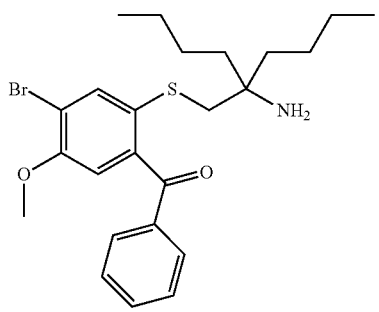 [SMILES: CCCCC(N)(CCCC)CSc1cc(Br)c(OC)cc1C(=O)c1ccccc1]

A suspension of S—[5-bromo-4-(methyloxy)-2-(phenylcarbonyl)phenyl]diethylthiocarbamate (Intermediate 29) (15 g, 35.5 mmol) in EtOH (75 mL) was treated with 6M KOH (23.68 mL, 142 mmol) then heated at reflux for 3 h. The reaction was diluted with additional EtOH (200 mL) then heated at 70° C. for 15 h. The reaction was concentrated until a thick dark red oil. In a separate flask, the 2-amino-2-butylhexanesyl hydrogen sulfate (9.90 g, 39.1 mmol) was dissolved in H$_2$O (25 mL) then heated to 85° C. whereupon the solution of thiophenolate in H$_2$O was added via pipette. Residual thiophenolate was transferred with minimal EtOH and H$_2$O. The reaction mixture was stirred at 85° C. for 15 h then cooled to ambient temperature. The reaction was poured into H$_2$O and extracted with DCM (3×). The combined organic layers were washed with brine, dried (MgSO$_4$), filtered, and concentrated in vacuo to give a thick red oil. The residue was purified via silica gel chromatrophy using DCM/MeOH with 1% NH$_4$OH (gradient from 100/0% to 90:10 over 30 min) to give [2-[(2-amino-2-butylhexanesyl)thio]-4-bromo-5-(methyloxy)phenyl]phenyl)methanone (16.3 g, 96% yield) as a thick, red oil: $^1$H NMR (CDCl$_3$) δ ppm 7.76-7.83 (m, 3H), 7.60 (t, J=7.4 Hz, 1H), 7.47 (t, J=7.8 Hz, 2H), 6.84 (s, 1H), 3.88 (s, 3H), 2.81 (s, 2H), 0.78-1.55 (m, 18H); LC-MS (ES$^+$) m/z 478.2 [M+H], 480.2 [M+H],

Intermediate 31: [2-[(2-amino-2-butylhexanesyl)thio]-4-bromo-5-(methyloxy)phenyl]phenyl)methanone

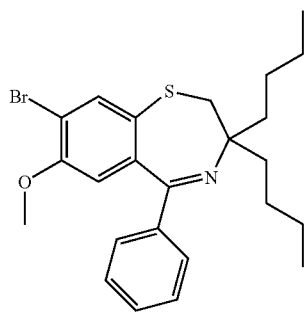 [SMILES: CCCCC1(CCCC)CSc2cc(Br)c(OC)cc2C(c2ccccc2)=N1]

A solution of [2-[(2-amino-2-butylhexanesyl)thio]-4-bromo-5-(methyloxy)phenyl]phenyl)methanone (16.3 g, 34.1 mmol) in toluene (341 mL) was treated with citric acid (0.327 g, 1.703 mmol) then heated at reflux for 15 h. The reaction was fitted with a Dean-Stark trap then heated at 130° C. for 10 h whereupon additional citric acid (325 mg) was added. Stirring was continued at 130° C. for 15 h then additional citric acid (100 mg) was added and stirring at 130° C. was continued for 10 h. The reaction was concentrated in vacuo then purified by SiO$_2$ chromatography using hexanes:EtOAc (100:0 to 80:20) as eluent to give 8-bromo-3,3-dibutyl-7-(methyloxy)-5-phenyl-2,3-dihydro-1,4-benzothiazepine (10 g, 63.7% yield) as an oil which solidified to a tan solid upon standing: $^1$H NMR (CDCl$_3$) δ ppm 7.79 (s, 1H), 7.53 (d, J=8.2 Hz, 2H), 7.30-7.44 (m, 3H), 6.59 (s, 1H), 3.71 (s, 3H), 3.23 (s, 2H), 1.16-1.66 (m, 12H), 0.86 (t, J=7.2 Hz, 6H); LC-MS (ES$^+$) m/z 460.2 [M+H], 462.2 [M+H],

Intermediate 32: methyl 3,3-dibutyl-7-(methyloxy)-5-phenyl-2,3-dihydro-1,4-benzothiazepine-8-carboxylate

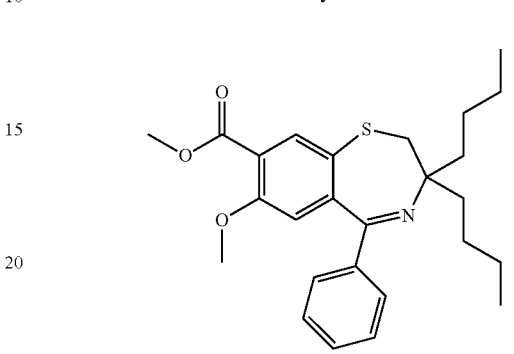

Carbon monoxide was bubbled through a mixture of 8-bromo-3,3-dibutyl-7-(methyloxy)-5-phenyl-2,3-dihydro-1,4-benzothiazepine (Intermediate 31) (10 g, 21.72 mmol), Pd(OAc)$_2$ (0.488 g, 2.172 mmol), and dppp (0.896 g, 2.172 mmol) in DMSO (71.6 mL) for 15 min. The reaction mixture was treated with MeOH (3.51 mL, 87 mmol) and TEA (4.54 mL, 32.6 mmol) then heated at 70° C. for 3 h after which time additional MeOH (3.51 mL, 87 mmol) was added. Heating under CO atmosphere was continued for 39 h. The reaction mixture was diluted with MTBE then filtered through a plug of celite washing with MTBE. The filtrate was poured into H$_2$O then the separated aqueous layer was extracted with MTBE (1×). The combined organic layers were washed with brine, dried (MgSO$_4$), filtered, and concentrated in vacuo. The residue was purified via SiO2 chromatography using hexanes; EtOAc (100:0 to 60:40) as eluent to give methyl 3,3-dibutyl-7-(methyloxy)-5-phenyl-2,3-dihydro-1,4-benzothiazepine-8-carboxylate (86% yield) as a light orange oil: $^1$H NMR (CDCl$_3$) δ ppm 8.01 (s, 1H), 7.53 (d, J=6.8 Hz, 2H), 7.30-7.44 (m, 3H), 6.69 (s, 1H), 3.93 (s, 3H), 3.72 (s, 3H), 3.22 (s, 2H), 1.14-1.65 (m, 12H), 0.86 (t, J=7.2 Hz, 6H); LC-MS (ES$^+$) m/z 440.3 [M+H].

Intermediate 33: [3,3-dibutyl-7-(methyloxy)-5-phenyl-2,3-dihydro-1,4-benzothiazepin-8-yl]methanol

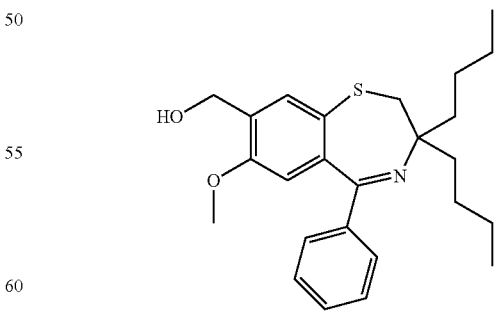

A solution of methyl 3,3-dibutyl-7-(methyloxy)-5-phenyl-2,3-dihydro-1,4-benzothiazepine-8-carboxylate (8.2 g, 18.65 mmol) in THF (34.0 mL) at 25° C. was treated with 2M LAH in THF (13.99 mL, 28.0 mmol) in a dropwise fashion. The reaction was stirred for 15 min then quenched with H$_2$O (1.1 mL), 15% NaOH (1.1 mL), and H$_2$O (3.4 mL). After stirring for 30 min, the reaction was filtered through a pad of celite washing with THF. The filtrate was concentrated in vacuo to give [3,3-dibutyl-7-(methyloxy)-5-phenyl-2,3-dihydro-1,4-benzothiazepin-8-yl]methanol (7.7 g, 100% yield): $^1$H NMR (CDCl$_3$) δ ppm 7.49-7.59 (m, 3H), 7.30-7.42 (m, 3H), 6.58 (s, 1H), 3.68 (s, 3H), 3.22 (s, 2H), 1.13-1.65 (m, 12H), 0.86 (t, J=7.2 Hz, 6H); LC-MS (ES$^+$) m/z 412.3 [M+H].

Intermediate 34: [3,3-dibutyl-7-(methyloxy)-5-phenyl-2,3,4,5-tetrahydro-1,4-benzothiazepin-8-yl]methanol

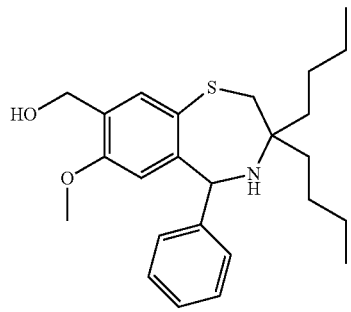 [SMILES: CCCCC1(CCCC)CSc2cc(CO)c(OC)cc2C(c2ccccc2)N1]

A solution of [3,3-dibutyl-7-(methyloxy)-5-phenyl-2,3-dihydro-1,4-benzothiazepin-8-yl]methanol (7.7 g, 18.71 mmol) in THF (51.1 mL) at 25° C. was treated with 1M BH$_3$·THF (20.58 mL, 20.58 mmol) in a dropwise fashion then the reaction was stirred for 2 h. The reaction was quenched with MeOH (30 mL) then concentrated under reduced pressure to give a crude white foam. Purification of the residue by SiO$_2$ chromatography using 6:1/hexanes:EtOAc to 2:1/hexanes:EtOAc gradient provided a mixture of unreacted starting material and product (approximately 85:15, respectively) This material was resubjected to identical conditions and purified in a similar fashion to give [3,3-dibutyl-7-(methyloxy)-5-phenyl-2,3,4,5-tetrahydro-1,4-benzothiazepin-8-yl]methanol (6.56 g, 85% yield) containing 5-10% imine: $^1$H NMR (CDCl$_3$) δ ppm 7.50 (s, 1H), 7.24-7.47 (m, 5H), 6.09 (s, 1H), 5.78 (s, 1H), 4.59 (d, J=3.1 Hz, 2H), 3.49 (s, 3H), 2.76 (d, J=14.2 Hz, 1H), 2.50 (d, J=14.2 Hz, 1H), 2.01-2.24 (m, 2H), 0.08-1.72 (m, 10H), 0.90 (t, J=6.9 Hz, 3H), 0.85 (t, J=7.2 Hz, 3H); LC-MS (ES$^+$) m/z 414.3 [M+H].

Intermediate 35: [3,3-dibutyl-7-(methyloxy)-1,1-dioxido-5-phenyl-2,3,4,5-tetrahydro-1,4-benzothiazepin-8-yl]methanol

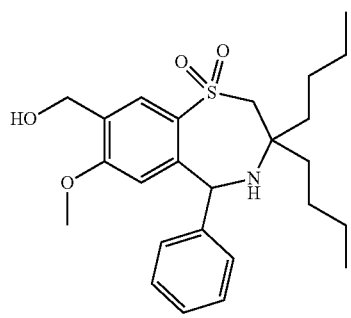 [SMILES: CCCCC1(CCCC)CS(=O)(=O)c2cc(CO)c(OC)cc2C(c2ccccc2)N1]

A solution of [3,3-dibutyl-7-(methyloxy)-5-phenyl-2,3,4,5-tetrahydro-1,4-benzothiazepin-8-yl]methanol (6.56 g, 15.86 mmol) in TFA (52.4 mL) at 25° C. was treated with 30% H$_2$O$_2$ (3.24 mL, 31.7 mmol), and the rxn was stirred for 1 h. After cooling in an ice bath, H$_2$O (300 mL) and THF (120 mL) were added followed by 15% NaOH then 6N NaOH until the solution reached pH 12. After stirring for 1 h, a solution of 10% Na$_2$SO$_3$ (60 mL) was added, and the solution was stirred until bubbling ceased. The reaction was treated with DCM, and the layers were separated. The aqueous layer was extracted with DCM (2×) then the combined organic layers were washed with brine, dried (MgSO$_4$), filtered, and concentrated in vacuo. The residue was purified by SiO$_2$ chromatography using a DCM/MeOH gradient (100:0 to 95:5) to give [3,3-dibutyl-7-(methyloxy)-1,1-dioxido-5-phenyl-2,3,4,5-tetrahydro-1,4-benzothiazepin-8-yl]methanol (6.7 g, 95% yield) as a white solid. The material contained 10-15% imine: $^1$H NMR (CDCl$_3$) δ ppm 8.05 (s, 1H), 7.29-7.49 (m, 5H), 6.19 (s, 1H), 6.08 (br. s., 1H), 4.56-4.76 (m, 2H), 3.56 (s, 3H), 3.44 (d, J=14.8 Hz, 1H), 3.07 (d, J=14.8 Hz, 1H), 2.05-2.30 (m, 1H), 1.85 (m, 1H), 1.02-1.64 (m, 10H), 0.91 (t, J=6.8 Hz, 3H), 0.84 (t, J=7.0 Hz, 3H); LC-MS (ES$^+$) m/z 446.3 [M+H].

Intermediate 36: 3,3-dibutyl-7-(methyloxy)-5-phenyl-2,3,4,5-tetrahydro-1,4-benzothiazepine-8-carbaldehyde 1,1-dioxide

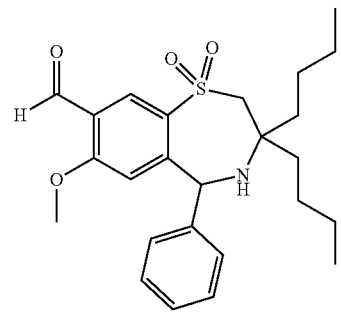 [SMILES: CCCCC1(CCCC)CS(=O)(=O)c2cc(C=O)c(OC)cc2C(c2ccccc2)N1]

A solution of [3,3-dibutyl-7-(methyloxy)-1,1-dioxido-5-phenyl-2,3,4,5-tetrahydro-1,4-benzothiazepin-8-yl]methanol (415 mg, 0.931 mmol) in DCM (9313 µl) at 25° C. was treated with Dess-Martin Periodinane (415 mg, 0.978 mmol) and stirred for 1 h. The reaction was filtered through a thin pad of SiO$_2$ washing with EtOAC then the filtrate was concentrated in vacuo to give a white solid. The residue was purified by SiO$_2$ chromatography using hexanes/EtOAc gradient to give 3,3-dibutyl-7-(methyloxy)-5-phenyl-2,3,4,5-tetrahydro-1,4-benzothiazepine-8-carbaldehyde 1,1-dioxide (310 mg, 75% yield) as a white solid: $^1$H NMR (CDCl$_3$) δ ppm 10.35 (s, 1H), 8.55 (s, 1H), 7.32-7.56 (m, 5H), 6.30 (s, 1H), 6.13 (d, J=7.8 Hz, 1H), 3.63 (s, 3H), 3.47 (d, J=15.0 Hz, 1H), 3.05 (d, J=15.0 Hz, 1H), 2.12-2.29 (m, 1H), 1.78-1.92 (m, 1H), 1.03-1.61 (m, 10H), 0.91 (t, J=7.0 Hz, 3H), 0.82 (t, J=7.1 Hz, 3H); LC-MS (ES$^+$) m/z 444.2 [M+H].

Intermediate 37: diethyl {[3,3-dibutyl-7-(methyloxy)-1,1-dioxido-5-phenyl-2,3,4,5-tetrahydro-1,4-benzothiazepin-8-yl]methyl}phosphonate

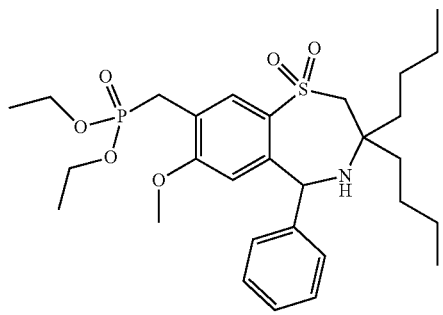 [SMILES: CCCCC1(CCCC)CS(=O)(=O)c2cc(CP(=O)(OCC)OCC)c(OC)cc2C(c2ccccc2)N1]

Step 1: A solution of imidazole (306 mg, 4.49 mmol) in DCM (2.7 mL) at 0° C. was treated with triphenylphosphine (589 mg, 2.244 mmol) followed by Br$_2$ (116 μl, 2.244 mmol). After stirring for 5 min, a solution of [3,3-dibutyl-7-(methyloxy)-1,1-dioxido-5-phenyl-2,3,4,5-tetrahydro-1,4-benzothiazepin-8-yl]methanol (Intermediate 35) (500 mg, 1.122 mmol) in DCM (2.7 mL) was slowly added then the reaction was stirred at 0° C. for 2 h. The reaction was treated with 10% aq. Na$_2$SO$_3$, the layers were separated, and the aqueous layer was extracted with DCM. The combined organic layers were dried (Na$_2$SO$_4$), filtered through a pad of SiO$_2$, and concentrated in vacuo to give 8-(bromomethyl)-3,3-dibutyl-7-(methyloxy)-5-phenyl-2,3,4,5-tetrahydro-1,4-benzothiazepine 1,1-dioxide (571 mg, >99% yield).

Step 2: A solution of 8-(bromomethyl)-3,3-dibutyl-7-(methyloxy)-5-phenyl-2,3,4,5-tetrahydro-1,4-benzothiazepine 1,1-dioxide (571 mg, 1.123 mmol) in toluene (5.3 mL) at 25° C. was treated with triethyl phosphite (295 μl, 1.684 mmol) then heated at reflux for 18 h. The reaction was concentrated in vacuo to an oil then purified by SiO$_2$ chromatography using 4:1/EtOAc:hexanes to 100% EtOAc to give diethyl {[3,3-dibutyl-7-(methyloxy)-1,1-dioxido-5-phenyl-2,3,4,5-tetrahydro-1,4-benzothiazepin-8-yl]methyl}phosphonate (285 mg, 44.9% yield): $^1$H NMR (CDCl$_3$) δ ppm 7.99 (d, J=2.7 Hz, 1H), 7.29-7.68 (m, 5H), 6.16 (s, 1H), 6.06 (br. s., 1H), 3.95-4.18 (m, 4H), 3.53 (s, 3H), 3.43 (d, J=14.8 Hz, 1H), 3.15-3.26 (m, 2H), 3.04 (d, J=14.8 Hz, 1H), 2.09-2.30 (m, 1H), 1.79-1.94 (m, 1H), 1.04-1.63 (m, 16H), 0.92 (t, J=6.8 Hz, 3H), 0.83 (t, J=7.1 Hz, 3H); LC-MS (ES$^+$) m/z 566.4 [M+H].

Intermediate 38: (3R,5R)-3-butyl-3-ethyl-8-(methyloxy)-1,1-dioxido-5-phenyl-2,3,4,5-tetrahydro-1,4-benzothiazepin-7-yl trifluoromethanesulfonate

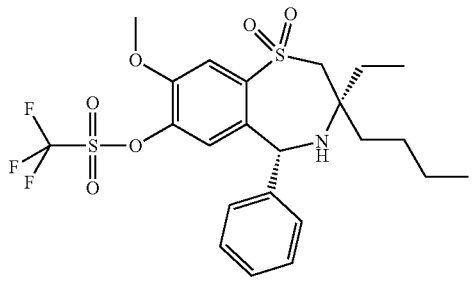 [SMILES: CCCC[C@]1(CC)CS(=O)(=O)c2cc(OC)c(OS(=O)(=O)C(F)(F)F)cc2[C@@H](c2ccccc2)N1]

A solution of (3R,5R)-3-butyl-3-ethyl-8-(methyloxy)-5-phenyl-2,3,4,5-tetrahydro-1,4-benzothiazepin-7-ol 1,1-dioxide (9.24 g, 22.90 mmol) and pyridine dissolved in DCM (300 mL) was treated with triflic anhydride (4.64 mL, 27.5 mmol) dissolved in DCM (80 mL) dropwise with stirring and cooling in an ice bath. The reaction mixture was allowed to warm to ambient temperature and stirred for 1 h after which time LCMS indicated complete conversion. The reaction mixture was washed twice with dilute HCl, dried over MgSO$_4$, filtered and concentrated to an orange foam: $^1$H NMR (400 MHz, DMSO-d$_6$) δ ppm 0.75 (t, J=7.0 Hz, 3H), 0.81 (t, J=7.3 Hz, 3H), 0.94-1.29 (m, 4H), 1.47 (q, J=7.3 Hz, 2H), 1.67-1.80 (m, 1H), 1.95-2.07 (m, 1H), 2.80 (d, J=9.6 Hz, 1H), 3.27 (d, J=15.2 Hz, 1H), 3.76 (d, J=15.2 Hz, 1H), 3.99 (s, 3H), 5.86 (d, J=9.6 Hz, 1H), 6.34 (s, 1H), 7.27-7.52 (m, 5H), 7.79 (s, 1H).

Intermediate 39: (3R,5R)-3-butyl-3-ethyl-N,N-dimethyl-8-(methyloxy)-5-phenyl-2,3,4,5-tetrahydro-1,4-benzothiazepin-7-amine 1,1-dioxide

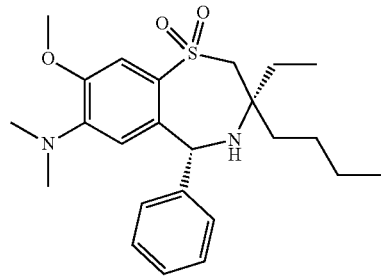 [SMILES: CCCC[C@]1(CC)CS(=O)(=O)c2cc(OC)c(N(C)C)cc2[C@@H](c2ccccc2)N1]

(3R,5R)-3-butyl-3-ethyl-8-(methyloxy)-1,1-dioxido-5-phenyl-2,3,4,5-tetrahydro-1,4-benzothiazepin-7-yl trifluoromethanesulfonate (5.57 g, 10.40 mmol), Pd$_2$(dba)$_3$ (0.286 g, 0.312 mmol), 2-biphenylyl-di-tert-butylphosphine (0.372 g, 1.248 mmol), and K$_3$PO$_4$ (2.318 g, 10.92 mmol) were combined in 1,2-Dimethoxyethane (DME) (10 mL) and stirred for 10 min while purging with N$_2$. 2M dimethylamine in THF (40 mL, 80 mmol) was added, and the mixture was heated for 16 h at 100° C. in an oil bath after which time LCMS indicated >90% conversion with significant phenol formation. The reaction mixture was filtered through Celite, and the filtrate was concentrated to dryness. The residue was partitioned between DCM and aq. NaHCO$_3$, and the organic phase was isolated, dried over MgSO$_4$, filtered, and concentrated to dryness. The residue was purified on 330 g silica gel eluting with 20 to 40% EtOAc/hexanes to give (3R,5R)-3-butyl-3-ethyl-N,N-dimethyl-8-(methyloxy)-5-phenyl-2,3,4,5-tetrahydro-1,4-benzothiazepin-7-amine 1,1-dioxide (3.12 g, 7.25 mmol, 69.7% yield) as a white solid: $^1$H NMR (400 MHz, DMSO-d$_6$) δ ppm 0.68-0.87 (m, 6H), 0.96-1.29 (m, 4H), 1.33-1.54 (m, 2H), 1.64-1.83 (m, 1H), 2.00-2.12 (m, 1H), 2.46 (d, J=10.0 Hz, 1H), 2.53 (s, 6H), 3.06 (d, J=14.6 Hz, 1H), 3.51 (d, J=14.6 Hz, 1H), 3.82 (s, 3H), 5.85 (d, J=9.8 Hz, 1H), 5.94 (s, 1H), 7.26-7.34 (m, 1H), 7.34-7.46 (m, 5H); LC-MS (ES$^+$) m/z 431.33 [M+H].

Intermediate 40: (3R,5R)-3-butyl-7-(dimethylamino)-3-ethyl-5-phenyl-2,3,4,5-tetrahydro-1,4-benzothiazepin-8-ol 1,1-dioxide

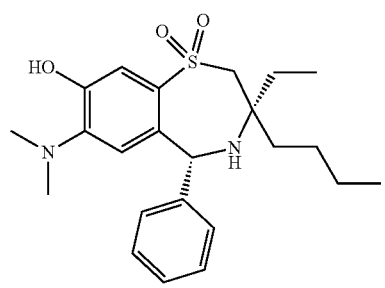

(3R,5R)-3-butyl-3-ethyl-N,N-dimethyl-8-(methyloxy)-5-phenyl-2,3,4,5-tetrahydro-1,4-benzothiazepin-7-amine 1,1-dioxide (5.25 g, 12.19 mmol) dissolved in DCM (100 mL) was treated with aluminium chloride (6.50 g, 48.8 mmol) for 2 h at 23° C. after which time LCMS indicated complete conversion but with formation of significant byproduct. The mixture was quenched with ice H$_2$O, and the mixture was stirred vigorously for 15 min. The mixture was extracted four times with DCM, and the combined organics were dried over MgSO$_4$, filtered and concentrated to dryness. The pH of the aqueous phase was adjusted to 13 with 6N NaOH, the mixture was extracted four times with DCM, and the combined organics were dried over MgSO$_4$, filtered and concentrated to dryness. The pH 1 extracts (1.47 g) and pH 13 extracts (1.01 g) were combined and purified on 220 g silica gel eluting with 15 to 45% EtOAc/hexanes to give (3R,5R)-3-butyl-7-(dimethylamino)-3-ethyl-5-phenyl-2,3,4,5-tetrahydro-1,4-benzothiazepin-8-ol 1,1-dioxide (1.76 g, 4.22 mmol, 34.7% yield) as a tan glass. $^1$H NMR (400 MHz, DMSO-d$_6$) δ ppm 0.69-0.83 (m, 6H), 0.96-1.28 (m, 4H), 1.31-1.54 (m, 2H), 1.65-1.77 (m, 1H), 2.00-2.12 (m, 1H), 2.38 (d, J=9.8 Hz, 1H), 3.04 (d, J=14.8 Hz, 1H), 3.33 (s, 6H), 3.45 (d, J=14.8 Hz, 1H), 5.80 (d, J=9.8 Hz, 1H), 5.89 (s, 1H), 7.23-7.33 (m, 1H), 7.33-7.52 (m, 5H), 9.81 (s, 1H). LC-MS (ES$^-$) m/z 415.18 [M−1]; LC-MS (ES$^+$) m/z 417.20 [M+H].

Intermediate 41: (3R,5R)-3-butyl-7-(dimethylamino)-3-ethyl-1,1-dioxido-5-phenyl-2,3,4,5-tetrahydro-1,4-benzothiazepin-8-yl trifluoromethanesulfonate

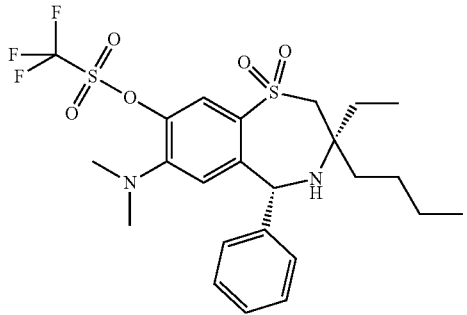 [SMILES: CCCC[C@]1(CC)CS(=O)(=O)c2cc(OS(=O)(=O)C(F)(F)F)c(N(C)C)cc2[C@@H](c2ccccc2)N1]

To a solution of (3R,5R)-3-butyl-7-(dimethylamino)-3-ethyl-5-phenyl-2,3,4,5-tetrahydro-1,4-benzothiazepin-8-ol 1,1-dioxide (1.24 g, 2.98 mmol) in DCM (10 mL) at 22° C. was added pyridine (0.602 mL, 7.44 mmol), followed by triflic anhydride (0.603 mL, 3.57 mmol), and the reaction mixture was stirred at ambient temperature overnight. The reaction mixture was washed twice with H$_2$O, and the organic layer was isolated, dried over MgSO$_4$, filtered, and concentrated to dryness. The residue was purified on 330 g silica eluting with DCM to give (3R,5R)-3-butyl-7-(dimethylamino)-3-ethyl-1,1-dioxido-5-phenyl-2,3,4,5-tetrahydro-1,4-benzothiazepin-8-yl trifluoromethanesulfonate (1.42 g, 2.59 mmol, 87% yield) as a white foam: LC-MS (ES$^+$) m/z 549.17 [M+H].

Intermediate 42: (3R,5R)-3-butyl-7-(dimethylamino)-3-ethyl-5-phenyl-2,3,4,5-tetrahydro-1,4-benzothiazepine-8-carbonitrile 1,1-dioxide

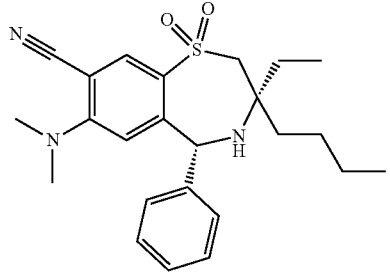 [SMILES: CCCC[C@]1(CC)CS(=O)(=O)c2cc(C#N)c(N(C)C)cc2[C@@H](c2ccccc2)N1]

(3R,5R)-3-butyl-7-(dimethylamino)-3-ethyl-1,1-dioxido-5-phenyl-2,3,4,5-tetrahydro-1,4-benzothiazepin-8-yl trifluoromethanesulfonate (1.42 g, 2.59 mmol) dissolved in DMF (5 mL) was combined with dicyanozinc (0.456 g, 3.88 mmol), Pd$_2$(dba)$_3$ (0.012 g, 0.013 mmol), and DPPF (0.016 g, 0.028 mmol) and purged with N$_2$. The mixture was heated at 80° C. for 16 h after which time LCMS indicated ~25% conversion. The reaction mixture was purged for 1 h with N$_2$, additional dicyanozinc (0.456 g, 3.88 mmol), Pd$_2$(dba)$_3$ (0.036 g, 0.039 mmol), and DPPF (0.050 g, 0.091 mmol) were added, and the mixture was purged an additional 30 min with N$_2$. The resultant mixture was heated at 80° C. for 40 h after which time LCMS indicated significant byproduct formation. The mixture was partitioned between EtOAc/H$_2$O and filtered through Celite. The organic phase was isolated, washed with H$_2$O and brine, dried over MgSO$_4$, filtered and concentrated to dryness. The residue was purified on 120 g silica gel eluted with 20 to 100% EtOAc/hexanes to give (3R,5R)-3-butyl-7-(dimethylamino)-3-ethyl-5-phenyl-2,3,4,5-tetrahydro-1,4-benzothiazepine-8-carbonitrile 1,1-dioxide (contaminated with phenol) (340 mg, 0.799 mmol, 30.9% yield: LC-MS (ES$^-$) m/z 424.18 [M−1], LC-MS (ES$^+$) m/z 426.35 [M+H].

Intermediate 43: (3R,5R)-3-butyl-7-(dimethylamino)-3-ethyl-5-phenyl-2,3,4,5-tetrahydro-1,4-benzothiazepine-8-carbaldehyde 1,1-dioxide

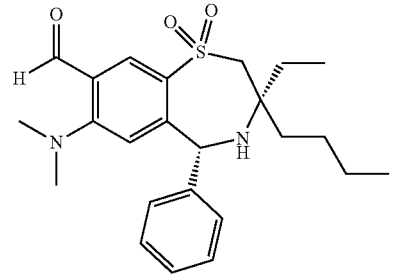 [SMILES: CCCC[C@]1(CC)CS(=O)(=O)c2cc(C=O)c(N(C)C)cc2[C@@H](c2ccccc2)N1]

(3R,5R)-3-butyl-7-(dimethylamino)-3-ethyl-5-phenyl-2,3,4,5-tetrahydro-1,4-benzothiazepine-8-carbonitrile 1,1-dioxide (340 mg, 0.799 mmol) dissolved in toluene (5 mL) was treated with 1M DIBAL-H in toluene (0.919 mL, 0.919 mmol) at 0° C. and stirred for 1 h. The mixture was warmed to ambient temperature and stirred overnight after which time LCMS indicated ~20% conversion. Additional 1M DIBAL-H (131 mg, 0.919 mmol) was added, and the reaction mixture was stirred for 2 h at ambient temperature after which time LCMS indicated >80% conversion. The reaction mixture was diluted with DCM and quenched with 1N HCl. The phases were separated, and the aqueous phase was extracted twice with DCM. The organics were combined, dried over MgSO$_4$, filtered and concentrated to dryness. The residue was purified on 40 g silica gel eluted with 20 to 40% EtOAc/hexanes to give (3R,5R)-3-butyl-7-(dimethylamino)-3-ethyl-5-phenyl-2,3,4,5-tetrahydro-1,4-benzothiazepine-8-carbaldehyde 1,1-dioxide (40 mg, 0.093 mmol, 11.7% yield): $^1$H NMR (400 MHz, DMSO-d$_6$) δ ppm 0.74 (t, J=6.9 Hz, 3H), 0.80 (t, J=7.4 Hz, 3H), 0.93-1.27 (m, 4H), 1.29-1.55 (m, 2H), 1.64-1.82 (m, 1H), 2.01-2.21 (m, 1H), 2.64-2.73 (m, 1H), 2.75 (s, 6H), 3.06 (d, J=14.8 Hz, 1H), 3.56 (d, J=14.6 Hz, 1H), 5.85-5.93 (m, 1H), 6.04 (s, 1H), 7.26-7.52 (m, 5H), 8.21 (s, 1H), 9.94 (s, 1H).

Intermediate 44: (3R,5R)-3-butyl-3-ethyl-N-methyl-N,7-bis(methyloxy)-5-phenyl-2,3,4,5-tetrahydro-1,4-benzothiazepine-8-carboxamide 1,1-dioxide

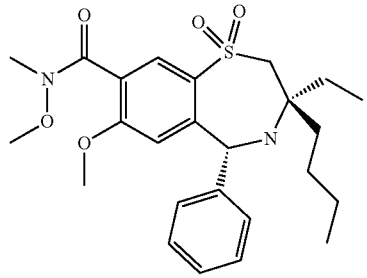 [SMILES: CCCC[C@]1(CC)CS(=O)(=O)c2cc(C(=O)N(C)OC)c(OC)cc2[C@@H](c2ccccc2)N1]

To a solution of (3R,5R)-3-butyl-3-ethyl-7-(methyloxy)-5-phenyl-2,3,4,5-tetrahydro-1,4-benzothiazepine-8-carboxylic acid 1,1-dioxide (Intermediate 4, 174 mg, 0.403 mmol) in N,N-dimethylformamide (5 mL) was added N,O-dimethylhydroxylamine hydrochloride (59.0 mg, 0.605 mmol), DIEA (0.282 mL, 1.613 mmol) and HATU (307 mg, 0.806 mmol). The reaction mixture was stirred at room temperature overnight then partitioned between H₂O and EtOAc. The organic layer was washed with saturated brine, dried, filtered, and concentrated under reduced pressure. Purification via SiO₂ chromatography (EtOAc:Hex=1:3 to 3:1) afforded the title compound (168 mg, 95% pure, 83%) as a light yellow oil: ES-LCMS m/z 475 (M+H)⁺.

Intermediate 45: diethyl {[(3R,5R)-3-butyl-3-ethyl-7-(methyloxy)-1,1-dioxido-5-phenyl-2,3,4,5-tetrahydro-1,4-benzothiazepin-8-yl]methylidene}propanedioate

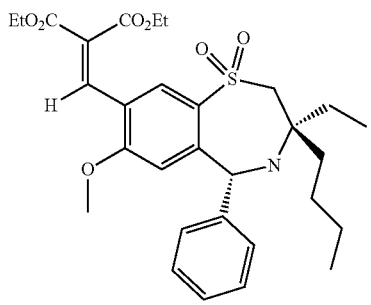 [SMILES: CCCC[C@]1(CC)CS(=O)(=O)c2cc(C=C(C(=O)OCC)C(=O)OCC)c(OC)cc2[C@@H](c2ccccc2)N1]

To a solution of (3R,5R)-3-butyl-3-ethyl-7-(methyloxy)-5-phenyl-2,3,4,5-tetrahydro-1,4-benzothiazepine-8-carbaldehyde 1,1-dioxide (Intermediate 9, 109 mg, 0.262 mmol) in toluene (3 mL) was added diethyl malonate (0.048 mL, 0.315 mmol) and piperidine (0.013 mL, 0.131 mmol). The reaction mixture was stirred at 100° C. overnight, cooled to room temperature, and concentrated under reduced pressure. Purification via SiO₂ chromatography (EtOAc/Hex=10:90 to 80:20) afforded the title compound (146 mg, 90% pure, 90%) as a light yellow oil: ES-LCMS m/z 558 (M+H)⁺.

Intermediate 46

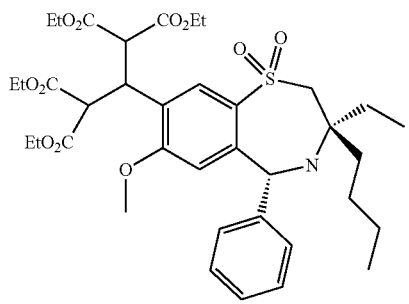 [SMILES: CCCC[C@]1(CC)CS(=O)(=O)c2cc(C(C(C(=O)OCC)C(=O)OCC)C(C(=O)OCC)C(=O)OCC)c(OC)cc2[C@@H](c2ccccc2)N1]

To a solution of diethyl malonate (0.096 mL, 0.628 mmol) in ethanol (3 mL) was added sodium ethoxide (0.254 mL, 0.681 mmol). The reaction mixture was stirred at room temperature for 20 min and treated with a solution of diethyl {[(3R,5R)-3-butyl-3-ethyl-7-(methyloxy)-1,1-dioxido-5-phenyl-2,3,4,5-tetrahydro-1,4-benzothiazepin-8-yl]methylidene}propanedioate (Intermediate 45, 146 mg, 0.262 mmol) in ethanol (2 mL). The reaction mixture was stirred at room temperature overnight, acidified with acetic acid to pH 3-4 and partially concentrated under reduced pressure to remove the organic solvents under reduced pressure. The residue was partitioned between water and dichloromethane. The organic layer was washed with saturated brine, dried, (Na₂SO₄), filtered, and concentrated under reduced pressure. Purification using silica gel (EtOAc:Hex=1:5 to 2:1) afforded the title compound (78, 120 mg, 84% pure, 53%) as a colorless oil: ¹H NMR (400 MHz, CDCl₃) δ ppm 7.97 (s, 1H), 7.26-7.48 (m, 5H), 6.08 (s, 1H), 5.97 (s, 1H), 4.43 (br s, 1H), 4.04-4.20 (m, 6H), 3.86-4.03 (m, 4H), 3.37 (d, J=14.9 Hz, 1H), 2.90 (d, J=14.9 Hz, 1H), 2.07-2.23 (m, 2H), 2.04 (d, J=14.7 Hz, 1H), 1.74-1.90 (m, 1H), 1.34-1.54 (m, 2H), 1.17-1.27 (m, 8H), 0.97-1.10 (m, 6H), 0.66-0.92 (m, 6H); ES-LCMS m/z 718 (M+H)⁺.

Intermediate 47: dimethyl 3-({[(3R,5R)-3-butyl-3-ethyl-7-(methyloxy)-1,1-dioxido-5-phenyl-2,3,4,5-tetrahydro-1,4-benzothiazepin-8-yl]carbonyl}amino)pentanedioate

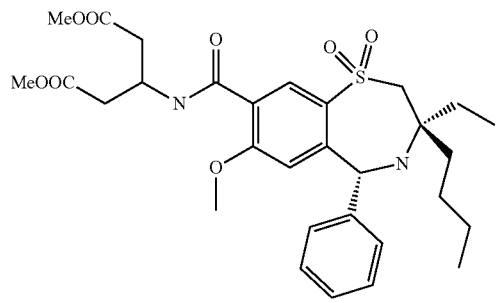 [SMILES: CCCC[C@]1(CC)CS(=O)(=O)c2cc(C(=O)NC(CC(=O)OC)CC(=O)OC)c(OC)cc2[C@@H](c2ccccc2)N1]

(3R,5R)-3-butyl-3-ethyl-7-(methyloxy)-5-phenyl-2,3,4,5-tetrahydro-1,4-benzothiazepine-8-carboxylic acid 1,1-dioxide (Intermediate 4, 100 mg, 0.232 mmol) in dichloromethane (5 mL) was added DIPEA (0.202 mL, 1.159 mmol) and HATU (88 mg, 0.232 mmol). The reaction mixture was stirred at room temperature for 20 min, followed by addition of dimethyl 3-aminopentanedioate (81 mg, 0.463 mmol), and stirred at room temperature overnight. The reaction mixture was then partitioned between water and dichloromethane. The organic layer was washed with saturated brine, dried (Na$_2$SO$_4$), filtered, and concentrated under reduced pressure. Purification on silica gel using MeOH:DCM=0:100 to 10:90 afforded the title compound (212 mg, 63% pure, 98%): ES-LCMS m/z 589 (M+H)$^+$.

Intermediate 48: Dimethyl 3-aminopentanedioate

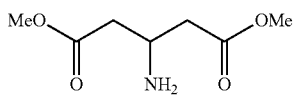 [SMILES: COC(=O)CC(N)CC(=O)OC]

Dimethyl (2Z)-3-amino-2-pentenedioate (613 g, 3.54 mol) was added in portions to TFA (3.15 L) with stirring while maintaining the reaction temperature below 30° C. with external cooling. After most of the solids were dissolved, 1M BH$_3$-THF (1.53 L, 1.53 mol) was added dropwise over 1 h while maintaining the reaction temperature between 18-21° C. The reaction mixture was cooled to 10° C. and quenched by dropwise addition of water (500 mL) over 5 min while maintaining the reaction temperature between 10-15° C. The reaction was stirred at ambient temperature for 30 min and then filtered. The filtrate was concentrated to remove most of the TFA, and the resulting material was dissolved in CH$_2$Cl$_2$ (4 L). The CH$_2$Cl$_2$ solution was added slowly to a stirred solution of K$_3$PO$_4$ (3 kg) in water (3 L) at ambient temperature and the mixture was stirred rapidly for 10 min. The layers were separated and the aqueous phase was extracted with CH$_2$Cl$_2$ (2 L). The combined CH$_2$Cl$_2$ layers were dried over MgSO$_4$, filtered and concentrated to afford dimethyl 3-aminopentanedioate (568 g) as a golden liquid: $^1$H NMR (DMSO-d$_6$) δ ppm 3.56 (s, 6H), 3.35 (m, 1H), 2.42 (dd, J=16 Hz, J=5.3 Hz, 2H), 2.29 (dd, J=16 Hz, J=8 Hz, 2H), 1.93 (br s, 2H).

Intermediate 49: Dimethyl 3-aminopentanedioate (acetic acid salt)

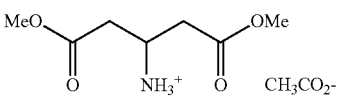

A solution of dimethyl 3-aminopentanedioate (568 g, 3.24 mol) in tert-butyl methyl ether (2.3 L) was cooled in an ice bath and glacial acetic acid (195, 3.24 mol) was added dropwise while maintaining the reaction temp at ca. 15° C. The resulting mixture was seeded with a small quantity of the desired crystalline product and stirred for 90 min with cooling to 5° C. The resulting precipitate was collected by filtration and washed with 1:1 tert-butyl methyl ether/heptane. The filter cake was dried under vacuum to afford the acetic acid salt of dimethyl 3-aminopentanedioate as an off-white solid (640 g): $^1$H NMR (DMSO-d$_6$) δ ppm 5.30 (br s, 3H), 3.56 (s, 6H), 3.36 (m, 1H), 2.44 (dd, J=16, J=5, 2H), 2.31 (dd, J=16, J=8, 2H), 1.86 (s, 3H).

Intermediate 50: Dimethyl 3-({[(3R,5R)-3-butyl-3-ethyl-7-(methyloxy)-1,1-dioxido-5-phenyl-2,3,4,5-tetrahydro-1,4-benzothiazepin-8-yl]methyl}amino)pentanedioate

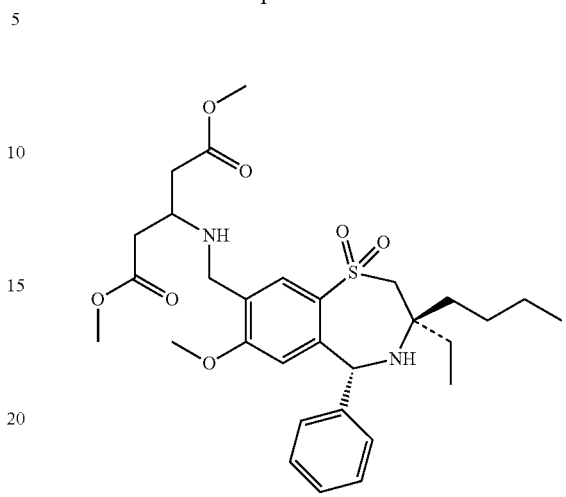

Glacial acetic acid (420 g, 6.99 mol) was added to a stirred mixture of (3R,5R)-3-butyl-3-ethyl-7-(methyloxy)-5-phenyl-2,3,4,5-tetrahydro-1,4-benzothiazepine-8-carbaldehyde 1,1-dioxide (857 g, 2.06 mol) in i-PrOAc (8 L) followed by addition of the acetic acid salt of dimethyl 3-aminopentanedioate (645 g, 2.74 mol). Sodium triacetoxyborohydride (656 g, 3.09 mol) was added portion-wise over 45 min while maintaining the reaction temperature below 22° C. After 1 h, the reaction mixture was washed with water (8 L) and 10% Na$_2$CO$_3$ (8 L). The organic phase was dried over MgSO$_4$, filtered and concentrated to afford dimethyl 3-({[(3R,5R)-3-butyl-3-ethyl-7-(methyloxy)-1,1-dioxido-5-phenyl-2,3,4,5-tetrahydro-1,4-benzothiazepin-8-yl]methyl}amino)pentanedioate as an oil (1.2 kg): $^1$H NMR (DMSO-d$_6$) δ ppm 7.90 (s, 1H), 7.42-7.34 (m, 4H), 7.34-7.26 (m, 1H), 6.04 (s, 1 H), 5.91 (d, J=9.87 Hz, 1H), 3.67-3.53 (m, 3H), 3.55 (s, 3H), 3.54 (s, 3H), 3.50 (d, J=15 Hz, 1H), 3.40 (s, 3H), 3.23 (m, 1H), 3.01 (d, J=15 Hz, 1H), 2.58-2.39 (m, 4H), 2.03 (m, 1H), 2.16 (br s, 1H), 1.76-1.66 (m, 1H), 1.50-1.30 (m, 2H), 1.27-0.96 (m, 4H), 0.77 (t, J=7.5 Hz, 3H), 0.73 (t, J=7.0 Hz, 3H).

II. Preparation of Compounds of the Invention

Example 1

3-({[(3R,5R)-3-butyl-3-ethyl-7-(methyloxy)-1,1-dioxido-5-phenyl-2,3,4,5-tetrahydro-1,4-benzothiazepin-8-yl]carbonyl}amino)-2,2-dimethylpropanoic acid

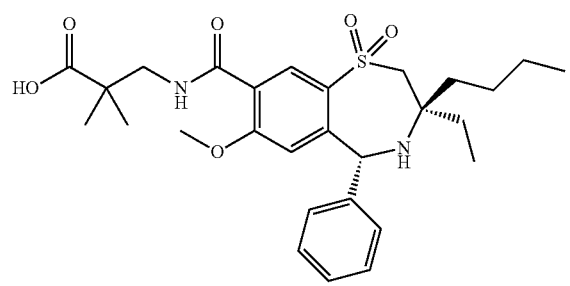 [SMILES: CCCC[C@]1(CC)CS(=O)(=O)c2cc(C(=O)NCC(C)(C)C(=O)O)c(OC)cc2[C@@H](c2ccccc2)N1]

Step 1: To a DMF (0.5 mL) solution of (3R,5R)-3-butyl-3-ethyl-7-(methyloxy)-5-phenyl-2,3,4,5-tetrahydro-1,4-benzothiazepine-8-carboxylic acid-1,1-dioxide (0.025 g, 0.058 mmol) and ethyl 3-amino-2,2-dimethylpropanoate (prepared as described in U.S. Pat. No. 2,370,015) (0.009 g, 0.064 mmol) at 0° C. was added HATU (0.024 g, 0.064 mmol) followed by DIEA (0.012 mL, 0.070 mmol). The reaction was stirred for 10 min then warmed to room temperature. After 1 h the reaction was concentrated to half volume, and $H_2O$ (3 mL) was added. The precipitant was filtered and dried then used without further purification in the next step.

Step 2: The material was dissolved in THF (0.500 mL), and $H_2O$ (0.250 mL) was added along with excess LiOH (7 mg, 0.174 mmol). The reaction was stirred at room temperature for 3 h then concentrated. The residue was purified by silica chromatography using DCM/MeOH to give the title compound (0.020 g, 63%): $^1$H NMR (400 MHz, $CDCl_3$) δ ppm 8.71 (s, 1H) 8.13 (br. s., 1H) 7.27-7.52 (m, 5H) 6.21 (br. s., 1H) 6.08 (br. s., 1H) 3.31-3.70 (m, 7H) 3.11 (br. s., 1H) 2.18 (br. s., 1H) 1.83 (br. s., 1H) 0.99-1.65 (m, 12H) 0.71-0.96 (m, 6H); LC-MS m/z 531 $(M+H)^+$.

Example 2

({[(3R,5R)-3-butyl-3-ethyl-7-(methyloxy)-1,1-dioxido-5-phenyl-2,3,4,5-tetrahydro-1,4-benzothiazepin-8-yl]carbonyl}amino)methanesulfonic acid

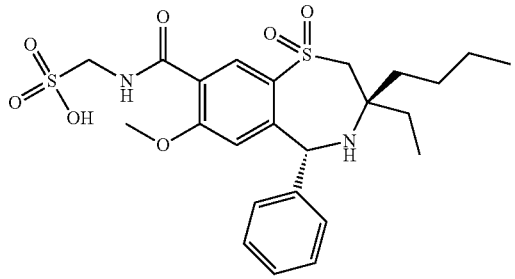 [SMILES: CCCC[C@]1(CC)CS(=O)(=O)c2cc(C(=O)NCS(=O)(=O)O)c(OC)cc2[C@@H](c2ccccc2)N1]

Prepared in analogous fashion to Example 1 step 1 via HATU amide-coupling using aminomethanesulfonic acid (0.013 g, 0.116 mmol) and (3R,5R)-3-butyl-3-ethyl-7-(methyloxy)-5-phenyl-2,3,4,5-tetrahydro-1,4-benzothiazepine-8-carboxylic acid-1,1-dioxide (50 mg, 0.12 mmol) to give the title compound (45 mg, 73%): $^1$H NMR (400 MHz, $CDCl_3$) δ ppm 8.47 (s, 1H) 8.28 (partially resolved t, J=5.72 Hz, 1H) 7.47 (d, J=3.62 Hz, 5H) 6.29 (br. s., 1H) 6.02 (br. s., 1H) 3.43-4.72 (m, 6H+ $H_2O$) 3.22 (br. s., 1H) 2.14 (br. s., 1H) 1.80 (br. s., 1H) 1.45 (br. s., 2H) 0.93-1.32 (m, 5H) 0.63-0.93 (m, 6H); ES-LCMS m/z 525 $(M+H)^+$.

Example 3

2-({[(3R,5R)-3-butyl-3-ethyl-7-(methyloxy)-1,1-dioxido-5-phenyl-2,3,4,5-tetrahydro-1,4-benzothiazepin-8-yl]carbonyl}amino)ethanesulfonic acid trifluoroacetate

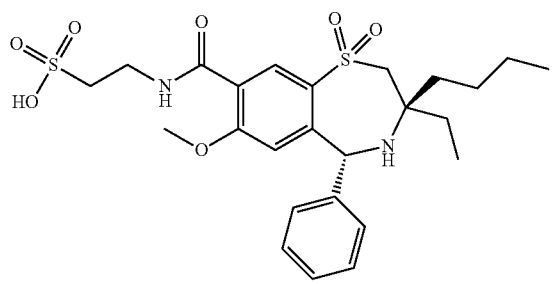 [SMILES: CCCC[C@]1(CC)CS(=O)(=O)c2cc(C(=O)NCCS(=O)(=O)O)c(OC)cc2[C@@H](c2ccccc2)N1]

Prepared in an analogous fashion to Example 1 step 1 via HATU amide-coupling using taurine (0.014 g, 0.116 mmol) and (3R,5R)-3-butyl-3-ethyl-7-(methyloxy)-5-phenyl-2,3,4,5-tetrahydro-1,4-benzothiazepine-8-carboxylic acid-1,1-dioxide (0.050 g, 0.116 mmol). Purification via RP-HPLC (30× 150 $H_2O$ Sunfire C18 Column) using MeCN/$H_2O$ 10-100% with 0.1% TFA as mobile phase over 8 min provided the title compound (0.015 g, 19%): $^1$H NMR (400 MHz, MeOH-$d_4$) δ ppm 8.74 (s, 1H) 7.48-7.72 (m, 5H) 6.68 (s, 1H) 6.47 (s, 1H) 4.02 (d, J=15.83 Hz, 1H) 3.75-3.83 (m, 2H) 3.72 (s, 3H) 3.55 (d, J=15.83 Hz, 1H) 2.91-3.02 (m, 2H) 2.77 (br. s., 1H) 2.13 (br. s., 2H) 1.66 (s, 1H) 1.43 (d, J=6.55 Hz, 3H) 1.02 (partially resolved t, J=7.48 Hz, 4H) 0.91 (t, J=7.13 Hz, 3H); ES-LCMS m/z 539 $(M+H)^+$.

Example 4

2,2'-({[(3R,5R)-3-butyl-3-ethyl-7-(methyloxy)-1,1-dioxido-5-phenyl-2,3,4,5-tetrahydro-1,4-benzothiazepin-8-yl]carbonyl}imino)diacetic acid hydrochloride

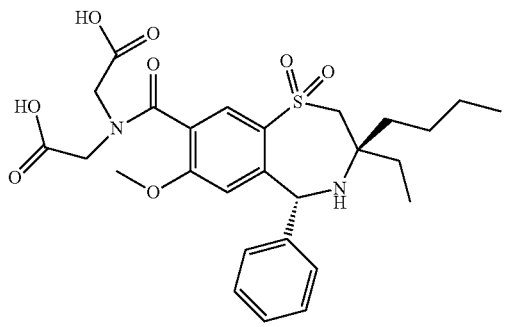 [SMILES: CCCC[C@]1(CC)CS(=O)(=O)c2cc(C(=O)N(CC(=O)O)CC(=O)O)c(OC)cc2[C@@H](c2ccccc2)N1]

Prepared in analogous fashion to Example 1 via HATU amide-coupling using diethyliminoacetate (0.022 g, 0.116 mmol) and (3R,5R)-3-butyl-3-ethyl-7-(methyloxy)-5-phenyl-2,3,4,5-tetrahydro-1,4-benzothiazepine-8-carboxylic acid-1,1-dioxide (0.050 g, 0.116 mmol) followed by LiOH (10 mg, 0.24 mmol) hydrolysis conditions to give the title compound (0.045 g, 63%): $^1$H NMR (400 MHz, DMSO-$d_6$) δ ppm 12.76 (br. s., 2H) 7.73 (s, 1H) 7.22-7.60 (m, 5H) 6.15 (s, 1H) 5.97 (br. s., 1H) 4.15 (br. s., 2H) 3.86 (br. s., 2H) 3.01-3.53 (m, 4H+ $H_2O$) 2.08 (br. s., 1H) 1.66-1.91 (m, 1H) 0.95-1.63 (m, 7H) 0.64-0.92 (m, 6H); ES-LCMS m/z 547 $(M+H)^+$.

Example 5

[3R,5R)-3-butyl-3-ethyl-7-(methyloxy)-1,1-dioxido-5-phenyl-2,3,4,5-tetrahydro-1,4-benzothiazepin-8-yl]methanesulfonic acid trifluoroacetate salt

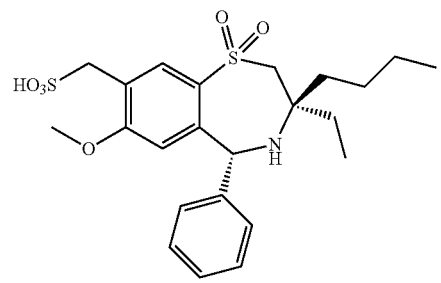 [SMILES: CCCC[C@]1(CC)CS(=O)(=O)c2cc(CS(=O)(=O)O)c(OC)cc2[C@@H](c2ccccc2)N1]

To a solution of (3R,5R)-8-(bromomethyl)-3-butyl-3-ethyl-7-(methyloxy)-5-phenyl-2,3,4,5-tetrahydro-1,4-benzothiazepine-1,1-dioxide (0.100 g, 0.21 mmol) in 1,4-dioxane (1 mL) was added a solution of sodium sulfite (131 mg, 1.04 mmol) in H₂O (1 mL). The mixture was stirred under reflux overnight then concentrated under vacuum, and the crude reaction mixture was washed with 1N HCl. The supernatant was decanted leaving a white gummy solid which was triturated with DCM and hexanes to give a solid that was collected via filtration. Purification was accomplished using the Agilent prep-HPLC(C18 packing with MeCN, H₂O w/0.1% TFA as the mobile phase) to give the title compound (83 mg, 66%) as a trifluoroacetate salt: ¹H NMR (400 MHz, DMSO-d₆) δ ppm 8.17 (br. s., 1H) 7.59 (br. s., 5H) 6.33 (br. s., 2H) 3.14-4.46 (m, 6H+ H₂O) 2.02 (br. s., 2H) 1.60 (br. s., 1H) 1.33 (br. s., 3H) 0.62-1.13 (m, 7H); ES-LCMS m/z 482 (M+H)⁺.

Example 6

{[(3R,5R)-3-butyl-3-ethyl-7-(methyloxy)-1,1-dioxido-5-phenyl-2,3,4,5-tetrahydro-1,4-benzothiazepin-8-yl]methyl}phosphonic acid hydrochloride salt

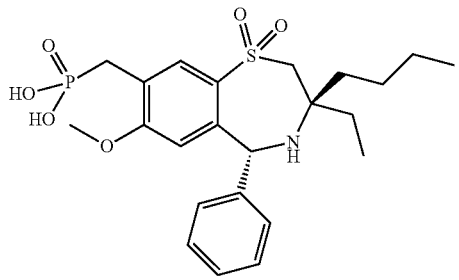 [SMILES: CCCC[C@]1(CC)CS(=O)(=O)c2cc(CP(=O)(O)O)c(OC)cc2[C@@H](c2ccccc2)N1]

Step 1: Prepared in analogous fashion to Example 5 via alkylation using triethyl phosphite (0.352 mL, 2.01 mmol) and (3R,5R)-8-(bromomethyl)-3-butyl-3-ethyl-7-(methyloxy)-5-phenyl-2,3,4,5-tetrahydro-1,4-benzothiazepine 1,1-dioxide (0.920 g, 1.92 mmol) in toluene (10 mL).

Step 2: The phosphonate ester from the previous step was dissolved in 2 mL 6N HCl and 1 mL EtOH then heated at reflux for 6 h. The reaction was cooled then concentrated. The residue was dissolved in EtOH then concentrated to give the title compound (0.86 g, 85%) as a hydrochloride salt: ¹H NMR (400 MHz, MeOH-d₄) δ ppm 8.04 (d, J=2.34 Hz, 1H) 7.57 (s, 5H) 6.46 (s, 1H) 6.36 (s, 1H) 3.79 (d, J=15.51 Hz, 1H) 3.58 (s, 3H) 3.45 (d, J=15.51 Hz, 1H) 3.16-3.25 (m, 1H) 2.99-3.12 (m, 2H) 2.68 (br. s., 1H) 1.97 (dd, J=14.15, 7.12 Hz, 2H) 1.64 (dd, J=14.15, 7.32 Hz, 1H) 1.23-1.46 (m, 3H) 0.98 (t, J=7.41 Hz, 4H) 0.89 (t, J=6.88 Hz, 3H); ES-LCMS m/z 482 (M+H)⁺.

Example 7

2,2'-({[(3R,5R)-3-butyl-3-ethyl-7-(methyloxy)-1,1-dioxido-5-phenyl-2,3,4,5-tetrahydro-1,4-benzothiazepin-8-yl]methyl}imino)diacetic acid hydrochloride salt

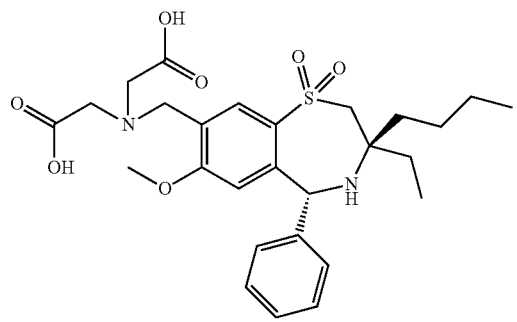 [SMILES: CCCC[C@]1(CC)CS(=O)(=O)c2cc(CN(CC(=O)O)CC(=O)O)c(OC)cc2[C@@H](c2ccccc2)N1]

Step 1: To an MeCN solution of (3R,5R)-8-(bromomethyl)-3-butyl-3-ethyl-7-(methyloxy)-5-phenyl-2,3,4,5-tetrahydro-1,4-benzothiazepine-1,1-dioxide (77 mg, 0.16 mmol) was added diethyl iminodiacetic acid (33 m, 0.18 mmol). The reaction mixture was heated at 65° C. for 4 h then cooled and concentrated to a thick oil. Chromatography on silica using hexanes/EtOAc provided a clear oil.

Step 2: H₂O and THF were added to the product from step 1 along with LiOH (15 mg, 0.36 mmol), and the mixture stirred for 2 h at ambient temp to hydrolyze the diacetic acid. The rxn mixture was concentrated to half volume, and 1N HCl added to acidify the reaction contents then the organics were extracted 2×DCM. The combined organics were washed with brine, dried (Na₂SO₄), filtered, and concentrated. The residue was triturated (DCM/EtOAc), filtered, and dried. The material was redissolved in DCM/EtOAc/MeOH then concentrated to a solid and kept under N₂ overnight to dry. Obtained the title compound as a hydrochloride salt as a white solid. (45 mg, 47% over 2 steps): ¹H NMR (400 MHz, DMSO-d₆) δ ppm 12.36 (br. s., 2H) 8.03 (s, 1H) 7.16-7.55 (m, 5H) 6.09 (s, 1H) 5.95 (br. s., 1H) 3.81 (br. s., 2H) 3.16-3.59 (m, 26H) 3.07 (d, J=14.83 Hz, 1H) 2.51 (br. s., 14H) 2.08 (br. s., 1H) 1.75 (br. s., 1H) 0.98-1.56 (m, 8H) 0.62-0.90 (m, 6H); ES-LCMS m/z 533 (M+H)⁺.

Example 8

(3R,5R)-3-butyl-3-ethyl-7-(methyloxy)-5-phenyl-2,3,4,5-tetrahydro-1,4-benzothiazepine-8-carboxamide-1,1-dioxide

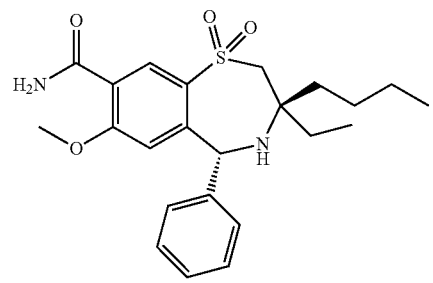 [SMILES: CCCC[C@]1(CC)CS(=O)(=O)c2cc(C(N)=O)c(OC)cc2[C@@H](c2ccccc2)N1]

A mixture of (3R,5R)-3-butyl-3-ethyl-7-(methyloxy)-5-phenyl-2,3,4,5-tetrahydro-1,4-benzothiazepine-8-carbonitrile-1,1-dioxide (38 mg, 0.092 mmol) and K₂O₃ (25 mg, 0.184 mmol) in DMSO (1 mL) was cooled to 0° C., and 30% w/w H₂O₂ (0.016 mL, 0.153 mmol) was added dropwise. The resulting mixture was warmed to room temperature then stirred for 2 h. H₂O was added then the resulting precipitant filtered and dried to give the title compound (40 mg, 95%): ¹H NMR (400 MHz, DMSO-d₆) δ ppm 7.81 (s, 1H) 6.51-6.76 (m, 5H) 5.58 (s, 1H) 5.31 (s, 1H) 2.85 (s, 3H) 2.74 (d, J=14.92 Hz, 1H) 2.36 (d, J=14.92 Hz, 1H) 1.87 (s, 2H) 1.41-1.55 (m, 1H) 0.96-1.13 (m, 1H) 0.75-0.91 (m, 1H) 0.61-0.75 (m, 1H) 0.25-0.59 (m, 4H) 0.13 (t, J=7.37 Hz, 3H) 0.03 (t, J=6.82 Hz, 3H); ES-LCMS m/z 431 (M+H)⁺.

Example 9

(2E)-3-[(3R,5R)-3-butyl-3-ethyl-7-(methyloxy)-1,1-dioxido-5-phenyl-2,3,4,5-tetrahydro-1,4-benzothiazepin-8-yl]-2-propenoic acid ammonium salt

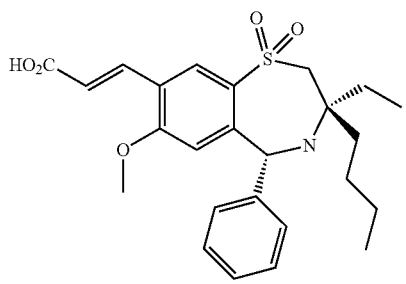 [SMILES: CCCC[C@]1(CC)CS(=O)(=O)c2cc(/C=C/C(=O)O)c(OC)cc2[C@@H](c2ccccc2)N1]

To a solution of ethyl (2E)-3-[(3R,5R)-3-butyl-3-ethyl-7-(methyloxy)-1,1-dioxido-5-phenyl-2,3,4,5-tetrahydro-1,4-benzothiazepin-8-yl]-2-propenoate (300 mg, 0.618 mmol) in a 1:1:1 mixture of THF/MeOH/H$_2$O (15 mL) was added lithium hydroxide (74.0 mg, 3.09 mmol), and the resulting reaction mixture was stirred at room temperature overnight. The reaction mixture was concentrated under reduced pressure to remove the organic solvents. The resulting aqueous layer was acidified to pH 1 with 1N hydrochloric acid then the aqueous layer was extracted with DCM. The organic layer was washed with H$_2$O, saturated brine, dried (Na$_2$SO$_4$), filtered, and concentrated under reduced pressure. Purification using HPLC (eluting with MeCN/H$_2$O with 0.5% NH$_3$—H$_2$O) afforded the title compound (201 mg, 65%, as an ammonium salt) as a white solid: $^1$H NMR (MeOH-d$_4$): δ ppm 8.06 (s, 1H), 7.27-7.48 (m, 5H), 6.30 (s, 1H), 6.06 (s, 1H), 4.26 (s, 2H), 3.65 (s, 1H), 3.58 (s, 3H), 3.49 (d, J=15.0 Hz, 1H), 3.07 (d, J=14.8 Hz, 1H), 2.52-2.76 (m, 4H), 2.11-2.28 (m, 1H), 1.69-1.84 (m, 1H), 1.56 (s, 1H), 1.42 (s, 1H), 1.04-1.33 (m, 4H), 0.87 (t, J=7.4 Hz, 3H), 0.78 (t, J=6.8 Hz, 3H); ES-LCMS m/z 458 (M+H)$^+$.

Example 10

3-[(3R,5R)-3-butyl-3-ethyl-7-(methyloxy)-1,1-dioxido-5-phenyl-2,3,4,5-tetrahydro-1,4-benzothiazepin-8-yl]propanoic acid

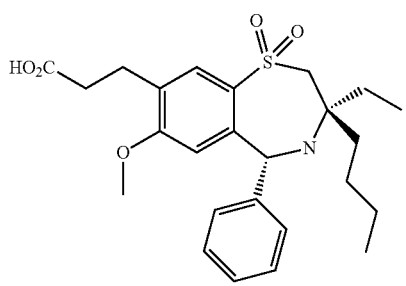 [SMILES: CCCC[C@]1(CC)CS(=O)(=O)c2cc(CCC(=O)O)c(OC)cc2[C@@H](c2ccccc2)N1]

Step 1: A mixture of ethyl (2E)-3-[(3R,5R)-3-butyl-3-ethyl-7-(methyloxy)-1,1-dioxido-5-phenyl-2,3,4,5-tetrahydro-1,4-benzothiazepin-8-yl]-2-propenoate (0.27 g, 0.556 mmol) and 10% Pd/C (0.012 g) in EtOH (10 mL) at room temperature was hydrogenated under an atmosphere of hydrogen at 1 atm. overnight. The reaction mixture was filtered through diatomaceous earth and washed with EtOH. The filtrate was concentrated under reduced pressure to give ethyl 3-[(3R,5R)-3-butyl-3-ethyl-7-(methyloxy)-1,1-dioxido-5-phenyl-2,3,4,5-tetrahydro-1,4-benzothiazepin-8-yl]propanoate (182 mg, 57%) as a clear oil: ES-LCMS m/z 488 (M+H)$^+$.

Step 2: To a solution of ethyl 3-[(3R,5R)-3-butyl-3-ethyl-7-(methyloxy)-1,1-dioxido-5-phenyl-2,3,4,5-tetrahydro-1,4-benzothiazepin-8-yl]propanoate (172 mg, 0.353 mmol) in a 1:1:2 mixture of THF/MeOH/H$_2$O (12 mL) was added lithium hydroxide (84 mg, 3.53 mmol). The reaction mixture was stirred at room temperature overnight then partially concentrated under reduced pressure to remove organic solvents. The resulting aqueous layer was then acidified to pH 1-2 with 1N hydrochloric acid and extracted with DCM. The organic layer was washed with saturated brine, dried (Na$_2$SO$_4$), filtered, and concentrated under reduced pressure to give the title compound (149 mg, 87%) as a white solid: $^1$H NMR (CDCl$_3$): δ ppm 7.85 (s, 1H), 7.41 (d, J=7.0 Hz, 5H), 5.97-6.32 (m, 2H), 3.50 (s, 3H), 3.41 (d, J=15.0 Hz, 1H), 2.78-2.95 (m, 2H), 2.48-2.66 (m, 2H), 2.09-2.39 (m, 1H), 1.77-1.97 (m, 1H), 1.13-1.38 (m, 5H), 0.98-1.14 (m, 1H), 0.88 (t, J=7.3 Hz, 3H), 0.81 (t, J=7.0 Hz, 3H); ES-LCMS m/z 458 (M–H)$^-$.

Example 11

3-[(3R,5R)-3-butyl-3-ethyl-7-(methyloxy)-1,1-dioxido-5-phenyl-2,3,4,5-tetrahydro-1,4-benzothiazepin-8-yl]-N-(methylsulfonyl)propanamide

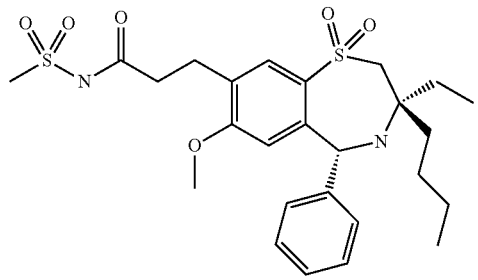 [SMILES: CCCC[C@]1(CC)CS(=O)(=O)c2cc(CCC(=O)NS(C)(=O)=O)c(OC)cc2[C@@H](c2ccccc2)N1]

To a solution of 3-[(3R,5R)-3-butyl-3-ethyl-7-(methyloxy)-1,1-dioxido-5-phenyl-2,3,4,5-tetrahydro-1,4-benzothiazepin-8-yl]propanoic acid (50 mg, 0.109 mmol) in a 2:1 mixture of DCM/THF (6 mL) was added EDC (25.03 mg, 0.131 mmol), DMAP (15.95 mg, 0.131 mmol) and methanesulfonamide (12.42 mg, 0.131 mmol). The reaction mixture was stirred at room temperature overnight and partitioned between H$_2$O and DCM. The organic layer was washed with saturated brine, dried (Na$_2$SO$_4$), filtered, and concentrated under reduced pressure. Purification with HPLC (eluting with MeCN/H$_2$O with 0.05% TFA-H$_2$O and 0.05% TFA-MeCN) afforded the title compound (25 mg, 34%, TFA salt) as a white solid: $^1$H NMR (CDCl$_3$) δ ppm 7.84 (s, 1H), 7.44-7.65 (m, 5H), 6.61 (s, 2H), 6.39 (s, 1H), 3.84 (d, J=15.6 Hz, 1H), 3.55 (s, 3H), 3.43 (d, J=15.6 Hz, 1H), 3.27 (s, 3H), 3.05-3.20 (m, 1H), 2.73-2.85 (m, 1H), 2.46-2.67 (m, 2H), 2.25-2.39 (m, 1H), 2.06-2.20 (m, 1H), 1.69-1.96 (m, 2H), 1.26-1.48 (m, 3H), 0.94 (t, J=7.3 Hz, 3H), 0.86 (t, J=7.0 Hz, 3H); ES-LCMS m/z 537 (M+H)$^+$.

Example 12

3-[(3R,5R)-3-butyl-3-ethyl-7-(methyloxy)-1,1-dioxido-5-phenyl-2,3,4,5-tetrahydro-1,4-benzothiazepin-8-yl]-N-hydroxypropanamide

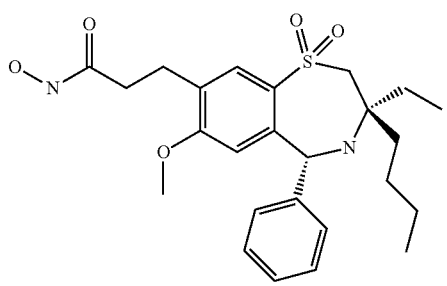 [SMILES: CCCC[C@]1(CC)CS(=O)(=O)c2cc(CCC(=O)NO)c(OC)cc2[C@@H](c2ccccc2)N1]

To a solution of 3-[(3R,5R)-3-butyl-3-ethyl-7-(methyloxy)-1,1-dioxido-5-phenyl-2,3,4,5-tetrahydro-1,4-benzothiazepin-8-yl]propanoic acid (50.1 mg, 0.109 mmol) in THF (5 mL) was added EDC (41.8 mg, 0.218 mmol), DMAP (39.9 mg, 0.327 mmol) and hydroxylamine hydrochloride (37.9 mg, 0.545 mmol). The reaction mixture was stirred at room temperature overnight and concentrated under reduced pressure. The residue was partitioned between $H_2O$ and DCM and the organic layer was washed with saturated brine, dried ($Na_2SO_4$), filtered, and concentrated under reduced pressure. Purification with HPLC (eluting with MeCN/$H_2O$ with 0.05% TFA-$H_2O$ and 0.05% TFA-MeCN) afforded the title compound (24 mg, 35%, TFA salt) as a white solid: $^1$H NMR (CDCl$_3$): δ ppm 7.74-7.85 (m, 1H), 7.40-7.68 (m, 5H), 6.60 (s, 1H), 6.39 (s, 1H), 3.84 (d, J=15.4 Hz, 1H), 3.51-3.63 (m, 3H), 3.46 (d, J=15.4 Hz, 1H), 2.84-3.05 (m, 1H), 2.45-2.79 (m, 2H), 2.23-2.42 (m, 1H), 1.69-2.23 (m, 4H), 1.28-1.52 (m, 3H), 0.92-1.13 (m, 4H), 0.76-0.92 (m, 3H); ES-LCMS m/z 475 (M+H)$^+$.

Example 13

({3-[(3R,5R)-3-butyl-3-ethyl-7-(methyloxy)-1,1-dioxido-5-phenyl-2,3,4,5-tetrahydro-1,4-benzothiazepin-8-yl]propanoyl}amino)methanesulfonic acid

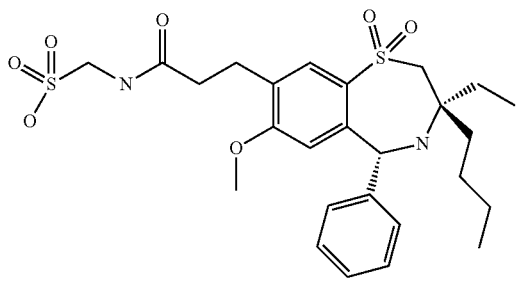 [SMILES: CCCC[C@]1(CC)CS(=O)(=O)c2cc(CCC(=O)NCS(=O)(=O)O)c(OC)cc2[C@@H](c2ccccc2)N1]

To a solution of 3-[(3R,5R)-3-butyl-3-ethyl-7-(methyloxy)-1,1-dioxido-5-phenyl-2,3,4,5-tetrahydro-1,4-benzothiazepin-8-yl]propanoic acid (50 mg, 0.109 mmol) in a 2:1 mixture of DCM/THF (6 mL) was added EDC (62.6 mg, 0.326 mmol), DMAP (39.9 mg, 0.326 mmol) and EDC (62.6 mg, 0.326 mmol). The reaction mixture was stirred at room temperature overnight then partitioned between $H_2O$ and DCM. The organic layer was washed with saturated brine, dried ($Na_2SO_4$), filtered, and concentrated under reduced pressure. Purification with HPLC (eluting with MeCN/$H_2O$ with 0.05% TFA-$H_2O$ and 0.05% TFA-MeCN) afforded the title compound (11.4 mg, 18%, TFA salt) as a white solid: $^1$H NMR (CDCl$_3$) δ ppm 7.85 (s, 1H), 7.35-7.77 (m, 5H), 6.51 (d, J=8.1 Hz, 2H), 3.85 (d, J=15.2 Hz, 2H), 3.67 (s, 3H), 3.21-3.50 (m, 2H), 2.92 (br. s., 1H), 2.58-2.80 (m, 2H), 2.12-2.52 (m, 2H), 1.69-1.97 (m, 2H), 1.31 (m, 3H), 0.63-0.99 (m, 6H); ES-LCMS m/z 553 (M+H)$^+$.

Example 14

N-{3-[(3R,5R)-3-butyl-3-ethyl-7-(methyloxy)-1,1-dioxido-5-phenyl-2,3,4,5-tetrahydro-1,4-benzothiazepin-8-yl]propanoyl}glycine

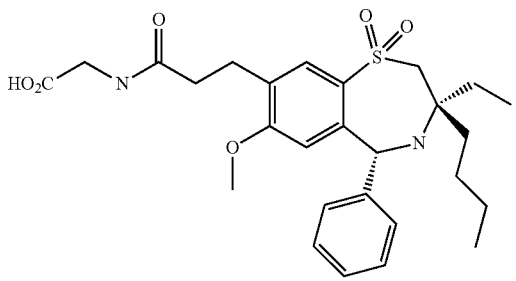 [SMILES: CCCC[C@]1(CC)CS(=O)(=O)c2cc(CCC(=O)NCC(=O)O)c(OC)cc2[C@@H](c2ccccc2)N1]

Step 1: To a solution of 3-[(3R,5R)-3-butyl-3-ethyl-7-(methyloxy)-1,1-dioxido-5-phenyl-2,3,4,5-tetrahydro-1,4-benzothiazepin-8-yl]propanoic acid (50 mg, 0.109 mmol) in DCM (4 mL) was added DIPEA (0.095 mL, 0.544 mmol), HATU (124 mg, 0.326 mmol) and glycine methyl ester hydrochloride (19.39 mg, 0.218 mmol). The reaction mixture was stirred at room temperature overnight then partitioned between $H_2O$ and DCM. The organic layer was washed with saturated brine, dried ($Na_2SO_4$), filtered, and concentrated under reduced pressure. Purification on silica gel (MeOH:DCM=0:100 to 10:90) afforded methyl N-{3-[(3R,5R)-3-butyl-3-ethyl-7-(methyloxy)-1,1-dioxido-5-phenyl-2,3,4,5-tetrahydro-1,4-benzothiazepin-8-yl]propanoyl}glycinate (45 mg, 76%) as a clear oil: ES-LCMS m/z 531 (M+H)$^+$.

Step 2: To a solution of methyl N-{3-[3R,5R)-3-butyl-3-ethyl-7-(methyloxy)-1,1-dioxido-5-phenyl-2,3,4,5-tetrahydro-1,4-benzothiazepin-8-yl]propanoyl}glycinate (43 mg, 0.081 mmol) in a mixture of 2:1:1 THF/MeOH/$H_2O$ (8 mL) was added lithium hydroxide (1.941 mg, 0.081 mmol). The reaction mixture was stirred at room temperature overnight then partially concentrated to remove the organic solvents. The resulting aqueous layer was diluted with $H_2O$ and acidified to pH 1 with 1N hydrochloric acid. The aqueous layer was extracted with DCM. The organic layer was washed with saturated brine, dried ($Na_2SO_4$), filtered, and concentrated under reduced pressure. Purification on silica gel (MeOH:DCM=0:100 to 10:90) afforded the title product (21 mg, 47%) as a white solid: $^1$H NMR (CDCl$_3$) δ ppm 7.83 (s, 1H), 7.31-7.62 (m, 5H), 6.02-6.37 (m, 3H), 3.89 (br. s., 2H), 3.49 (s, 3H), 3.34-3.44 (m, 1H), 3.14-3.33 (m, 1H), 3.02 (d, J=6.8 Hz, 1H), 2.70-2.90 (m, 1H), 2.27-2.66 (m, 3H), 1.76-1.96 (m, 1H), 0.49-0.93 (m, 13H); ES-LCMS m/z 515 (M−H)$^-$.

Example 15

2-({3-[(3R,5R)-3-butyl-3-ethyl-7-(methyloxy)-1,1-dioxido-5-phenyl-2,3,4,5-tetrahydro-1,4-benzothiazepin-8-yl]propanoyl}amino)ethanesulfonic acid

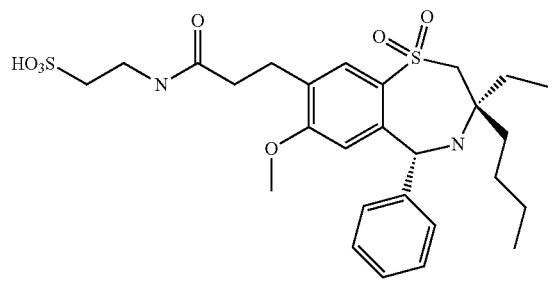 [SMILES: CCCC[C@]1(CC)CS(=O)(=O)c2cc(CCC(=O)NCCS(=O)(=O)O)c(OC)cc2[C@@H](c2ccccc2)N1]

To a solution of 3-[(3R,5R)-3-butyl-3-ethyl-7-(methyloxy)-1,1-dioxido-5-phenyl-2,3,4,5-tetrahydro-1,4-benzothiazepin-8-yl]propanoic acid (50 mg, 0.109 mmol) in a 2:1 mixture of DCM/THF (6 mL) was added EDC (25.03 mg, 0.131 mmol), DMAP (15.95 mg, 0.131 mmol) and taurine (16.34 mg, 0.131 mmol). The reaction mixture was stirred at room temperature overnight then partitioned between $H_2O$ and DCM. The organic layer was washed with saturated brine, dried ($Na_2SO_4$), filtered, and concentrated under reduced pressure. Purification with HPLC (eluting with MeCN/$H_2O$ with 0.05% TFA-$H_2O$ and 0.05% TFA-MeCN) afforded the title compound (4.6 mg, 7%, TFA salt) as a white solid: $^1$H NMR (CDCl$_3$) δ ppm 7.40-8.17 (m, 6H), 6.59 (br. s., 1H), 6.46 (br. s., 1H), 5.79-6.18 (m, 1H), 3.05-4.00 (m, 7H), 1.68-2.97 (m, 12H), 1.34-1.38 (m, 3H), 0.62-1.12 (m, 6H); ES-LCMS m/z 567 (M+H)$^+$.

Example 16

N-{3-[(3R,5R)-3-butyl-3-ethyl-7-(methyloxy)-1,1-dioxido-5-phenyl-2,3,4,5-tetrahydro-1,4-benzothiazepin-8-yl]propanoyl}-2-methylalanine

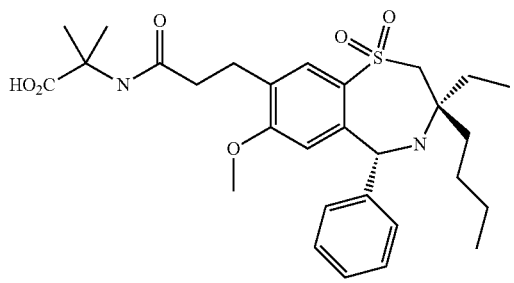 [SMILES: CCCC[C@]1(CC)CS(=O)(=O)c2cc(CCC(=O)NC(C)(C)C(=O)O)c(OC)cc2[C@@H](c2ccccc2)N1]

Step 1: To a solution of 3-[(3R,5R)-3-butyl-3-ethyl-7-(methyloxy)-1,1-dioxido-5-phenyl-2,3,4,5-tetrahydro-1,4-benzothiazepin-8-yl]propanoic acid (50 mg, 0.109 mmol) in DCM (4 mL) was added DIPEA (0.057 mL, 0.326 mmol), HATU (62.0 mg, 0.163 mmol) and methyl alpha-aminoisobutyrate hydrochloride (20.05 mg, 0.131 mmol). The reaction mixture was stirred at room temperature overnight and partitioned between $H_2O$ and DCM. The organic layer was washed with saturated brine, dried ($Na_2SO_4$), filtered, and concentrated under reduced pressure. Purification using silica gel (MeOH:DCM=0:100 to 10:90) afforded the methyl N-{3-[(3R,5R)-3-butyl-3-ethyl-7-(methyloxy)-1,1-dioxido-5-phenyl-2,3,4,5-tetrahydro-1,4-benzothiazepin-8-yl]propanoyl}-2-methylalaninate (56.8 mg, 89%) as a clear oil: ES-LCMS m/z 559 (M+H)$^+$.

Step 2: To a solution of methyl N-{3-[(3R,5R)-3-butyl-3-ethyl-7-(methyloxy)-1,1-dioxido-5-phenyl-2,3,4,5-tetrahydro-1,4-benzothiazepin-8-yl]propanoyl}-2-methylalaninate (54 mg, 0.097 mmol) in a 2:1:1 mixture of THF/MeOH/$H_2O$ (8 mL) was added lithium hydroxide (23.15 mg, 0.966 mmol). The reaction mixture was stirred at room temperature overnight then concentrated under reduced pressure to remove the organic solvents. The resulting aqueous layer was diluted with $H_2O$ and acidified to pH 1 with 1N hydrochloric acid. The aqueous layer was extracted with DCM. The organic layer was washed with saturated brine, dried ($Na_2SO_4$), filtered, and concentrated under reduced pressure. Purification using silica gel (MeOH:DCM=0:100 to 10:90) afforded the title compound (40 mg, 72%) as a white solid: $^1$H NMR (CDCl$_3$) δ ppm 7.82 (s, 1H), 7.29-7.55 (m, 5H), 6.11 (s, 1H), 6.01 (s, 1H), 5.87 (s, 1H), 3.48 (s, 3H), 3.38 (d, J=14.8 Hz, 2H), 3.06 (d, J=14.8 Hz, 2H), 2.84-2.99 (m, 3H), 2.78 (s, 1H), 2.37-2.55 (m, 2H), 2.17 (br. s., 1H), 1.83 (d, J=4.0 Hz, 1H), 1.51 (s, 3H), 1.48 (s, 3H), 1.00-1.34 (m, 9H), 0.86 (t, J=7.3 Hz, 3H), 0.80 (t, J=7.1 Hz, 4H); ES-LCMS m/z 545 (M+H)$^+$.

Example 17

3-({3-[(3R,5R)-3-butyl-3-ethyl-7-(methyloxy)-1,1-dioxido-5-phenyl-2,3,4,5-tetrahydro-1,4-benzothiazepin-8-yl]propanoyl}amino)pentanedioic acid trifluoroacetate salt

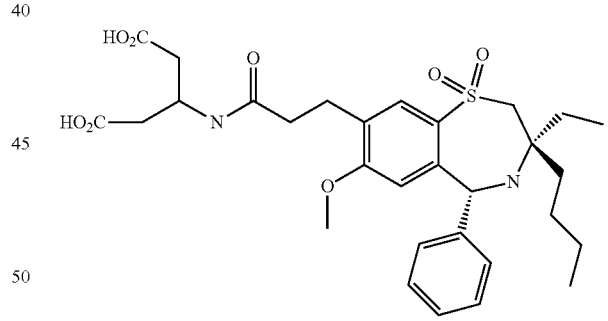

Step 1: To a solution of 3-[(3R,5R)-3-butyl-3-ethyl-7-(methyloxy)-1,1-dioxido-5-phenyl-2,3,4,5-tetrahydro-1,4-benzothiazepin-8-yl]propanoic acid (100 mg, 0.218 mmol) in DCM (6 mL) was added DIPEA (0.190 mL, 1.088 mmol) and HATU (165 mg, 0.435 mmol). The reaction mixture was stirred at room temperature for 20 min then treated with diethyl 3-aminopentanedioate (66.3 mg, 0.326 mmol). The reaction mixture was stirred at room temperature overnight then concentrated under reduced pressure. Purification on silica gel (EtOAc:hexanes=1:3 to 3:1) afforded diethyl 3-({3-[(3R,5R)-3-butyl-3-ethyl-7-(methyloxy)-1,1-dioxido-5-phenyl-2,3,4,5-tetrahydro-1,4-benzothiazepin-8-yl]propanoyl}amino)pentanedioate (137 mg, 96%) as a colorless oil: ES-LCMS m/z 645 (M+H)$^+$.

Step 2: To a solution of diethyl 3-({3-[(3R,5R)-3-butyl-3-ethyl-7-(methyloxy)-1,1-dioxido-5-phenyl-2,3,4,5-tetrahydro-1,4-benzothiazepin-8-yl]propanoyl}amino)pentanedioate (137 mg, 0.212 mmol) in a 1:1:1 mixture of THF/MeOH/H₂O (6 mL) was added lithium hydroxide (25.4 mg, 1.062 mmol). The reaction mixture was stirred at room temperature overnight, acidified with acetic acid to pH 3-4, and concentrated under reduced pressure. Purification by RP-HPLC (eluting with MeGN/H₂O with 0.05% TFA-H₂O and 0.05% TFA-MeCN) afforded the title product (92 mg, 60%, TFA salt) as white solid: ¹H NMR (MeOH-d₄) δ ppm 7.90 (s, 1H), 7.48-7.62 (m, 5H), 6.44 (s, 1H), 6.37 (s, 1H), 4.33-4.48 (m, 1H), 3.81 (d, J=15.6 Hz, 1H), 3.57 (s, 3H), 3.46 (d, J=15.6 Hz, 2H), 2.78-3.03 (m, 2H), 2.60-2.75 (m, 1H), 2.48-2.58 (m, 4H), 2.37-2.46 (m, 2H), 1.86-2.13 (m, 2H), 1.49-1.67 (m, 1H), 1.33-1.39 (m, 3H), 0.96 (t, J=7.4 Hz, 3H), 0.87 (t, J=7.0 Hz, 3H); ES-LCMS m/z 589 (M+H)⁺.

Example 18

2,2'-({3-[(3R,5R)-3-butyl-3-ethyl-7-(methyloxy)-1,1-dioxido-5-phenyl-2,3,4,5-tetrahydro-1,4-benzothiazepin-8-yl]propanoyl}imino)diacetic acid

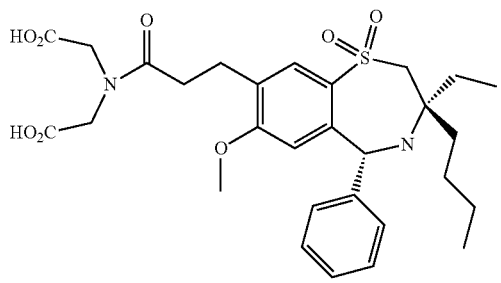 [SMILES: CCCC[C@]1(CC)CS(=O)(=O)c2cc(CCC(=O)N(CC(=O)O)CC(=O)O)c(OC)cc2[C@@H](c2ccccc2)N1]

Step 1: To a solution of 3-[(3R,5R)-3-butyl-3-ethyl-7-(methyloxy)-1,1-dioxido-5-phenyl-2,3,4,5-tetrahydro-1,4-benzothiazepin-8-yl]propanoic acid (50 mg, 0.109 mmol) in a 2:1 mixture of DCM/THF (6 mL) was added DMAP (39.9 mg, 0.326 mmol), EDC (62.6 mg, 0.326 mmol) and diethyl 2,2'-iminodiacetate (41.2 mg, 0.218 mmol). The reaction mixture was stirred at room temperature overnight then partitioned between H₂O and DCM. The organic layer was washed with saturated brine, dried (Na₂SO₄), filtered, and concentrated under reduced pressure. Purification using silica gel (EtOAc:hexanes=10:90 to 50:50) afforded diethyl 2,2'-({3-[(3R,5R)-3-butyl-3-ethyl-7-(methyloxy)-1,1-dioxido-5-phenyl-2,3,4,5-tetrahydro-1,4-benzothiazepin-8-yl]propanoyl}imino)diacetate (44.8 mg, 65%) as a clear oil: ES-LCMS m/z 631 (M+H)⁺.

Step 2: To a solution of diethyl 2,2'-({3-[(3R,5R)-3-butyl-3-ethyl-7-(methyloxy)-1,1-dioxido-5-phenyl-2,3,4,5-tetrahydro-1,4-benzothiazepin-8-yl]propanoyl}imino)diacetate (44.8 mg, 0.071 mmol) in a 1:1:1 mixture of THF/MeOH/H₂O (9 mL) was added lithium hydroxide (85 mg, 3.55 mmol). The reaction mixture was stirred at room temperature overnight, acidified with 1N hydrochloric acid to pH 1 and concentrated under reduced pressure. Purification with HPLC (eluting with MeCN/H₂O with 0.05% TFA-H₂O and 0.05% TFA-MeCN) afforded the title product (23 mg, 53%, TFA salt) as a white solid: ¹H NMR (CDCl₃) δ ppm 7.84 (s, 1H), 7.61-7.75 (m, 2H), 7.37-7.59 (m, 3H), 6.54 (br. s., 1H), 6.42 (s, 1H), 3.96-4.25 (m, 2H), 3.72-3.88 (m, J=8.6 Hz, 2H), 3.23-3.70 (m, 11H), 2.97-3.13 (m, 1H), 2.50-2.95 (m, 2H), 2.31-2.48 (m, J=14.1 Hz, 1H), 1.69-2.09 (m, 3H), 0.55-1.45 (m, 8H); ES-LCMS m/z 575 (M+H)⁺.

Example 19

3-[(3R,5R)-3-butyl-3-ethyl-7-(methyloxy)-1,1-dioxido-5-phenyl-2,3,4,5-tetrahydro-1,4-benzothiazepin-8-yl]-1-propanol

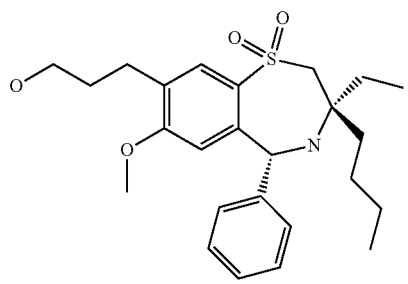 [SMILES: CCCC[C@]1(CC)CS(=O)(=O)c2cc(CCCO)c(OC)cc2[C@@H](c2ccccc2)N1]

To an ice-cold solution of 3-[(3R,5R)-3-butyl-3-ethyl-7-(methyloxy)-1,1-dioxido-5-phenyl-2,3,4,5-tetrahydro-1,4-benzothiazepin-8-yl]propanoic acid (100 mg, 0.218 mmol) in THF (5 mL) was added borane-THF complex (0.653 mL, 0.653 mmol). The reaction mixture was stirred at room temperature overnight then quenched by dropwise addition of MeOH. The reaction mixture was stirred for 30 min then concentrated under reduced pressure. The residue was taken up with MeOH and evaporated under reduced pressure again. The residue was purified using silica gel (MeOH:DCM=0:100 to 10:90) afforded the title compound (96 mg, 94%) as a colorless oil: ¹H NMR (CDCl₃) δ ppm 7.84 (s, 1H), 7.26-7.48 (m, 5H), 6.11 (s, 1H), 6.01 (s, 1H), 3.58 (t, J=6.2 Hz, 2H), 3.48 (s, 3H), 3.40 (d, J=14.8 Hz, 1H), 3.00 (d, J=14.8 Hz, 1H), 2.56-2.75 (m, 2H), 2.02-2.25 (m, 1H), 1.69-1.92 (m, 3H), 0.99-1.52 (m, 14H), 0.86 (t, J=7.3 Hz, 3H), 0.80 (t, J=7.0 Hz, 3H); ES-LCMS m/z 446 (M+H)⁺.

Example 20

3-[(3R,5R)-3-butyl-3-ethyl-7-(methyloxy)-1,1-dioxido-5-phenyl-2,3,4,5-tetrahydro-1,4-benzothiazepin-8-yl]-1-propanesulfonic acid

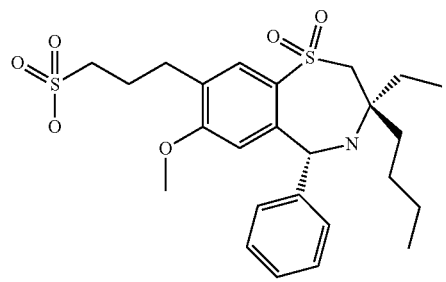 [SMILES: CCCC[C@]1(CC)CS(=O)(=O)c2cc(CCCS(=O)(=O)O)c(OC)cc2[C@@H](c2ccccc2)N1]

To a solution of (3R,5R)-8-(3-bromopropyl)-3-butyl-3-ethyl-7-(methyloxy)-5-phenyl-2,3,4,5-tetrahydro-1,4-benzothiazepine 1,1-dioxide (70 mg, 0.138 mmol) in a 1:1 mixture of EtOH/H₂O (10 mL) was added sodium sulfite (868 mg, 6.88 mmol). The reaction mixture was stirred at reflux overnight, cooled to room temperature, and partially concentrated under reduced pressure to remove the organic solvents. The aqueous layer was then acidified to pH 1 with 1N hydrochloric acid. The aqueous layer was extracted with DCM. The combined organic layers were washed with saturated brine, dried (Na$_2$SO$_4$), filtered, and concentrated under reduced pressure. Purification on silica gel (MeOH:DCM=0:100 to 20:80) afforded the title compound (27.2 mg, 38%) as a white solid: $^1$H NMR (CDCl$_3$) δ ppm (br. s., 1H), 7.16-7.60 (m, 5H), 6.06 (br. s., 2H), 2.33-3.63 (m, 14H), 0.47-2.26 (m, 12H); ES-LCMS m/z 510 (M+H)$^+$.

Example 21

{3-[(3R,5R)-3-butyl-3-ethyl-7-(methyloxy)-1,1-di-oxido-5-phenyl-2,3,4,5-tetrahydro-1,4-benzothiaz-epin-8-yl]propyl}phosphonic acid trifluoroacetate salt

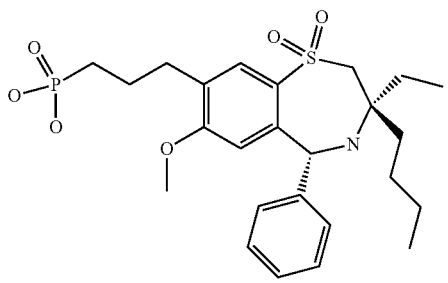 [SMILES: CCCC[C@]1(CC)CS(=O)(=O)c2cc(CCCP(=O)(O)O)c(OC)cc2[C@@H](c2ccccc2)N1]

Step 1: To a solution of diethylphosphite (119 mg, 0.859 mmol) in THF (5 mL) was added sodium hydride (27.5 mg, 0.687 mmol). The reaction mixture was stirred for 30 min, followed by dropwise addition of 3-[(3R,5R)-3-butyl-3-ethyl-7-(methyloxy)-1,1-dioxido-5-phenyl-2,3,4,5-tetrahydro-1,4-benzothiazepin-8-yl]propyl methanesulfonate (90 mg, 0.172 mmol) in THF (5 mL). The reaction mixture was stirred at room temperature overnight then concentrated under reduced pressure. The residue was partitioned between 1N hydrochloric acid and EtOAc. The organic layer was washed with saturated brine, dried (Na$_2$SO$_4$), filtered, and concentrated under reduced pressure. Purification using silica gel (EtOAc:hexanes=10:90 to 100:0) afforded diethyl {3-[(3R,5R)-3-butyl-3-ethyl-7-(methyloxy)-1,1-dioxido-5-phenyl-2,3,4,5-tetrahydro-1,4-benzothiazepin-8-yl]propyl}phosphonate (55 mg, 53%) as a white solid: ES-LCMS m/z 566 (M+H)$^+$.

Step 2: To a solution of diethyl {3-[3R,5R)-3-butyl-3-ethyl-7-(methyloxy)-1,1-dioxido-5-phenyl-2,3,4,5-tetrahydro-1,4-benzothiazepin-8-yl]propyl}phosphonate (50 mg, 0.088 mmol) in DCM (5 mL) was added bromotrimethylsilane (0.115 mL, 0.884 mmol). The reaction mixture was stirred at room temperature overnight then concentrated under reduced pressure. Purification by RP-HPLC (eluting with MeCN/H$_2$O with 0.05% TFA-H$_2$O and 0.05% TFA-MeCN) afforded the title compound (25 mg, 43%, TFA salt) as a white solid: $^1$H NMR (MeOH-d$_4$) δ ppm 7.90 (s, 1H), 7.39-7.60 (m, 5H), 6.42 (s, 1H), 6.32 (s, 1H), 3.79 (d, J=15.6 Hz, 1H), 3.55 (s, 3H), 3.37 (d, J=15.6 Hz, 1H), 2.73 (t, J=7.4 Hz, 2H), 2.51-2.66 (m, 1H), 1.75-2.10 (m, 4H), 1.48-1.72 (m, 3H), 1.20-1.45 (m, 3H), 0.99-1.13 (m, 1H), 0.95 (t, J=7.4 Hz, 3H), 0.86 (t, J=7.0 Hz, 3H); ES-LCMS m/z 510 (M+H)$^+$.

Example 22

2-({3-[(3R,5R)-3-butyl-3-ethyl-7-(methyloxy)-1,1-dioxido-5-phenyl-2,3,4,5-tetrahydro-1,4-benzothiaz-epin-8-yl]propyl}amino)ethanesulfonic acid

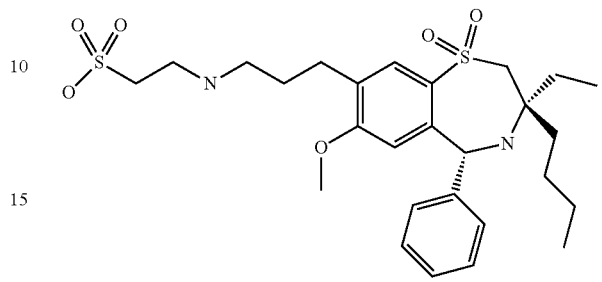

To a solution of 3-[(3R,5R)-3-butyl-3-ethyl-7-(methyloxy)-1,1-dioxido-5-phenyl-2,3,4,5-tetrahydro-1,4-benzothiazepin-8-yl]propyl methanesulfonate (90 mg, 0.172 mmol) in DMF (5 mL) was added potassium carbonate (238 mg, 1.719 mmol) and taurine (108 mg, 0.859 mmol). The reaction mixture was stirred at 60° C. overnight, cooled to room temperature, acidified with 1N hydrochloric acid to pH 1 and concentrated under reduced pressure. Purification by RP-HPLC (eluting with MeCN/H$_2$O with 0.05% TFA-H$_2$O and 0.05% TFA-MeCN) afforded the title compound (22 mg, 15%, TFA salt) as a white solid: $^1$H NMR (MeOH-d$_4$) δ ppm 7.42-7.65 (m, 5H), 6.48 (s, 1H), 6.34 (s, 1H), 3.77 (d, J=15.4 Hz, 1H), 3.58 (s, 3H), 3.47 (d, J=15.6 Hz, 1H), 2.95-3.12 (m, 4H), 2.51-2.88 (m, 3H), 1.84-2.11 (m, 4H), 1.54-1.69 (m, 7.4 Hz, 1H), 1.23-1.45 (m, 3H), 1.00-1.10 (m, 1H), 0.95 (t, J=7.4 Hz, 3H), 0.87 (t, J=6.8 Hz, 3H); ES-LCMS m/z 553 (M+H)$^+$.

Example 23

4-[(3R,5R)-3-butyl-3-ethyl-7-(methyloxy)-1,1-di-oxido-5-phenyl-2,3,4,5-tetrahydro-1,4-benzothiaz-epin-8-yl]butanoic acid trifluoroacetate salt

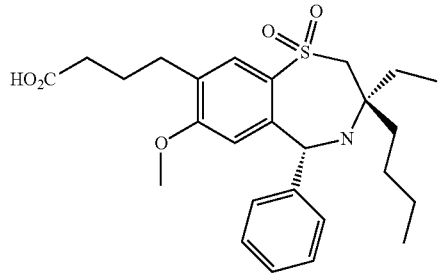 [SMILES: CCCC[C@]1(CC)CS(=O)(=O)c2cc(CCCC(=O)O)c(OC)cc2[C@@H](c2ccccc2)N1]

A mixture of 4-[(3R,5R)-3-butyl-3-ethyl-7-(methyloxy)-1,1-dioxido-5-phenyl-2,3,4,5-tetrahydro-1,4-benzothiaz-epin-8-yl]butanenitrile (40 mg, 0.088 mmol) and 37% hydrochloric acid (4 mL) was stirred at 100° C. overnight, cooled to room temperature and concentrated under reduced pressure. MeOH was added to transfer the residue to a flask, and the solution was concentrated under reduced pressure. Purification by RP-HPLC (eluting with MeCN/H$_2$O with 0.05% TFA-H$_2$O and 0.05% TFA-MeCN) afforded trace amount of desired acid. The majority was the methyl ester of the acid, which was hydrolyzed in the presence of excess lithium hydroxide. Purification by RP-HPLC (MeCN/H$_2$O with 0.05% TFA) afforded the title compound (10 mg, 18%, TFA salt) as a white solid: $^1$H NMR (CDCl$_3$) δ ppm 7.87 (s, 1H), 7.41-7.65 (m, 5H), 6.59 (s, 1H), 6.32 (s, 1H), 3.65 (d, J=15.6 Hz, 1H), 3.45 (d, J=15.4 Hz, 1H), 2.83-2.97 (m, 1H), 2.40-2.66 (m, 2H), 2.26-2.38 (m, 1H), 1.62-2.25 (m, 5H), 1.26-1.47 (m, 3H), 0.96 (t, J=7.4 Hz, 4H), 0.86 (t, J=7.0 Hz, 3H); ES-LCMS m/z 474 (M+H)$^+$.

Example 24

4-[(3R,5R)-3-butyl-3-ethyl-7-(methyloxy)-1,1-dioxido-5-phenyl-2,3,4,5-tetrahydro-1,4-benzothiazepin-8-yl]butanamide trifluoroacetate salt

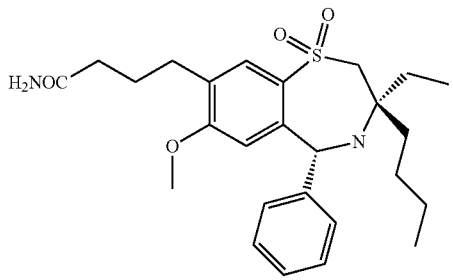 [SMILES: CCCC[C@]1(CC)CS(=O)(=O)c2cc(CCCC(N)=O)c(OC)cc2[C@@H](c2ccccc2)N1]

To a solution of 4-[(3R,5R)-3-butyl-3-ethyl-7-(methyloxy)-1,1-dioxido-5-phenyl-2,3,4,5-tetrahydro-1,4-benzothiazepin-8-yl]butanenitrile (40 mg, 0.088 mmol) in DMSO (4 mL) was added potassium carbonate (48.6 mg, 0.352 mmol). The reaction flask was immersed in an ice-cold H$_2$O bath, and hydrogen peroxide (0.449 mL, 4.40 mmol) was added dropwise. The reaction mixture was warmed to room temperature and stirred for 2 hrs. H$_2$O was added, and the solids collected by filtration. Purification by RP-HPLC (eluting with MeCN/H$_2$O with 0.05% TFA-H$_2$O and 0.05% TFA-MeCN) afforded the title compound (32 mg, 58%, TFA salt) as a white solid: $^1$H NMR (MeOH-d$_4$) δ ppm 7.76 (s, 1H), 7.25-7.51 (m, 5H), 6.17 (s, 1H), 6.01 (s, 1H), 3.40-3.55 (m, 4H), 3.06 (d, J=14.8 Hz, 1H), 2.48-2.69 (m, 2H), 2.07-2.29 (m, 3H), 1.67-1.91 (m, 3H), 1.49-1.64 (m, 1H), 1.35-1.48 (m, 1H), 0.99-1.34 (m, 5H), 0.86 (t, J=7.4 Hz, 3H), 0.78 (t, J=6.8 Hz, 3H); ES-LCMS m/z 475 (M+H)$^+$.

Example 25

N-{[(3R,5R)-3-butyl-3-ethyl-7-(methyloxy)-1,1-dioxido-5-phenyl-2,3,4,5-tetrahydro-1,4-benzothiazepin-8-yl]methyl}glycine

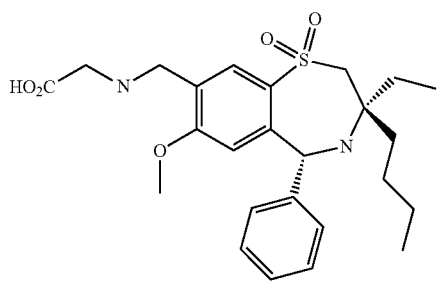 [SMILES: CCCC[C@]1(CC)CS(=O)(=O)c2cc(CNCC(=O)O)c(OC)cc2[C@@H](c2ccccc2)N1]

Step 1: To a solution of (3R,5R)-3-butyl-3-ethyl-7-(methyloxy)-5-phenyl-2,3,4,5-tetrahydro-1,4-benzothiazepine-8-carbaldehyde 1,1-dioxide (8.35 g, 20.09 mmol) in DCE (300 mL) was added 1,1-dimethylethyl glycinate (3.95 g, 30.1 mmol) and acetic acid (5.75 mL, 100 mmol). The reaction mixture was stirred at room temperature for 1 hr then treated with NaHB(OAc)$_3$ (10.65 g, 50.2 mmol). The reaction mixture was stirred at room temperature for 1 hr then treated with aqueous sodium carbonate solution and stirred for 1 hr. The layers were separated, and the aqueous layer was extracted with DCM. The combined organic layers were washed with H$_2$O, saturated brine, dried (Na$_2$SO$_4$), filtered, and concentrated under reduced pressure. Purification using silica gel (EtOAc/hexanes=20:80 to 60:40) afforded 1,1-dimethylethyl N-{[(3R,5R)-3-butyl-3-ethyl-7-(methyloxy)-1,1-dioxido-5-phenyl-2,3,4,5-tetrahydro-1,4-benzothiazepin-8-yl]methyl}glycinate (8.0 g, 71'/0) as a white solid; $^1$H NMR (CDCl$_3$) δ ppm 7.98 (s, 1H), 7.30-7.48 (m, 5H), 6.17 (s, 1H), 6.08 (s, 1H), 3.78 (s, 2H), 3.54 (s, 3H), 3.43 (d, J=14.9 Hz, 1H), 3.29 (d, J=2.0 Hz, 2H), 3.03 (d, J=14.7 Hz, 1H), 2.10-2.24 (m, 1H), 1.78-1.92 (m, 2H), 1.39-1.57 (m, 12H), 1.03-1.38 (m, 5H), 0.90 (t, J=7.4 Hz, 3H), 0.84 (t, J=7.0 Hz, 3H); ES-LCMS m/z 531 (M+H)$^+$.

Step 2: To a mixture of 1,1-dimethylethyl N-{[(3R,5R)-3-butyl-3-ethyl-7-(methyloxy)-1,1-dioxido-5-phenyl-2,3,4,5-tetrahydro-1,4-benzothiazepin-8-yl]methyl}glycinate (6.7 g, 12.62 mmol) in 1,4-dioxane (5 mL) was added 4N hydrogen chloride in 1,4-dioxane (95 mL, 379 mmol). The reaction mixture was stirred at room temperature for 16 h when concentrated. The residue was taken up in H$_2$O (200 mL), and the solution was adjusted to pH 4-5 with acetic acid. The white precipitate was collected via filtration. Acetonitrile was added, and the mixture was heated to reflux to dissolve all the solids, cooled to room temperature and stored for 2 days with no crystals. The solution was then evaporated under reduced pressure until solids precipitate out of the solution. The mixture was then heated to dissolve all the solids then let stand for 30 min. Solids were collected by multiple filtrations, combined, and dried under high vacuum at 50° C. for 3 hrs to give the title compound (5.0 g, 82%) as a white solid: $^1$H NMR (MeOH-d$_4$) δ ppm 8.06 (s, 1H), 7.25-7.50 (m, 5H), 6.30 (s, 1H), 6.06 (s, 1H), 4.22 (s, 2H), 3.58 (s, 3H), 3.50 (d, J=14.8 Hz, 1H), 3.42 (s, 2H), 3.08 (d, J=15.0 Hz, 1H), 2.12-2.31 (m, 1H), 1.67-1.86 (m, 1H), 1.49-1.64 (m, 1H), 1.34-1.48 (m, 1H), 1.01-1.34 (m, 4H), 0.87 (t, J=7.4 Hz, 3H), 0.78 (t, J=6.8 Hz, 3H); ES-LCMS m/z 475 (M+H)$^+$.

Example 26

3-({[(3R,5R)-3-butyl-3-ethyl-7-(methyloxy)-1,1-dioxido-5-phenyl-2,3,4,5-tetrahydro-1,4-benzothiazepin-8-yl]methyl}amino)pentanedioic acid

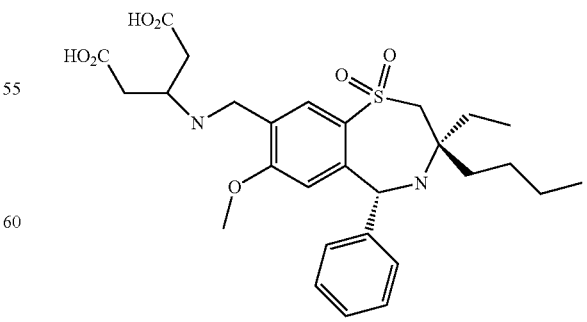

Method 1, Step 1: To a solution of (3R,5R)-3-butyl-3-ethyl-7-(methyloxy)-5-phenyl-2,3,4,5-tetrahydro-1,4-benzothiazepine-8-carbaldehyde 1,1-dioxide (683 mg, 1.644 mmol) in 1,2-dichloroethane (20 mL) was added diethyl 3-aminopentanedioate (501 mg, 2.465 mmol) and acetic acid (0.188 mL, 3.29 mmol). The reaction mixture was stirred at room temperature for 1 hr then treated with NaHB(OAc)$_3$ (697 mg, 3.29 mmol). The reaction mixture was then stirred at room temperature overnight and quenched with aqueous potassium carbonate solution. The mixture was extracted with DCM. The combined organic layers were washed with H$_2$O, saturated brine, dried (Na$_2$SO$_4$), filtered, and concentrated under reduced pressure to give diethyl 3-({[(3R,5R)-3-butyl-3-ethyl-7-(methyloxy)-1,1-dioxido-5-phenyl-2,3,4,5-tetrahydro-1,4-benzothiazepin-8-yl]methyl}amino)pentanedioate (880 mg, 88%) as a light yellow oil: MS-LCMS m/z 603 (M+H)$^+$.

Method 1, Step 2: To a solution of diethyl 3-({[(3R,5R)-3-butyl-3-ethyl-7-(methyloxy)-1,1-dioxido-5-phenyl-2,3,4,5-tetrahydro-1,4-benzothiazepin-8-yl]methyl}amino)pentanedioate (880 mg, 1.460 mmol) in a 1:1:1 mixture of THF/MeOH/H$_2$O (30 mL) was added lithium hydroxide (175 mg, 7.30 mmol). The reaction mixture was stirred at room temperature overnight then concentrated under reduced pressure. H$_2$O and MeCN was added to dissolve the residue. The solution was acidified with acetic acid to pH 4-5, partially concentrated to remove MeCN under reduced pressure, and left to stand for 30 min. The white precipitate was collected by filtration and dried under reduced pressure at 50° C. overnight to give the title compound (803 mg, 100%) as a white solid: $^1$H NMR (MeOH-d$_4$) δ ppm 8.05 (s, 1H), 7.27-7.49 (m, 5H), 6.29 (s, 1H), 6.06 (s, 1H), 4.25 (s, 2H), 3.60-3.68 (m, 1H), 3.58 (s, 3H), 3.47 (d, J=14.8 Hz, 1H), 3.09 (d, J=14.8 Hz, 1H), 2.52-2.73 (m, 4H), 2.12-2.27 (m, 1H), 1.69-1.84 (m, 1H), 1.48-1.63 (m, 1H), 1.05-1.48 (m, 5H), 0.87 (t, J=7.4 Hz, 3H), 0.78 (t, J=7.0 Hz, 3H); ES-LCMS m/z 547 (M+H)$^+$.

Method 2: A solution of dimethyl 3-({[(3R,5R)-3-butyl-3-ethyl-7-(methyloxy)-1,1-dioxido-5-phenyl-2,3,4,5-tetrahydro-1,4-benzothiazepin-8-yl]methyl}amino)pentanedioate (~600 g) in THF (2.5 L) and MeOH (1.25 L) was cooled in an ice-bath and a solution of NaOH (206 g, 5.15 mol) in water (2.5 L) was added dropwise over 20 min (10-22° C. reaction temperature). After stirring 20 min, the solution was concentrated (to remove THF/MeOH) and acidified to pH-4 with concentrated HCl. The precipitated product was aged with stirring, collected by filtration and air dried overnight. A second 600 g batch of dimethyl 3-({[(3R,5R)-3-butyl-3-ethyl-7-(methyloxy)-1,1-dioxido-5-phenyl-2,3,4,5-tetrahydro-1,4-benzothiazepin-8-yl]methyl}amino)pentanedioate was saponified in a similar fashion. The combined crude products (~2 mol theoretical) were suspended in CH$_3$CN (8 L) and water (4 L) and the stirred mixture was heated to 65° C. A solution formed which was cooled to 10° C. over 2 h while seeding a few times with an authentic sample of the desired crystalline product. The resulting slurry was stirred at 10° C. for 2 h, and the solid was collected by filtration. The filter cake was washed with water and air-dried overnight. Further drying to constant weight in a vacuum oven at 55° C. afforded crystalline 3-({[(3R,5R)-3-butyl-3-ethyl-7-(methyloxy)-1,1-dioxido-5-phenyl-2,3,4,5-tetrahydro-1,4-benzothiazepin-8-yl]methyl}amino)pentanedioic acid as a white solid (790 g).

Method 3: (3R,5R)-3-butyl-3-ethyl-7-(methyloxy)-5-phenyl-2,3,4,5-tetrahydro-1,4-benzothiazepine-8-carbaldehyde 1,1-dioxide (1802 grams, 4.336 moles) and dimethyl 3-aminopentanedioate (1334 grams, 5.671 moles) were slurried in iPrOAc (13.83 kgs). A nitrogen atmosphere was applied to the reactor. To the slurry at 20° C. was added glacial acetic acid (847 mL, 14.810 moles), and the mixture was stirred until complete dissolution was observed. Solid sodium triacetoxyborohydride (1424 grams, 6.719 moles) was next added to the reaction over a period of 7 minutes. The reaction was held at 20° C. for a total of 3 hours at which time LC analysis of a sample indicated complete consumption of the (3R,5R)-3-butyl-3-ethyl-7-(methyloxy)-5-phenyl-2,3,4,5-tetrahydro-1,4-benzothiazepine-8-carbaldehyde 1,1-dioxide. Next, water (20.36 kgs) and brine (4.8 kgs) were added to the reactor. The contents of the reactor were stirred for 10 minutes and then settled for 10 minutes. The bottom, aqueous layer was then removed and sent to waste. A previously prepared, 10% (wt/wt) aqueous solution of sodium bicarbonate (22.5 L) was added to the reactor. The contents were stirred for 10 minutes and then settled for 10 minutes. The bottom, aqueous layer was then removed and sent to waste. To the reactor was added a second wash of 10% (wt/wt) aqueous, sodium bicarbonate (22.5 L). The contents of the reactor were stirred for 10 minutes and settled for 10 minutes. The bottom, aqueous layer was then removed and sent to waste. The contents of the reactor were then reduced to an oil under vacuum distillation. To the oil was added THF (7.15 kgs) and MeOH (3.68 kgs). The contents of the reactor were heated to 55° C. and agitated vigorously until complete dissolution was observed. The contents of the reactor were then cooled to 25° C. whereupon a previously prepared aqueous solution of NaOH [6.75 kgs of water and 2.09 kgs of NaOH (50% wt/wt solution)] was added with cooling being applied to the jacket. The contents of the reactor were kept below 42° C. during the addition of the NaOH solution. The temperature was readjusted to 25° C. after the NaOH addition, and the reaction was stirred for 75 minutes before HPLC analysis indicated the reaction was complete. Heptane (7.66 kgs) was added to the reactor, and the contents were stirred for 10 minutes and then allowed to settle for 10 minutes. The aqueous layer was collected in a clean nalgene carboy. The heptane layer was removed from the reactor and sent to waste. The aqueous solution was then returned to the reactor, and the reactor was prepared for vacuum distillation. Approximately 8.5 liters of distillate was collected during the vacuum distillation. The vacuum was released from the reactor, and the temperature of the contents was readjusted to 25° C. A 1N HCl solution (30.76 kgs) was added to the reactor over a period of 40 minutes. The resulting slurry was stirred at 25° C. for 10 hours then cooled to 5° C. over a period of 2 hours. The slurry was held at 5° C. for 4 hours before the product was collected in a filter crock by vacuum filtration. The filter cake was then washed with cold (5° C.) water (6 kgs). The product cake was air dried in the filter crock under vacuum for approximately 72 hours. The product was then transferred to three drying trays and dried in a vacuum oven at 50° C. for 79 hours. The temperature of the vacuum oven was then raised to 65° C. for 85 additional hours. The product was off-loaded as a single batch to give 2568 grams (93.4% yield) of intermediate grade 3-({[(3R,5R)-3-butyl-3-ethyl-7-(methyloxy)-1,1-dioxido-5-phenyl-2,3,4,5-tetrahydro-1,4-benzothiazepin-8-yl]methyl}amino)pentanedioic acid as an off-white solid.

Intermediate grade 3-({[(3R,5R)-3-butyl-3-ethyl-7-(methyloxy)-1,1-dioxido-5-phenyl-2,3,4,5-tetrahydro-1,4-benzothiazepin-8-yl]methyl}amino)pentanedioic acid was dissolved (4690 g) in a mixture of glacial acetic acid (8850 g) and purified water (4200 g) at 70° C. The resulting solution was transferred through a 5 micron polishing filter while maintaining the temperature above 30° C. The reactor and filter were rinsed through with a mixture of glacial acetic acid (980 g) and purified water (470 g). The solution temperature was adjusted to 50° C. Filtered purified water (4230 g) was added to the solution. The cloudy solution was then seeded with crystalline 3-({[(3R,5R)-3-butyl-3-ethyl-7-(methyloxy)-1,1-dioxido-5-phenyl-2,3,4,5-tetrahydro-1,4-benzothiazepin-8-yl]methyl}amino)pentanedioic acid (10 g). While maintaining the temperature at 50° C., filtered purified water was charged to the slurry at a controlled rate (11030 g over 130 minutes). Additional filtered purified water was then added to the slurry at a faster controlled rate (20740 g over 100 minutes). A final charge of filtered purified water (3780 g) was made to the slurry. The slurry was then cooled to 10° C. at a linear rate over 135 minutes. The solids were filtered over sharkskin filter paper to remove the mother liquor. The cake was then rinsed with filtered ethyl acetate (17280 g) then the wash liquors were removed by filtration. The resulting wet-cake was isolated into trays and dried under vacuum at 50° C. for 23 hours. The temperature was then increased to 60° C. and drying was continued for an additional 24 hours to afford crystalline 3-({[(3R,5R)-3-butyl-3-ethyl-7-(methyloxy)-1,1-dioxido-5-phenyl-2,3,4,5-tetrahydro-1,4-benzothiazepin-8-yl]methyl}amino)pentanedioic acid (3740 g, 79.7% yield) as a white solid.

To a slurry of this crystalline 3-({[(3R,5R)-3-butyl-3-ethyl-7-(methyloxy)-1,1-dioxido-5-phenyl-2,3,4,5-tetrahydro-1,4-benzothiazepin-8-yl]methyl}amino)pentanedioic acid (3660 g) and filtered purified water (3.6 L) was added filtered glacial acetic acid (7530 g). The temperature was increased to 60° C. and full dissolution was observed. The temperature was reduced to 55° C., filtered, and treated with purified water (3.2 L). The solution was then seeded with crystalline 3-({[(3R,5R)-3-butyl-3-ethyl-7-(methyloxy)-1,1-dioxido-5-phenyl-2,3,4,5-tetrahydro-1,4-benzothiazepin-8-yl]methyl}amino)pentanedioic acid (18 g) to afford a slurry. Filtered purified water was charged to the slurry at a controlled rate (9 L over 140 minutes). Additional filtered purified water was then added to the slurry at a faster controlled rate (18 L over 190 minutes). The slurry was then cooled to 10° C. at a linear rate over 225 minutes. The solids were filtered over sharkskin filter paper to remove the mother liquor. The cake was then rinsed with filtered purified water (18 L), and the wash liquors were removed by filtration. The resulting wetcake was isolated into trays and dried under vacuum at 60° C. for 18.5 hours to afford a crystalline 3-({[(3R,5R)-3-butyl-3-ethyl-7-(methyloxy)-1,1-dioxido-5-phenyl-2,3,4,5-tetrahydro-1,4-benzothiazepin-8-yl]methyl}amino)pentanedioic acid (3330 g, 90.8% yield) as a white solid which was analyzed for crystallinity as summarized below.

Example 27

N-{[(3R,5R)-3-butyl-3-ethyl-7-(methyloxy)-1,1-dioxido-5-phenyl-2,3,4,5-tetrahydro-1,4-benzothiazepin-8-yl]methyl}-L-aspartic acid trifluoroacetate salt

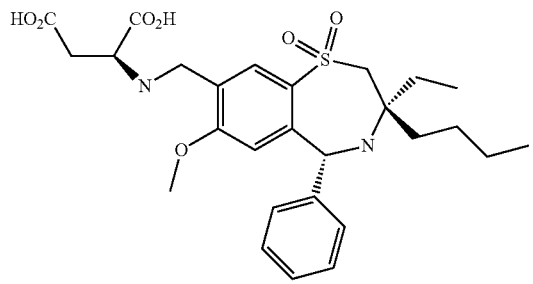 [SMILES: CCCC[C@]1(CC)CS(=O)(=O)c2cc(CN[C@@H](CC(=O)O)C(=O)O)c(OC)cc2[C@@H](c2ccccc2)N1]

Step 1: To a solution of (3R,5R)-3-butyl-3-ethyl-7-(methyloxy)-5-phenyl-2,3,4,5-tetrahydro-1,4-benzothiazepine-8-carbaldehyde 1,1-dioxide (33 mg, 0.079 mmol) in 1,2-dichloroethane (3 mL) was added dimethyl L-aspartate (12.80 mg, 0.079 mmol) and NaHB(OAc)$_3$ (33.7 mg, 0.159 mmol). The reaction mixture was stirred at room temperature overnight then treated with aqueous potassium carbonate solution. The layers were separated, and the aqueous layer was extracted with DCM. The combined organic layers were washed with H$_2$O, saturated brine, dried (Na$_2$SO$_4$), filtered, and concentrated under reduced pressure. Purification by RP-HPLC (eluting with MeCN/H$_2$O with 0.05% TFA-H$_2$O and 0.05% TFA-MeCN) twice afforded dimethyl N-{[(3R,5R)-3-butyl-3-ethyl-7-(methyloxy)-1,1-dioxido-5-phenyl-2,3,4,5-tetrahydro-1,4-benzothiazepin-8-yl]methyl}-L-aspartate (21 mg, 46%) as a colorless oil: ES-LCMS m/z 561 (M+H)$^+$.

Step 2: To a solution of dimethyl N-{[(3R,5R)-3-butyl-3-ethyl-7-(methyloxy)-1,1-dioxido-5-phenyl-2,3,4,5-tetrahydro-1,4-benzothiazepin-8-yl]methyl}-L-aspartate (21 mg, 0.037 mmol) in a 1:1:1 mixture of THF/MeOH/H$_2$O (3 mL) was added lithium hydroxide (17.94 mg, 0.749 mmol). The reaction mixture was stirred at room temperature overnight, treated with trifluoroacetic acid, and concentrated to 1 mL. Purification by RP-HPLC (eluting with MeCN/H$_2$O with 0.05% TFA-H$_2$O and 0.05% TFA-MeCN) afforded the title compound (25.4 mg, 89%, TFA salt) as a white solid: $^1$H NMR (MeOH-d$_4$) δ ppm 8.10 (s, 1H), 7.32-7.56 (m, 5H), 6.40 (s, 1H), 6.17 (s, 1H), 4.38 (d, J=7.6 Hz, 2H), 4.19 (dd, J=6.8, 4.3 Hz, 1H), 3.55-3.66 (m, 4H), 3.23 (d, J=15.0 Hz, 1H), 2.88-3.13 (m, 2H), 2.38 (d, J=4.1 Hz, 1H), 1.79-1.95 (m, 1H), 1.62-1.77 (m, 1H), 1.42-1.58 (m, 1H), 1.03-1.40 (m, 4H), 0.91 (t, J=7.4 Hz, 3H), 0.81 (t, J=6.8 Hz, 3H); ES-LCMS m/z 533 (M+H)$^+$.

Example 28

N-{[(3R,5R)-3-butyl-3-ethyl-7-(methyloxy)-1,1-dioxido-5-phenyl-2,3,4,5-tetrahydro-1,4-benzothiazepin-8-yl]methyl}-D-aspartic acid trifluoroacetate salt

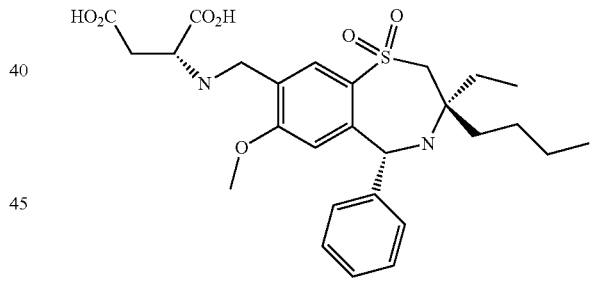

Step 1: To a solution of (3R,5R)-3-butyl-3-ethyl-7-(methyloxy)-5-phenyl-2,3,4,5-tetrahydro-1,4-benzothiazepine-8-carbaldehyde 1,1-dioxide (33 mg, 0.079 mmol) in 1,2-dichloroethane (3 mL) was added dimethyl D-aspartate (12.80 mg, 0.079 mmol) and NaHB(OAc)$_3$ (33.7 mg, 0.159 mmol). The reaction mixture was stirred at room temperature overnight then treated with an aqueous potassium carbonate solution. The layers were separated, and the aqueous layer was extracted with DCM. The combined organic layers were washed with H$_2$O, saturated brine, dried (Na$_2$SO$_4$), filtered, and concentrated under reduced pressure. Purification by RP-HPLC (MeCN/H$_2$O with 0.05% TFA) afforded dimethyl N-{[(3R,5R)-3-butyl-3-ethyl-7-(methyloxy)-1,1-dioxido-5-phenyl-2,3,4,5-tetrahydro-1,4-benzothiazepin-8-yl]methyl}-D-aspartate (22 mg, 48%) as a colorless oil: ES-LCMS m/z 561 (M+H)$^+$.

Step 2: To a solution of dimethyl N-{[(3R,5R)-3-butyl-3-ethyl-7-(methyloxy)-1,1-dioxido-5-phenyl-2,3,4,5-tetrahydro-1,4-benzothiazepin-8-yl]methyl}-D-aspartate (22 mg, 0.039 mmol) in a 1:1:1 mixture of THF/MeOH/H₂O (3 mL) was added lithium hydroxide (18.79 mg, 0.785 mmol). The reaction mixture was stirred at room temperature overnight, treated with trifluoroacetic acid, and concentrated under reduced pressure. Purification by RP-HPLC (MeCN/H₂O with 0.05% TFA) afforded the title compound (10.9 mg, 37%, TFA salt) as a white solid: $^1$H NMR (MeOH-d₄) δ ppm 8.10 (s, 1H), 7.33-7.54 (m, 5H), 6.42 (s, 1H), 6.18 (s, 1H), 4.31-4.45 (m, 2H), 4.13-4.24 (m, 1H), 3.58-3.67 (m, 4H), 2.92-3.14 (m, 2H), 1.80-1.96 (m, 1H), 1.58-1.78 (m, 1H), 1.43-1.57 (m, 1H), 1.04-1.41 (m, 4H), 0.91 (t, J=7.4 Hz, 3H), 0.83 (t, J=6.8 Hz, 3H); ES-LCMS m/z 533 (M+H)⁺.

Example 29

N-{[(3R,5R)-3-butyl-3-ethyl-7-(methyloxy)-1,1-dioxido-5-phenyl-2,3,4,5-tetrahydro-1,4-benzothiazepin-8-yl]methyl}-N-methyl-β-alanine trifluoroacetate salt

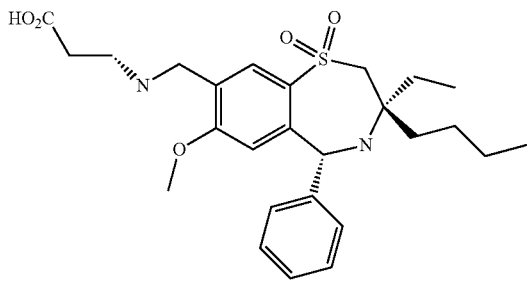

Step 1: To a solution of (3R,5R)-3-butyl-3-ethyl-7-(methyloxy)-5-phenyl-2,3,4,5-tetrahydro-1,4-benzothiazepine-8-carbaldehyde 1,1-dioxide (200 mg, 0.481 mmol) in 1,2-dichloroethane (10 mL) was added 1,1-dimethylethyl β-alaninate (175 mg, 0.963 mmol) and acetic acid (0.276 mL, 4.81 mmol). After 1 hr of stirring, NaHB(OAc)₃ (255 mg, 1.203 mmol) was added to the reaction mixture. The reaction mixture was stirred at room temperature for 1 hr then treated with an aqueous sodium carbonate solution. The layers were separated, and the aqueous layer was extracted with DCM. The combined organic layers were washed with H₂O, saturated brine, dried (Na₂SO₄), filtered, and concentrated under reduced pressure to affored 1,1-dimethylethyl N-{[(3R,5R)-3-butyl-3-ethyl-7-(methyloxy)-1,1-dioxido-5-phenyl-2,3,4,5-tetrahydro-1,4-benzothiazepin-8-yl]methyl}-β-alaninate (210 mg, 80%) as an oil: ES-LCMS m/z 559 (M+H)⁺.

Step 2: To 1,1-dimethylethyl N-{[(3R,5R)-3-butyl-3-ethyl-7-(methyloxy)-1,1-dioxido-5-phenyl-2,3,4,5-tetrahydro-1,4-benzothiazepin-8-yl]methyl}-β-alaninate (210 mg, 0.289 mmol) was added 4N hydrogen chloride (3.61 mL, 4N solution in 1,4-dioxane, 14.46 mmol). The reaction mixture was stirred at room temperature overnight then concentrated under reduced pressure. Purification by RP-HPLC (MeCN/H₂O with 0.05% TFA) afforded the title compound (143 mg, 82%, TFA salt) as a white solid: $^1$H NMR (CDCl₃) δ ppm 8.13 (s, 1H), 7.35-7.62 (m, 5H), 6.35 (s, 1H), 6.24 (s, 1H), 4.12-4.42 (m, 2H), 3.62 (s, 3H), 3.33-3.52 (m, 2H), 3.25 (br. s., 2H), 2.79 (br. s., 2H), 2.35 (br. s., 1H), 1.89-2.10 (m, 1H), 1.68-1.82 (m, 1H), 1.51-1.68 (m, 1H), 1.18-1.46 (m, 3H), 1.00-1.17 (m, 1H), 0.92 (t, J=7.2 Hz, 3H), 0.86 (t, J=6.8 Hz, 3H); ES-LCMS m/z 503 (M+H)⁺.

Examples 30 and 31

4-({[(3R,5R)-3-butyl-3-ethyl-7-(methyloxy)-1,1-dioxido-5-phenyl-2,3,4,5-tetrahydro-1,4-benzothiazepin-8-yl]methyl}amino)butanoic acid trifluoroacetate salt and 1-{[(3R,5R)-3-butyl-3-ethyl-7-(methyloxy)-1,1-dioxido-5-phenyl-2,3,4,5-tetrahydro-1,4-benzothiazepin-8-yl]methyl}-2-pyrrolidinone trifluoroacetate salt

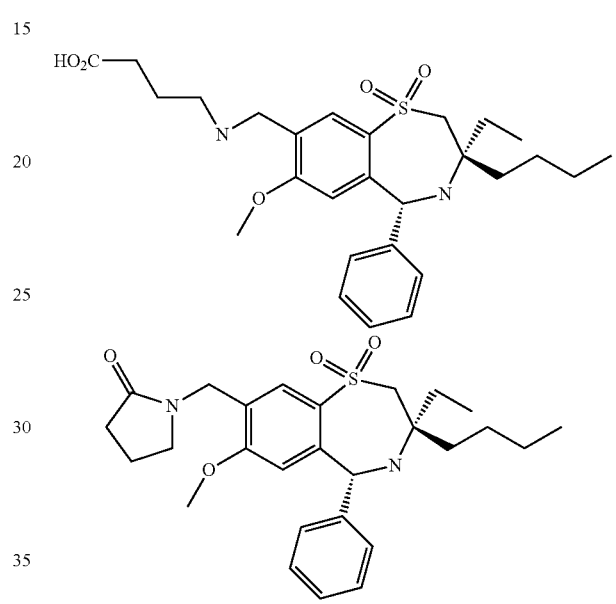

Step 1: To a solution of (3R,5R)-3-butyl-3-ethyl-7-(methyloxy)-5-phenyl-2,3,4,5-tetrahydro-1,4-benzothiazepine-8-carbaldehyde 1,1-dioxide (200 mg, 0.481 mmol) in 1,2-dichloroethane (5 mL) was added methyl 4-aminobutanoate (111 mg, 0.722 mmol) and acetic acid (0.276 mL, 4.81 mmol). The reaction mixture was stirred at room temperature overnight, treated with NaHB(OAc)₃ (255 mg, 1.203 mmol), and stirred for 1 hr. The reaction mixture was treated with aqueous sodium carbonate solution and extracted with DCM. The organic layer was washed with H₂O, saturated brine, dried (Na₂SO₄), filtered, and concentrated under reduced pressure. Purification using silica gel (EtOAc:Hexanes=20:80 to 60:40) afforded 4-({[(3R,5R)-3-butyl-3-ethyl-7-(methyloxy)-1,1-dioxido-5-phenyl-2,3,4,5-tetrahydro-1,4-benzothiazepin-8-yl]methyl}amino)butanoic acid (210 mg, 83%) as a light yellow oil: ES-LCMS m/z 517 (M+H)⁺.

Step 2: To a solution of 4-({[(3R,5R)-3-butyl-3-ethyl-7-(methyloxy)-1,1-dioxido-5-phenyl-2,3,4,5-tetrahydro-1,4-benzothiazepin-8-yl]methyl}amino)butanoic acid (210 mg, 0.406 mmol) in a 1:1:1 mixture of THF/MeOH/H₂O (3 mL) was added lithium hydroxide (9.73 mg, 0.406 mmol). The reaction mixture was stirred at room temperature overnight then concentrated under reduced pressure. Purification by RP-HPLC (eluting with MeCN/H₂O with 0.05% TFA-H₂O and 0.05% TFA-MeCN) afforded Example 30 (45.6 mg, 44%) trifluoroacetate salt as a white solid: $^1$H NMR (DMSO-d₆) δ ppm 8.67 (br. s., 2H), 8.09 (s, 1H), 7.30-7.56 (m, 5H), 6.18 (s, 1H), 5.97 (s, 1H), 4.16 (br. s., 2H), 3.63 (d, J=14.8 Hz, 1H), 3.49 (s, 3H), 3.09 (d, J=15.0 Hz, 1H), 2.88-3.01 (m, 2H), 2.33 (t, J=7.2 Hz, 2H), 1.99-2.15 (m, 1H), 1.67-1.90 (m, 3H), 1.35-1.61 (m, 2H), 0.96-1.32 (m, 4H), 0.81 (t, J=7.2 Hz, 3H), 0.76 (t, J=6.6 Hz, 3H); ES-LCMS m/z 503 (M+H)+ and Example 31 (47.8 mg, 48%) trifluoroacetate salt as a white solid: $^1$H NMR (DMSO-d$_6$) δ ppm 7.69 (s, 1H), 7.30-7.61 (m, 5H), 6.22 (br. s., 1H), 6.04 (br. s., 1H), 4.23-4.44 (m, 2H), 3.49 (s, 3H), 2.12-2.34 (m, 3H), 1.75-2.02 (m, 3H), 1.35-1.74 (m, 2H), 1.11-1.34 (m, 3H), 0.94-1.10 (m, 1H), 0.64-0.89 (m, 6H); ES-LCMS m/z 485 (M+H)+.

Example 32

N-{[(3R,5R)-3-butyl-3-ethyl-7-(methyloxy)-1,1-dioxido-5-phenyl-2,3,4,5-tetrahydro-1,4-benzothiazepin-8-yl]methyl}-2-methylalanine trifluoroacetate salt

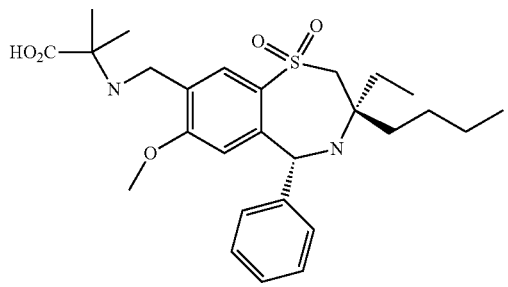 [SMILES: CCCC[C@]1(CC)CS(=O)(=O)c2cc(CNC(C)(C)C(=O)O)c(OC)cc2[C@@H](c2ccccc2)N1]

Step 1: To a solution of (3R,5R)-3-butyl-3-ethyl-7-(methyloxy)-5-phenyl-2,3,4,5-tetrahydro-1,4-benzothiazepine-8-carbaldehyde 1,1-dioxide (200 mg, 0.481 mmol) in 1,2-dichloroethane (300 mL) was added methyl 2-methylalaninate (113 mg, 0.963 mmol) and acetic acid (0.138 mL, 2.406 mmol). The reaction mixture was stirred at room temperature for 1 hr. NaHB(OAc)$_3$ (255 mg, 1.203 mmol) was added, and the reaction mixture was stirred at room temperature for 1 hr. Aqueous sodium carbonate solution was added to the reaction mixture which was then extracted with DCM. The organic layer was washed with H$_2$O, saturated brine, dried, (Na$_2$SO$_4$), filtered, and concentrated under reduced pressure. Purification using silica gel (EtOAc:Hexanes=20:80 to 60:40) afforded methyl N-{[(3R,5R)-3-butyl-3-ethyl-7-(methyloxy)-1,1-dioxido-5-phenyl-2,3,4,5-tetrahydro-1,4-benzothiazepin-8-yl]methyl}-2-methylalaninate (230 mg, 91%): ES-LCMS m/z 517 (M+H)+.

Step 2: To a solution of methyl N-{[(3R,5R)-3-butyl-3-ethyl-7-(methyloxy)-1,1-dioxido-5-phenyl-2,3,4,5-tetrahydro-1,4-benzothiazepin-8-yl]methyl}-2-methylalaninate (230 mg, 0.245 mmol) in a 1:1:1 mixture of THF/MeOH/H$_2$O (15 mL) was added lithium hydroxide (5.6 mg, 0.245 mmol). The reaction mixture was stirred at room temperature overnight then partially concentrated under reduced pressure to remove the organic solvents. The residue was acidified with trifluoroacetic acid. Purification by RP-HPLC (eluting with MeCN/H$_2$O with 0.05% TFA-H$_2$O and 0.05% TFA-MeCN) afforded the title compound (102 mg, 66%, TFA salt) as a white solid: $^1$H NMR (DMSO-d$_6$) δ ppm 8.10 (s, 1H), 7.28-7.55 (m, 5H), 6.18 (s, 1H), 6.00 (s, 1H), 4.14 (d, J=17.6 Hz, 2H), 3.64 (d, J=15.0 Hz, 1H), 3.49 (s, 3H), 3.13 (d, J=14.8 Hz, 1H), 2.46-2.55 (m, 1H), 2.00-2.23 (m, 1H), 1.70-1.86 (m, 1H), 1.35-1.49 (m, 1H), 0.98-1.31 (m, 4H), 0.82 (t, J=7.2 Hz, 3H), 0.77 (t, J=6.8 Hz, 3H); ES-LCMS m/z 503 (M+H)+.

Example 33

[2-({[(3R,5R)-3-butyl-3-ethyl-7-(methyloxy)-1,1-dioxido-5-phenyl-2,3,4,5-tetrahydro-1,4-benzothiazepin-8-yl]methyl}amino)ethyl]phosphonic acid trifluoroacetate salt

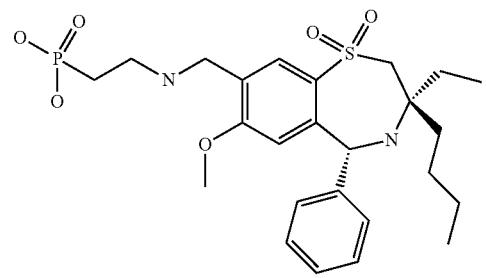 [SMILES: CCCC[C@]1(CC)CS(=O)(=O)c2cc(CNCCP(=O)(O)O)c(OC)cc2[C@@H](c2ccccc2)N1]

Step 1: To a solution of (3R,5R)-3-butyl-3-ethyl-7-(methyloxy)-5-phenyl-2,3,4,5-tetrahydro-1,4-benzothiazepine-8-carbaldehyde 1,1-dioxide (50 mg, 0.120 mmol) in 1,2-dichloroethane (3 mL) was added diethyl (2-aminoethyl)phosphonate (109 mg, 0.602 mmol). The reaction mixture was stirred for 3 h then treated with NaHB(OAc)$_3$ (128 mg, 0.602 mmol). The reaction mixture was stirred at room temperature for 2 hr then treated with H$_2$O and 1N hydrochloric acid solution. The resulting mixture was concentrated under reduced pressure. Purification by RP-HPLC (eluting with MeCN/H$_2$O with 0.05% TFA-H$_2$O and 0.05% TFA-MeCN) afforded diethyl [2-({[(3R,5R)-3-butyl-3-ethyl-7-(methyloxy)-1,1-dioxido-5-phenyl-2,3,4,5-tetrahydro-1,4-benzothiazepin-8-yl]methyl}amino)ethyl]phosphonate (70 mg, 71%) as a white solid: ES-LCMS m/z 581 (M+H)+.

Step 2: To a solution of diethyl [2-({[(3R,5R)-3-butyl-3-ethyl-7-(methyloxy)-1,1-dioxido-5-phenyl-2,3,4,5-tetrahydro-1,4-benzothiazepin-8-yl]methyl}amino)ethyl]phosphonate (70 mg, 0.121 mmol) in DCM (3 mL) was added bromotrimethylsilane (0.065 mL, 0.499 mmol). The reaction mixture was stirred at room temperature overnight. Additional bromotrimethylsilane (0.16 mL, 1.21 mmol) was added. The reaction mixture was stirred overnight, concentrated under reduced pressure and treated with H$_2$O. Purification by RP-HPLC (eluting with MeCN/H$_2$O with 0.05% TFA-H$_2$O and 0.05% TFA-MeCN) afforded the title product (51 mg, 55%, TFA salt) as a white solid: $^1$H NMR (MeOH-d$_4$) δ ppm 8.09 (s, 1H), 7.30-7.53 (m, 5H), 6.39 (s, 1H), 6.15 (s, 1H), 4.12-4.35 (m, 2H), 3.57-3.65 (m, 4H), 3.14-3.24 (m, 3H), 2.23-2.40 (m, 1H), 1.76-2.06 (m, 3H), 1.59-1.75 (m, 1H), 1.38-1.55 (m, 1H), 1.00-1.38 (m, 4H), 0.90 (t, J=7.4 Hz, 3H), 0.81 (t, J=7.0 Hz, 3H); ES-LCMS m/z 525 (M+H)+.

Example 34 ethyl hydrogen [2-({[(3R,5R)-3-butyl-3-ethyl-7-(methyloxy)-1,1-dioxido-5-phenyl-2,3,4,5-tetrahydro-1,4-benzothiazepin-8-yl]methyl}amino)ethyl]phosphonate trifluoroacetate salt

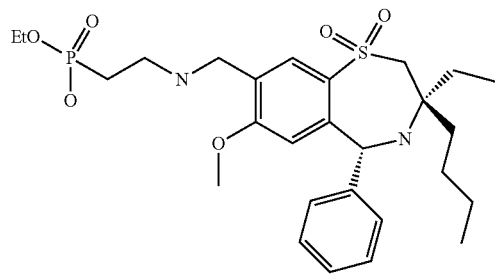 [SMILES: CCCC[C@]1(CC)CS(=O)(=O)c2cc(CNCCP(=O)(O)OCC)c(OC)cc2[C@@H](c2ccccc2)N1]

To a solution {[(3R,5R)-3-butyl-3-ethyl-7-(methyloxy)-1,1-dioxido-5-phenyl-2,3,4,5-tetrahydro-1,4-benzothiazepin-8-yl]methyl}amine (50 mg, 0.120 mmol) in DMF (4 mL) was added potassium carbonate (49.8 mg, 0.360 mmol) and diethyl (2-bromoethyl)phosphonate (17.65 mg, 0.072 mmol). The reaction mixture was heated at 90° C. overnight, cooled to room temperature, and concentrated under reduced pressure. To the residue was added trifluoroacetic acid, and the solution was concentrated under reduced pressure. Purification by RP-HPLC (MeCN/H$_2$O with 0.05% TFA) afforded the title product (34 mg, 95%, TFA salt) as a white solid: $^1$H NMR (MeOH-d$_4$) δ ppm 8.04 (s, 1H), 7.27-7.59 (m, 5H), 6.38 (s, 1H), 6.04-6.21 (m, 2H), 3.88-4.24 (m, 4H), 3.50-3.68 (m, 4H), 3.16-3.35 (m, 3H), 2.20-2.49 (m, 1H), 1.78-1.95 (m, 1H), 1.60-1.75 (m, 1H), 1.41-1.58 (m, 1H), 1.01-1.36 (m, 7H), 0.89 (t, J=7.6 Hz, 3H), 0.81 (t, J=6.8 Hz, 3H); ES-LCMS m/z 553 (M+H)$^+$.

Example 35

2-({[(3R,5R)-3-butyl-3-ethyl-7-(methyloxy)-1,1-dioxido-5-phenyl-2,3,4,5-tetrahydro-1,4-benzothiazepin-8-yl]methyl}amino)ethanesulfonic acid ammonium salt

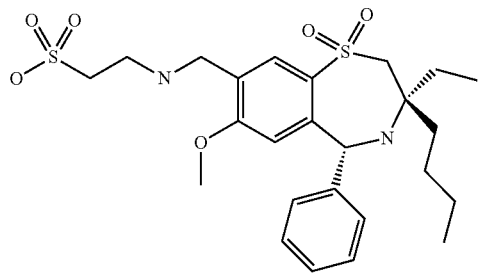 [SMILES: CCCC[C@]1(CC)CS(=O)(=O)c2cc(CNCCS(=O)(=O)O)c(OC)cc2[C@@H](c2ccccc2)N1]

To a solution of {[(3R,5R)-3-butyl-3-ethyl-7-(methyloxy)-1,1-dioxido-5-phenyl-2,3,4,5-tetrahydro-1,4-benzothiazepin-8-yl]methyl}amine (100 mg, 0.240 mmol) in DMF (4 mL) was added 2-bromoethane sulfonic acid sodium salt (25.3 mg, 0.120 mmol). The reaction mixture was stirred at 70° C. overnight, cooled to room temperature, acidified with trifluoroacetic acid, and concentrated under reduced pressure. Purification by RP-HPLC (MeCN/H$_2$O with 0.05% TFA), followed by further purification with RP-HPLC (eluting with MeCN/H$_2$O with 0.5% ammonium hydroxide in H$_2$O) afforded the title compound (27.6 mg, 54%, ammonium salt) as a white solid: $^1$H NMR (MeOH-d$_4$) δ ppm 8.03 (s, 1H), 7.19-7.54 (m, 5H), 6.30 (s, 1H), 6.06 (s, 1H), 4.20 (s, 2H), 3.58 (s, 3H), 3.49 (d, J=15.0 Hz, 1H), 3.30-3.38 (m, 2H), 2.96-3.15 (m, 3H), 2.09-2.31 (m, 1H), 1.71-1.88 (m, J=5.1 Hz, 1H), 1.49-1.70 (m, 1H), 1.34-1.49 (m, 1H), 1.05-1.32 (m, 4H), 0.87 (t, J=7.4 Hz, 3H), 0.78 (t, J=6.6 Hz, 3H); ES-LCMS m/z 525 (M+H)$^+$.

Example 36

2,2'-({[(3R,5R)-3-butyl-3-ethyl-7-(methyloxy)-1,1-dioxido-5-phenyl-2,3,4,5-tetrahydro-1,4-benzothiazepin-8-yl]methyl}imino)diethanesulfonic acid trifluoroacetate salt

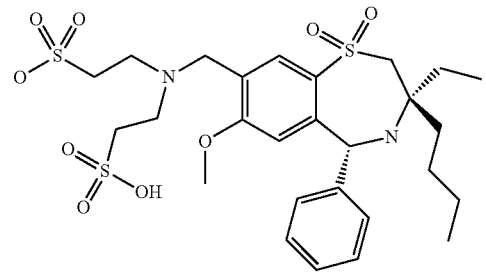 [SMILES: CCCC[C@]1(CC)CS(=O)(=O)c2cc(CN(CCS(=O)(=O)O)CCS(=O)(=O)O)c(OC)cc2[C@@H](c2ccccc2)N1]

To a solution of {[(3R,5R)-3-butyl-3-ethyl-7-(methyloxy)-1,1-dioxido-5-phenyl-2,3,4,5-tetrahydro-1,4-benzothiazepin-8-yl]methyl}amine (25 mg, 0.060 mmol) in DMF (2 mL) was added 2-bromoethane sulfonic acid sodium salt (127 mg, 0.600 mmol). The reaction mixture was stirred at 70° C. overnight, cooled to room temperature, acidified to pH 3-4 with acetic acid, and concentrated under reduced pressure. Purification by RP-HPLC (MeCN/H$_2$O with 0.05% TFA) afforded the title product (13 mg, 24%, TFA salt) as a white solid: $^1$H NMR (MeOH-d$_4$) δ ppm 8.23 (s, 1H), 7.42-7.80 (m, 5H), 6.68 (s, 1H), 6.53 (s, 1H), 4.72 (d, J=13.3 Hz, 1H), 4.40 (d, J=13.5 Hz, 1H), 3.95 (d, J=15.8 Hz, 1H), 3.41-3.83 (m, 8H), 2.60-2.85 (m, 1H), 1.85-2.27 (m, 2H), 1.57-1.80 (m, 1H), 1.22-1.53 (m, 3H), 0.71-1.17 (m, 7H); ES-LCMS m/z 633 (M+H)$^+$.

Example 37

2-({[(3R,5R)-3-butyl-3-ethyl-7-(methyloxy)-1,1-dioxido-5-phenyl-2,3,4,5-tetrahydro-1,4-benzothiazepin-8-yl]methyl}amino)-2-oxoethanesulfonic acid

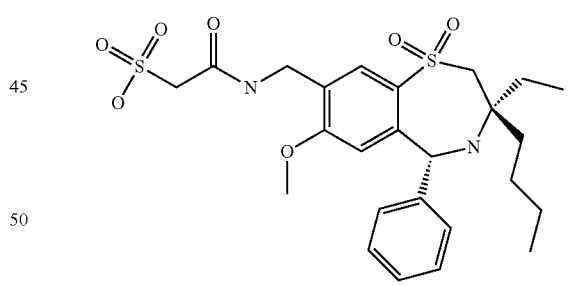

To a solution of N-{[(3R,5R)-3-butyl-3-ethyl-7-(methyloxy)-1,1-dioxido-5-phenyl-2,3,4,5-tetrahydro-1,4-benzothiazepin-8-yl]methyl}-2-chloroacetamide (55 mg, 0.112 mmol) in a 1:1 mixture of ethanol/H$_2$O (6 mL) was added sodium sulfite (141 mg, 1.115 mmol). The reaction mixture was stirred at 80° C. overnight, cooled to room temperature, acidified with acetic acid to pH 3-4, and concentrated under reduced pressure. Purification using silica gel (MeOH:DCM=0:100 to 30:70) afforded the title compound (32 mg, 52%) as an off-white solid: $^1$H NMR (MeOH-d$_4$) δ ppm 7.94 (s, 1H), 7.16-7.68 (m, 5H), 6.28 (br. s., 1H), 6.06 (br. s., 1H), 4.39 (br. s., 2H), 3.63-3.78 (m, 2H), 3.43-3.59 (m, 4H), 2.06-2.49 (m, 1H), 1.01-1.94 (m, 7H), 0.89 (t, J=7.4 Hz, 3H), 0.81 (t, J=6.6 Hz, 3H); ES-LCMS m/z 539 (M+H)$^+$.

Example 38

[2-({[(3R,5R)-3-butyl-3-ethyl-7-(methyloxy)-1,1-dioxido-5-phenyl-2,3,4,5-tetrahydro-1,4-benzothiazepin-8-yl]methyl}amino)-2-oxoethyl]phosphonic acid trifluoroacetate salt

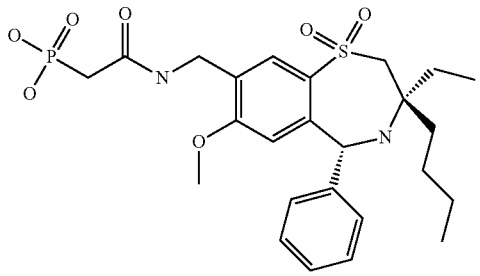 [SMILES: CCCC[C@]1(CC)CS(=O)(=O)c2cc(CNC(=O)CP(=O)(O)O)c(OC)cc2[C@@H](c2ccccc2)N1]

Step 1: A mixture of N-{[(3R,5R)-3-butyl-3-ethyl-7-(methyloxy)-1,1-dioxido-5-phenyl-2,3,4,5-tetrahydro-1,4-benzothiazepin-8-yl]methyl}-2-chloroacetamide (82 mg, 0.166 mmol) and triethyl phosphite (2.9 mL, 16.63 mmol) was stirred at 135° C. overnight, cooled to room temperature, and concentrated under reduced pressure. The crude diethyl [2-({[(3R,5R)-3-butyl-3-ethyl-7-(methyloxy)-1,1-dioxido-5-phenyl-2,3,4,5-tetrahydro-1,4-benzothiazepin-8-yl]methyl}amino)-2-oxoethyl]phosphonate (99 mg, 98%) was used in the next step without further purification: ES-LCMS m/z 595 (M+H)$^+$.

Step 2: To a solution of diethyl [2-({[(3R,5R)-3-butyl-3-ethyl-7-(methyloxy)-1,1-dioxido-5-phenyl-2,3,4,5-tetrahydro-1,4-benzothiazepin-8-yl]methyl}amino)-2-oxoethyl]phosphonate (99 mg, 0.166 mmol) in DCM (5 mL) was added bromotrimethylsilane (0.065 mL, 0.499 mmol), and the reaction mixture was stirred at room temperature overnight. Additional bromotrimethylsilane (0.216 mL, 1.66 mmol) was added, and the reaction mixture was stirred overnight. The reaction mixture was then concentrated under reduced pressure and treated with H$_2$O. Purification by RP-HPLC (MeCN/H$_2$O with 0.05% TFA) afforded the title compound (69 mg, 63%, TFA salt) as a gray white solid: $^1$H NMR (MeOH-d$_4$) δ ppm 8.01 (s, 1H), 7.35-7.75 (m, 5H), 6.51 (s, 1H), 6.42 (s, 1H), 4.43 (d, J=14.8 Hz, 1H), 4.24 (d, J=14.1 Hz, 1H), 3.85 (d, J=15.4 Hz, 1H), 3.66 (br. s., 1H), 3.61 (s, 3H), 2.57-2.87 (m, 3H), 1.96-2.13 (m, 2H), 1.56-1.75 (m, 1H), 1.22-1.49 (m, 3H), 0.99 (t, J=7.4 Hz, 3H), 0.89 (t, J=6.8 Hz, 3H); ES-LCMS m/z 539 (M+H)$^+$.

Example 39

N-[2-({[(3R,5R)-3-butyl-3-ethyl-7-(methyloxy)-1,1-dioxido-5-phenyl-2,3,4,5-tetrahydro-1,4-benzothiazepin-8-yl]methyl}amino)-2-oxoethyl]glycine trifluoroacetate salt

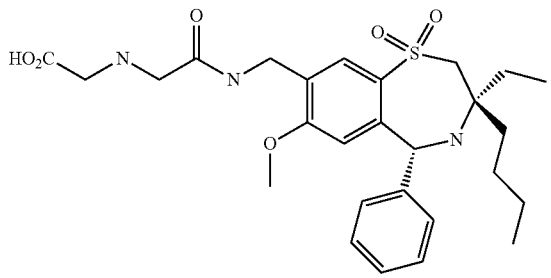 [SMILES: CCCC[C@]1(CC)CS(=O)(=O)c2cc(CNC(=O)CNCC(=O)O)c(OC)cc2[C@@H](c2ccccc2)N1]

Step 1: To a solution of N-{[(3R,5R)-3-butyl-3-ethyl-7-(methyloxy)-1,1-dioxido-5-phenyl-2,3,4,5-tetrahydro-1,4-benzothiazepin-8-yl]methyl}-2-chloroacetamide (50 mg, 0.101 mmol) in DMF (3 mL) was added potassium carbonate (56.1 mg, 0.406 mmol), glycine methyl ester hydrochloride salt (63.7 mg, 0.507 mmol) and potassium iodide (67.3 mg, 0.406 mmol). The reaction mixture was stirred at 60° C. overnight, cooled to room temperature, and partitioned between H$_2$O and EtOAc. The organic layer was washed with saturated brine, dried (Na$_2$SO$_4$), filtered, and concentrated under reduced pressure. Purification using silica gel (MeOH:DCM=0:100 to 20:80) afforded methyl N-[2-({[(3R,5R)-3-butyl-3-ethyl-7-(methyloxy)-1,1-dioxido-5-phenyl-2,3,4,5-tetrahydro-1,4-benzothiazepin-8-yl]methyl}amino)-2-oxoethyl]glycinate (50 mg, 90%) as a colorless oil: ES-LCMS m/z 546 (M+H)$^+$.

Step 2: To a solution of methyl N-[2-({[(3R,5R)-3-butyl-3-ethyl-7-(methyloxy)-1,1-dioxido-5-phenyl-2,3,4,5-tetrahydro-1,4-benzothiazepin-8-yl]methyl}amino)-2-oxoethyl]glycinate (50 mg, 0.092 mmol) in a 1:1:1 mixture of THF/MeOH/H$_2$O (9 mL) was added lithium hydroxide (54.9 mg, 2.291 mmol). The reaction mixture was stirred at room temperature overnight, concentrated under reduced pressure to remove the organic solvents, and acidified with trifluoroacetic acid. Purification by RP-HPLC (MeCN/H$_2$O with 0.05% TFA) afforded the title compound (15 mg, 21%, TFA salt) as a white solid: $^1$H NMR (MeOH-d$_4$) δ ppm 7.90 (s, 1H), 7.25-7.57 (m, 5H), 6.33 (s, 1H), 6.16 (s, 1H), 4.39 (s, 2H), 3.89 (d, J=5.9 Hz, 3H), 3.61 (d, J=15.2 Hz, 1H), 3.55 (s, 3H), 2.27-2.49 (m, 1H), 1.79-1.98 (m, 1H), 1.62-1.79 (m, 1H), 1.42-1.58 (m, 1H), 1.17-1.38 (m, 3H), 0.99-1.17 (m, 1H), 0.90 (t, J=7.4 Hz, 3H), 0.82 (t, J=6.8 Hz, 3H); ES-LCMS m/z 532 (M+H)$^+$.

Example 40

(2-{[2-({[(3R,5R)-3-butyl-3-ethyl-7-(methyloxy)-1,1-dioxido-5-phenyl-2,3,4,5-tetrahydro-1,4-benzothiazepin-8-yl]methyl}amino)-2-oxoethyl]amino}ethyl)phosphonic acid trifluoroacetate salt

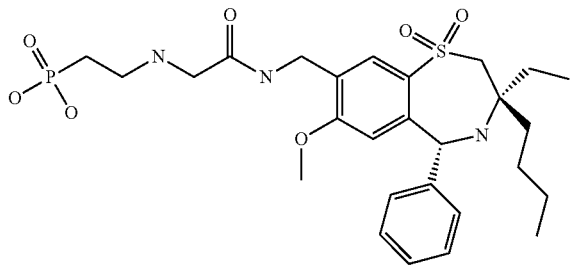 [SMILES: CCCC[C@]1(CC)CS(=O)(=O)c2cc(CNC(=O)CNCCP(=O)(O)O)c(OC)cc2[C@@H](c2ccccc2)N1]

Step 1: To a solution of N-{[(3R,5R)-3-butyl-3-ethyl-7-(methyloxy)-1,1-dioxido-5-phenyl-2,3,4,5-tetrahydro-1,4-benzothiazepin-8-yl]methyl}-2-chloroacetamide (50 mg, 0.101 mmol) in DMF (3 mL) was added potassium carbonate (28.0 mg, 0.203 mmol) and diethyl (2-aminoethyl)phosphonate (20.21 mg, 0.112 mmol). The reaction mixture was stirred at 60° C. overnight. Potassium iodide (33.7 mg, 0.203 mmol) was added, and the reaction mixture was stirred at 60° C. overnight, cooled to room temperature, and partitioned between H$_2$O and EtOAc. The organic layer was washed with saturated brine, dried (Na$_2$SO$_4$), filtered, and concentrated under reduced pressure. Purification using silica gel (MeOH:DCM=0:100 to 20:80) afforded diethyl (2-{[2-({[(3R,5R)-3-butyl-3-ethyl-7-(methyloxy)-1,1-dioxido-5-phenyl-2,3,4,5-tetrahydro-1,4-benzothiazepin-8-yl]methyl}amino)-2-oxoethyl]amino}ethyl)phosphonate (27 mg, 40%) as a colorless oil: ES-LCMS m/z 638 (M+H)$^+$.

Step 2: To a solution of diethyl (2-{[2-({[(3R,5R)-3-butyl-3-ethyl-7-(methyloxy)-1,1-dioxido-5-phenyl-2,3,4,5-tetrahydro-1,4-benzothiazepin-8-yl]methyl}amino)-2-oxoethyl]amino}ethyl)phosphonate (25 mg, 0.039 mmol) in DCM (5 mL) was added bromotrimethylsilane (0.102 mL, 0.784 mmol). The reaction mixture was stirred at room temperature overnight, concentrated under reduced pressure, and acidified with 1N hydrochloric acid. The residue was concentrated under reduced pressure and purified by RP-HPLC (MeCN/H$_2$O with 0.05% TFA afforded the title compound (15 mg, 46%, TFA salt) as a white solid: $^1$H NMR (MeOH-d$_4$) δ ppm 7.96 (s, 1H), 7.33-7.61 (m, 5H), 6.41 (s, 1H), 6.22 (s, 1H), 4.25-4.50 (m, 2H), 3.75-3.84 (m, 2H), 3.69 (d, J=15.2 Hz, 1H), 3.58 (s, 3H), 3.34 (d, J=15.2 Hz, 1H), 3.05-3.22 (m, 2H), 2.42-2.65 (m, 1H), 1.71-2.02 (m, 4H), 1.51-1.69 (m, 1H), 1.14-1.44 (m, 4H), 0.97-1.14 (m, 1H), 0.92 (t, J=7.4 Hz, 3H), 0.83 (t, J=6.8 Hz, 3H); ES-LCMS m/z 582 (M+H)$^+$.

Example 41

3-{[2-({[(3R,5R)-3-butyl-3-ethyl-7-(methyloxy)-1,1-dioxido-5-phenyl-2,3,4,5-tetrahydro-1,4-benzothiazepin-8-yl]methyl}amino)-2-oxoethyl]amino}pentanedioic acid trifluoroacetate salt

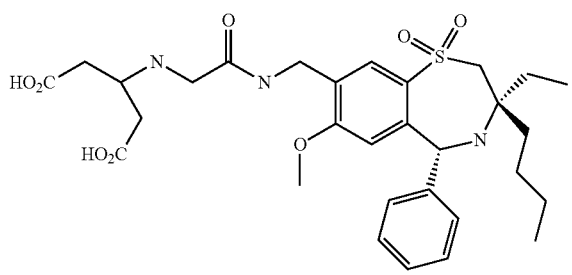 [SMILES: CCCC[C@]1(CC)CS(=O)(=O)c2cc(CNC(=O)CNC(CC(=O)O)CC(=O)O)c(OC)cc2[C@@H](c2ccccc2)N1]

Step 1: To a solution of N-{[(3R,5R)-3-butyl-3-ethyl-7-(methyloxy)-1,1-dioxido-5-phenyl-2,3,4,5-tetrahydro-1,4-benzothiazepin-8-yl]methyl}-2-chloroacetamide (55 mg, 0.112 mmol) in DMF (3 mL) was added potassium carbonate (61.7 mg, 0.446 mmol) and potassium iodide (74.1 mg, 0.446 mmol). The reaction mixture was stirred at 60° C. overnight, cooled to room temperature, and partitioned between H$_2$O and EtOAc. The organic layer was washed with saturated brine, dried (Na$_2$SO$_4$), filtered, and concentrated under reduced pressure. Purification using silica gel (MeOH:DCM=0:100 to 10:90) afforded diethyl 3-{[2-({[(3R,5R)-3-butyl-3-ethyl-7-(methyloxy)-1,1-dioxido-5-phenyl-2,3,4,5-tetrahydro-1,4-benzothiazepin-8-yl]methyl}amino)-2-oxoethyl]amino}pentanedioate (75 mg, 100%) as a yellow oil: ES-LCMS m/z 660 (M+H)$^+$.

Step 2: To a solution of diethyl 3-{[2-({[(3R,5R)-3-butyl-3-ethyl-7-(methyloxy)-1,1-dioxido-5-phenyl-2,3,4,5-tetrahydro-1,4-benzothiazepin-8-yl]methyl}amino)-2-oxoethyl]amino}pentanedioate (73.9 mg, 0.112 mmol) in a 1:1:1 mixture of THF/MeOH/H$_2$O 6 mL) was added lithium hydroxide (134 mg, 5.60 mmol). The reaction mixture was stirred at room temperature overnight, acidified with acetic acid, and concentrated under reduced pressure. Purification by RP-HPLC (MeCN/H$_2$O with 0.05% TFA) afforded the title compound (20 mg, 21%, TFA salt) as a white solid: $^1$H NMR (MeOH-d$_4$) δ ppm 7.95 (s, 1H), 7.34-7.66 (m, 5H), 6.45 (s, 1H), 6.30 (s, 1H), 4.41 (d, J=3.3 Hz, 2H), 3.82-4.00 (m, 3H), 3.74 (d, J=15.4 Hz, 1H), 3.58 (s, 3H), 3.46 (d, J=15.4 Hz, 1H), 2.85 (d, J=5.7 Hz, 3H), 2.45-2.72 (m, 2H), 1.77-2.11 (m, 2H), 1.49-1.72 (m, 1H), 1.24-1.45 (m, 3H), 0.97-1.13 (m, 1H), 0.93 (t, J=7.4 Hz, 3H), 0.86 (t, J=6.8 Hz, 3H); ES-LCMS m/z 604 (M+H)$^+$.

Example 42

3-({[(3R,5R)-3-butyl-3-ethyl-7-(methyloxy)-1,1-dioxido-5-phenyl-2,3,4,5-tetrahydro-1,4-benzothiazepin-8-yl]methyl}amino)-3-oxo-1-propanesulfonic

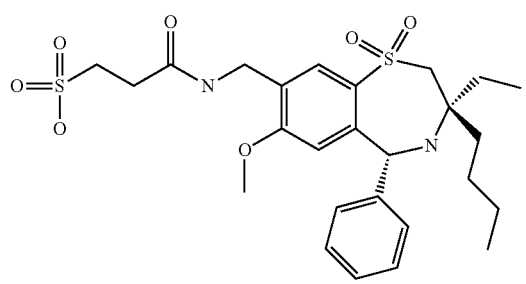 [SMILES: CCCC[C@]1(CC)CS(=O)(=O)c2cc(CNC(=O)CCS(=O)(=O)O)c(OC)cc2[C@@H](c2ccccc2)N1]

Step 1: To an ice-cold solution of {[(3R,5R)-3-butyl-3-ethyl-7-(methyloxy)-1,1-dioxido-5-phenyl-2,3,4,5-tetrahydro-1,4-benzothiazepin-8-yl]methyl}amine (150 mg, 0.233 mmol) in DCM (10 mL) was added pyridine (0.132 mL, 1.629 mmol) and 3-chloropropanoyl chloride (0.045 mL, 0.465 mmol). The reaction mixture was stirred at room temperature for 4 hrs then partitioned between H$_2$O and DCM. Purification via silica gel (MeOH:DCM=0:100 to 3:97) afforded N-{[(3R,5R)-3-butyl-3-ethyl-7-(methyloxy)-1,1-dioxido-5-phenyl-2,3,4,5-tetrahydro-1,4-benzothiazepin-8-yl]methyl}-3-chloropropanamide (105 mg, 89%) as a colorless oil: ES-LCMS m/z 508 (M+H)$^+$.

Step 2: To a solution of N-{[(3R,5R)-3-butyl-3-ethyl-7-(methyloxy)-1,1-dioxido-5-phenyl-2,3,4,5-tetrahydro-1,4-benzothiazepin-8-yl]methyl}-3-chloropropanamide (150 mg, 0.296 mmol) in a 1:1 mixture of ethanol/H$_2$O (10 mL) was added sodium sulfite (186 mg, 1.479 mmol). The reaction mixture was stirred at 60° C. overnight, cooled to room temperature, acidified with acetic acid, and concentrated under reduced pressure. Purification by RP-HPLC (MeCN/H$_2$O with 0.5% NH$_4$OH) afforded the title compound (27 mg, 15%, NH$_3$ salt) as a white solid: $^1$H NMR (MeOH-d$_4$) δ ppm 8.31-8.49 (m, 1H), 7.86 (s, 1H), 7.13-7.55 (m, 5H), 6.20 (s, 1H), 6.04 (s, 1H), 4.18-4.37 (m, 2H), 3.51 (s, 3H), 3.44 (d, J=14.8 Hz, 1H), 2.95-3.11 (m, 3H), 2.57-2.73 (m, 2H), 2.08-2.31 (m, 1H), 1.67-1.85 (m, 1H), 1.48-1.66 (m, 1H), 1.32-1.46 (m, 1H), 1.03-1.32 (m, 4H), 0.86 (t, J=7.4 Hz, 3H), 0.78 (t, J=6.8 Hz, 3H); ES-LCMS m/z 553 (M+H)$^+$.

Example 43

3-({[(3R,5S)-3-butyl-3-ethyl-7-(methyloxy)-1,1-dioxido-5-phenyl-2,3,4,5-tetrahydro-1,4-benzothiazepin-8-yl]methyl}amino)pentanedioic acid

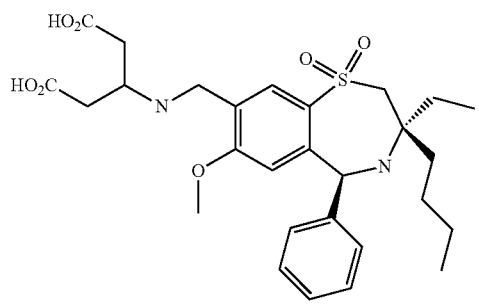 [SMILES: CCCC[C@]1(CC)CS(=O)(=O)c2cc(CNC(CC(=O)O)CC(=O)O)c(OC)cc2[C@H](c2ccccc2)N1]

Step 1: A solution of (3R,5S)-3-butyl-3-ethyl-7-(methyloxy)-5-phenyl-2,3,4,5-tetrahydro-1,4-benzothiazepine-8-carbaldehyde 1,1-dioxide (100 mg, 0.241 mmol) and dimethyl 3-aminopentanedioate (63.2 mg, 0.361 mmol) in 1,2-dichloroethane (4 mL) was stirred for 30 min then treated with acetic acid (0.069 mL, 1.203 mmol). The reaction mixture was stirred for 1 hr, treated with NaHB(OAc)$_3$ (102 mg, 0.481 mmol), stirred at room temperature overnight, and quenched with 2N aq. sodium carbonate solution. After stirring for 30 min, the mixture was extracted with DCM. The organic layer was washed with saturated brine, dried (Na$_2$SO$_4$), filtered, and concentrated under reduced pressure. Purification using silica gel (EtOAc/hexanes=1:4 to 1:1) afforded dimethyl 3-({[(3R,5S)-3-butyl-3-ethyl-7-(methyloxy)-1,1-dioxido-5-phenyl-2,3,4,5-tetrahydro-1,4-benzothiazepin-8-yl]methyl}amino)pentanedioate (92.7 mg, 67%) as a colorless oil: $^1$H NMR (CDCl$_3$) δ ppm 7.99 (s, 1H), 7.21-7.52 (m, 5H), 6.12 (s, 1H), 6.06 (s, 1H), 3.74 (d, J=5.3 Hz, 2H), 3.66 (s, 6H), 3.50 (s, 3H), 3.23-3.44 (m, 2H), 3.05 (d, J=14.6 Hz, 1H), 2.56 (d, J=6.2 Hz, 4H), 2.26-2.44 (m, 1H), 1.67-1.87 (m, 2H), 1.03-1.56 (m, 7H), 0.89 (t, J=6.6 Hz, 3H), 0.76 (t, J=7.2 Hz, 3H); ES-LCMS m/z 575 (M+H)$^+$.

Step 2: To a solution of dimethyl 3-({[(3R,5S)-3-butyl-3-ethyl-7-(methyloxy)-1,1-dioxido-5-phenyl-2,3,4,5-tetrahydro-1,4-benzothiazepin-8-yl]methyl}amino)pentanedioate (92 mg, 0.160 mmol) in a 1:1:1 mixture of THF/MeOH/H$_2$O (6 mL) was added lithium hydroxide monohydrate (67.2 mg, 1.601 mmol). The reaction mixture was stirred at room temperature overnight then partially concentrated under reduced pressure to remove the organic solvents. The aqueous phase was adjusted to pH 5 with 1N hydrochloric acid. A white precipitate was collected by filtration and air-dried to give the title compound (42 mg, 45%) as a white solid: $^1$H NMR (DMSO-d$_6$) δ ppm 7.94 (s, 1H), 7.41 (d, J=4.3 Hz, 4H), 7.26-7.38 (m, 1H), 6.10 (s, 1H), 5.93 (br. s., 1H), 3.80 (s, 2H), 3.55 (d, J=14.9 Hz, 1H), 3.08 (d, J=14.9 Hz, 1H), 2.57-2.76 (m, 1H), 2.31-2.47 (m, 3H), 2.04-2.21 (m, 1H), 1.55-1.82 (m, 1H), 1.07-1.51 (m, 7H), 0.86 (t, J=6.6 Hz, 3H), 0.66 (t, J=7.2 Hz, 3H); ES-LCMS m/z 547 (M+H)$^+$.

Example 44

N-{[(3R,5S)-3-butyl-3-ethyl-7-(methyloxy)-1,1-dioxido-5-phenyl-2,3,4,5-tetrahydro-1,4-benzothiazepin-8-yl]methyl}glycine trifluoroacetate salt

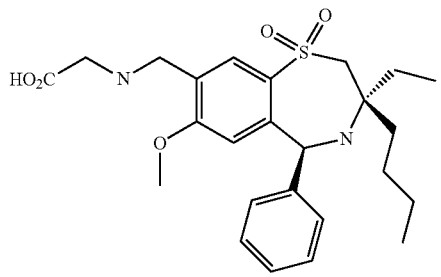 [SMILES: CCCC[C@]1(CC)CS(=O)(=O)c2cc(CNCC(=O)O)c(OC)cc2[C@H](c2ccccc2)N1]

Step 1: To a solution of (3R,5S)-3-butyl-3-ethyl-7-(methyloxy)-5-phenyl-2,3,4,5-tetrahydro-1,4-benzothiazepine-8-carbaldehyde 1,1-dioxide (100 mg, 0.241 mmol) in 1,2-dichloroethane (4 mL) was added 1,1-dimethylethyl glycinate (47.3 mg, 0.361 mmol) and acetic acid (0.069 mL, 1.203 mmol). The reaction mixture was stirred at room temperature for 1 hr, treated with NaHB(OAc)$_3$ (102 mg, 0.481 mmol), and stirred at room temperature overnight. The reaction mixture was added 2M aq. sodium carbonate solution and extracted with DCM. The combined organic layers were washed with saturated brine, dried (Na$_2$SO$_4$), filtered, and concentrated under reduced pressure. Purification using silica gel (EtOAc:hexanes=1:4 to 1:1) afforded 1,1-dimethylethyl N-{[(3R,5S)-3-butyl-3-ethyl-7-(methyloxy)-1,1-dioxido-5-phenyl-2,3,4,5-tetrahydro-1,4-benzothiazepin-8-yl]methyl}glycinate (35.8 mg, 28.0%) as a colorless oil: $^1$H NMR (CDCl$_3$) δ ppm 7.97 (s, 1H), 7.30-7.58 (m, 6H), 6.15 (s, 1H), 6.07 (s, 1H), 3.77 (s, 2H), 3.52 (s, 3H), 3.42 (d, J=14.7 Hz, 1H), 3.27 (s, 2H), 3.06 (d, J=14.7 Hz, 1H), 2.26-2.48 (m, 1H), 1.72-1.92 (m, 2H), 1.06-1.41 (m, 8H), 0.90 (t, J=6.2 Hz, 3H), 0.78 (t, J=7.2 Hz, 3H); ES-LCMS m/z 531 (M+H)$^+$.

Step 2: A mixture of 1,1-dimethylethyl N-{[(3R,5S)-3-butyl-3-ethyl-7-(methyloxy)-1,1-dioxido-5-phenyl-2,3,4,5-tetrahydro-1,4-benzothiazepin-8-yl]methyl}glycinate (34.0 mg, 0.064 mmol) was treated with 4N hydrogen chloride in 1,4-dioxane (1.600 mL, 6.40 mmol). The reaction mixture was stirred at room temperature overnight then concentrated under reduced pressure. Purification by RP-HPLC (eluting with MeCN/H$_2$O with 0.05% TFA-H$_2$O and 0.05% TFA-MeCN) afforded the title compound (35 mg, 77%, TFA salt) as a white solid: $^1$H NMR (DMSO-d$_6$) δ ppm 9.01-9.40 (m, 2H), 8.07 (s, 1H), 7.17-7.56 (m, 5H), 6.16 (s, 1H), 5.95 (br. s., 1H), 4.10-4.31 (m, 2H), 3.84 (br. s., 2H), 3.62 (d, J=14.3 Hz, 1H), 3.56-3.72 (m, 1H), 3.48 (s, 3H), 3.11 (d, J=14.6 Hz, 1H), 2.09-2.26 (m, 1H), 2.07 (s, 1H), 1.62-1.84 (m, 1H), 1.00-1.56 (m, 6H), 0.86 (t, J=6.6 Hz, 3H), 0.68 (t, J=7.0 Hz, 3H); ES-LCMS m/z 475 (M+H)$^+$.

Example 45

{[(3R,5S)-3-butyl-3-ethyl-7-(methyloxy)-1,1-dioxido-5-phenyl-2,3,4,5-tetrahydro-1,4-benzothiazepin-8-yl]methyl}phosphonic acid trifluoroacetate salt

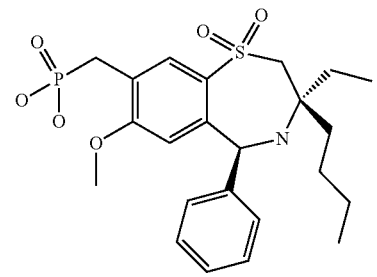 [SMILES: CCCC[C@]1(CC)CS(=O)(=O)c2cc(CP(=O)(O)O)c(OC)cc2[C@H](c2ccccc2)N1]

Step 1: To an ice-cold solution of imidazole (130 mg, 1.916 mmol) in DCM (5 mL) was added triphenylphosphine (251 mg, 0.958 mmol) followed by dropwise addition of bromine (0.049 mL, 0.958 mmol). A solution of [(3R,5S)-3-butyl-3-ethyl-7-(methyloxy)-1,1-dioxido-5-phenyl-2,3,4,5-tetrahydro-1,4-benzothiazepin-8-yl]methanol (200 mg, 0.479 mmol) in DCM (5 mL) was added slowly. The reaction mixture was stirred at 0° C. for 2 hrs. Aqueous sodium sulfite solution was added, and the resulting mixture separated. The aqueous layer was extracted with DCM, and the combined organic layers were dried (Na$_2$SO$_4$), filtered and concentrated. Purification using silica gel (EtOAc/hexanes=1:10 to 1:2) afforded (3R,5S)-8-(bromomethyl)-3-butyl-3-ethyl-7-(methyloxy)-5-phenyl-2,3,4,5-tetrahydro-1,4-benzothiazepine 1,1-dioxide (149 mg, 64%) as a white solid: $^1$H NMR (CDCl₃) δ ppm 8.06 (s, 1H), 7.28-7.54 (m, 5H), 6.17 (s, 1H), 6.07 (s, 1H), 4.38-4.62 (m, 2H), 3.58 (s, 3H), 3.44 (d, J=14.9 Hz, 1H), 3.09 (d, J=14.9 Hz, 1H), 2.38 (dd, J=14.9, 7.4 Hz, 1H), 1.81 (dd, J=14.7, 7.4 Hz, 1H), 1.11-1.59 (m, 8H), 0.91 (t, J=6.6 Hz, 3H), 0.78 (t, J=7.2 Hz, 3H); ES-LCMS m/z 482 (M+H)⁺.

Step 2: To a solution of (3R,5S)-8-(bromomethyl)-3-butyl-3-ethyl-7-(methyloxy)-5-phenyl-2,3,4,5-tetrahydro-1,4-benzothiazepine 1,1-dioxide (149 mg, 0.310 mmol) in toluene (10 mL) was added triethyl phosphite (0.163 mL, 0.930 mmol). The reaction mixture was heated at reflux overnight, cooled to room temperature, and concentrated under reduced pressure. Purification using silica gel (EtOAc:hexanes=50:50 to 100:0) afforded diethyl {[(3R,5S)-3-butyl-3-ethyl-7-(methyloxy)-1,1-dioxido-5-phenyl-2,3,4,5-tetrahydro-1,4-benzothiazepin-8-yl]methyl}phosphonate (132 mg, 79%) as a clear oil: ¹H NMR (CDCl₃) δ ppm 7.97 (d, J=2.7 Hz, 1H), 7.28-7.50 (m, 5H), 6.13 (s, 1H), 6.04 (s, 1H), 3.88-4.25 (m, 5H), 3.51 (s, 3H), 3.40 (d, J=14.8 Hz, 1H), 3.10-3.27 (m, 2H), 3.03 (d, J=14.8 Hz, 1H), 2.37 (dd, J=14.6, 7.4 Hz, 1H), 1.79 (dd, J=14.6, 7.4 Hz, 1H), 1.41-1.58 (m, 2H), 1.10-1.40 (m, 12H), 0.89 (t, J=6.8 Hz, 3H), 0.75 (t, J=7.2 Hz, 3H)

Step 3: To an ice-cold solution of diethyl {[(3R,5S)-3-butyl-3-ethyl-7-(methyloxy)-1,1-dioxido-5-phenyl-2,3,4,5-tetrahydro-1,4-benzothiazepin-8-yl]methyl}phosphonate (132 mg, 0.246 mmol) in DCM (5 mL) was added bromotrimethylsilane (0.159 mL, 1.228 mmol). The reaction mixture was warmed to room temperature, stirred overnight, and concentrated under reduced pressure. The residue was partitioned between H₂O and DCM. The organic layer was washed with saturated brine, dried (Na₂SO₄), filtered, and concentrated under reduced pressure. Purification by RP-HPLC (eluting with MeCN/H₂O with 0.05% TFA-H₂O and 0.05% TFA-MeCN) afforded the title compound (49 mg, 32%, TFA salt) as a white solid: ¹H NMR (CDCl₃) δ ppm 7.87 (br. s., 1H), 7.31-7.70 (m, 5H), 5.95-6.46 (m, 2H), 3.46-3.62 (m, 3H), 3.20-3.43 (m, 2H), 2.38-2.90 (m, 2H), 1.76 (br. s., 1H), 1.07-1.53 (m, 5H), 0.96 (t, J=6.6 Hz, 3H), 0.81 (t, J=7.2 Hz, 3H); ES-LCMS m/z 482 (M+H)⁺.

Example 46

N-{[(3R,5R)-3-butyl-3-ethyl-4-hydroxy-7-(methyloxy)-1,1-dioxido-5-phenyl-2,3,4,5-tetrahydro-1,4-benzothiazepin-8-yl]methyl}glycine

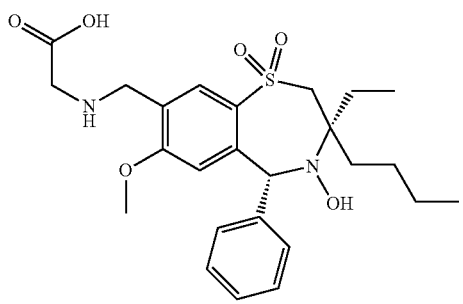 [SMILES: CCCC[C@]1(CC)CS(=O)(=O)c2cc(CNCC(=O)O)c(OC)cc2[C@@H](c2ccccc2)N1O]

(3R,5R)-3-butyl-3-ethyl-4-hydroxy-7-(methyloxy)-5-phenyl-2,3,4,5-tetrahydro-1,4-benzothiazepine-8-carbaldehyde 1,1-dioxide (410 mg, 0.95 mmol) and 1,1-dimethylethyl glycinate (187 mg, 1.43 mmol) were combined in DCM (210 mL) and stirred for 30 min at ambient temperature. The mixture was treated with NaHB(OAc)₃ (403 mg, 1.90 mmol), and the reaction mixture was stirred for 2 days at ambient temperature after which time LCMS indicated conversion to the desired product. The mixture was partitioned between DCM and brine, and the phases were separated. The aqueous phase was extracted with DCM, and the organic phases were combined, dried over MgSO₄, filtered, and concentrated to a clear oil. The residue was purified on 40 g silica eluting with 20 to 60% EtOAc/hexanes to give the t-butyl ester intermediate as a clear oil: LC-MS (ES⁺) m/z 547.40 [M+H].

The intermediate was dissolved in diethyl ether (20 mL) and treated with 4N HCl in dioxane (20 mL, 66 mmol) at ambient temperature. The mixture was stirred overnight after which time the mixture was concentrated to dryness and purified by RP-HPLC (30×150 Sunfire column; 47.5 mL/min; MeCN+0.05% TFA & H₂O+0.05% TFA) to give N-{[(3R,5R)-3-butyl-3-ethyl-4-hydroxy-7-(methyloxy)-1,1-dioxido-5-phenyl-2,3,4,5-tetrahydro-1,4-benzothiazepin-8-yl]methyl}glycine (306 mg, 65.6% yield) as a white solid: ¹H NMR (400 MHz, DMSO-d₆) δ ppm 0.79 (t, J=7.0 Hz, 3H), 0.86 (t, J=7.3 Hz, 3H), 1.01-1.53 (m, 5H), 1.58-1.72 (m, 1H), 1.78-1.92 (m, 1H), 1.96-2.15 (m, 1H), 3.28-3.45 (m, 2H), 3.45 (s, 3H), 3.74 (s, 1H), 3.80-4.31 (m, 4H), 6.18 (s, 1H), 6.38 (s, 1H), 7.33-7.40 (m, 1H), 7.44 (t, J=7.4 Hz, 2H), 7.47-7.69 (m, 2H), 8.04 (s, 1H), 8.14 (s, 1H), 9.19 (br. s., 1H), 9.34 (br. s., 1H) (one extra proton observed); LC-MS (ES⁻) m/z 489.4 [M−1]; LC-MS (ES⁺) m/z 491.3 [M+H].

Example 47

(2S)-2-({[(3R,5R)-3-butyl-3-ethyl-7-(methyloxy)-1,1-dioxido-5-phenyl-2,3,4,5-tetrahydro-1,4-benzothiazepin-8-yl]methyl}amino)-4-(methylsulfonyl)butanoic acid

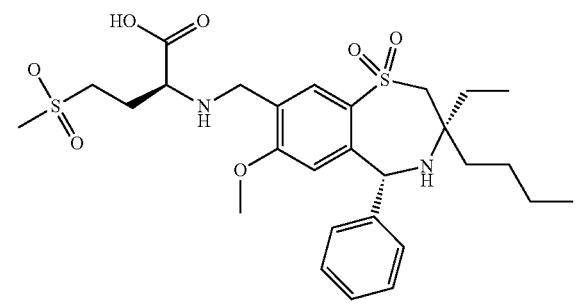

1,1-dimethylethyl N-{[(3R,5R)-3-butyl-3-ethyl-7-(methyloxy)-1,1-dioxido-5-phenyl-2,3,4,5-tetrahydro-1,4-benzothiazepin-8-yl]methyl}-L-methioninate (270 mg, 0.45 mmol) dissolved in TFA (3.4 mL, 44.6 mmol) was cooled in an ice bath and treated with dropwise addition of H₂O₂ (100 μl, 0.982 mmol). The mixture was allowed to warm to 22° C. and was stirred overnight after which time LCMS indicated complete conversion to the desired product with a very small amount of sulfoxide impurity. The reaction mixture was concentrated to dryness and purified by RP-HPLC to give (2S)-2-({[(3R,5R)-3-butyl-3-ethyl-7-(methyloxy)-1,1-dioxido-5-phenyl-2,3,4,5-tetrahydro-1,4-benzothiazepin-8-yl]methyl}amino)-4-(methylsulfonyl)butanoic acid (207 mg, 80% yield) as a white solid: ¹H NMR (400 MHz, DMSO-d₆) δ ppm 0.75 (t, J=7.0 Hz, 3H) 0.80 (t, J=7.4 Hz, 3H) 0.97-1.28 (m, 4H) 1.32-1.54 (m, 2H) 1.68-1.80 (m, 1H) 1.88-2.13 (m, 3H) 2.59 (d, 1H) 2.98 (s, 3H) 3.06 (d, J=14.9 Hz, 1H) 3.11-3.27 (m, 3H) 3.44 (s, 3H) 3.55 (d, J=15.0 Hz, 1H) 3.66-3.74 (m, 1H) 3.76-3.86 (m, 1H) 5.94 (d, J=9.2 Hz, 1H) 6.10 (s, 1H) 7.27-7.37 (m, 1H) 7.37-7.47 (m, 4H) 8.00 (s, 1H) (2 protons not observed); LC-MS (ES⁺) m/z 581.3 [M+H].

Example 48

N-{[(3R,5R)-3-butyl-3-ethyl-7-(methyloxy)-1,1-dioxido-5-phenyl-2,3,4,5-tetrahydro-1,4-benzothiazepin-8-yl]methyl}-N-hydroxyglycine

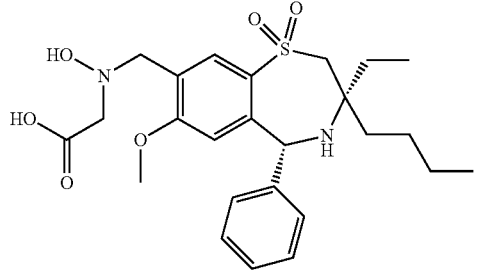 [SMILES: CCCC[C@]1(CC)CS(=O)(=O)c2cc(CN(O)CC(=O)O)c(OC)cc2[C@@H](c2ccccc2)N1]

1,1-dimethylethyl N-{[(3R,5R)-3-butyl-3-ethyl-7-(methyloxy)-1,1-dioxido-5-phenyl-2,3,4,5-tetrahydro-1,4-benzothiazepin-8-yl]methyl}glycinate (80 mg, 0.15 mmol) dissolved in DCM (5 mL) was treated with m-CPBA (33.8 mg, 0.15 mmol) then stirred at 22° C. for 16 h. The mixture was diluted with DCM and stirred with 10% aq. $Na_2SO_3$ for 15 min. The organic phase was isolated, dried over $MgSO_4$, filtered, and concentrated to dryness. The residue was purified on 40 g silica eluting with 30 to 100% EtOAc/hexanes to give two separate products that were not characterized further. Both products were separately converted to the title compound using the procedure below.

The first product (35 mg, 0.064 mmol) dissolved in DCM (1.5 mL) and MeOH (1.5 mL) was treated with acetic acid (0.011 mL, 0.20 mmol) and $NaCNBH_4$ (12 mg, 0.19 mmol) at 22° C. for 2 h after which time LCMS indicated clean conversion to the intermediate t-Bu-ester. Trifluoroacetic acid (4.95 μL, 0.064 mmol) was added, and the mixture was stirred at 22° C. for 16 h after which time LCMS indicated conversion to products of MW=474 and 490. The reaction mixture was concentrated to dryness and the residue was purified by RP-HPLC (30×50 Sunfire column at 55 mL/min; MeCN+0.05% TFA & $H_2O$+0.05% TFA were used as the eluants; 10% to 100% over 8 minutes) to give N-{[(3R,5R)-3-butyl-3-ethyl-7-(methyloxy)-1,1-dioxido-5-phenyl-2,3,4,5-tetrahydro-1,4-benzothiazepin-8-yl]methyl}-N-hydroxyglycine (18.9 mg, 60.0% yield): LC-MS (ES⁻) m/z 489.2 [M−1]. LC-MS (ES⁺) m/z 490.9 [M+H]. The ¹H NMR of the material was uninterpretable due to the physical properties of the title compound.

The second product (15 mg, 0.028 mmol) was subjected to similar conditions to give the title compound that was identical to the title compound prepared above: LC-MS (ES⁻) m/z 489.1 [M−1]. LC-MS (ES⁺) m/z 491.2 [M+H].

Example 49

N-{[(3R,5R)-3-butyl-3-ethyl-7-(methyloxy)-1,1-dioxido-5-phenyl-2,3,4,5-tetrahydro-1,4-benzothiazepin-8-yl]methyl}-N-methylglycine ammonium salt

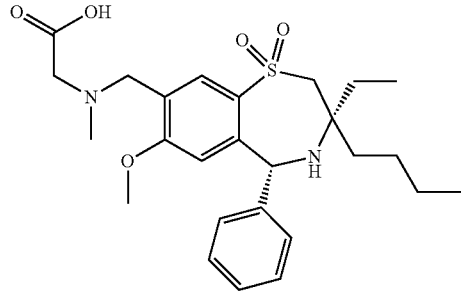 [SMILES: CCCC[C@]1(CC)CS(=O)(=O)c2cc(CN(C)CC(=O)O)c(OC)cc2[C@@H](c2ccccc2)N1]

A slurry of 1,1-dimethylethyl N-methylglycinate.HCl (164 mg, 0.902 mmol) in DCM (3 mL) was treated with TEA (0.126 mL, 0.90 mmol) at ambient temperature for 15 min after which time (3R,5R)-3-butyl-3-ethyl-7-(methyloxy)-5-phenyl-2,3,4,5-tetrahydro-1,4-benzothiazepine-8-carbaldehyde 1,1-dioxide (250 mg, 0.60 mmol) was added, and the mixture was stirred for 1 h. $NaHB(OAc)_3$ (255 mg, 1.20 mmol) was added, and the reaction mixture was stirred for 16 h at ambient temperature after which time LCMS indicated conversion to desired product. The mixture was partitioned between DCM and brine, and the phases were separated. The aqueous phase was extracted with DCM, and the organic phases were combined, dried over $MgSO_4$, filtered, and concentrated to a clear oil. The residue was purified on 40 g silica eluting with 20 to 60% EtOAc/hexanes to give the t-butyl ester intermediate (196 mg) as a white solid: ¹H NMR (400 MHz, DMSO-$d_6$) δ ppm 0.75 (t, J=7.0 Hz, 3H) 0.80 (t, J=7.4 Hz, 3H) 0.97-1.27 (m, 4H) 1.33-1.55 (m, 2H) 1.42 (s, 9H) 1.67-1.79 (m, 1H) 2.00-2.11 (m, 1H) 2.26 (s, 3H) 2.60 (d, J=9.8 Hz, 1H) 3.06 (d, J=14.8 Hz, 1H) 3.20 (s, 2H) 3.42 (s, 3H) 3.53 (d, J=14.8 Hz, 1H) 3.57-3.68 (m, 2H) 5.93 (d, J=9.8 Hz, 1H) 6.09 (s, 1H) 7.29-7.37 (m, 1H) 7.41 (d, J=4.3 Hz, 4H) 7.95 (s, 1H).

The ester was dissolved in diethyl ether (20 mL) and treated with 4N HCl in dioxane (20 mL, 80 mmol) at ambient temperature. The mixture was stirred overnight after which time LCMS indicated ~80% conversion to the acid. The reaction mixture was stirred an additional 24 h after which time LCMS indicated complete conversion. The mixture was concentrated to dryness and purified by RP-HPLC (30×100 XBridge column; Acetonitrile+0.2% $NH_4OH$ and $H_2O$+0.2% $NH_4OH$ were used as the solvent system; 10% to 70% over 8 minutes, 100% to 100% to 10 minutes) to give N-{[(3R,5R)-3-butyl-3-ethyl-7-(methyloxy)-1,1-dioxido-5-phenyl-2,3,4,5-tetrahydro-1,4-benzothiazepin-8-yl]methyl}-N-methylglycine (130 mg, 44.2% yield) ammonium salt as a white solid: ¹H NMR (400 MHz, DMSO-$d_6$) δ ppm 0.75 (t, J=7.0 Hz, 3H) 0.80 (t, J=7.4 Hz, 3H) 0.96-1.28 (m, 4H) 1.32-1.53 (m, 2H) 1.68-1.80 (m, 1H) 1.99-2.11 (m, 1H) 2.30 (s, 3H) 2.62 (d, J=9.4 Hz, 1H) 3.07 (d, J=14.9 Hz, 1H) 3.24 (s, 2H) 3.42 (s, 3H) 3.54 (d, J=14.9 Hz, 1H) 3.69 (s, 2H) 5.93 (d, J=8.2 Hz, 1H) 6.10 (s, 1H) 7.33 (dq, J=8.5, 4.2 Hz, 1H) 7.41 (d, J=4.3 Hz, 4H) 7.98 (s, 1H) (COOH proton not observed); LC-MS (ES⁺) m/z 489.3 [M+H].

Example 50

3-({[(3R,5R)-3-butyl-3-ethyl-4-hydroxy-7-(methyloxy)-1,1-dioxido-5-phenyl-2,3,4,5-tetrahydro-1,4-benzothiazepin-8-yl]methyl}amino)pentanedioic acid trifluoroacetate salt

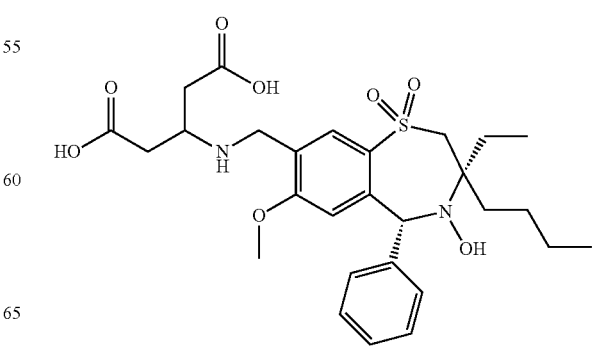

Dimethyl 3-({[(3R,5R)-3-butyl-3-ethyl-4-hydroxy-7-(methyloxy)-1,1-dioxido-5-phenyl-2,3,4,5-tetrahydro-1,4-benzothiazepin-8-yl]methyl}amino)pentanedioate (304 mg, 0.52 mmol) dissolved in THF (5 mL) was treated with 1M LiOH (5.15 mL, 5.15 mmol) at ambient temperature then vigorously stirred for 2 h. The reaction mixture was concentrated to remove the THF, and the remaining aqueous portion was treated with 1N HCl until material initiated precipitation (pH=5). The gummy mixture was extracted three times with DCM, and the organics were combined, dried over $MgSO_4$, filtered, and concentrated to dryness. The residue was purified by RP-HPLC (30×150 Sunfire column at 47.5 mL/min; MeCN+0.05% TFA & $H_2O$+0.05% TFA were used as the solvent system; 10% to 80% over 10 minutes) to give 3-({[(3R,5R)-3-butyl-3-ethyl-4-hydroxy-7-(methyloxy)-1,1-dioxido-5-phenyl-2,3,4,5-tetrahydro-1,4-benzothiazepin-8-yl]methyl}amino)pentanedioic acid (273.5 mg, 94% yield) as a white solid. $^1$H NMR (400 MHz, DMSO-$d_6$) δ ppm 0.79 (t, J=7.1 Hz, 3H), 0.85 (t, J=7.4 Hz, 3H), 1.06-1.37 (m, 4H), 1.37-1.50 (m, 1H), 1.58-1.71 (m, 1H), 1.78-1.93 (m, 1H), 2.00-2.14 (m, 1H), 2.67-2.88 (m, 4H), 3.16 (s, 1H), 3.26-3.45 (m, 2H), 3.46 (s, 3H), 3.71-3.85 (m, 1H), 4.26 (br. s., 2H), 6.16 (s, 1H), 6.38 (s, 1H), 7.32-7.40 (m, 1H), 7.44 (t, J=7.5 Hz, 2H), 7.46-7.65 (m, 2H), 8.05 (s, 1H), 8.16 (s, 1H), 8.62 (br. s., 2H), 12.92 (br. s., 2H) (2 extra protons observed). LC-MS (ES$^-$) m/z 561.20 [M−1].

Example 51

{2-[(3R,5R)-3-butyl-3-ethyl-7-(methyloxy)-1,1-dioxido-5-phenyl-2,3,4,5-tetrahydro-1,4-benzothiazepin-8-yl]ethyl}phosphonic acid bis-ammonium salt

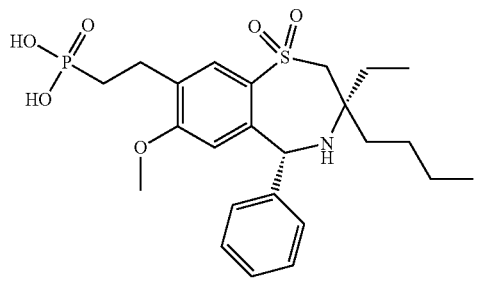 [SMILES: CCCC[C@]1(CC)CS(=O)(=O)c2cc(CCP(=O)(O)O)c(OC)cc2[C@@H](c2ccccc2)N1]

Diethyl {(E)-2-[(3R,5R)-3-butyl-3-ethyl-7-(methyloxy)-1,1-dioxido-5-phenyl-2,3,4,5-tetrahydro-1,4-benzothiazepin-8-yl]ethenyl}phosphonate (240 mg, 0.44 mmol) dissolved in EtOH (20 mL) was treated with 10% palladium on carbon (46.5 mg, 0.44 mmol) under a balloon of hydrogen gas at 23° C. overnight. The catalyst was filtered off, and the filtrate was concentrated to dryness to give the intermediate phosphonate as a clear oil. The residue was dissolved in DCM (10 mL) and treated with bromotrimethylsilane (0.227 mL, 1.75 mmol) for 16 h at 23° C. with stirring. The reaction mixture was concentrated to dryness then purified by RP-HPLC (30×100 XBridge column, MeCN/$H_2O$ containing 0.2% $NH_4OH$ buffer, 10 to 80 to 100% over 8 min) to give {2-[(3R,5R)-3-butyl-3-ethyl-7-(methyloxy)-1,1-dioxido-5-phenyl-2,3,4,5-tetrahydro-1,4-benzothiazepin-8-yl]ethyl}phosphonic acid (88 mg, 40.7 yield) bis-ammonium salt as a white solid: $^1$H NMR (400 MHz, DMSO-$d_6$) δ ppm 0.70-0.85 (m, 6H) 0.97-1.30 (m, 4H) 1.29-1.64 (m, 4H) 1.67-1.81 (m, 1H) 2.00-2.12 (m, 1H) 2.58 (d, J=9.8 Hz, 1H) 2.63-2.79 (m, 2H) 3.05 (d, J=14.9 Hz, 1H) 3.39 (s, 3H) 3.50 (d, J=14.9 Hz, 1H) 5.92 (d, J=9.6 Hz, 1H) 6.05 (s, 1H) 7.26-7.36 (m, 1H) 7.36-7.46 (m, 4H) 7.65 (s, 1H) (phosphonic acid protons not observed); LC-MS (ES$^+$) m/z 496.3 [M+H].

Example 52

N-{[(3R,5R)-3-butyl-3-ethyl-7-(methyloxy)-1,1-dioxido-5-phenyl-2,3,4,5-tetrahydro-1,4-benzothiazepin-8-yl]methyl}-L-serine bis-ammonium salt

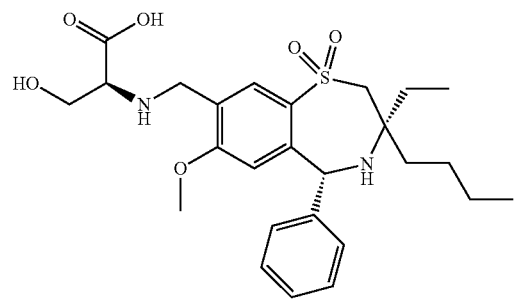 [SMILES: CCCC[C@]1(CC)CS(=O)(=O)c2cc(CN[C@@H](CO)C(=O)O)c(OC)cc2[C@@H](c2ccccc2)N1]

A slurry of 1,1-dimethylethyl L-serinate.HCl (238 mg, 1.20 mmol) in DCM (8 mL) was treated with TEA (0.168 mL, 1.20 mmol) at ambient temperature for 15 min after which time (3R,5R)-3-butyl-3-ethyl-7-(methyloxy)-5-phenyl-2,3,4,5-tetrahydro-1,4-benzothiazepine-8-carbaldehyde 1,1-dioxide (250 mg, 0.60 mmol) was added, and the mixture was stirred for 1 h. NaHB(OAc)$_3$ (319 mg, 1.504 mmol) was added, and the reaction mixture was stirred for 16 h at ambient temperature. The mixture was partitioned between DCM and brine, and the phases were separated. The aqueous phase was extracted with DCM, and the organic phases were combined, dried over $MgSO_4$, filtered, and concentrated to a clear oil. The residue was treated with 4N HCl in dioxane (10 mL, 40.0 mmol) at 22° C. with stirring overnight. The reaction mixture was concentrated to dryness then purified by RP-HPLC (30× 100 XBridge column, MeCN/$H_2O$ containing 0.2% $NH_4OH$ buffer, 10 to 70 to 100% over 8 min) to give N-{[(3R,5R)-3-butyl-3-ethyl-7-(methyloxy)-1,1-dioxido-5-phenyl-2,3,4,5-tetrahydro-1,4-benzothiazepin-8-yl]methyl}-L-serine (194 mg, 63.9% yield) bis-ammonium salt as a white solid: $^1$H NMR (400 MHz, DMSO-$d_6$) δ ppm 0.75 (t, J=7.0 Hz, 3H) 0.80 (t, J=7.4 Hz, 3H) 0.96-1.29 (m, 4H) 1.32-1.54 (m, 2H) 1.66-1.82 (m, 1H) 1.98-2.13 (m, 1H) 2.62 (d, J=9.6 Hz, 1H) 3.06 (d, J=15.0 Hz, 1H) 3.16 (t, J=5.2 Hz, 1H) 3.45 (s, 3H) 3.56 (d, J=14.9 Hz, 1H) 3.65 (qd, J=11.1, 5.2 Hz, 2H) 3.79-3.94 (m, 2H) 5.02 (br. s., 1H) 5.94 (d, J=9.6 Hz, 1H) 6.10 (s, 1H) 7.28-7.37 (m, 1H) 7.37-7.47 (m, 4H) 8.02 (s, 1H) (2 exchangables not observed); LC-MS (ES$^+$) m/z 505.3 [M+H].

Example 53

N-{[(3R,5R)-3-butyl-3-ethyl-7-(methyloxy)-1,1-dioxido-5-phenyl-2,3,4,5-tetrahydro-1,4-benzothiazepin-8-yl]methyl}-L-cystine bis-ammonium salt

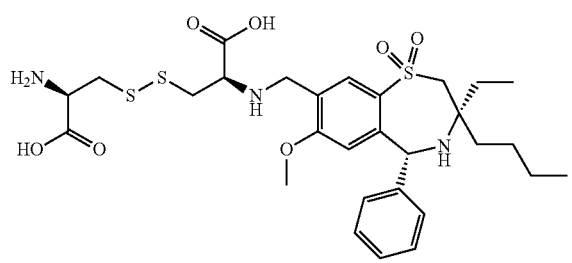 [SMILES: CCCC[C@]1(CC)CS(=O)(=O)c2cc(CN[C@@H](CSSC[C@H](N)C(=O)O)C(=O)O)c(OC)cc2[C@@H](c2ccccc2)N1]

Dimethyl N-{[(3R,5R)-3-butyl-3-ethyl-7-(methyloxy)-1,1-dioxido-5-phenyl-2,3,4,5-tetrahydro-1,4-benzothiazepin-8-yl]methyl}-L-cystinate (167 mg, 0.25 mmol) dissolved in THF (5 mL) was treated with 1M LiOH (5 mL, 5.0 mmol) then vigorously stirred stirring for 1 h. The mixture was neutralized with 1N HCl (5 mL) and concentrated to remove the THF. The residue was extracted twice with DCM, and the organic phases were combined, dried over MgSO₄, filtered, and concentrated to dryness. A portion of the residue was purified by RP-HPLC (30×100 XBridge column; MeCN+0.2% NH₄OH and H₂O+0.2% NH₄OH were used as the solvent system; 10% to 70% over 8 minutes) to give N-{[(3R,5R)-3-butyl-3-ethyl-7-(methyloxy)-1,1-dioxido-5-phenyl-2,3,4,5-tetrahydro-1,4-benzothiazepin-8-yl]methyl}-L-cystine (20.5 mg, 0.032 mmol, 12.81% yield) as a white solid: LC-MS (ES⁻) m/z 638.25 [M−1]; LC-MS (ES⁺) m/z 640.27 [M+H].

Example 54

{[(3R,5R)-3-butyl-3-ethyl-4-hydroxy-7-(methyloxy)-1,1-dioxido-5-phenyl-2,3,4,5-tetrahydro-1,4-benzothiazepin-8-yl]methyl}phosphonic acid

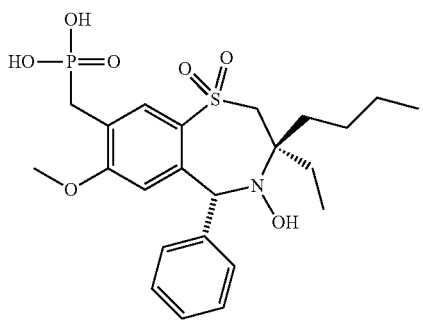 [SMILES: CCCC[C@]1(CC)CS(=O)(=O)c2cc(CP(=O)(O)O)c(OC)cc2[C@@H](c2ccccc2)N1O]

Diethyl {[(3R,5R)-3-butyl-3-ethyl-4-hydroxy-7-(methyloxy)-1,1-dioxido-5-phenyl-2,3,4,5-tetrahydro-1,4-benzothiazepin-8-yl]methyl}phosphonate (48.5 mg, 0.088 mmol) dissolved in DCM (1 mL) was treated with bromo(trimethyl)silane (67.1 mg, 0.44 mmol) at ambient temperature for 16 h. The reaction mixture was concentrated to dryness then purified by RP-HPLC (30×75 Sunfire column at 55 mL/min; MeCN+0.05% TFA & H₂O+0.05% TFA were used as the solvent system; 10% to 80% over 11 minutes) to give {[(3R,5R)-3-butyl-3-ethyl-4-hydroxy-7-(methyloxy)-1,1-dioxido-5-phenyl-2,3,4,5-tetrahydro-1,4-benzothiazepin-8-yl]methyl}phosphonic acid (35.3 mg, 81% yield) as a white solid: ¹H NMR (400 MHz, DMSO-d₆) δ ppm 0.79 (t, J=7.3 Hz, 3H), 0.82-0.94 (m, 3H), 1.05-1.52 (m, 5H), 1.55-1.67 (m, 1H), 1.77-2.02 (m, 1H), 2.02-2.15 (m, 1H), 2.83-3.10 (m, 2H), 3.26-3.43 (m, 2H), 3.38 (s, 3H), 3.96 (s, 0H), 6.09 (s, 1H), 6.33 (s, 1H), 7.30-7.38 (m, 1H), 7.42 (t, J=7.6 Hz, 2H), 7.45-7.58 (m, 2H), 7.84 (d, J=2.5 Hz, 1H), 8.00-8.05 (m, 1H); LC-MS (ES⁻) m/z 496-38 [M−1]. LC-MS (ES⁺) m/z 498.18 [M+H].

Example 55

{(E)-2-[(3R,5R)-3-butyl-3-ethyl-7-(methyloxy)-1,1-dioxido-5-phenyl-2,3,4,5-tetrahydro-1,4-benzothiazepin-8-yl]ethenyl}phosphonic acid bis-ammonium salt

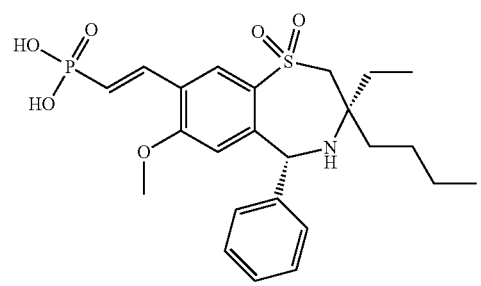 [SMILES: CCCC[C@]1(CC)CS(=O)(=O)c2cc(/C=C/P(=O)(O)O)c(OC)cc2[C@@H](c2ccccc2)N1]

Diethyl {(E)-2-[(3R,5R)-3-butyl-3-ethyl-7-(methyloxy)-1,1-dioxido-5-phenyl-2,3,4,5-tetrahydro-1,4-benzothiazepin-8-yl]ethenyl}phosphonate (95 mg, 0.173 mmol) was dissolved in DCM (4 mL) and treated with bromotrimethylsilane (0.090 mL, 0.69 mmol) at 22° C. overnight with stirring. The reaction mixture was concentrated to dryness, and the crude product was purified by RP-HPLC (30×100 XBridge column, MeCN/H₂O containing 0.2% NH₄OH buffer, 10 to 50 to 100% over 8 min) to give {(E)-2-[(3R,5R)-3-butyl-3-ethyl-7-(methyloxy)-1,1-dioxido-5-phenyl-2,3,4,5-tetrahydro-1,4-benzothiazepin-8-yl]ethenyl}phosphonic acid (51 mg, 59.8% yield) bis-ammonium salt as a white solid: ¹H NMR (400 MHz, DMSO-d₆) δ ppm 0.76 (t, J=7.0 Hz, 3H) 0.81 (t, J=7.4 Hz, 3H) 0.98-1.30 (m, 4H) 1.31-1.55 (m, 2H) 1.67-1.81 (m, 1H) 2.00-2.14 (m, 1H) 2.65 (d, J=10.2 Hz, 1H) 3.08 (d, J=14.9 Hz, 1H) 3.43 (s, 3H) 3.55 (d, J=14.9 Hz, 1H) 5.94 (d, J=10.0 Hz, 1H) 6.10 (s, 1H) 6.31 (dd, J=17.4, 13.9 Hz, 1H) 7.13 (dd, J=19.3, 17.8 Hz, 1H) 7.28-7.37 (m, 1H) 7.42 (d, J=4.5 Hz, 4H) 7.93 (s, 1H) (acidic protons not observed). Large coupling constant (17.57 Hz) suggests E isomer; LC-MS (ES⁺) m/z 494.3 [M+H].

Example 56

N-{[(3R,5R)-3-butyl-3-ethyl-7-(methyloxy)-1,1-dioxido-5-phenyl-2,3,4,5-tetrahydro-1,4-benzothiazepin-8-yl]methyl}-L-threonine ammonium salt

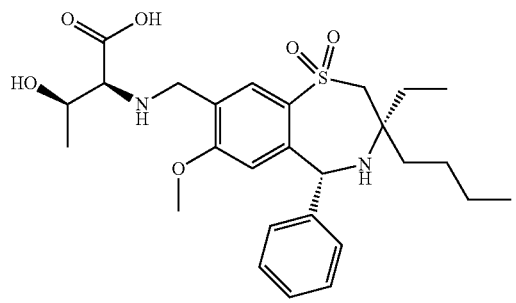 [SMILES: CCCC[C@]1(CC)CS(=O)(=O)c2cc(CN[C@H](C(=O)O)[C@@H](C)O)c(OC)cc2[C@@H](c2ccccc2)N1]

A slurry of 1,1-dimethylethyl L-threoninate (255 mg, 1.20 mmol) in DCM (3 mL) was treated with TEA (0.168 mL, 1.20 mmol) at ambient temperature for 15 min after which time (3R,5R)-3-butyl-3-ethyl-7-(methyloxy)-5-phenyl-2,3,4,5-tetrahydro-1,4-benzothiazepine-8-carbaldehyde 1,1-dioxide (250 mg, 0.602 mmol) was added, and the mixture was stirred for 1 h. NaHB(OAc)$_3$ (255 mg, 1.20 mmol) was added, and the reaction mixture was stirred for 16 h. The mixture was partitioned between DCM and brine, and the phases were separated. The aqueous phase was extracted with DCM, and the organic phases were combined, dried over MgSO$_4$, filtered, and concentrated to give the intermediate ester as a clear oil. The residue was treated with 4N HCl in 1,4-dioxane (10 mL, 40.0 mmol) at ambient temperature overnight. The mixture was concentrated to dryness then purified by RP-HPLC (30×100 XBridge column, MeCN/H$_2$O containing 0.2% NH$_4$OH buffer, 10 to 70 to 100% over 10 min) to give N-{[(3R,5R)-3-butyl-3-ethyl-7-(methyloxy)-1,1-dioxido-5-phenyl-2,3,4,5-tetrahydro-1,4-benzothiazepin-8-yl]methyl}-L-threonine (188 mg, 60.2% yield) ammonium salt as a white solid: $^1$H NMR (400 MHz, DMSO-d$_6$) δ ppm 0.75 (t, J=7.0 Hz, 3H) 0.80 (t, J=7.4 Hz, 3H) 0.97-1.28 (m, 4H) 1.16 (d, J=6.4 Hz, 3H) 1.33-1.54 (m, 2H) 1.68-1.79 (m, 1H) 2.00-2.12 (m, 1H) 2.59 (d, J=9.8 Hz, 1H) 2.96 (d, J=4.7 Hz, 1H) 3.06 (d, J=14.9 Hz, 1H) 3.44 (s, 3H) 3.54 (d, J=14.9 Hz, 1H) 3.67-3.93 (m, 3H) 5.94 (d, J=9.4 Hz, 1H) 6.09 (s, 1H) 7.29-7.37 (m, 1H) 7.37-7.46 (m, 4H) 8.03 (s, 1H) (3 exchangeable protons not observed); LC-MS (ES$^+$) m/z 519.3 [M+H].

Example 57

1-{[(3R,5R)-3-butyl-3-ethyl-7-(methyloxy)-1,1-dioxido-5-phenyl-2,3,4,5-tetrahydro-1,4-benzothiazepin-8-yl]methyl}-D-proline ammonium salt

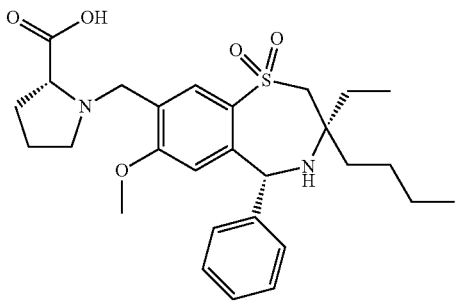 [SMILES: CCCC[C@]1(CC)CS(=O)(=O)c2cc(CN3CCC[C@@H]3C(=O)O)c(OC)cc2[C@@H](c2ccccc2)N1]

1,1-Dimethylethyl D-prolinate (206 mg, 1.20 mmol) and (3R,5R)-3-butyl-3-ethyl-7-(methyloxy)-5-phenyl-2,3,4,5-tetrahydro-1,4-benzothiazepine-8-carbaldehyde 1,1-dioxide (250 mg, 0.60 mmol) were combined in DCM (5 mL), and the mixture was stirred for 1 h. NaHB(OAc)$_3$(319 mg, 1.50 mmol) was added, and the reaction mixture was stirred for 3 days at ambient temperature. The mixture was partitioned between DCM and H$_2$O, and the phases were separated. The aqueous phase was extracted with DCM, and the organic phases were combined, dried over MgSO$_4$, filtered, and concentrated to a clear oil.

The residue was treated with TFA (4 mL, 51.9 mmol) at ambient temperature for 3 h. The reaction mixture was concentrated to dryness then purified by RP-HPLC (30×100 XBridge column; MeCN+0.1% NH$_4$OH and H$_2$O+0.1% NH$_4$OH were used as the solvent system; 10% to 70% over 8 minutes) to give 1-{[(3R,5R)-3-butyl-3-ethyl-7-(methyloxy)-1,1-dioxido-5-phenyl-2,3,4,5-tetrahydro-1,4-benzothiazepin-8-yl]methyl}-D-proline ammonium salt (333 mg, >99% yield) as a white solid: $^1$H NMR (400 MHz, DMSO-d$_6$) δ ppm 0.75 (t, J=7.0 Hz, 3H), 0.81 (t, J=7.4 Hz, 3H), 0.95-1.31 (m, 4H), 1.34-1.56 (m, 2H), 1.67-2.14 (m, 5H), 2.36-2.47 (m, 1H), 2.58-2.81 (m, 1H), 3.06 (d, J=15.0 Hz, 1H), 3.14-3.27 (m, 1H), 3.35-3.47 (m, 1H), 3.49 (s, 3H), 3.62 (d, J=15.0 Hz, 1H), 4.17-4.30 (m, 1H), 4.36 (d, J=13.1 Hz, 1H), 4.50 (d, J=13.1 Hz, 1H), 5.96 (br. s., 1H), 6.17 (s, 1H), 7.31-7.55 (m, 5H), 8.09 (s, 1H), 9.84 (br. s., 1H); LC-MS (ES$^-$) m/z 513.6 [M−1]. LC-MS (ES$^+$) m/z 515.3 [M+H].

Example 58

N$^2$-{[(3R,5R)-3-butyl-3-ethyl-7-(methyloxy)-1,1-dioxido-5-phenyl-2,3,4,5-tetrahydro-1,4-benzothiazepin-8-yl]methyl}-L-lysine ammonium salt

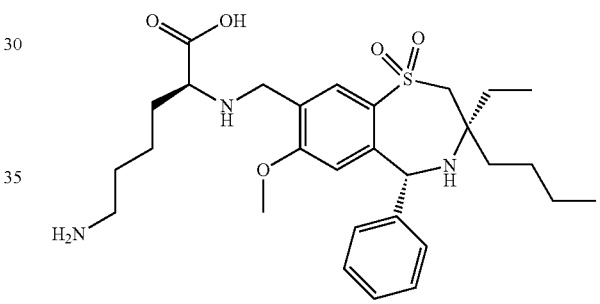

A slurry of 1,1-dimethylethyl N$^6$-{[(1,1-dimethylethyl)oxy]carbonyl}-L-lysinate.HCl (890 mg, 2.63 mmol) in DCM (10 mL) was treated with TEA (0.380 mL, 2.73 mmol) at ambient temperature for 15 min after which time (3R,5R)-3-butyl-3-ethyl-7-(methyloxy)-5-phenyl-2,3,4,5-tetrahydro-1,4-benzothiazepine-8-carbaldehyde 1,1-dioxide (600 mg, 1.444 mmol) was added, and the mixture was stirred for 1 h. NaHB(OAc)$_3$ (765 mg, 3.61 mmol) was added, and the reaction mixture was stirred for 16 h at ambient temperature. The mixture was partitioned between DCM and brine, and the phases were separated. The aqueous phase was extracted with DCM, and the organic phases were combined, dried over MgSO$_4$, filtered, and concentrated to a clear oil. The residue was treated with 4N HCl in 1,4-dioxane (10 mL, 40.0 mmol) at 22° C. with stirring overnight. The mixture was concentrated to dryness and purified by RP-HPLC (30×100 XBridge column, MeCN/H$_2$O containing 0.2% NH$_4$OH buffer, 10 to 80 to 100% over 10 min) to give N$^2$-{[(3R,5R)-3-butyl-3-ethyl-7-(methyloxy)-1,1-dioxido-5-phenyl-2,3,4,5-tetrahydro-1,4-benzothiazepin-8-yl]methyl}-L-lysine (297 mg, 37.7% yield) ammonium salt as a pink foam: $^1$H NMR (400 MHz, DMSO-d$_6$) δ ppm 0.75 (t, J=7.0 Hz, 3H) 0.80 (t, J=7.4 Hz, 3H) 0.97-1.60 (m, 12H) 1.67-1.80 (m, 1H) 1.99-2.14 (m, 1H) 2.54 (d, J=9.8 Hz, 1H) 2.64-2.78 (m, 3H) 3.06 (d, J=14.9

Hz, 1H) 3.41 (s, 3H) 3.50 (dd, J=15.0, 9.3 Hz, 2H) 3.65 (d, J=15.0 Hz, 1H) 5.94 (d, J=9.6 Hz, 1H) 6.06 (s, 1H) 7.32 (dq, J=8.5, 4.2 Hz, 1H) 7.41 (d, J=4.5 Hz, 4H) 7.99 (s, 1H) (4 exchangeable protons not observed); LC-MS (ES$^+$) m/z 546.4 [M+H].

Example 59

N$^2$-{[(3R,5R)-3-butyl-3-ethyl-7-(methyloxy)-1,1-dioxido-5-phenyl-2,3,4,5-tetrahydro-1,4-benzothiazepin-8-yl]methyl}-N$^6$,N$^6$-dimethyl-L-lysine ammonium salt

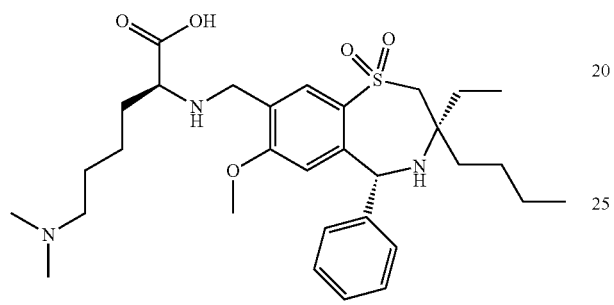

A slurry of N$^6$,N$^6$-dimethyl-L-lysine (250 mg, 1.187 mmol) in DCM (3 mL) was treated with TEA (0.165 mL, 1.19 mmol) at ambient temperature for 15 min after which time (3R,5R)-3-butyl-3-ethyl-7-(methyloxy)-5-phenyl-2,3,4,5-tetrahydro-1,4-benzothiazepine-8-carbaldehyde 1,1-dioxide (250 mg, 0.60 mmol) and THF (3.00 mL) were added, and the mixture was stirred for 1 h. NaHB(OAc)$_3$ (255 mg, 1.203 mmol) was added, and the reaction mixture was stirred for 16 h at ambient temperature. The reaction mixture was partitioned between DCM and H$_2$O, and the phases were isolated. While the organic phase showed a mix of aldehyde and alcohol by LCMS, the aqueous phase showed presence of desired product. The aqueous phase was isolated, and the pH was adjusted to 10 with 1M aq. Na$_2$CO$_3$. The aqueous layer was extracted five times with DCM, and the organic phases were combined, dried over MgSO$_4$, filtered, and concentrated to dryness to give the crude product as a brown oil. The crude material was purified by RP-HPLC (30×100 XBridge column, MeCN/H$_2$O containing 0.2% NH$_4$OH buffer, 10 to 80 to 100% over 10 min) to give N$^2$-{[(3R,5R)-3-butyl-3-ethyl-7-(methyloxy)-1,1-dioxido-5-phenyl-2,3,4,5-tetrahydro-1,4-benzothiazepin-8-yl]methyl}-N$^6$,N$^6$-dimethyl-L-lysine ammonium salt (23.5 mg, 6.8% yield) as a white solid: $^1$H NMR (400 MHz, DMSO-d$_6$) δ ppm 0.75 (t, J=7.0 Hz, 3H) 0.80 (t, J=7.4 Hz, 3H) 0.98-1.66 (m, 12H) 1.68-1.80 (m, 1H) 1.99-2.09 (m, 1H) 2.11 (s, 6H) 2.14-2.23 (m, 2H) 2.58 (d, J=9.8 Hz, 1H) 2.99-3.09 (m, 2H) 3.43 (s, 3H) 3.54 (d, J=14.9 Hz, 1H) 3.59-3.83 (m, 2H) 5.94 (d, J=9.4 Hz, 1H) 6.09 (s, 1H) 7.28-7.38 (m, 1H) 7.38-7.46 (m, 4H) 8.02 (s, 1H) (2 exchangeable protons not observed); LC-MS (ES$^+$) m/z 574.4 [M+H].

Examples 60 and 61

[({[(3R,5R)-3-butyl-3-ethyl-7-(methyloxy)-1,1-dioxido-5-phenyl-2,3,4,5-tetrahydro-1,4-benzothiazepin-8-yl]methyl}imino)dimethanediyl]bis(phosphonic acid) tetraammonium salt and [({[(3R,5R)-3-butyl-3-ethyl-7-(methyloxy)-1,1-dioxido-5-phenyl-2,3,4,5-tetrahydro-1,4-benzothiazepin-8-yl]methyl}{[(ethyloxy)(hydroxy)phosphoryl]methyl}amino)methyl]phosphonic acid triammonium salt

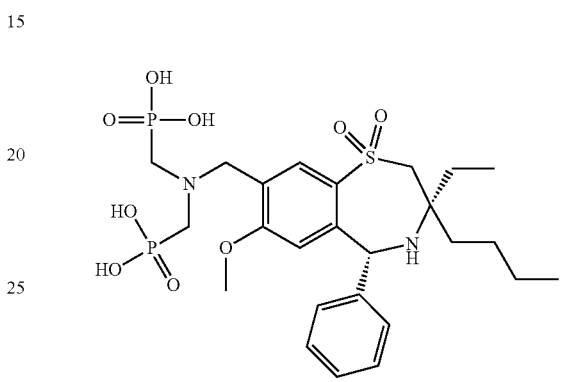

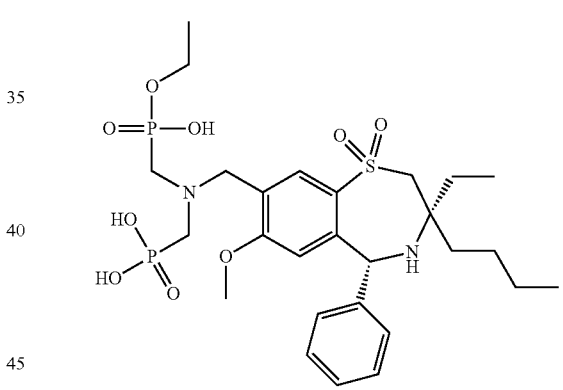

Tetraethyl [({[(3R,5R)-3-butyl-3-ethyl-7-(methyloxy)-1,1-dioxido-5-phenyl-2,3,4,5-tetrahydro-1,4-benzothiazepin-8-yl]methyl}imino)dimethanediyl]bis(phosphonate) (100 mg, 0.14 mmol) dissolved in DCM (5 mL) was treated with bromo(trimethyl)silane (171 mg, 1.116 mmol) at 23° C. overnight. The mixture was concentrated to dryness, and the crude product was purified by RP-HPLC (30×100 XBridge column under basic conditions; MeCN+0.1% NH$_4$OH and H$_2$O+0.1% NH$_4$OH were used as the solvent system; 10% to 55% over 6 minutes, 100% to 100% to 8 minutes) to give [({[(3R,5R)-3-butyl-3-ethyl-7-(methyloxy)-1,1-dioxido-5-phenyl-2,3,4,5-tetrahydro-1,4-benzothiazepin-8-yl]methyl}imino)dimethanediyl]bis(phosphonic acid) (45.4 mg, 53.8% yield) tetraammonium salt: $^1$H NMR (400 MHz, DMSO-d$_6$) δ ppm 0.75 (t, J=6.9 Hz, 3H) 0.80 (t, J=7.5 Hz, 3H) 0.97-1.29 (m, 4H) 1.32-1.55 (m, 2H) 1.68-1.81 (m, 1H)

1.98-2.14 (m, 1H) 2.58-2.77 (m, 5H) 3.09 (d, J=14.8 Hz, 1H) 3.41 (s, 3H) 3.52 (d, J=15.0 Hz, 1H) 3.75-3.96 (m, 2H) 5.94 (d, J=8.6 Hz, 1H) 6.08 (s, 1H) 7.25-7.37 (m, 1H) 7.36-7.49 (m, 4H) 7.90 (s, 1H) (phosphonic acid protons not observed); LC-MS (ES$^+$) m/z 605.2 [M+H]) and [({[(3R,5R)-3-butyl-3-ethyl-7-(methyloxy)-1,1-dioxido-5-phenyl-2,3,4,5-tetrahydro-1,4-benzothiazepin-8-yl]methyl}{[(ethyloxy)(hydroxy)phosphoryl]methyl}amino)methyl]phosphonic acid (10.8 mg, 12.2% yield) triammonium salt: ($^1$H NMR (400 MHz, DMSO-d$_6$) δ ppm 0.75 (t, J=7.0 Hz, 3H) 0.80 (t, J=7.4 Hz, 3H) 0.96-1.28 (m, 4H) 1.08 (t, J=7.0 Hz, 3H) 1.31-1.54 (m, 2H) 1.68-1.80 (m, 1H) 1.99-2.11 (m, 1H) 2.61-2.79 (m, 5H) 3.06 (d, J=14.9 Hz, 1H) 3.41 (s, 3H) 3.53 (d, J=14.9 Hz, 1H) 3.64-3.76 (m, 2H) 3.76-3.93 (m, 2H) 5.94 (d, J=9.6 Hz, 1H) 6.08 (s, 1H) 7.26-7.36 (m, 1H) 7.36-7.48 (m, 4H) 7.94 (s, 1H) (phosphonic acid protons not observed); LC-MS (ES$^+$) m/z 633.3 [M+H]).

Example 62

[({[(3R,5R)-3-butyl-3-ethyl-7-(methyloxy)-1,1-dioxido-5-phenyl-2,3,4,5-tetrahydro-1,4-benzothiazepin-8-yl]methyl}amino)methyl]phosphonic acid trifluoroacetate salt

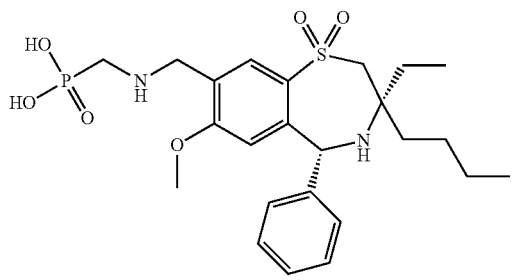 [SMILES: CCCC[C@]1(CC)CS(=O)(=O)c2cc(CNCP(=O)(O)O)c(OC)cc2[C@@H](c2ccccc2)N1]

Diethyl [({[(3R,5R)-3-butyl-3-ethyl-7-(methyloxy)-1,1-dioxido-5-phenyl-2,3,4,5-tetrahydro-1,4-benzothiazepin-8-yl]methyl}amino)methyl]phosphonate (36.3 mg, 0.064 mmol) dissolved in DCM (1 mL) was treated with bromo(trimethyl)silane (100 mg, 0.65 mmol) at 23° C. for 18 h. The mixture was concentrated to dryness, and the crude product was purified by RP-HPLC (30×75, C18, 5 um H$_2$O Sunfire Column at 55 mL/min; MeCN+0.05% TFA & H$_2$O+0.05% TFA were used as the solvent system; 10 to 100 over 8 min., 100 to 100 to 10 min) to give [({[(3R,5R)-3-butyl-3-ethyl-7-(methyloxy)-1,1-dioxido-5-phenyl-2,3,4,5-tetrahydro-1,4-benzothiazepin-8-yl]methyl}amino)methyl]phosphonic acid (6.0 mg, 18.4% yield) trifluoroacetate salt as a white glass: $^1$H NMR (400 MHz, DMSO-d$_6$) δ ppm 0.75 (t, J=7.0 Hz, 3H) 0.81 (t, J=7.4 Hz, 3H) 0.95-1.32 (m, 4H) 1.33-1.56 (m, 2H) 1.68-1.80 (m, 1H) 1.98-2.12 (m, 1H) 2.63-2.73 (m, 1H) 3.00-3.13 (m, 2H) 3.48 (s, 3H) 3.57-3.66 (m, 2H) 4.14-4.30 (m, 2H) 5.86-6.02 (m, 1H) 6.15 (s, 1H) 7.31-7.50 (m, 5H) 8.10 (s, 1H) (3 exchangable protons not observed); LC-MS (ES$^-$) m/z 509.5 [M−1]. LC-MS (ES$^+$) m/z 511.2 [M+H].

Example 63

1-{[(3R,5R)-3-butyl-3-ethyl-7-(methyloxy)-1,1-dioxido-5-phenyl-2,3,4,5-tetrahydro-1,4-benzothiazepin-8-yl]methyl}-L-proline ammonium salt

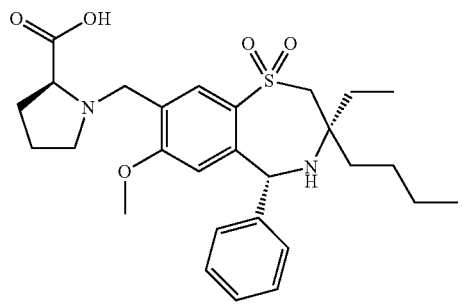 [SMILES: CCCC[C@]1(CC)CS(=O)(=O)c2cc(CN3CCC[C@H]3C(=O)O)c(OC)cc2[C@@H](c2ccccc2)N1]

1,1-Dimethylethyl L-prolinate.HCl (206 mg, 1.203 mmol) and (3R,5R)-3-butyl-3-ethyl-7-(methyloxy)-5-phenyl-2,3,4,5-tetrahydro-1,4-benzothiazepine-8-carbaldehyde 1,1-dioxide (250 mg, 0.60 mmol) were combined in DCM (5 mL), and the mixture was stirred for 1 h. NaHB(OAc)$_3$ (319 mg, 1.504 mmol) was added, and the reaction mixture was stirred for 16 h at ambient temperature. The mixture was partitioned between DCM and brine, and the phases were separated. The aqueous phase was extracted with DCM, and the organic phases were combined, dried over MgSO$_4$, filtered, and concentrated to a clear oil. The residue was treated with 4N HCl in 1,4-dioxane (10 mL, 40.0 mmol) at ambient temperature overnight. The reaction mixture was concentrated to dryness and purified by RP-HPLC (30×100 XBridge column; MeCN+0.2% NH$_4$OH and H$_2$O+0.2% NH$_4$OH were used as the solvent system; 10% to 70% over 8 minutes, 100% to 100% to 10 minutes) to give 1-{[(3R,5R)-3-butyl-3-ethyl-7-(methyloxy)-1,1-dioxido-5-phenyl-2,3,4,5-tetrahydro-1,4-benzothiazepin-8-yl]methyl}-L-proline (260 mg, 84% yield) ammonium salt as a white solid: $^1$H NMR (400 MHz, DMSO-d$_6$) δ ppm 0.75 (t, J=7.0 Hz, 3H) 0.80 (t, J=7.4 Hz, 3H) 0.96-1.29 (m, 4H) 1.32-1.53 (m, 2H) 1.64-1.94 (m, 4H) 1.99-2.16 (m, 2H) 2.62 (d, J=10.0 Hz, 1H) 2.98-3.12 (m, 2H) 3.26-3.37 (m, 2H) 3.44 (s, 3H) 3.55 (d, J=15.0 Hz, 1H) 3.82 (d, J=14.1 Hz, 1H) 3.89-4.00 (m, 1H) 5.94 (d, J=9.2 Hz, 1H) 6.10 (s, 1H) 7.27-7.37 (m, 1H) 7.42 (d, J=4.5 Hz, 4H) 7.99 (s, 1H) (COOH proton not observed); LC-MS (ES$^+$) m/z 513.5 [M+H].

Example 64

({[(3R,5R)-3-butyl-3-ethyl-7-(methyloxy)-1,1-dioxido-5-phenyl-2,3,4,5-tetrahydro-1,4-benzothiazepin-8-yl]methyl}amino)(oxo)acetic acid

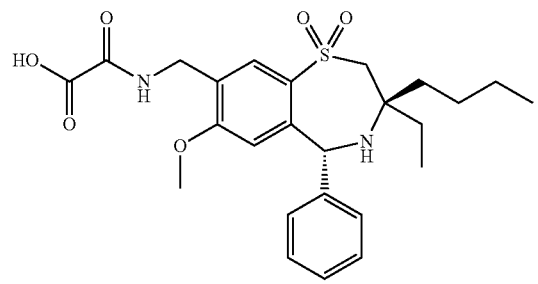 [SMILES: CCCC[C@]1(CC)CS(=O)(=O)c2cc(CNC(=O)C(=O)O)c(OC)cc2[C@@H](c2ccccc2)N1]

Step 1: A solution of {[(3R,5R)-3-butyl-3-ethyl-7-(methyloxy)-1,1-dioxido-5-phenyl-2,3,4,5-tetrahydro-1,4-benzothiazepin-8-yl]methyl}amine (77 mg, 0.19 mmol) in DCM (924 µl) at 0° C. was treated with Et₃N (56.7 µl, 0.407 mmol) followed by methyl chloro(oxo)acetate (18.7 µl, 0.203 mmol). The reaction was stirred for 30 min then warmed to 25° C. and stirred for an additional 1 h. LCMS indicated 92:8/prod:SM. Added additional acid chloride (2 ul) then stirred at 25° C. for 2 h. The reaction was diluted with DCM and H₂O, the layers separated, and the aqueous layer extracted with DCM (3×). The combined organic layers were dried (MgSO₄), filtered, and concentrated in vacuo to give methyl ({[(3R,5R)-3-butyl-3-ethyl-7-(methyloxy)-1,1-dioxido-5-phenyl-2,3,4,5-tetrahydro-1,4-benzothiazepin-8-yl]methyl}amino)(oxo)acetate (93 mg, 100% yield) which was used as is in the next step: ¹H NMR (CDCl₃) δ 7.96 (s, 1H), 7.28-7.54 (m, 6H), 6.18 (s, 1H), 6.06 (s, 1H), 4.48 (d, J=6.0 Hz, 2H), 3.87 (s, 3H), 3.54 (s, 3H), 3.41 (d, J=14.8 Hz, 1H), 2.96-3.10 (m, 2H), 2.06-2.22 (m, 1H), 1.76-1.90 (m, 1H), 1.03-1.58 (m, 6H), 0.88 (t, J=7.4 Hz, 3H), 0.81 (t, J=7.0 Hz, 3H); LC-MS (ES⁺) m/z 503 [M+H].

Step 2: A solution of methyl ({[(3R,5R)-3-butyl-3-ethyl-7-(methyloxy)-1,1-dioxido-5-phenyl-2,3,4,5-tetrahydro-1,4-benzothiazepin-8-yl]methyl}amino)(oxo)acetate (93 mg, 0.185 mmol) in THF (694 µl) and H₂O (231 µl) at 0° C. was treated with 1M aq. LiOH (204 µl, 0.204 mmol). The reaction was stirred at 0° C. for 60 min then warmed to 25° C. and stirred for 1 h. The reaction was diluted with EtOAc and acidified with dilute HCl. The layers were separated, and the aqueous layer was extracted with EtOAc (3×). The combined organic layers were washed with brine, dried (MgSO₄), filtered, and conc. in vacuo. Triturated the residue with hexanes/Et₂O then collected a white solid by filtration. Obtained ({[(3R,5R)-3-butyl-3-ethyl-7-(methyloxy)-1,1-dioxido-5-phenyl-2,3,4,5-tetrahydro-1,4-benzothiazepin-8-yl]methyl}amino)(oxo)acetic acid (79 mg, 87% yield) as a white solid: ¹H NMR (DMSO-d₆) δ ppm 9.37 (br. s., 1H), 7.75 (br. s., 1H), 7.27-7.65 (m, 5H), 6.17 (br. s., 1H), 5.92 (br. s., 1H), 4.16-4.38 (m, 2H), 3.48 (m 4H), 3.03 (br s, 1H), 1.95-2.26 (m, 1H), 1.62-1.88 (m, 1H), 0.94-1.61 (m, 6H), 0.46-0.95 (m, 61-1) LC-MS (ES⁺) m/z 489 [M+H].

Example 65

3-({[3,3-dibutyl-7-(methyloxy)-1,1-dioxido-5-phenyl-2,3,4,5-tetrahydro-1,4-benzothiazepin-8-yl]methyl}amino)pentanedioic acid trifluoroacetate salt

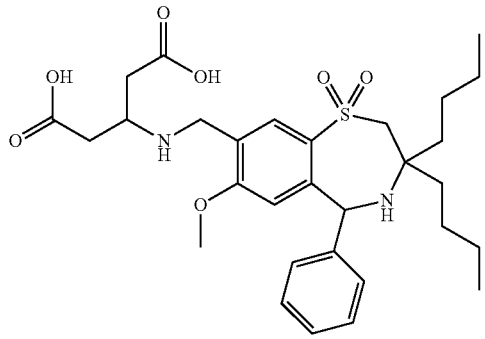 [SMILES: CCCCC1(CCCC)CS(=O)(=O)c2cc(CNC(CC(=O)O)CC(=O)O)c(OC)cc2C(c2ccccc2)N1]

Step 1: A solution of 3,3-dibutyl-7-(methyloxy)-5-phenyl-2,3,4,5-tetrahydro-1,4-benzothiazepine-8-carbaldehyde 1,1-dioxide (150 mg, 0.338 mmol) and dimethyl 3-aminopentanedioate (89 mg, 0.507 mmol) in 1,2-dichloroethane (DCE) (3.36 mL) was treated with acetic acid (19.36 µl, 0.338 mmol) and stirred at 25° C. for 1 h. The reaction was treated with NaHB(OAc)₃ (71.7 mg, 0.338 mmol) then stirred for 15 h. The reaction was treated with additional NaHB(OAc)₃ (71.7 mg, 0.338 mmol) then stirred for 4 h. The rxn was poured into DCM and 10% aq. Na₂CO₃. The layers were separated, and the aqueous layer was extracted with DCM (2×). The combined organic layers were washed with brine, dried (MgSO₄), filtered, and concentrated in vacuo. The residue was purified by preparative SiO₂ chromatography using hexanes:EtOAc as eluent to give dimethyl 3-({[3,3-dibutyl-7-(methyloxy)-1,1-dioxido-5-phenyl-2,3,4,5-tetrahydro-1,4-benzothiazepin-8-yl]methyl}amino)pentanedioate (142 mg, 69.7% yield).

Step 2: A solution of dimethyl 3-({[3,3-dibutyl-7-(methyloxy)-1,1-dioxido-5-phenyl-2,3,4,5-tetrahydro-1,4-benzothiazepin-8-yl]methyl}amino)pentanedioate (140 mg, 0.232 mmol) in THF (1.05 mL) and H₂O (348 µl) at 25° C. was treated with 1N LiOH (929 µl, 0.929 mmol) then stirred for 4 h. THF was removed under reduced pressure then the residue was lyophilized to a white solid. The material was purified via RP-HPLC purification (30×150 mm, C18 5 um H₂O Sunfire Column; MeCN+0.05% TFA & H₂O+0.05% TFA were used as the solvent system; 10 to 100% over 10 min.) to give 3-({[3,3-dibutyl-7-(methyloxy)-1,1-dioxido-5-phenyl-2,3,4,5-tetrahydro-1,4-benzothiazepin-8-yl]methyl}amino)pentanedioic acid (81 mg, 50.6% yield) trifluoroacetate salt as an amorphous white solid: ¹H NMR (DMSO-d₆) δ ppm 12.79 (br. s., 1H), 8.75 (br. s., 1H), 8.48 (br. s., 1H), 8.10 (s, 1H), 7.28-7.56 (m, 5H), 6.17 (s, 1H), 5.98 (s, 1H), 4.27 (br. s., 2H), 3.69-3.80 (m, 1H), 3.62 (d, J=14.8 Hz, 1H), 3.49 (s, 3H), 3.10 (d, J=14.8 Hz, 1H), 2.62-2.89 (m, 4H), 2.07 (br. s., 1H), 1.76 (br. s., 1H), 0.99-1.55 (m, 10H), 0.86 (t, J=6.6 Hz, 3H), 0.76 (t, J=6.9 Hz, 3H); LC-MS (ES⁺) m/z 575.1 [M+H].

Example 66

N-{[3,3-dibutyl-7-(methyloxy)-1,1-dioxido-5-phenyl-2,3,4,5-tetrahydro-1,4-benzothiazepin-8-yl]methyl}glycine trifluoroacetate salt

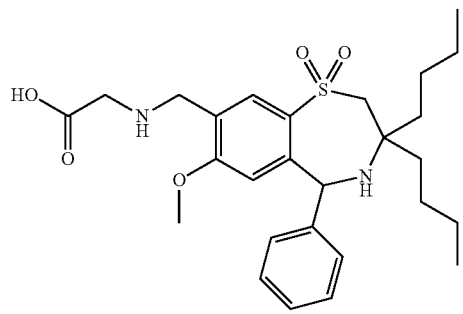 [SMILES: CCCCC1(CCCC)CS(=O)(=O)c2cc(CNCC(=O)O)c(OC)cc2C(c2ccccc2)N1]

Step 1: A solution of 3,3-dibutyl-7-(methyloxy)-5-phenyl-2,3,4,5-tetrahydro-1,4-benzothiazepine-8-carbaldehyde 1,1-dioxide (150 mg, 0.338 mmol) and 1,1-dimethylethyl glycinate (44.4 mg, 0.338 mmol) in 1,2-dichloroethane (DCE) (3.36 mL) was treated with acetic acid (19.36 µl, 0.338 mmol) and stirred at 25° C. for 1 h. The reaction was treated with NaHB(OAc)₃ (71.7 mg, 0.338 mmol) then stirred for 5 h. Additional NaHB(OAc)₃ (71.7 mg, 0.338 mmol) was added then stirring was continued at 25° C. for 4 h. The rxn was poured into DCM and 10% aq. Na₂CO₃. The layers were separated. and the aqueous layer was extracted with DCM (2×). The combined organic layers were washed with brine, dried (MgSO₄), filtered, and concentrated in vacuo. The residue was purified by preparative SiO₂ chromatography using hexanes:EtOAc as eluent to give 1,1-dimethylethyl N-{[3,3-dibutyl-7-(methyloxy)-1,1-dioxido-5-phenyl-2,3,4,5-tetrahydro-1,4-benzothiazepin-8-yl]methyl}glycinate (100 mg, 52.9% yield).

Step 2: A solution of 1,1-dimethylethyl N-{[3,3-dibutyl-7-(methyloxy)-1,1-dioxido-5-phenyl-2,3,4,5-tetrahydro-1,4-benzothiazepin-8-yl]methyl}glycinate (130 mg, 0.233 mmol) in DCM (2 mL) at 25° C. was treated with excess 4M HCl in 1,4-dioxane (3.53 mL, 116 mmol) then stirred for 15 h. The reaction was concentrated in vacuo then the residue was triturated with Et$_2$O. A white solid was collected by filtration then purified by RP-HPLC (30×150 mm, C18 5 um H$_2$O Sunfire Column; MeCN+0.05% TFA & H$_2$O+0.05% TFA as the solvent system; 10 to 100% over 10 min.) to give N-{[3,3-dibutyl-7-(methyloxy)-1,1-dioxido-5-phenyl-2,3,4,5-tetrahydro-1,4-benzothiazepin-8-yl]methyl}glycine (70 mg, 48.8% yield) trifluoroacetate salt as an amorphous white solid: $^1$H NMR (DMSO-d$_6$) δ ppm 13.72 (br. s., 1H), 8.76-9.61 (m, 2H), 8.07 (s, 1H), 7.26-7.52 (m, 5H), 6.17 (s, 1H), 5.75-6.04 (br s, 1H), 4.05-4.28 (m, 2H), 3.84 (br. s., 2H), 3.63 (d, J=14.9 Hz, 1H), 3.48 (s, 3H), 3.10 (d, J=14.9 Hz, 1H), 1.99-2.15 (m, 1H), 1.64-1.84 (m, 1H), 0.99-1.52 (m, 10H), 0.87 (t, J=6.6 Hz, 3H), 0.75 (t, J=6.9 Hz, 3H); LC-MS (ES$^+$) m/z 503.1 [M+H].

Example 67

{[3,3-dibutyl-7-(methyloxy)-1,1-dioxido-5-phenyl-2,3,4,5-tetrahydro-1,4-benzothiazepin-8-yl]methyl}phosphonic acid trifluoroacetate salt

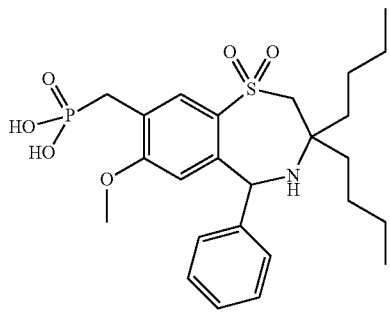 [SMILES: CCCCC1(CCCC)CS(=O)(=O)c2cc(CP(=O)(O)O)c(OC)cc2C(c2ccccc2)N1]

A solution of diethyl {[3,3-dibutyl-7-(methyloxy)-1,1-dioxido-5-phenyl-2,3,4,5-tetrahydro-1,4-benzothiazepin-8-yl]methyl}phosphonate (200 mg, 0.354 mmol) in DCM (6.9 mL) at 25° C. was treated with TMSBr (213 µl, 1.640 mmol) then stirred at 25° C. for 15 h. The reaction was concentrated in vacuo then triturated with Et$_2$O/hexanes. A white solid was collected by filtration which was purified via preparative RP-HPLC (30×150 mm, C18 5 um H$_2$O Sunfire Column; MeCN+0.05% TFA & H$_2$O+0.05% TFA were used as the solvent system; 10 to 80% over 12 min.) to give {[3,3-dibutyl-7-(methyloxy)-1,1-dioxido-5-phenyl-2,3,4,5-tetrahydro-1,4-benzothiazepin-8-yl]methyl}phosphonic acid (60 mg, 27.2% yield) trifluoroacetate salt as a white solid: $^1$H NMR (CDCl$_3$) δ ppm 7.87 (br. s., 1H), 7.50-7.73 (m, 5H), 6.58 (s, 1H), 6.50 (s, 1H), 3.89 (d, J=15.0 Hz, 1H), 3.61 (s, 3H), 3.34-3.66 (m, 3H), 2.83-3.06 (m, 1H), 2.44-2.75 (m, 1H), 1.18-2.02 (m, 10H), 0.74-1.04 (m, 6H); LC-MS (ES$^+$) m/z 510.4 [M+H].

Example 68

N-{[(3R,5R)-3-butyl-7-(dimethylamino)-3-ethyl-1,1-dioxido-5-phenyl-2,3,4,5-tetrahydro-1,4-benzothiazepin-8-yl]methyl}glycine trifluoroacetate salt

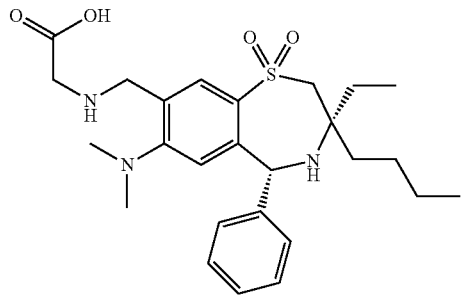 [SMILES: CCCC[C@]1(CC)CS(=O)(=O)c2cc(CNCC(=O)O)c(N(C)C)cc2[C@@H](c2ccccc2)N1]

(3R,5R)-3-butyl-7-(dimethylamino)-3-ethyl-5-phenyl-2,3,4,5-tetrahydro-1,4-benzothiazepine-8-carbaldehyde 1,1-dioxide (22 mg, 0.051 mmol) and 1,1-dimethylethyl glycinate (33.7 mg, 0.257 mmol) were combined in DCM (4 mL) and stirred for 1 h at ambient temperature. The mixture was treated with NaHB(OAc)$_3$ (76 mg, 0.359 mmol) then stirred for 2 days at ambient temperature. The reaction mixture was partitioned between DCM and brine, and the phases were separated. The aqueous phase was extracted with DCM, and the organic phases were combined, dried over MgSO$_4$, filtered, and concentrated to a clear oil. The residue was purified on 4 g silica gel eluting with 30 to 100% EtOAc/hexanes to give the t-butyl ester intermediate (18 mg, 0.033 mmol, 64.2% yield) as a clear oil. LC-MS (ES$^+$) m/z 544.34 [M+H]. The ester was treated with 4N HCl in 1,4-dioxane (1.283 mL, 5.13 mmol) at ambient temperature. The mixture was stirred overnight then concentrated to dryness. The material was purified by RP-HPLC (30×75 Sunfire column; 55 mL/min; 10% to 100% MeCN in H$_2$O with 0.05% TFA buffer over 8 minutes) to give N-{[(3R,5R)-3-butyl-7-(dimethylamino)-3-ethyl-1,1-dioxido-5-phenyl-2,3,4,5-tetrahydro-1,4-benzothiazepin-8-yl]methyl}glycine trifluoroacetate salt (17.1 mg, 0.024 mmol, 46.5% yield) as a clear oil: $^1$H NMR (400 MHz, DMSO-d$_6$) δ ppm 0.77 (t, J=7.0 Hz, 3H), 0.82 (t, J=7.3 Hz, 3H), 0.94-1.30 (m, 4H), 1.36-1.63 (m, 2H), 1.70-1.86 (m, 1H), 2.02-2.20 (m, 1H), 2.44 (s, 6H), 3.16 (s, 1H), 3.56-3.80 (m, 1H), 3.91 (br. s., 2H), 4.14-4.40 (m, 2H), 5.94 (br. s., 1H), 6.27 (s, 1H), 7.16-7.65 (m, 5H), 8.13 (s, 1H), 9.35 (br. s., 2H) (amine proton not observed); LC-MS (ES$^-$) m/z 486.4 [M−1]. LC-MS (ES$^+$) m/z 488.3 [M+H].

Example 69

3-({[(3R,5R)-3-butyl-7-(dimethylamino)-3-ethyl-1,1-dioxido-5-phenyl-2,3,4,5-tetrahydro-1,4-benzothiazepin-8-yl]methyl}amino)pentanedioic acid bis-ammonium salt

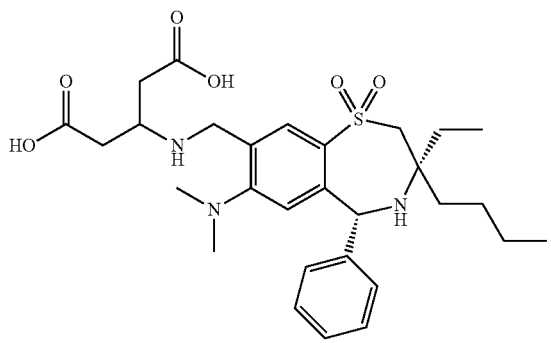 [SMILES: CCCC[C@]1(CC)CS(=O)(=O)c2cc(CNC(CC(=O)O)CC(=O)O)c(N(C)C)cc2[C@@H](c2ccccc2)N1]

(3R,5R)-3-butyl-7-(dimethylamino)-3-ethyl-5-phenyl-2,3,4,5-tetrahydro-1,4-benzothiazepine-8-carbaldehyde 1,1-dioxide (22 mg, 0.051 mmol) and dimethyl 3-aminopentanedioate (45.0 mg, 0.257 mmol) were combined in DCM (4 mL) and stirred for 1 h at ambient temperature. The mixture was treated with NaHB(OAc)₃ (76 mg, 0.359 mmol) then stirred for 2 days at ambient temperature. The mixture was partitioned between DCM and brine, and the phases were separated. The aqueous phase was extracted with DCM, and the organic phases were combined, dried over MgSO₄, filtered, and concentrated to a clear oil. The residue was purified on 40 g silica eluted with 30 to 100% EtOAc/hexanes to give the intermediate bis methyl ester as a clear oil. LC-MS (ES⁺) m/z 588.29 [M+H]. The ester was dissolved in THF (0.5 mL) and treated with 1M LiOH (0.513 mL, 0.513 mmol) at ambient temperature. The mixture was stirred overnight. The mixture was concentrated to dryness and purified by RP-HPLC (30×100 XBridge column at 55 mL/min; 10% to 100% MeCN in H₂O with 0.1% NH₄OH buffer over 8 minutes) to give 3-({[(3R,5R)-3-butyl-7-(dimethylamino)-3-ethyl-1,1-dioxido-5-phenyl-2,3,4,5-tetrahydro-1,4-benzothiazepin-8-yl]methyl}amino)pentanedioic acid bis-ammonium salt (11.2 mg, 0.019 mmol, 36.7% yield) as a white solid: ¹H NMR (400 MHz, DMSO-d₆) δ ppm 0.75 (t, J=7.1 Hz, 3H), 0.79 (t, J=7.6 Hz, 3H), 0.94-1.29 (m, 4H), 1.31-1.52 (m, 2H), 1.65-1.82 (m, 1H), 1.66-1.83 (m, 1H), 1.96-2.15 (m, 1H), 2.26-2.40 (m, 4H), 2.47 (s, 6H), 2.60 (d, J=9.8 Hz, 1H), 3.06 (d, J=14.9 Hz, 1H), 3.16 (t, J=6.2 Hz, 1H), 3.52 (d, J=15.0 Hz, 1H), 3.78 (s, 2H), 5.88 (d, J=9.6 Hz, 1H), 6.11 (s, 1H), 7.26-7.35 (m, 1H), 7.35-7.48 (m, 4H), 7.94 (s, 1H) (acid protons not observed); LC-MS (ES⁻) m/z 558.3 [M−1]. LC-MS (ES⁺) m/z 560.2 [M+H].

Example 70

3-({[(3R,5R)-3-butyl-3-ethyl-7-(methyloxy)-1,1-dioxido-5-phenyl-2,3,4,5-tetrahydro-1,4-benzothiazepin-8-yl]carbonyl}amino)pentanedioic acid

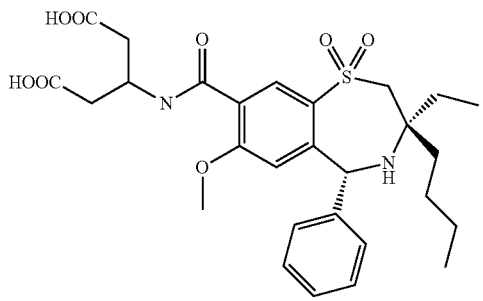 [SMILES: CCCC[C@]1(CC)CS(=O)(=O)c2cc(C(=O)NC(CC(=O)O)CC(=O)O)c(OC)cc2[C@@H](c2ccccc2)N1]

Dimethyl 3-({[(3R,5R)-3-butyl-3-ethyl-7-(methyloxy)-1,1-dioxido-5-phenyl-2,3,4,5-tetrahydro-1,4-benzothiazepin-8-yl]carbonyl}amino)pentanedioate (Intermediate 47, 212 mg, 0.227 mmol) in a 1:1:1 mixture of methanol/water/tetrahydrofuran (15 mL) was added lithium hydroxide monohydrate (28.6 mg, 0.681 mmol). The reaction mixture was stirred at room temperature overnight and partially concentrated under reduce pressure. The residue was then adjusted to pH=2 using 1N hydrochloric acid and partitioned between water and dichloromethane. The organic layer was washed with saturated brine, dried (Na₂SO₄), filtered, and concentrated under reduced pressure. Purification with HPLC (Medium Column: Gilson 845Z Prep. System; Sunfire C18 5 μM, 30×150 mm; Method: 10-100% MeCN/H₂O with 0.05% TFA over 10 min, 45 mL/min, A=220, 254 nm) afforded the title compound as a light yellow solid (61 mg, 95% pure, 38%) as a TFA salt: ¹H NMR (400 MHz, DMSO-d₆) δ 8.40-8.55 (m, 1H), 8.36 (s, 1H), 7.24-7.55 (m, 5H), 6.17-6.28 (m, 1H), 5.86-6.05 (m, 1H), 4.46-4.63 (m, 1H), 3.47-3.70 (m, 4H), 3.06-3.20 (m, 1H), 2.52-2.61 (m, 4H), 1.97-2.23 (m, 1H), 1.66-1.88 (m, 1H), 1.34-1.61 (m, 2H), 0.95-1.34 (m, 4H), 0.68-0.89 (m, 6H); ES-LCMS m/z 561 (M+H)⁺.

Example 71

1-[(3R,5R)-3-butyl-3-ethyl-7-(methyloxy)-1,1-dioxido-5-phenyl-2,3,4,5-tetrahydro-1,4-benzothiazepin-8-yl]ethanone

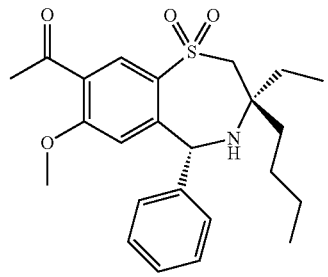 [SMILES: CCCC[C@]1(CC)CS(=O)(=O)c2cc(C(C)=O)c(OC)cc2[C@@H](c2ccccc2)N1]

To an ice-cold solution of (3R,5R)-3-butyl-3-ethyl-N-methyl-N,7-bis(methyloxy)-5-phenyl-2,3,4,5-tetrahydro-1,4-benzothiazepine-8-carboxamide 1,1-dioxide (Intermediate 44, 160 mg, 0.337 mmol) in tetrahydrofuran (5 mL) was added methylmagnesium bromide (0.337 mL, 1.011 mmol). The reaction mixture was stirred at room temperature for 1 hr, treated with a saturated ammonium hydrochloride solution, and extracted with EtOAc. The organic layer was washed with saturated brine, dried (Na₂SO₄), filtered, and concentrated under reduced pressure. Purification via SiO₂ chromatography (MeOH:DCM=0:100 to 3:97) afforded the title compound (78 mg, 94% pure, 50%) as a white solid: ¹H NMR (400 MHz, CDCl₃) δ ppm 8.43 (s, 1H), 7.30-7.51 (m, 5H), 6.25 (s, 1H), 6.09 (s, 1H), 3.57 (s, 3H), 3.43 (d, J=14.9 Hz, 1H), 3.00 (d, J=14.9 Hz, 1H), 2.54 (s, 2H), 2.11-2.26 (m, J=4.1 Hz, 1H), 1.77-1.93 (m, 1H), 1.57 (d, J=7.2 Hz, 1H), 1.38-1.51 (m, 2H), 1.01-1.35 (m, 5H), 0.87 (t, J=7.4 Hz, 3H), 0.81 (t, J=7.0 Hz, 3H); ES-LCMS m/z 430 (M+H)⁺.

Example 72

3-[(3R,5R)-3-butyl-3-ethyl-7-(methyloxy)-1,1-dioxido-5-phenyl-2,3,4,5-tetrahydro-1,4-benzothiazepin-8-yl]pentanedioic acid

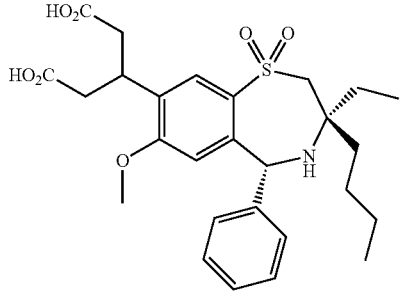 [SMILES: CCCC[C@]1(CC)CS(=O)(=O)c2cc(C(CC(=O)O)CC(=O)O)c(OC)cc2[C@@H](c2ccccc2)N1]

A mixture of tetraethyl 2-[(3R,5R)-3-butyl-3-ethyl-7-(methyloxy)-1,1-dioxido-5-phenyl-2,3,4,5-tetrahydro-1,4-benzothiazepin-8-yl]-1,1,3,3-propanetetracarboxylate (Intermediate 46, 120 mg, 0.167 mmol) and 37% hydrochloric acid (3 mL) was stirred at reflux for 20 h. LC-MS showed no starting material left, but instead a mixture of tri-acid and di-acid. Additional 37% hydrochloric acid (3 mL) was added, and the reaction mixture was heated at reflux overnight. The reaction mixture was cooled to room temperature then concentrated under reduced pressure. Purification with HPLC (eluting with MeCN/water with 0.05% TFA-H₂O and 0.05% TFA-MeCN)

afforded the title compound (76 mg, 95% pure, 68%) as a white solid: $^1$H NMR (400 MHz, DMSO-d$_6$) δ ppm 12.14 (br. s., 2H), 7.78 (br. s., 1H), 6.98-7.66 (m, 5H), 5.58-6.41 (m, 1H), 3.55-3.82 (m, 2H), 3.46 (s, 3H), 2.59 (d, J=7.2 Hz, 4H), 0.95-2.26 (m, 7H), 0.68-0.92 (m, 6H); ES-LCMS m/z 518 (M+H)$^+$.

Example 73

2-((3R,5R)-3-butyl-3-ethyl-7-(methyloxy)-5-phenyl-2,3,4,5-tetrahydro-1,4-benzothiazepine-8-carboxamido)acetic acid

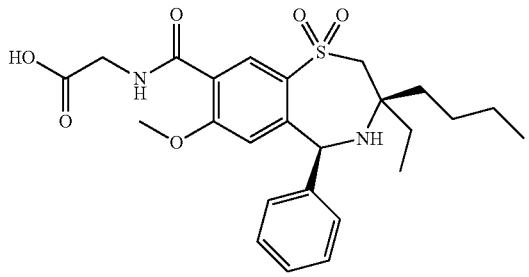 [SMILES: CCCC[C@]1(CC)CS(=O)(=O)c2cc(C(=O)NCC(=O)O)c(OC)cc2[C@H](c2ccccc2)N1]

To a DMF solution of (3R,5R)-3-butyl-3-ethyl-7-(methyloxy)-5-phenyl-2,3,4,5-tetrahydro-1,4-benzothiazepine-8-carboxylic acid 1,1-dioxide (Intermediate 4, 0.025 g, 0.058 mmol) and glycine methyl ester hydrochloride (0.008 g, 0.064 mmol) at 0° C. was added HATU (0.024 g, 0.064 mmol) followed by DIPEA (0.009 g, 0.070 mmol). The reaction was stirred for 10 min and then warmed to room temperature. After 1 h the reaction was concentrated to half volume and water (3 mL) was added. The precipitant was filtered, dried, and used without further purification. The material was dissolved in THF (0.500 mL) and H$_2$O (0.250 mL) was added followed by LiOH (0.007 g, 0.174 mmol). The reaction was stirred at room temperature for 3 h then concentrated in vacuo. The residue was chromatographed via SiO$_2$ chromatography using DCM/MeOH to give the title compound in 90% purity: $^1$H NMR (400 MHz, MeOH-d$_4$) δ ppm 8.63 (s, 1H), 7.38-7.58 (m, 5H), 6.46 (br. s., 1H), 6.20 (br. s., 1H), 4.04-4.21 (m, 2H), 3.68 (s, 3H), 2.39 (br. s., 1H), 1.90 (br. s., 1H), 1.75 (br. s., 1H), 1.52 (br. s., 1H), 1.05-1.43 (m, 6H), 0.94 (t, J=7.46 Hz, 3H), 0.84 (t, J=6.98 Hz, 3H); ES-LCMS m/z 489 (M+H)$^+$.

Method for Determination of Crystallinity:

Differential scanning calorimetry analysis was performed using a TA Instruments Q1000 DSC. A sample was loaded into a non-hermetically sealed aluminum pan and scanned under nitrogen purge at 10° C./min. The thermogravimetric analysis was performed using a TA instruments Q5000 TGA. The sample was loaded into a platinum pan and scanned from room temperature to past the onset of decomposition at 10° C./min.

A sample of the final crystalline Example 26 from Method 3 exhibited an onset of decomposition at approximately 207° C. TGA confirmed that the DSC endotherm was due to decomposition rather than a true melt. No significant weight loss (less than 0.5% w/w) prior to decomposition was observed by TGA.

A sample of the final crystalline Example 26 from Method 3 had significant diffraction peaks in the powder X-ray diffraction (PXRD) pattern at values in two-theta in degrees and d-spacing in Angstroms in parenthesis of 4.9 (18), 5.3 (17), 9.8 (9.0), 12.0 (7.4), 13.2 (6.7), 18.5 (4.8), 19.8 (4.5), 21.1 (4.2).

A powder X-ray diffraction scan was obtained by filling a 1-mm glass capillary with the sample. The PXRD scan was collected using a PANalytical X'Pert Pro MPD diffractometer equipped with a copper X-ray tube, an incident beam elliptical mirror and a PANalytical X' celerator detector. Silicon powder (NIST 640b) was used as an internal standard to correct, if necessary, for experimental 2theta errors. In addition, a short range low angle negative scan was compared to that of a short range low angle positive scan to estimate the error in two-theta for the lowest observed diffraction peaks (near 5 degrees two-theta) as well as verify that the capillary was properly aligned in the X-ray beam. Diffraction data was collected from 3.5 to 90 degrees two-theta. A separate scan of a capillary filled with pure sample (no internal standard) was collected from 3.5 to 50 degrees two-theta.

Method for Determination of Human iBAT Inhibition:

In preparation for measurement of bile acid uptake into cells expressing the ileal bile acid cotransporter (iBAT), HEK293 cells were cultured in DMEM/F12 supplemented with 10% FBS. Twenty four hours prior to running an experiment, cells were harvested when at a confluence of 80-90%. Cells were seeded in poly-d-lysine coated plates at 50,000 cells per well, and human iBAT Bacmam virus was added such that each well contains 3.67×10e6 pfu (73.4pfu/cell). Each assay plate was covered with Breathe Easy Seal and placed in an incubator for 24 hours to allow expression of the transporter.

On the day of the uptake experiment, 10 mM HEPES was added to Hank's Balanced Salt Solution, and the pH was adjusted to 7.4 with TRIS (HBSSH). The assay buffer was prepared by adding 100 μM [$^3$H]-taurocholate and 10 μM cold taurocholate to room temperature HBSSH. A separate washing buffer was prepared by adding 10 μM cold taurocholate to HBSSH (~30 ml per assay plate) and placed on ice. Using 100% DMSO, 8 point, 3-fold dilution curves for each test compound was prepared starting at 200 μM. Similarly, an 8 point dose response curve was prepared of the control compound [(3R,5R)-3-butyl-3-ethyl-7,8-bis(methyloxy)-5-phenyl-2,3,4,5-tetrahydro-1,4-benzothiazepine 1,1-dioxide (Brieaddy, L. E. WO9605188, 1996)] starting at 1.8 mM. Drug plates were created by adding 3 μL of each concentration to a v-bottom 96-well plate then diluted 60-fold with 177 μL of assay buffer. Plates were removed from the incubator and allowed to cool to ambient temperature. Media was aspirated, and wells were washed once with 300 μL HBSSH. 50 μL of each dose response curve concentration was added in triplicate by column to the assay plates, reserving column 10 for control (assay buffer+1.67% DMSO) and columns 11 and 12 for the control compound. Plates were incubated at ambient temperature for 90 minutes then the plates were aspirated then washed 1× with 300 μL of wash buffer. 220 μL of Microscint 20 was added to each well, and the plates were sealed. The amount of [$^3$H]-taurocholate in cell lysate was quantitated using a microplate scintillation counter on the following day.

Percent inhibition of uptake was determined using the following formula at each drug concentration: $100*(1-((T1-C2)/(C1-C2)))$; where T1 is average cpm for the test compound, C1 is average cpm observed in the absence of any added inhibitor, and C2 is average cpm observed in the presence of a substance known to elicit 100% inhibition of uptake (30 μM control compound). IC50's can be generated using the formula, $y=(Vmax*x\char`\^n)/(K\char`\^n+x\char`\^n)$.

The compounds of the invention were tested in the above assay and the results are summarized below where each number is a mean of at least 2 datapoints.

| Compound | iBAT IC$_{50}$ (nM) |
| --- | --- |
| Example 1 | 32 |
| Example 2 | 11 |
| Example 3 | 2 |
| Example 4 | 2540 |
| Example 5 | 4 |

-continued

| Compound | iBAT IC$_{50}$ (nM) |
|---|---|
| Example 6 | 23 |
| Example 7 | 145 |
| Example 8 | 73 |
| Example 9 | 3 |
| Example 10 | 17 |
| Example 11 | 20 |
| Example 12 | 68 |
| Example 13 | 167 |
| Example 14 | 276 |
| Example 15 | 504 |
| Example 16 | 731 |
| Example 17 | 3330 |
| Example 18 | 728 |
| Example 19 | 622 |
| Example 20 | 4 |
| Example 21 | 51 |
| Example 22 | 2440 |
| Example 23 | 2 |
| Example 24 | 73 |
| Example 25 | 6 |
| Example 26 | 43 |
| Example 27 | 47 |
| Example 28 | 55 |
| Example 29 | 367 |
| Example 30 | 1287 |
| Example 31 | 407 |
| Example 32 | 190 |
| Example 33 | 2698 |
| Example 34 | 2790 |
| Example 35 | 54 |
| Example 36 | 365 |
| Example 37 | 9 |
| Example 38 | 249 |
| Example 39 | 619 |
| Example 40 | 4670 |
| Example 41 | 3330 |
| Example 42 | 128 |
| Example 43 | 7679 |
| Example 44 | 648 |
| Example 45 | 1950 |
| Example 46 | 2 |
| Example 47 | 13 |
| Example 48 | 17 |
| Example 49 | 41 |
| Example 50 | 51 |
| Example 51 | 51 |
| Example 52 | 59 |
| Example 53 | 67 |
| Example 54 | 124 |
| Example 55 | 131 |
| Example 56 | 425 |
| Example 57 | 751 |
| Example 58 | 1458 |
| Example 59 | 3326 |
| Example 60 | 3330 |
| Example 61 | 3360 |
| Example 62 | 3900 |
| Example 63 | 8992 |
| Example 64 | 6 |
| Example 65 | 337 |
| Example 66 | 21 |
| Example 67 | 52 |
| Example 68 | 1 |
| Example 69 | 19 |
| Example 70 | 100 |
| Example 71 | 100 |
| Example 72 | >3000 |
| Example 73 | Not tested |

What is claimed is:

1. A compound of Formula I

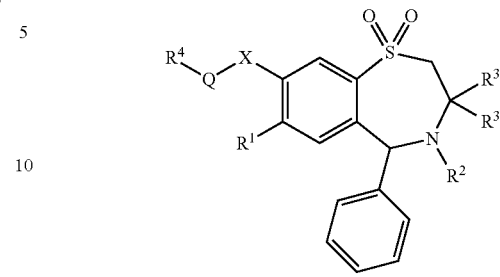

wherein $R^1$ is H, Cl, Br, $N(CH_3)_2$, or methoxy;
$R^2$ is H or OH;
each $R^3$ is independently $C_{1-6}$alkyl;
X is $CH_2$, C(O), or CH=CH;
Q is $C_{0-6}$alkyl;
$R^4$ is OH, $SO_3H$, $CO_2H$, $PO_3H_2$, $CONR^5R^5$, $NR^5R^5$; or $NHC(O)CH_2NR^5R^5$;
each $R^5$ is independently H, OH, $C_{1-6}$alkyl, $C_{0-6}$alkylCO$_2$H, $C_{0-6}$alkylSO$_3$H, $C_{0-6}$alkylPO$_3$H$_2$, $C(O)C_{0-6}$alkylCO$_2$H, $C(O)C_{0-6}$alkylSO$_3$H, $C(O)C_{0-6}$alkylPO$_3$H$_2$, or $CH(R^7)C_{0-6}$alkyCO$_2$H; and
$R^7$ is $C_{0-6}$alkylCO$_2$H, $C_{0-6}$alkylOH, $C_{0-6}$alkylSO$_3$H, or $C_{0-6}$alkylPO$_3$H$_2$.

2. A compound according to claim 1 wherein $R^1$ is methoxy.

3. A compound according to claim 2 wherein $R^2$ is H.

4. A compound according to claim 3 wherein X is $CH_2$.

5. A compound according to claim 1 wherein X is C(O).

6. A compound according to claim 1 wherein Q is $C_{0-2}$alkyl.

7. A compound according to claim 4 wherein Q is absent.

8. A compound according to claim 7 wherein each $R^3$ is independently $C_{2-4}$ alkyl.

9. A compound according to claim 8 wherein each $R^3$ is independently ethyl or n-butyl.

10. A compound according to claim 1 wherein $R^4$ is $PO_3H_2$.

11. A compound according to claim 9 wherein $R^4$ is $NR^5R^5$.

12. A compound according to claim 11 wherein one $R^5$ is H and the other is OH, methyl, $C_{1-4}$alkylCO$_2$H, $C_{0-2}$alkylSO$_3$H, $C_{1-2}$alkylPO$_3$H$_2$, $C(O)CO_2H$, $C(O)C_{1-2}$alkylSO$_3$H, $C(O)C_{1-2}$alkylPO$_3$H$_2$, or $CH(R^7)C_{0-1}$alkylCO$_2$H.

13. A compound according to claim 12 wherein one $R^5$ is H and the other is $CH_2CO_2H$, $CH_2SO_3H$, $CH_2CH_2SO_3H$, or $CH(R^7)C_{0-1}$alkyCO$_2$H.

14. A compound according to claim 13 wherein $R^7$ is $C_{0-1}$alkylCO$_2$H or $C_{0-2}$alkylSO$_3$H.

15. The compound

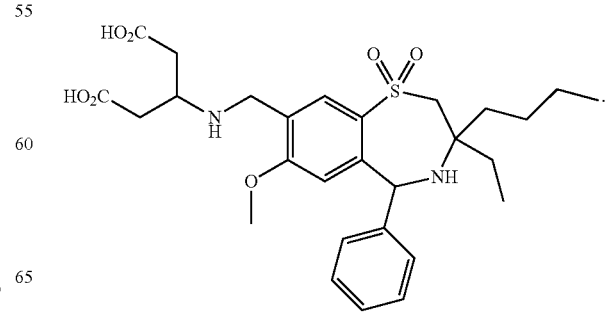

16. The compound

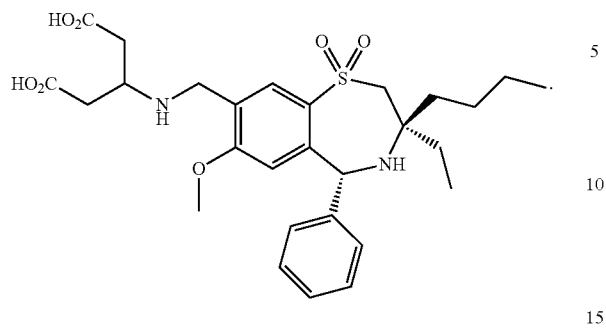

17. The compound of claim 16 wherein said compound is crystalline.

18. A pharmaceutically acceptable salt of a compound according to claim 1.

19. A pharmaceutical composition comprising a compound according to claim 16.

20. A method for treating diabetes mellitus (Type I or Type II) or obesity, in a human comprising administration of a composition according to claim 19.

21. The method of claim 20 wherein said method is for treating Type II diabetes mellitus.

22. The method of claim 21 wherein said method further comprises administration of metformin.

* * * * *